US012715867B2

(12) United States Patent
Shafeev et al.

(10) Patent No.: US 12,715,867 B2
(45) **Date of Patent: *Aug. 25, 2026**

(54) AGONISTS OF FREE FATTY ACID RECEPTOR 1 AND THEIR USE IN DISEASES ASSOCIATED WITH SAID RECEPTOR

(71) Applicant: HALO Therapeutics Ltd, Caerphilly (GB)

(72) Inventors: Mikhail Shafeev, Kyiv (UA); Daniel Josef Fitzgerald, Carouge (CH); Dominik Wolfgang Schelshorn, Geneva (CH); Igor I. Pervak, Kyiv (UA)

(73) Assignee: HALO Therapeutics Ltd, Caerphilly (GB)

( * ) Notice: Subject to any disclaimer, the term of this patent is extended or adjusted under 35 U.S.C. 154(b) by 591 days.

This patent is subject to a terminal disclaimer.

(21) Appl. No.: 18/032,963

(22) PCT Filed: Oct. 20, 2020

(86) PCT No.: PCT/EP2020/079530

§ 371 (c)(1),
(2) Date: Apr. 20, 2023

(87) PCT Pub. No.: WO2022/083853

PCT Pub. Date: Apr. 28, 2022

(65) Prior Publication Data

US 2024/0158382 A1 May 16, 2024

(51) Int. Cl.

| | |
|---|---|
| ***C07D 413/12*** | (2006.01) |
| ***A61K 31/506*** | (2006.01) |
| ***A61K 31/53*** | (2006.01) |
| ***A61P 3/08*** | (2006.01) |

(52) U.S. Cl.

CPC .......... *C07D 413/12* (2013.01); *A61K 31/506* (2013.01); *A61K 31/53* (2013.01); *A61P 3/08* (2018.01)

(58) Field of Classification Search

CPC ....... C07D 413/12; A61P 3/08; A61K 31/506; A61K 31/53

See application file for complete search history.

(56) References Cited

U.S. PATENT DOCUMENTS

2004/0006011 A1 1/2004 Gour
2022/0274968 A1* 9/2022 Shafeev ............... C07D 417/14
2023/0128972 A1* 4/2023 Viola ...................... A61P 25/28
514/249

OTHER PUBLICATIONS

Xu Li-Li et al: 11 Molecular similarity guided optimization of novel Nrf2 activators with 1,2,4-oxadiazole core; Bioorganic & Medicinal Chemistry vol. 24, No. 16, May 28, 2016 (May 28, 2016), pp. 3540-3547.

Daniel F. Kawano et al: Prospecting for New Inhibitors of Anaplastic Lymphoma Kinase, A Clinically Relevant Oncogenic Drug Target, Current Bioactive Compounds, vol. 13, No. 3, Jul. 24, 2017 (Jul. 24, 2017).

Duffy Margaret R et al: Identification of novel small molecule inhibitors of adenovirus gene transfer using a high throughput screening approach, Journal of Controlled Release, Elsevier, Amsterdam, NL, vol. 170, No. 1, May 20, 2013 (May 20, 2013), pp. 132-140.

Juxian Wang et al: Pharmacophore-Based Virtual Screening and Biological Evaluation of Small Molecule Inhibitors for Protein Arginine Methylation, Journal of Medicinal Chemistry, vol. 55, No. 18, Sep. 12, 2012 (Sep. 12, 2012), pp. 7978-7987.

Juxian Wang et al: Supporting Information, Pharmacophore-Based Virtual Screening and Biological Evaluation of Small Molecule Inhibitors for Protein Arginine Methylation, Aug. 28, 2012 (Aug. 28, 2012).

Yi-You Huang et al: Validation of Phosphodiesterase-10 as a Novel Target for Pulmonary Arterial Hypertension via Highly Selective and Subnanomolar Inhibitors, Journal of Medicinal Chemistry, vol. 62, No. 7, Mar. 19, 2019 (Mar. 19, 2019), pp. 3707-3721.

Yi-You Huang et al: Supporting Information Validation of Phosphodiesterase-10 as a Novel Target for Pulmonary Arterial Hypertension via Highly Selective and Subnanomolar Inhibitors, Mar. 19, 2019 (Mar. 19, 2019).

Jonas Bostrom et al: Oxadiazoles in Medicinal Chemistry, Journal of Medicinal Chemistry, vol. 55, No. 5, Mar. 8, 2012 (Mar. 8, 2012), pp. 1817-1830.

Ihor Zahanich et al: Phenoxymethyl 1,3-oxazoles and 1,2,4-oxadiazoles as potent and selective agonists of free fatty acid receptor 1 (GPR40), Biorganic & Medicinal Chemistry Letters, vol. 25, No. 16, Aug. 1, 2015 (Aug. 1, 2015), pp. 3105-3111.

Chemcats, Chemical Abstracts Service, Columbus, Ohio, USA, Nov. 12, 2019 (Nov. 12, 2019), XP002795546.

Chemcats, Chemical Abstracts Service, Columbus, Ohio, USA, Nov. 12, 2019 (Nov. 12, 2019), XP002795547.

International Search Report, PCT/EP2020/079530 (Mar. 17, 2021).

Written Opinion, PCT/EP2020/079530 (Mar. 17, 2021).

Covington et al.(2006) Biochem. Soc. Trans. 34 (Pt 5), 770-773.

Ang et al. (2017) The FASEB Journal. 32, 201700252RR. doi:10.1096/fj.

Davenport et al. (2013) International Union of Basic and Clinical Pharmacology. LXXXVIII. G protein-coupled receptor list: recommendations for new pairings with cognate ligands. Pharmacol. Rev., 65 (3), 967-86.

(Continued)

*Primary Examiner* — James H Alstrum-Acevedo
*Assistant Examiner* — Manahil Mirghani Ali Abdalhameed
(74) *Attorney, Agent, or Firm* — St. Onge Steward Johnston & Reens LLC; Stephen P. McNamara

(57) ABSTRACT

Novel free fatty acid receptor (FFAR) agonists, in particular agonists of FFAR1, and the use of said FFAR agonists as medicaments, in particular for treatment and/or prevention of conditions or diseases amenable to enhanced activity of FFAR1 such as conditions or diseases involving impaired control of glucose blood levels, metabolic syndrome, obesity, dyslipidemia, kidney diseases, fibrotic and sclerotic diseases as well as hepatic and biliary diseases. $R^1$—S—$CH_2$—OXA-$R^2$.

22 Claims, 46 Drawing Sheets

(56) References Cited

OTHER PUBLICATIONS

Stoddart et al. (2008) International Union of Pharmacology. LXXI. Free fatty acid receptors FFA1, -2, and -3: pharmacology and pathophysiological functions. Pharmacol. Rev., 60 (4): 405-17.
Briscoe et al. (2003) J Biol Chem 278, 11303-11311.
Itoh et al. (2003) Nature 422, 173-176.
Kotarsky et al. (2003) Biochem Biophys Res Commun 301, 406-410.
Hirasawa et al. (2005) Nat Med 11, 90-94.
Ichimura et al. (2012) Nature, 483 (7389) 350-354.
Oh et al. (2010) Cell, 142 (5), 687-98.
Brown et al. (2003) J Biol Chem 278, 11312-11319.
Le Poul et al. (2003) J Biol Chem 278, 25481-25489.
Nilsson et al. (2003) Biochem Biophys Res Commun 303, 1047-1052.
Srivastava et al. (2014) Nature 513 (7516), 124-127.
Burant et al. (2012) Lancet 379, 1403-1411.
Houze et al. (2012) Bioorg Med Chem Lett 22, 1267-1270.
Briscoe et al. (2006) British Journal of Pharmacology 148, 619-628.
Hara et al. (2009) Naunyn Schmiedebergs Arch Pharmacol 380, 247-255.
Sun et al. (2010) Mol Pharmacol 78, 804-810.
Martin et al. (2012) J Lipid Res 53, 2256-2265.
Shimpukade et al. (2012) J Med Chem 55, 4511-4515.

* cited by examiner

Z3465744373
nM EC50: 2.511886432 , -p(EC50,M): 8.6
% Activity: 38

Z3485538339
nM EC50: 3.981071706 , -p(EC50,M): 8.4
% Activity: 40

Z3485538343
nM EC50: 3.981071706 , -p(EC50,M): 8.4
% Activity: 40

Z3485538337
nM EC50: 6.309573445 , -p(EC50,M): 8.2
% Activity: 38

Z3397119007 nM EC50: 7.943282347 , -p(EC50,M): 8.1

% Activity: 27

Z3352693146 nM EC50: 7.943282347 , -p(EC50,M): 8.1

% Activity: 32

Z3465744378
nM EC50: 7.943282347 , -p(EC50,M): 8.1
% Activity: 38

Z3465744370
nM EC50: 10 , -p(EC50,M): 8
% Activity: 38

Z3352693158
nM EC50: 12.58925412 , -p(EC50,M): 7.9
% Activity: 35

Z3465744375
nM EC50: 12.58925412 , -p(EC50,M): 7.9
% Activity: 30

Z3485538344
nM EC50: 12.58925412 , -p(EC50,M): 7.9
% Activity: 40

Z3331727681
nM EC50: 15.84893192 , -p(EC50,M): 7.8
% Activity: 36

Z3397119001 nM EC50: 15.84893192 , -p(EC50,M): 7.8

% Activity: 27

Z3325085943 nM EC50: 19.95262315 , -p(EC50,M): 7.7

% Activity: 39

Z3397119008 nM EC50: 19.95262315 , -p(EC50,M): 7.7

% Activity: 29

Z3397119003 nM EC50: 19.95262315 , -p(EC50,M): 7.7

% Activity: 43

Z1558782315
nM EC50: 25.11886432 , -p(EC50,M): 7.6
% Activity: 29

Z1263951047
nM EC50: 25.11886432 , -p(EC50,M): 7.6
% Activity: 50

Z1263951043 nM EC50: 25.11886432 , -p(EC50,M): 7.6

% Activity: 37

Z3400108341 nM EC50: 25.11886432 , -p(EC50,M): 7.6

% Activity: 35

Z3465744387
nM EC50: 25.11886432 , -p(EC50,M): 7.6
% Activity: 38

Z1558775684
nM EC50: 31.6227766 , -p(EC50,M): 7.5
% Activity: 36

Z3379835076 nM EC50: 31.6227766 , -p(EC50,M): 7.5

% Activity: 34

Z1272945752 nM EC50: 31.6227766 , -p(EC50,M): 7.5

% Activity: 36

Z74373346
nM EC50: 31.6227766 , -p(EC50,M): 7.5
% Activity: 36

Z3400108335
nM EC50: 31.6227766 , -p(EC50,M): 7.5
% Activity: 37

Z3485538331 nM EC50: 31.6227766 , -p(EC50,M): 7.5

% Activity: 3

Z3379835080 nM EC50: 39.81071706 , -p(EC50,M): 7.4

% Activity: 28

Z3331727639 nM EC50: 39.81071706 , -p(EC50,M): 7.4

% Activity: 31

Z3352693152 nM EC50: 39.81071706 , -p(EC50,M): 7.4

% Activity: 40

Z3304784609
nM EC50: 39.81071706 , -p(EC50,M): 7.4
% Activity: 37

Z3304784620
nM EC50: 39.81071706 , -p(EC50,M): 7.4
% Activity: 36

Z3465744383
nM EC50: 39.81071706 , -p(EC50,M): 7.4
% Activity: 33

Z3397119002
nM EC50: 50.11872336 , -p(EC50,M): 7.3
% Activity: 35

Z3325085937
nM EC50: 50.11872336 , -p(EC50,M): 7.3
% Activity: 36

Z3331727663
nM EC50: 50.11872336 , -p(EC50,M): 7.3
% Activity: 37

Z3352693156
nM EC50: 50.11872336 , -p(EC50,M): 7.3
% Activity: 43

Z3352693154
nM EC50: 50.11872336 , -p(EC50,M): 7.3
% Activity: 37

Z3379835077 nM EC50: 50.11872336 , -p(EC50,M): 7.3

% Activity: 34

Z3352693149 nM EC50: 50.11872336 , -p(EC50,M): 7.3

% Activity: 34

Z3331727680
nM EC50: 50.11872336 , -p(EC50,M): 7.3
% Activity: 35

Z3400108326
nM EC50: 50.11872336 , -p(EC50,M): 7.3
% Activity: 38

Z3465744380 nM EC50: 50.11872336, -p(EC50,M): 7.3

% Activity: 38

Z3485538342 nM EC50: 50.11872336 , -p(EC50,M): 7.3

% Activity: 40

Z3304784612 nM EC50: 63.09573445 , -p(EC50,M): 7.2

% Activity: 44

Z1263951032 nM EC50: 63.09573445 , -p(EC50,M): 7.2

% Activity: 35

Z3379835078
nM EC50: 63.09573445 , -p(EC50,M): 7.2
% Activity: 34

Z3302950784
nM EC50: 63.09573445 , -p(EC50,M): 7.2
% Activity: 39

Z3397119006 nM EC50: 63.09573445 , -p(EC50,M): 7.2

% Activity: 38

Z855791334 nM EC50: 79.43282347 , -p(EC50,M): 7.1

% Activity: 30

Z3271681130 nM EC50: 79.43282347 , -p(EC50,M): 7.1

% Activity: 35

Z3379835074 nM EC50: 79.43282347 , -p(EC50,M): 7.1

% Activity: 25

Z1263951049
nM EC50: 79.43282347 , -p(EC50,M): 7.1
% Activity: 35

Z3400108327
nM EC50: 79.43282347 , -p(EC50,M): 7.1
% Activity: 35

Z3485538336
nM EC50: 79.43282347 , -p(EC50,M): 7.1
% Activity: 40

Z3375851526
nM EC50: 100 , -p(EC50,M):7
% Activity: 20

Z3379835075
nM EC50: 100 , -p(EC50,M): 7
% Activity: 41

Z3302950786
nM EC50: 100 , -p(EC50,M):7
% Activity: 33

Z3397119009
nM EC50: 100 , -p(EC50,M):7
% Activity: 5

Z3485538340
nM EC50:100 , -p(EC50,M): 7
% Activity: 20

Z3302950790
nM EC50: 125.8925412 , -p(EC50,M): 6.9
% Activity: 36

Z3399992230
nM EC50: 125.8925412 , -p(EC50,M): 6.9
% Activity: 37

Z3465744385
nM EC50: 125.8925412 , -p(EC50,M): 6.9
% Activity: 30

Z3331727652
nM EC50: 158.4893192 , -p(EC50,M): 6.8
% Activity: 35

Z3400108333
nM EC50: 158.4893192 , -p(EC50,M): 6.8
% Activity: 32

Z3400108334
nM EC50: 158.4893192 , -p(EC50,M): 6.8
% Activity: 37

Z3304784617 nM EC50: 199.5262315 , -p(EC50,M):6.7

% Activity: 40

Z3325085938 nM EC50: 199.5262315 , -p(EC50,M):6.7

% Activity: 24

Z3400108300
nM EC50: 199.5262315 , -p(EC50,M): 6.7
% Activity: 28

Z3400108303
nM EC50: 199.5262315 , -p(EC50,M): 6.7
% Activity: 37

Z3397119005
nM EC50: 199.5262315 , -p(EC50,M): 6.7
% Activity: 35

Z3465744366
nM EC50: 199.5262315 , -p(EC50,M): 6.7
% Activity: 21

Z1272945742
nM EC50: 251.1886432 , -p(EC50,M): 6.6
% Activity: 30

Z3352693410
nM EC50: 251.1886432 , -p(EC50,M): 6.6
% Activity: 21

Z1263936589
nM EC50: 251.1886432 , -p(EC50,M): 6.6
% Activity: 33

Z3302950788
nM EC50: 251.1886432 , -p(EC50,M): 6.6
% Activity: 45

Z3400108307
nM EC50: 251.1886432 , -p(EC50,M): 6.6
% Activity: 33

Z3446839939
nM EC50: 251.1886432 , -p(EC50,M): 6.6
% Activity: 59

Z855791540
nM EC50: 316.227766 , -p(EC50,M): 6.5
% Activity: 43

Z71175677
nM EC50: 316.227766 , -p(EC50,M): 6.5
% Activity: 26

Z3400108304
nM EC50: 316.227766 , -p(EC50,M): 6.5
% Activity: 29

Z1263928611
nM EC50: 398.1071706 , -p(EC50,M): 6.4
% Activity: 25

Z1143973826 nM EC50: 398.1071706 , -p(EC50,M): 6.4

% Activity: 11

Z3331727625 nM EC50: 398.1071706 , -p(EC50,M): 6.4

% Activity: 41

Z3331727576
nM EC50: 398.1071706 , -p(EC50,M): 6.4
% Activity: 5

Z3304784622
nM EC50: 398.1071706 , -p(EC50,M): 6.4% Activity: 47

Z92291581 nM EC50: 158.4893192 , -p(EC50,M): 6.8
% Activity: 30

Z74373790 nM EC50: 158.4893192 , -p(EC50,M): 6.8
% Activity: 30

Z74373573
nM EC50: 251.1886432 , -p(EC50,M): 6.6
% Activity: 26

AGONISTS OF FREE FATTY ACID RECEPTOR 1 AND THEIR USE IN DISEASES ASSOCIATED WITH SAID RECEPTOR

FIELD OF THE INVENTION

The present invention relates to novel free fatty acid receptor (FFAR) agonists, in particular agonists of FFAR1, and to the use of said FFAR agonists as medicaments, in particular for treatment and/or prevention of conditions or diseases amenable to enhanced activity of FFAR1 such as of conditions or diseases involving impaired control of glucose blood levels, metabolic syndrome, obesity, dyslipidemia, kidney diseases, fibrotic and sclerotic diseases as well as hepatic and biliary diseases.

BACKGROUND OF THE INVENTION

The free fatty acid receptors are G-protein coupled receptors which bind free fatty acids [1]. Free fatty acid receptors have broad tissue distribution, e.g., they are expressed in mouth (possibly for sensing fatty taste), digestive system (as energy sensors, and eating sensors), pancreatic Beta cells (to sense feeding), and even in CNS (of yet unknown function). There are at least four different FFARs, each encoded by a separate gene (FFAR1, FFAR2, FFAR3, FFAR4). Preliminary findings suggest that FFAR2 and FFAR3 may interact to form a FFAR2-FFAR3 receptor heteromer. [2] Free fatty acid receptors (FFA, nomenclature as agreed by the NC-IUPHAR Subcommittee on free fatty acid receptors [3,4]) are activated by free fatty acids. Long-chain saturated and unsaturated fatty acids (C14.0 (myristic acid), C16:0 (palmitic acid), C18:1 (oleic acid), C18:2 (linoleic acid), C18:3, (α-linolenic acid), C20:4 (arachidonic acid), C20:5,n−3 (EPA) and C22:6,n−3 (docosahexaenoic acid)) activate FFAR1 [5, 6, 7] and FFAR4 receptors [8, 9, 10]. while short chain fatty acids (C2 (acetic acid), C3 (propanoic acid), C4 (butyric acid) and C5 (pentanoic acid)) activate FFAR2 [11, 12, 13] and FFAR3 [11, 12] receptors. The crystal structure for agonist bound FFAR1 has been described in [14].

FFAR1 is also known as GPR40, FFAR4 is known as GPR120.

Several known FFAR1 (GPR40) agonists are under development as Type 2 diabetic drugs. An example is Fasiglifam (TAK-875) is a highly potent GPR40 agonist (low nanomolar EC50 on human GPR40) with marked selectivity over other FFA family receptors (i.e., GPR120). It stimulates insulin secretion independently of blood glucose levels, which led to the expectation that TAK-875, in contrast to other anti-diabetic medicines, would not induce hypoglycemia, while also causing less weight gain [15]. Although very promising, the development of TAK-875 was terminated in 2013 due to (liver) toxicity issues in phase III clinical trials. Also the clinical development of other FFAR1 (GPR40) agonists such as LY2881835 [16] and AMG 837 [17] was stopped because of toxicity issues.

Several agonists for FFAR4 (GPR120), are undergoing preliminary development. In the search for compounds binding and activating FFAR4 (GPR120): for example, GW9508, initially identified as a GPR40 agonist, was shown to also moderately activate GPR120 [17]. However, the dual specificity of GW9508 for GPR40 and GPR120 represents a confounding variable in the interpretation of results in studies using GW9508 as a result of off-target effects at GPR40. Further research identified several other potential agonists for GPR120 including the plant-derived compound grifolic acid which acts as a partially selective GPR120 agonist [18], and NCG21 [19] as well as GSK-137647A [20], which are reported to be selective for GPR120. Recently, TUG891 has been made commercially available as a GPR120 agonist. TUG891 is reported to be potent and selective for GPR120 demonstrating greater selectivity and potency to GPR120 than GPR40 [21].

The broad tissue distribution of FFARs and their apparently diverse physiological functions in the body has resulted in the target class being investigated for several types of diseases. The FFAR family's broad tissue distribution and involvement in multiple physiological processes also mean that target selectivity within the FFAR family is a major issue to consider in the context of development of therapeutic molecules. FFAR1/GPR40 has emerged as a target for treatment of (T2DM). T2DM is a disease in which blood sugar homeostasis is regulated improperly by insulin. Insulin is secreted from pancreatic b cells in response to elevated plasma glucose, with several additional types of signals combining to modify its insulin secretion rate from pancreatic b cells. One of those signals comes from free fatty acids circulating in the bloodstream, which typically accompany elevated blood glucose following feeding. In 2003, it was demonstrated [6] that FFAR1/GPR40 is abundantly expressed on the surface of pancreatic beta cells and functions as a receptor for long-chain FFAs, and that these FFAs amplify glucose-stimulated insulin secretion. Agonism of FFAR1/GPR40 in pancreatic beta cells was demonstrated to amplify insulin secretion over a period spanning hours, and even full agonism of the receptor did not appear to result in secretion of insulin levels sufficient to drive hypoglycemia. Hypoglycemia means low blood glucose, and severe hypoglycemia occurs when the blood glucose level becomes so low that a patient is unable to maintain normal activity, and it can result in loss of consciousness and be life threatening (due to oxygen deprivation in the brain which function crucially depends on appropriate glucose supply). Critically, available insulin stimulation drugs for treating T2DM generally have the potential to result in inappropriately high insulin secretion and trigger severe hypoglycemia. Since severe hypoglycemia cannot be triggered by agonizing PR40, GPR40 agonists therefore have a high potential for the treatment of T2DM.

The technical problem underlying the present invention is to provide agonists of FFARs, in particular agonists of FFAR1.

SUMMARY OF THE INVENTION

The technical problem underlying the present invention is to provide agonists of FFARs, in particular agonists of FFAR1.

The above technical problem is provided by the embodiments of the present invention as characterized in the claims, the present description and the drawings.

In particular, the present invention provides a compound of general formula (I)

$$R^1—S—CH_2—OXA\text{-}R^2 \qquad (I)$$

including enantiomers, diastereomers, hydrates, solvates, pharmaceutically acceptable cocrystals or salts, prodrugs and complexes thereof;

wherein

OXA is selected from the group consisting of 1,3-oxazolyl, 1,2,4-oxadiazolyl or 1,3,4-oxadiazolyl, with 1,3-oxazolyl being preferred;

when OXA is 1,3-oxazolyl, the group $R^1$—S—$CH_2$ is bound to $C^2$ of the 1,3-oxazolyl and the group $R^2$ is bound to C4 of the 1,3-oxazolyl;

when OXA is 1,2,4-oxadiazolyl the group $R^1$—S—$CH_2$ is bound to C5 of the 1,2,4-oxadiazolyl and the group $R^2$ is bound to C3 of the 1,2,4-oxadiazolyl;

when OXA is 1,3,4-oxadiazolyl the group $R^1$—S—$CH_2$ is bound to C5 of the 1,3,4-oxadiazolyl and the group $R^2$ is bound to $C^2$ of the 1,3,4-oxadiazolyl;

$R^1$ is a 6 membered heteroaryl group selected from the group consisting of 1,3,5-triazinyl and pyrimidinyl being independently substituted with one or more substituents selected from the group consisting of hydroxyl, amino, $C_1$-$C_6$-alkyl, $C_3$-$C_6$-cycloalkyl, $C_1$-$C_4$-alkoxy, N-mono- or N,N-di-substituted $C_1$-$C_3$-alkylamino, non-aromatic 5- to 6-membered heterocyclyl, 6-membered aryl and 5- to 6-membered heteroaryl which substituents may be unsubstituted or substituted with one or more groups selected from the group consisting of halide, cyano and $C_1$-$C_6$-alkyl, wherein the 6-membered aryl and 5- to 6-membered heteroaryl group, respectively, may be fused to said 1,3,5-triazinyl or pyrimidyl group, respectively, and $R^2$ is phenyl being unsubstituted or being substituted with one or more substituents selected from the group consisting of halide, cyano, amino, $C_1$-$C_6$-alkyl, $C_3$-$C_6$-cycloalkyl which may be optionally substituted with one or more halides, $C_1$-$C_4$-alkoxy which may optionally substituted with one or more halides, hydroxy-$C_1$-$C_6$-alkyl, sulfonyl-$C_1$-$C_6$-alkyl, sulphamidyl-N—$C_1$-$C_6$-alkyl and carboxamidyl-N-mono- or —N,N-di-$C_1$-$C_6$-alkyl;

with the proviso that the following compounds are excluded:

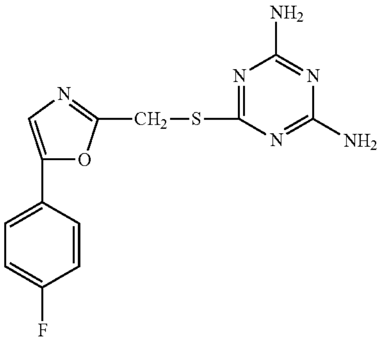

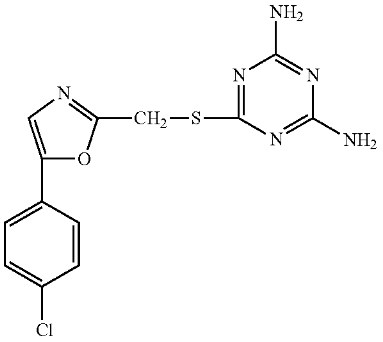

-continued

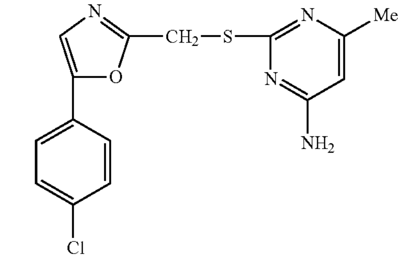

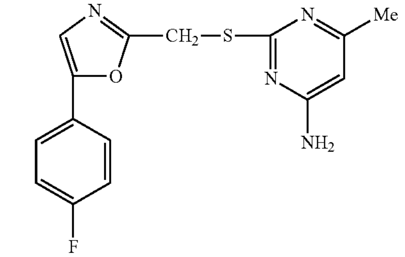

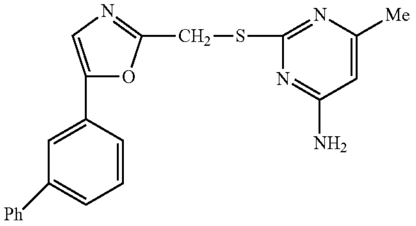

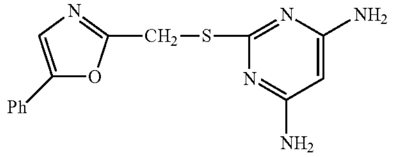

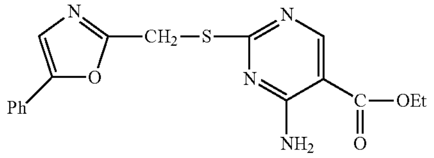

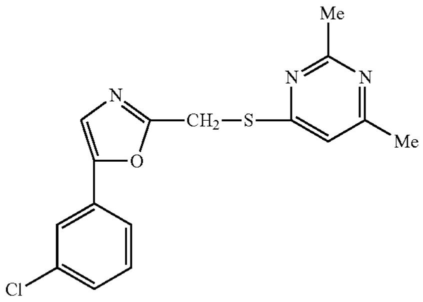

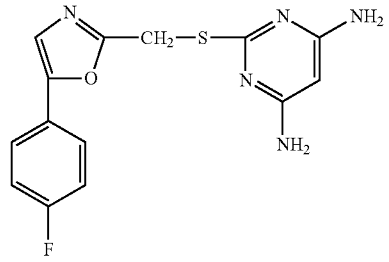

-continued

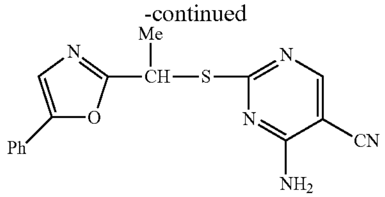

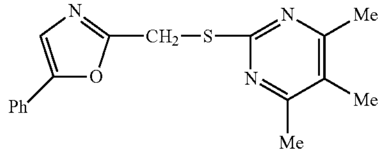

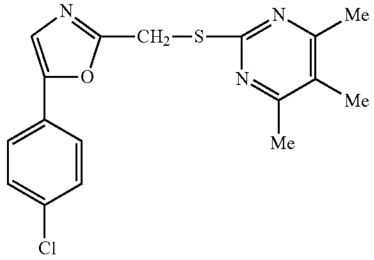

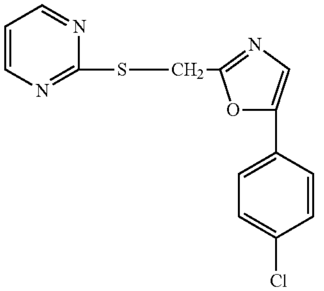

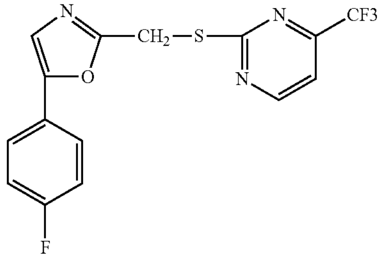

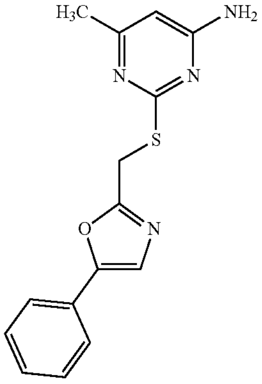

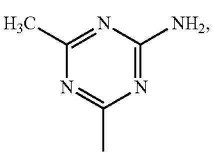,

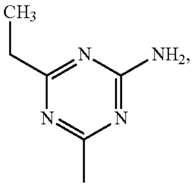,

Preferred halide substituents of the invention are selected from Cl, Brand F.

DETAILED DESCRIPTION OF THE INVENTION

Figure 1:
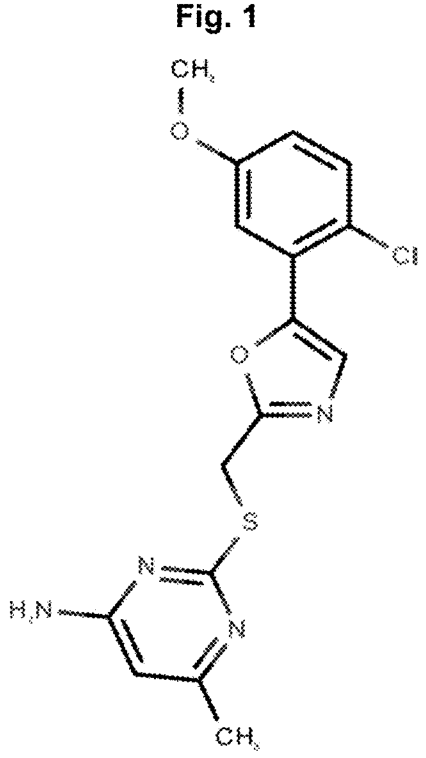
FIG. 1 shows preferred compounds of the invention. nM EC50, p(EC50,M) and % activation compared to AMG 837 are indicated.
Figure 1:
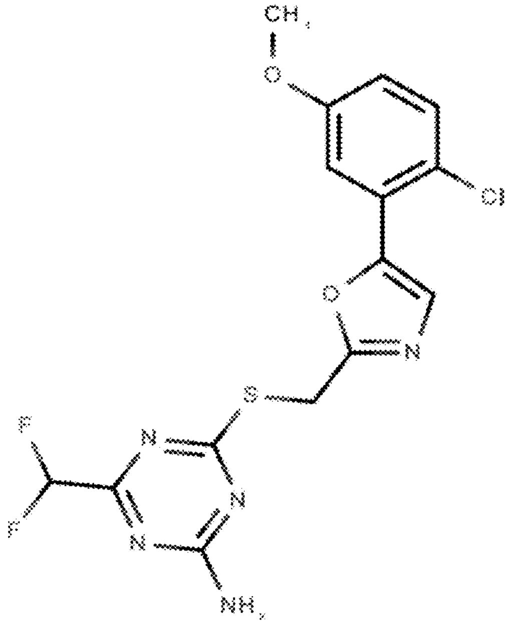
Figure 1:
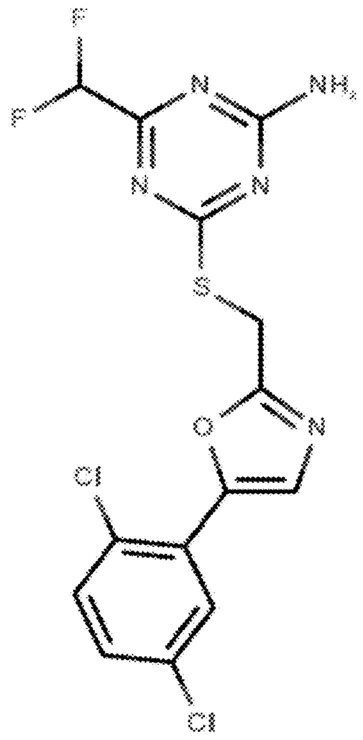
Figure 1:
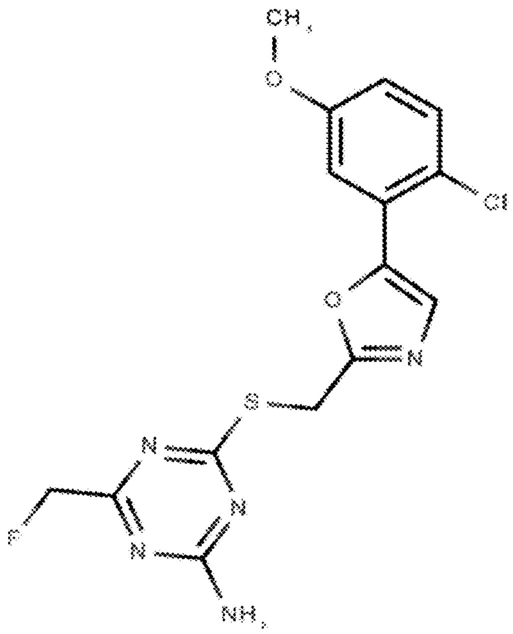
Figure 1:
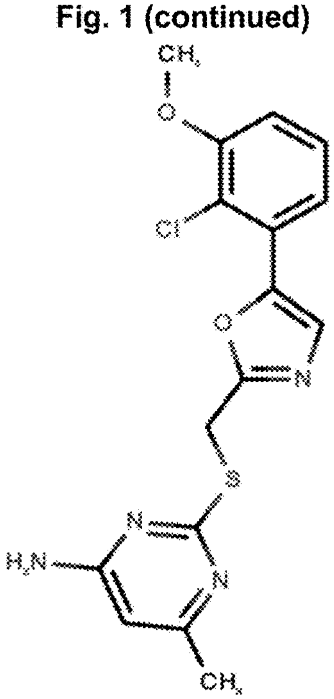
Figure 1:
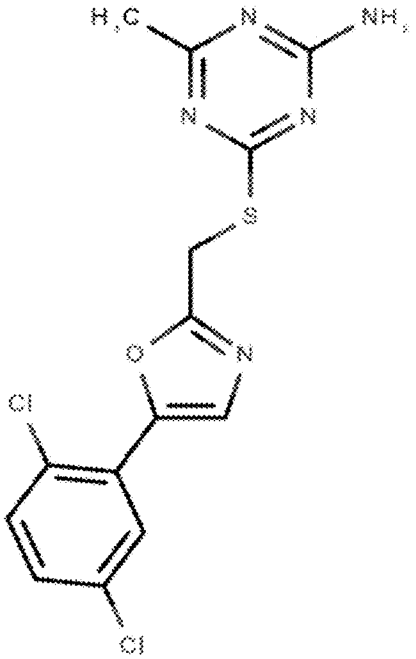
Figure 1:
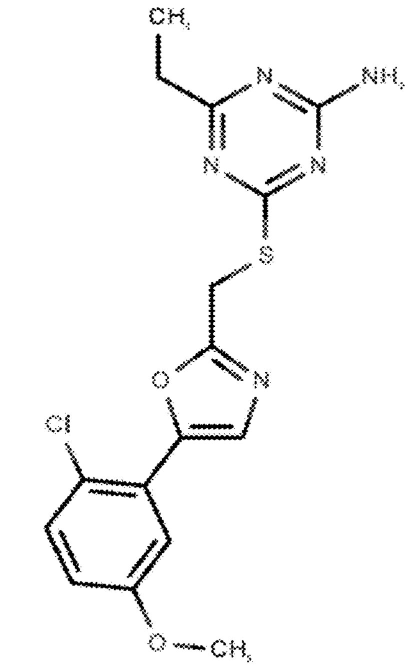
Figure 1:
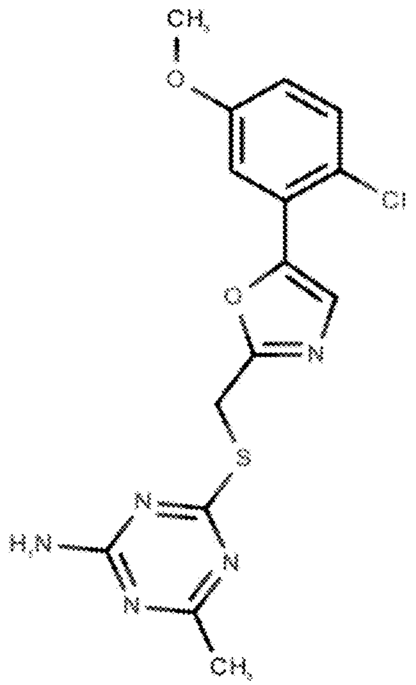
Figure 1:
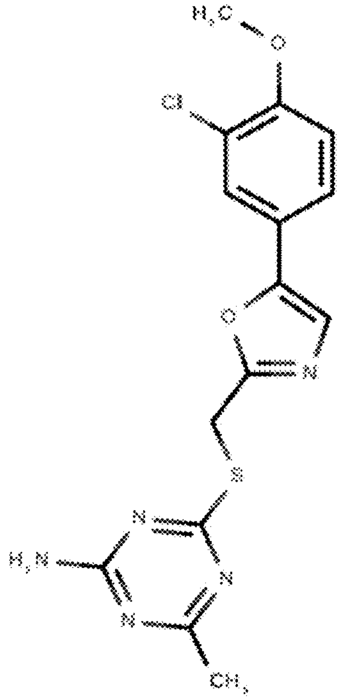
Figure 1:
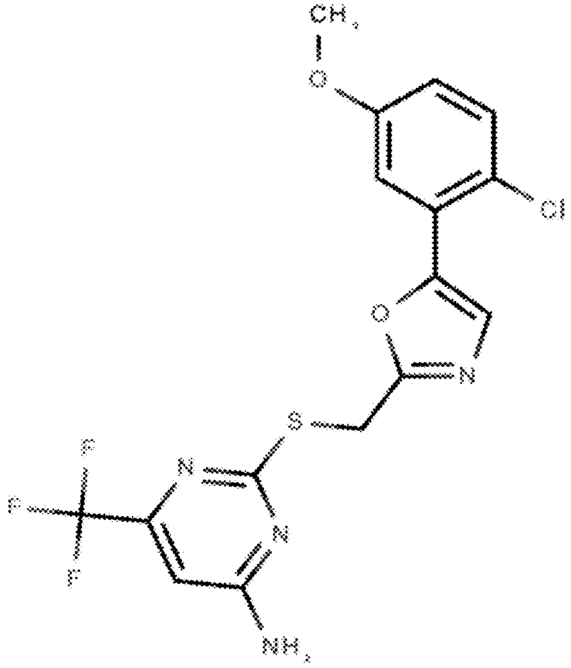
Figure 1:
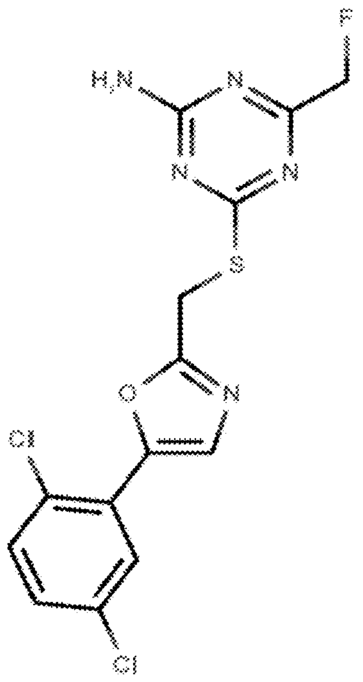
Figure 1:
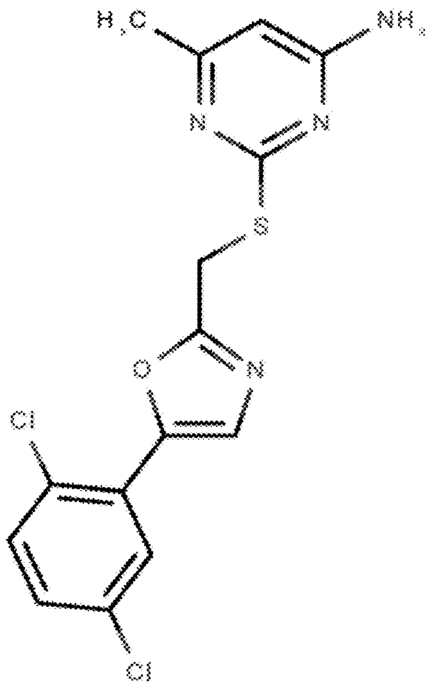
Figure 1:
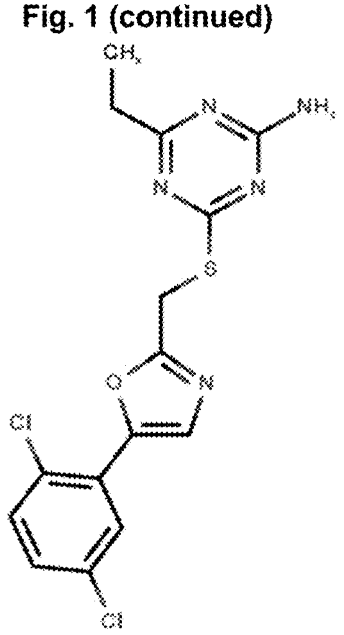
Figure 1:
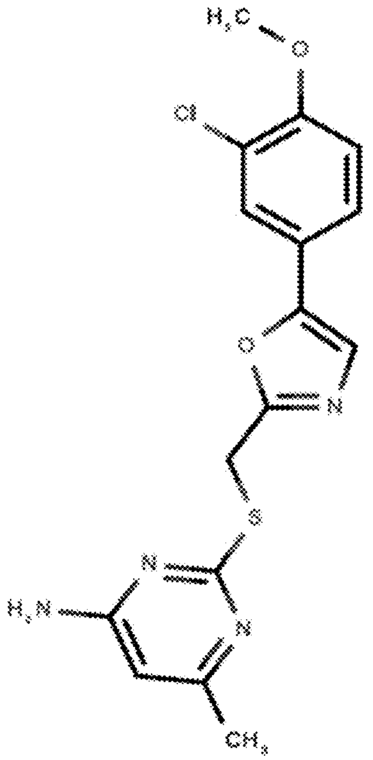
Figure 1:
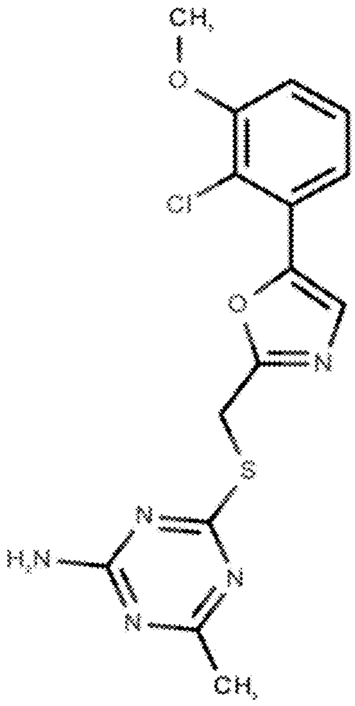
Figure 1:
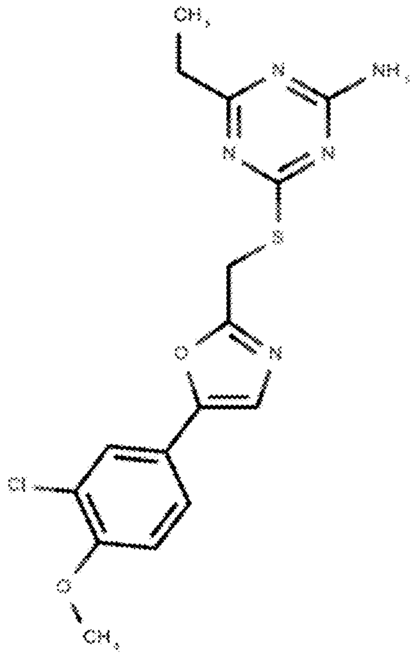
Figure 1:
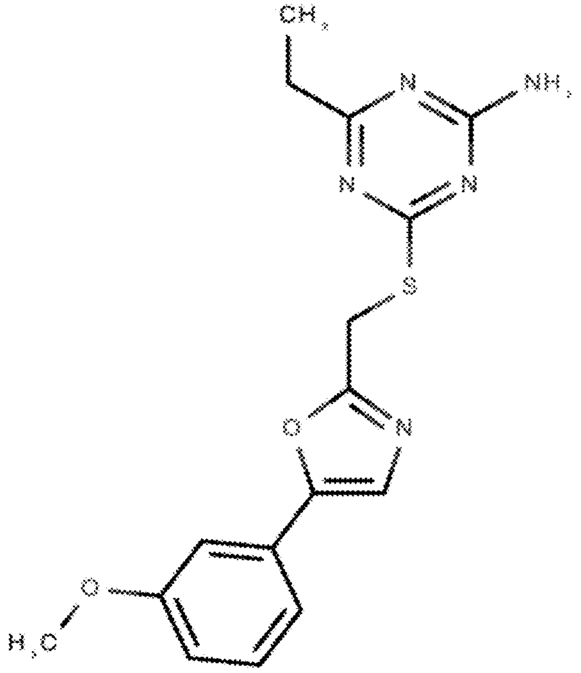
Figure 1:
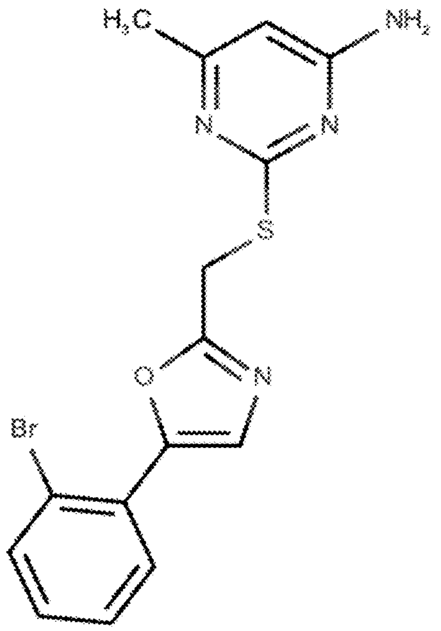
Figure 1:
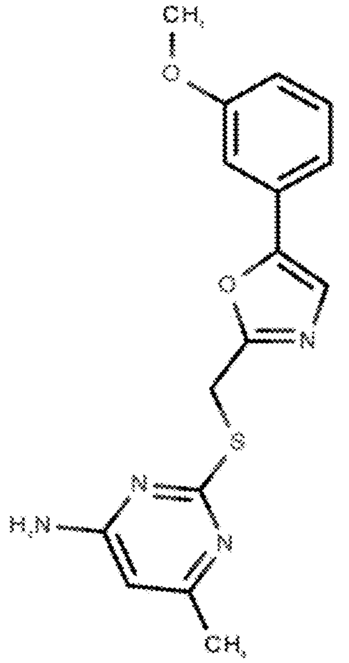
Figure 1:
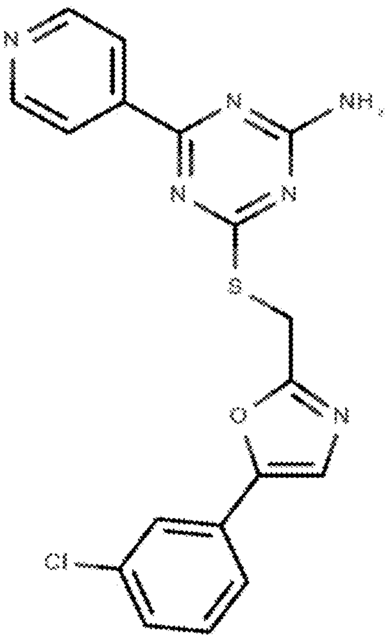
Figure 1:
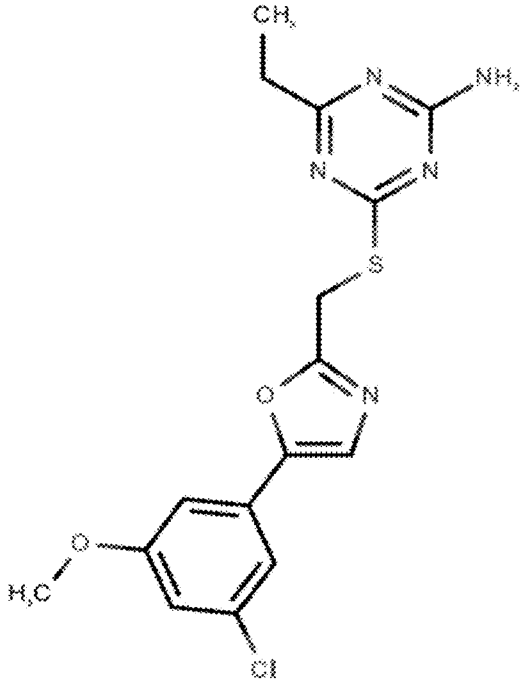
Figure 1:
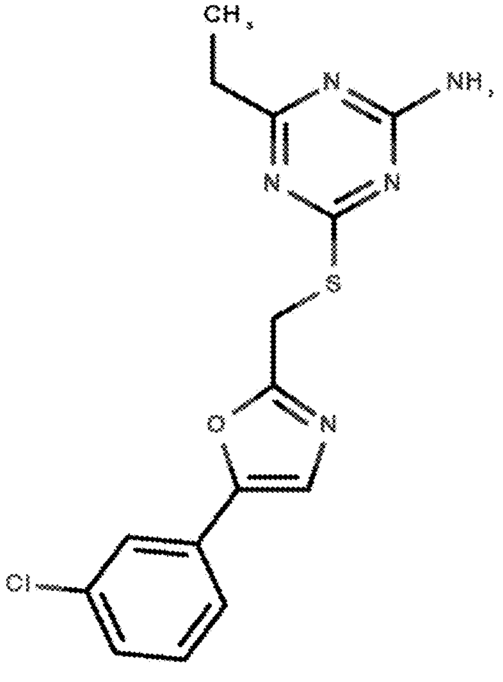
Figure 1:
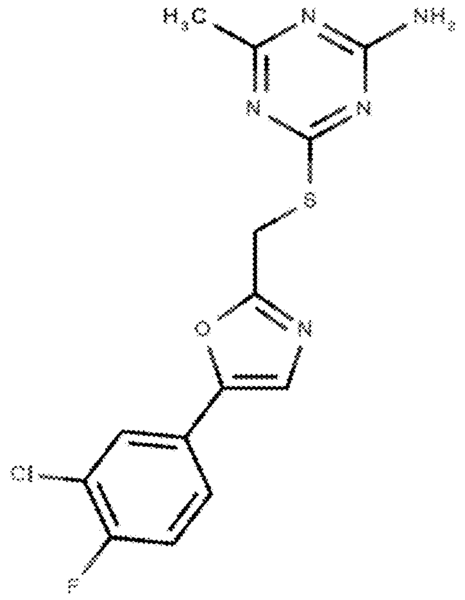
Figure 1:
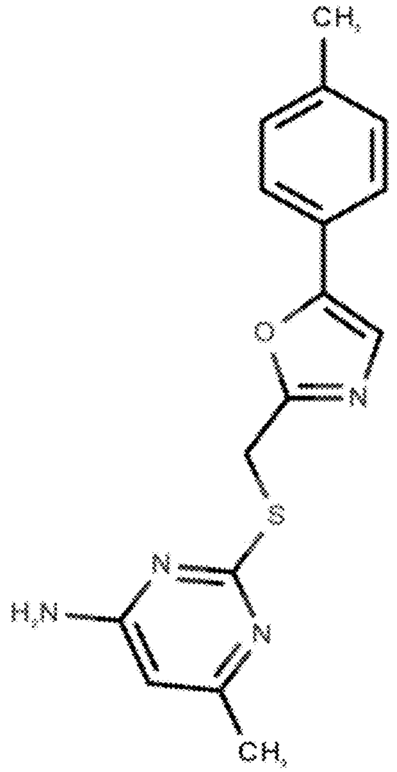
Figure 1:
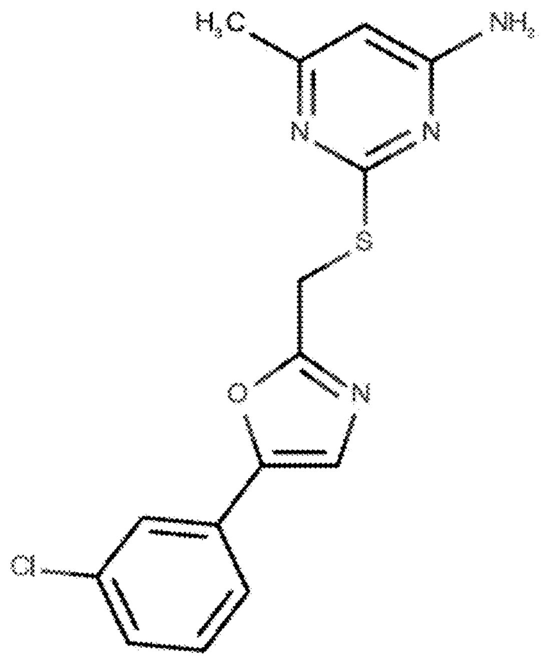
Figure 1:
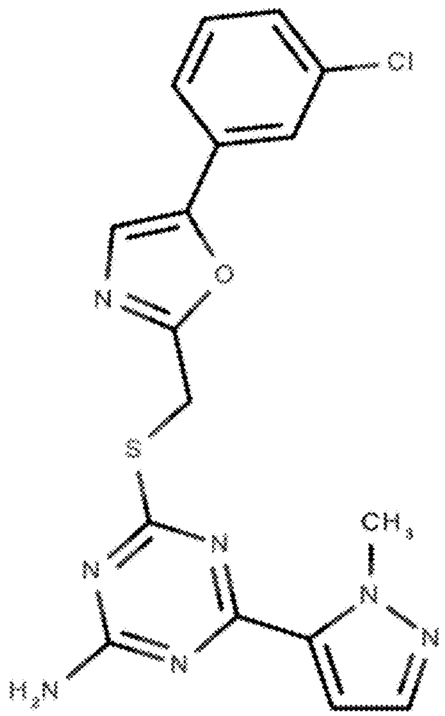
Figure 1:
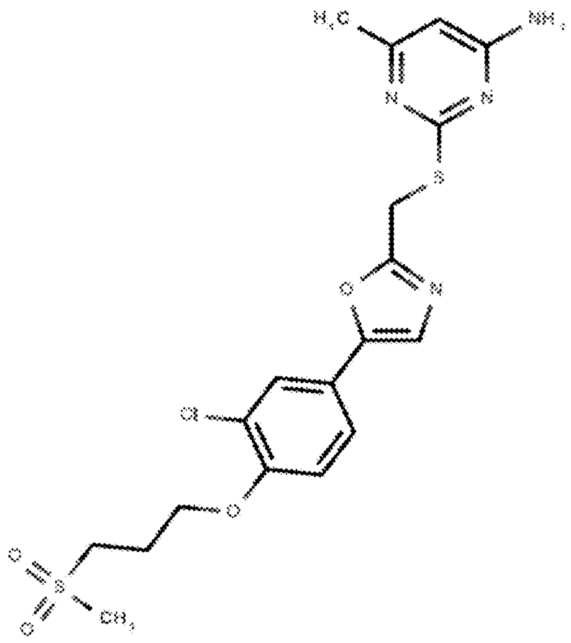
Figure 1:
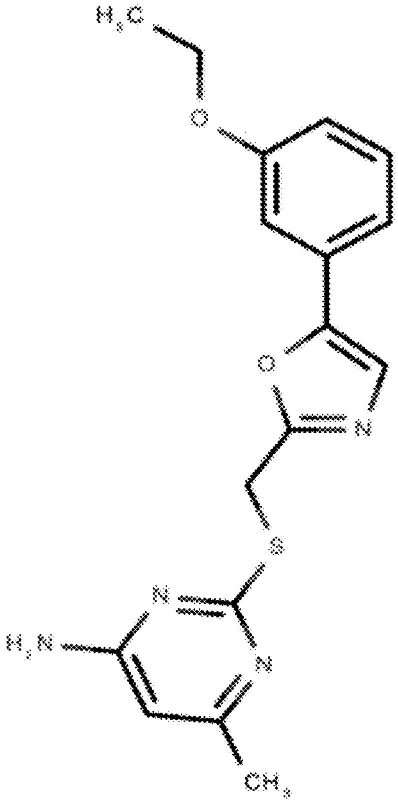
Figure 1:
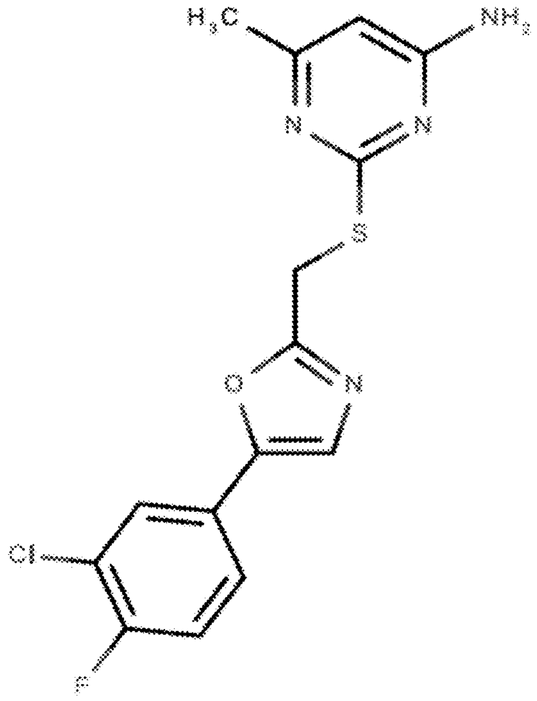
Figure 1:
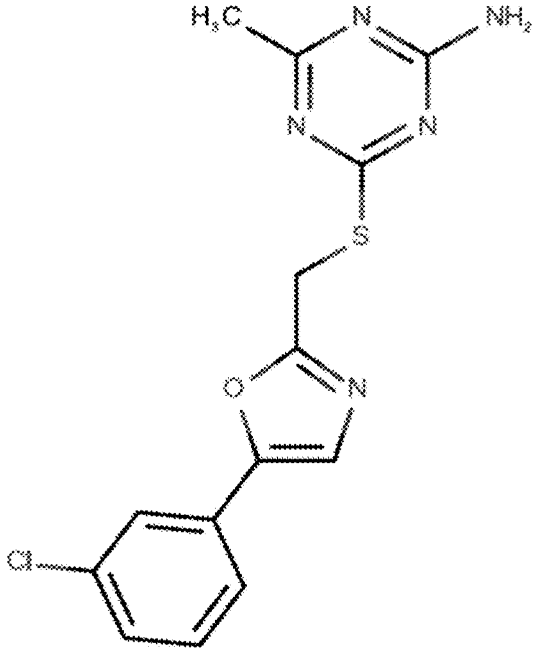
Figure 1:
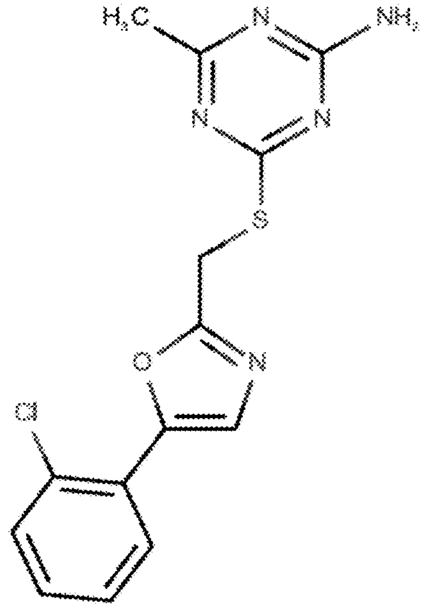
Figure 1:
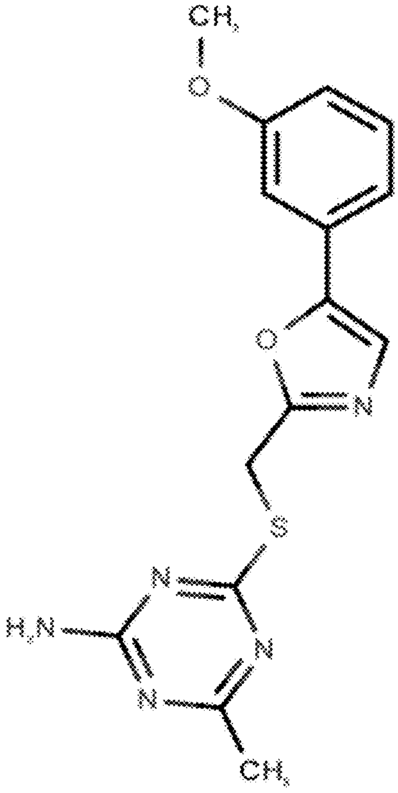
Figure 1:
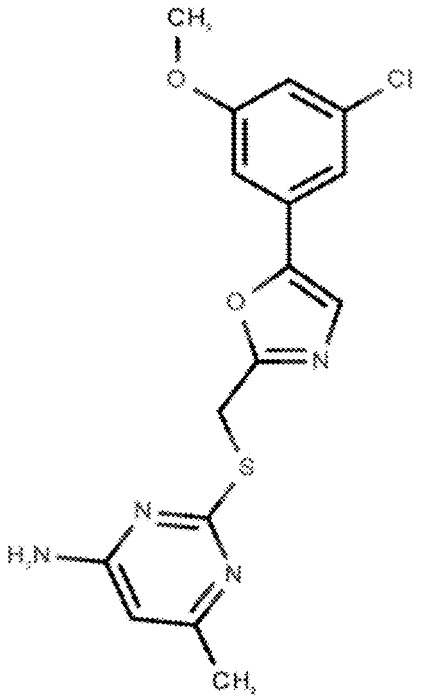
Figure 1:
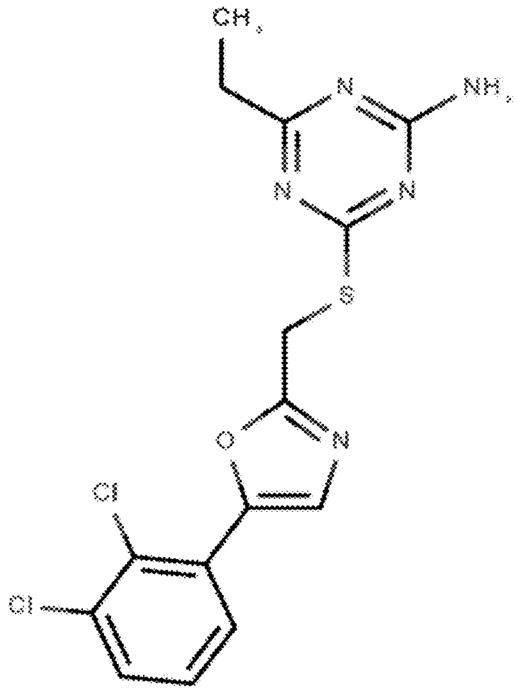
Figure 1:
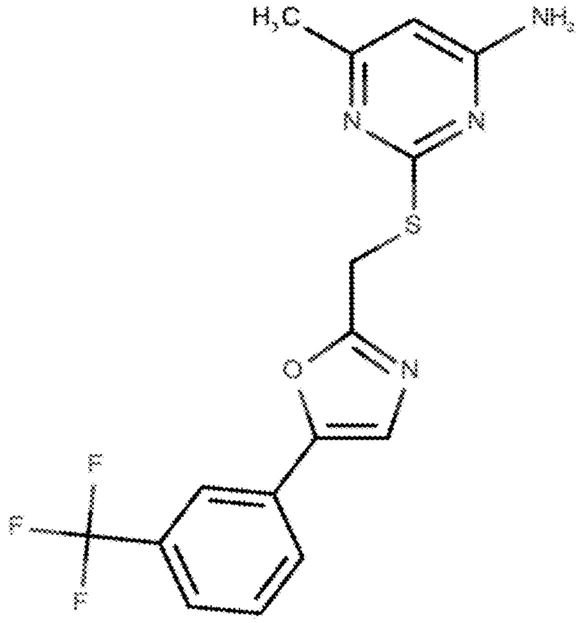
Figure 1:
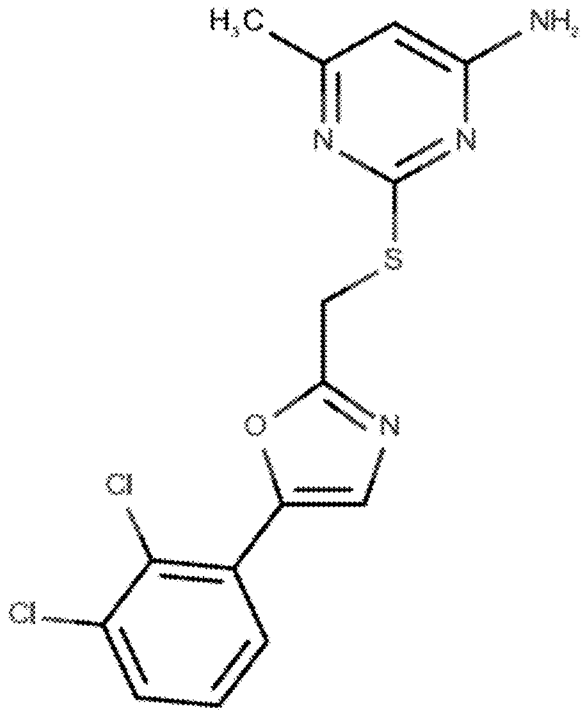
Figure 1:
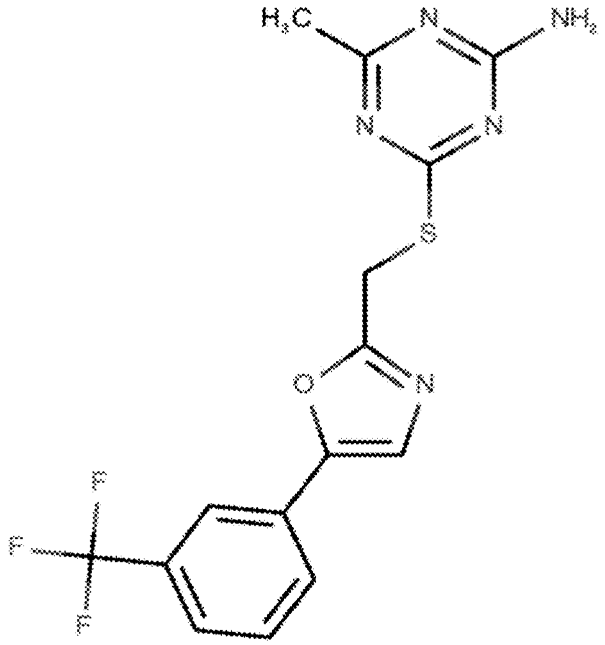
Figure 1:
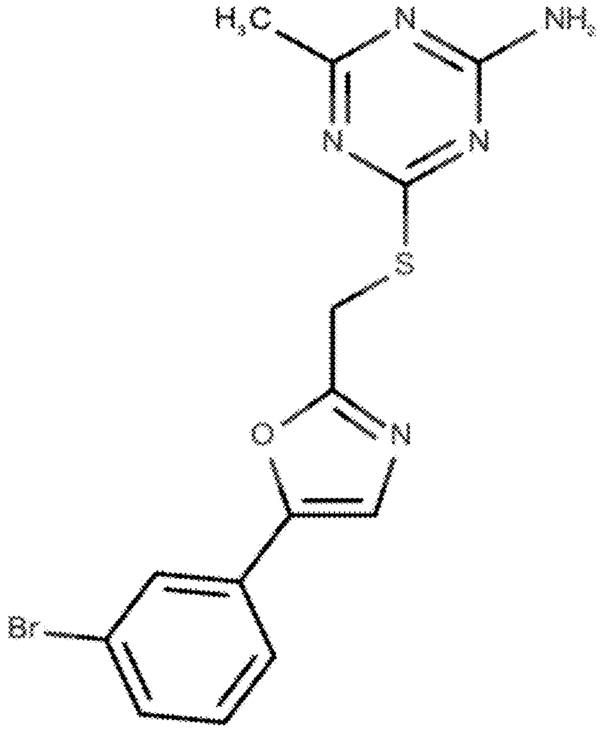
Figure 1:
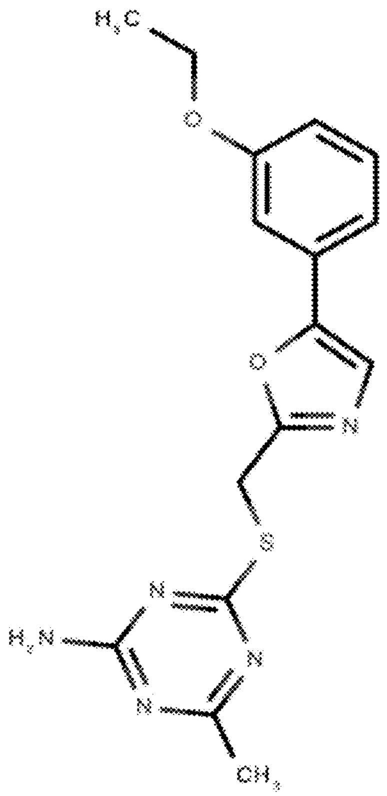
Figure 1:
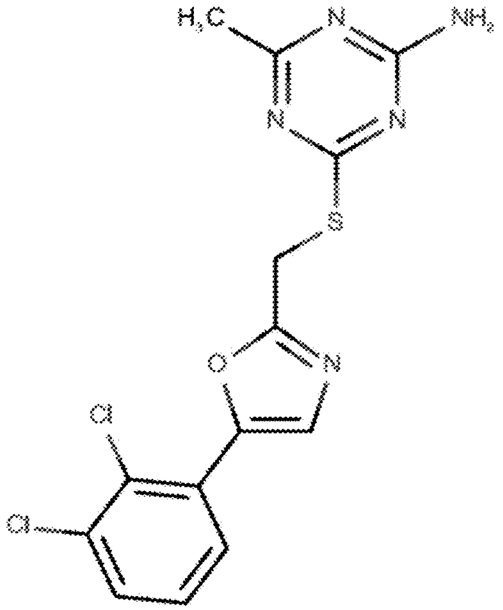
Figure 1:
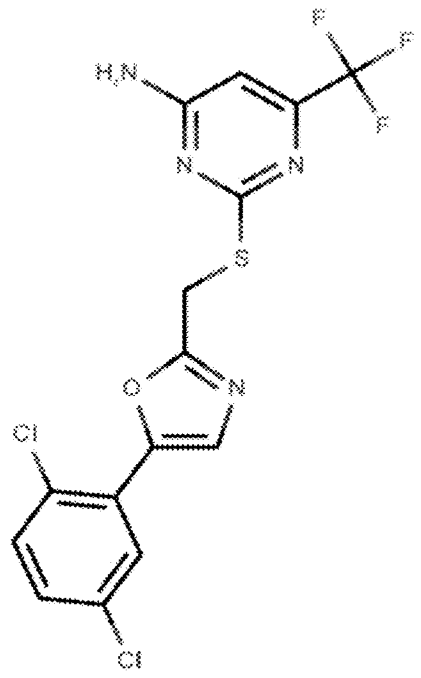
Figure 1:
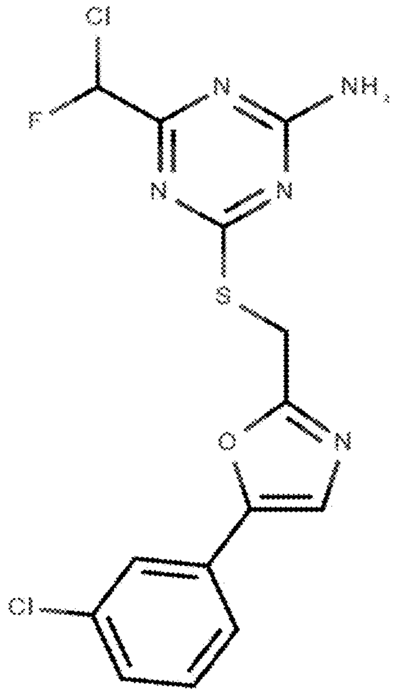
Figure 1:
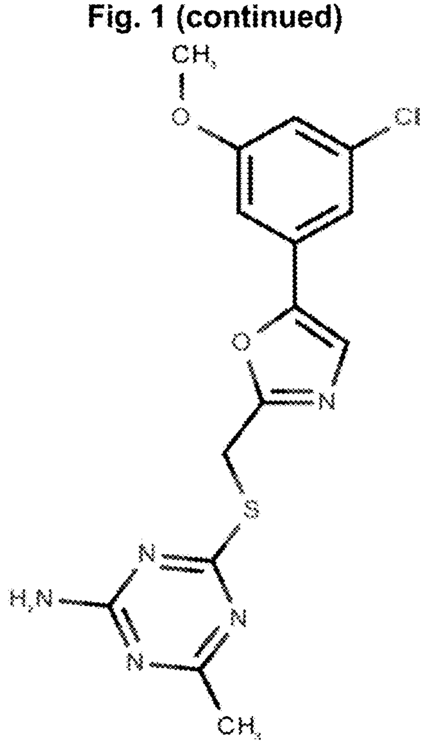
Figure 1:
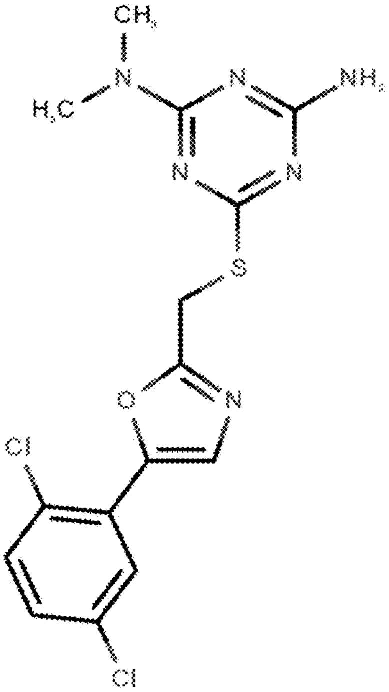
Figure 1:
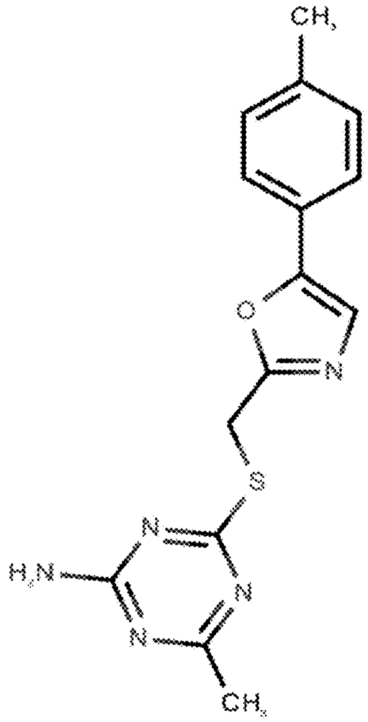
Figure 1:
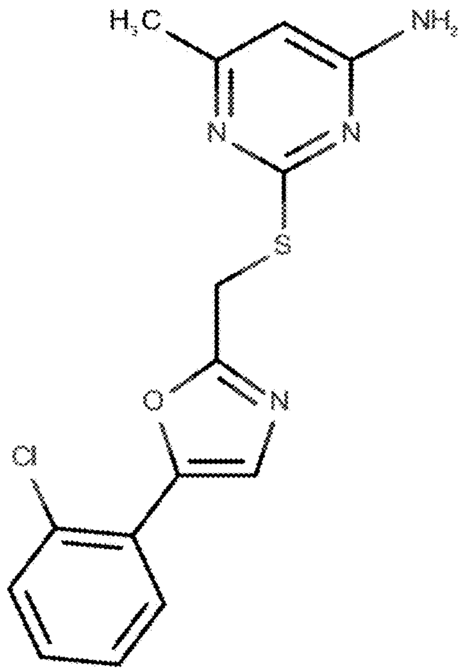
Figure 1:
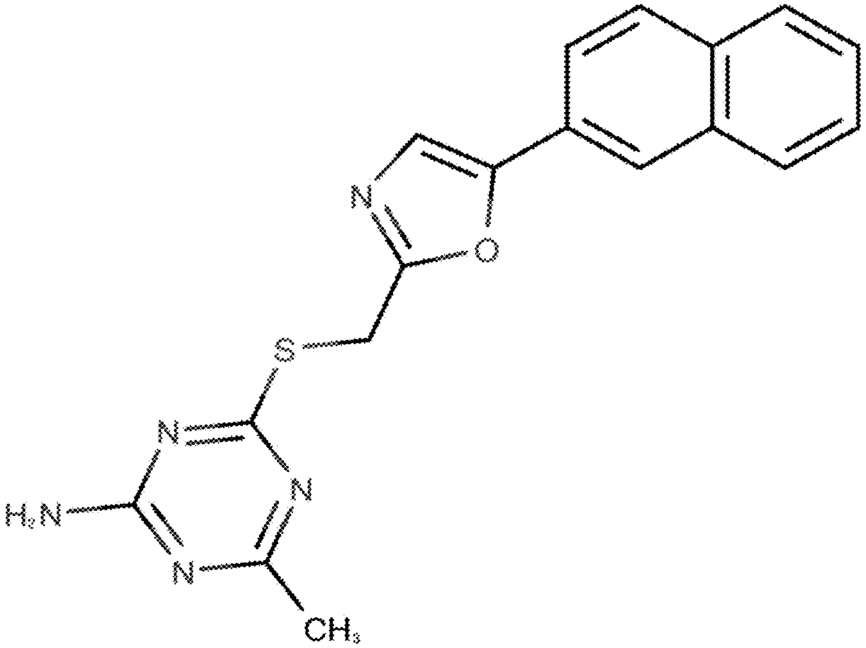
Figure 1:
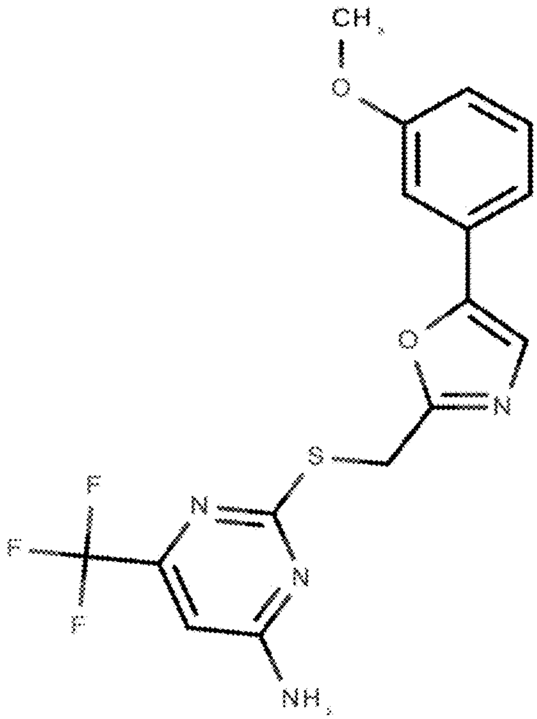
Figure 1:
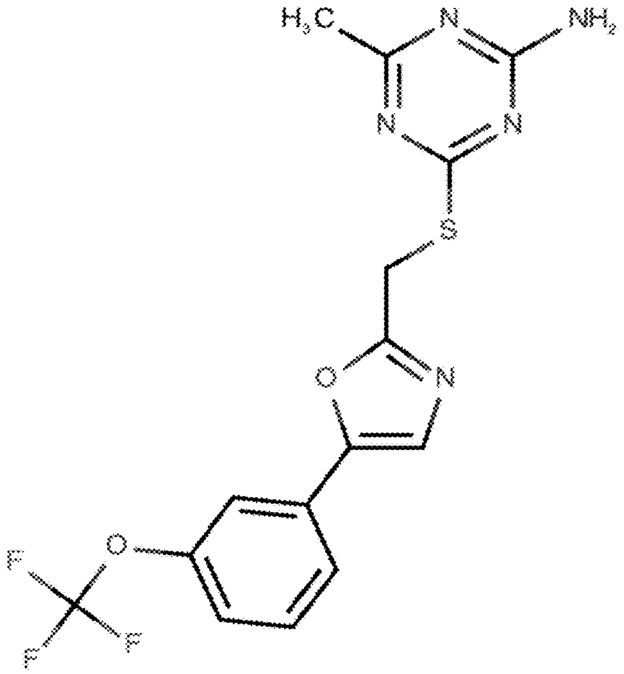
Figure 1:
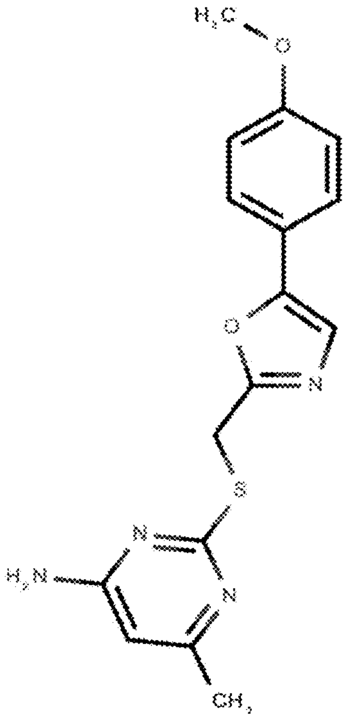
Figure 1:
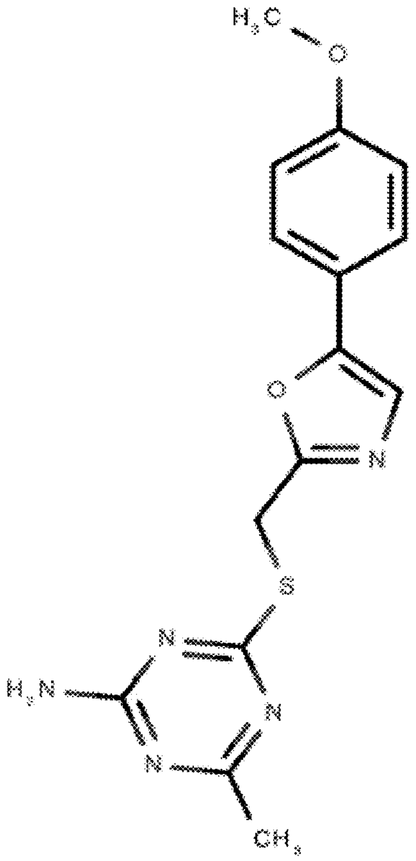
Figure 1:
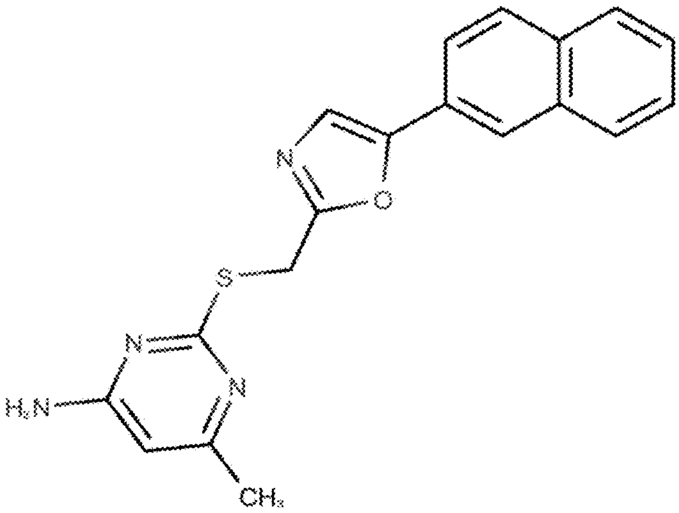
Figure 1:
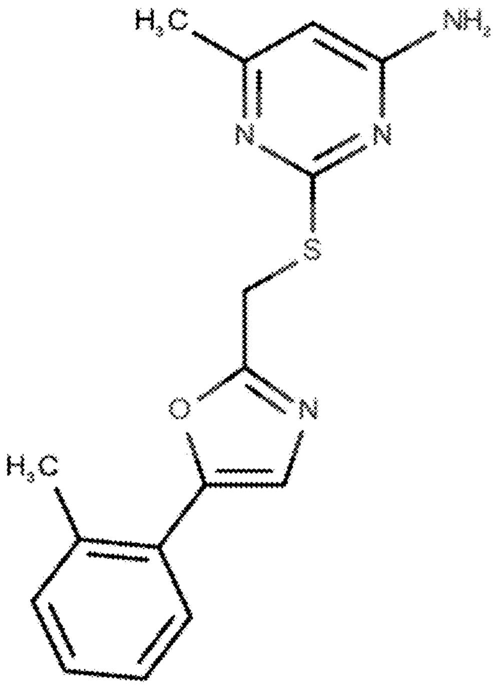
Figure 1:
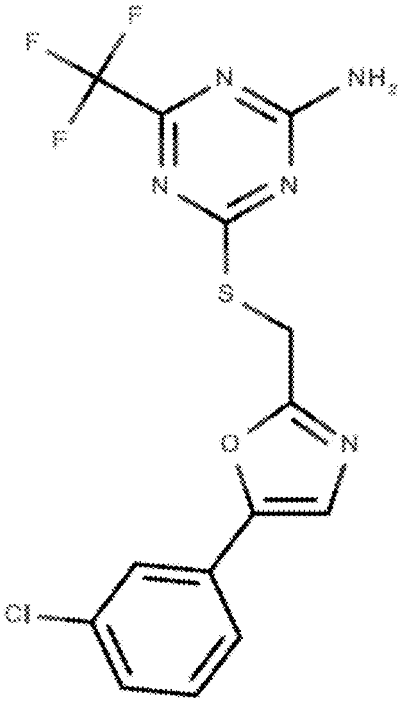
Figure 1:
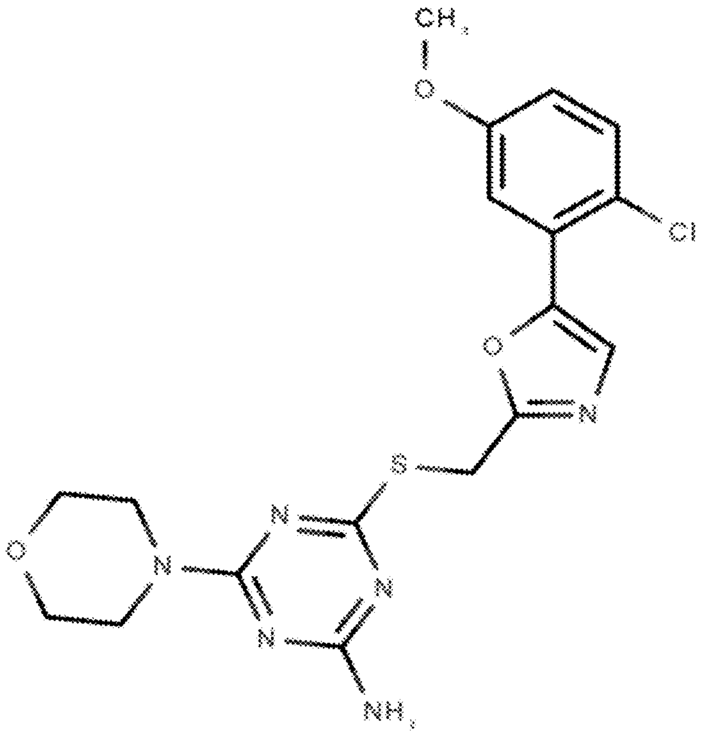
Figure 1:
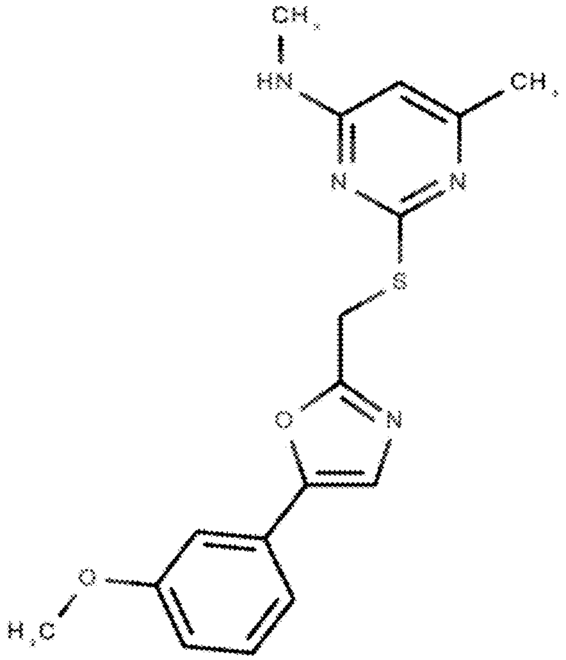
Figure 1:
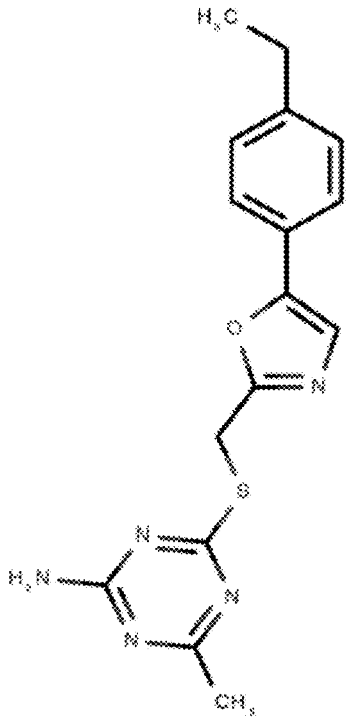
Figure 1:
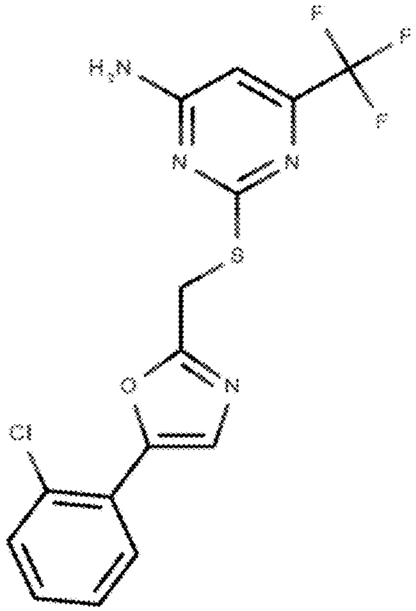
Figure 1:
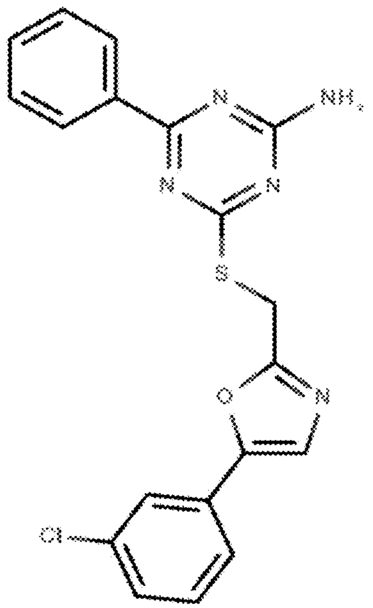
Figure 1:
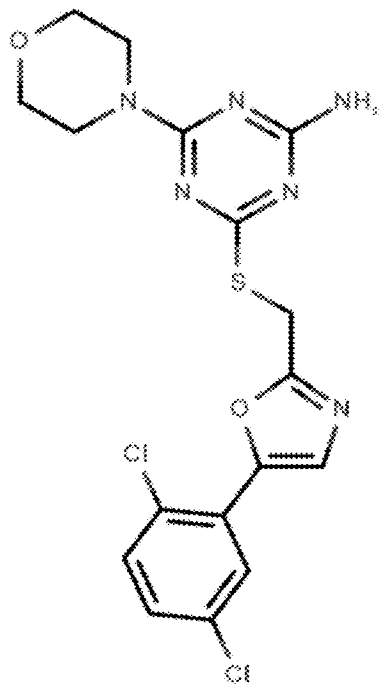
Figure 1:
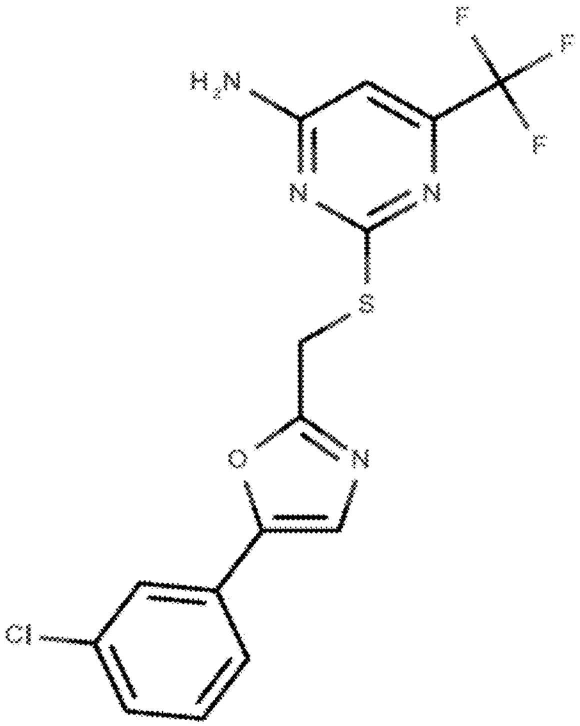
Figure 1:
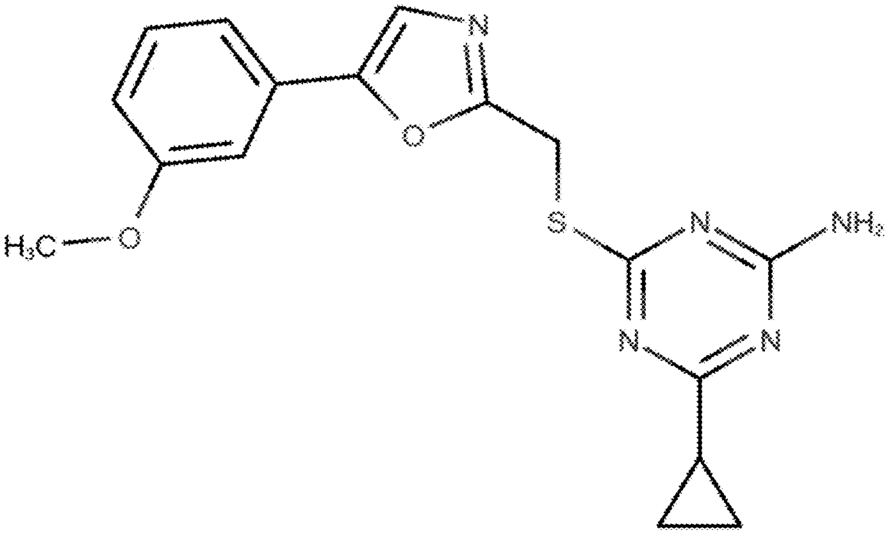
Figure 1:
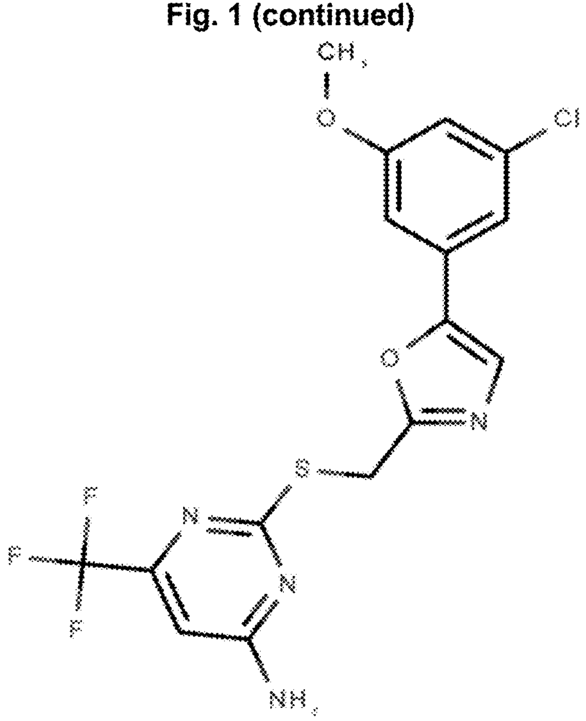
Figure 1:
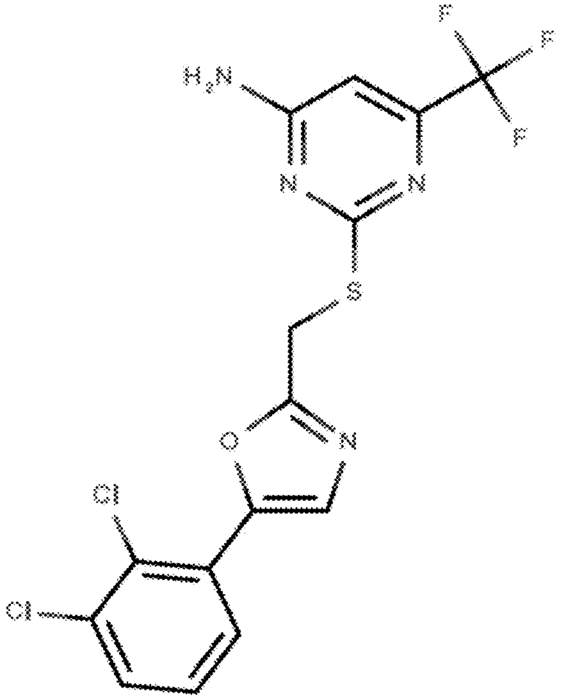
Figure 1:
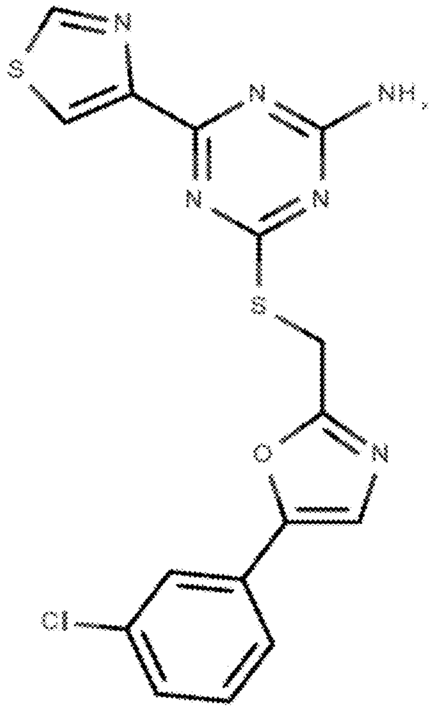
Figure 1:
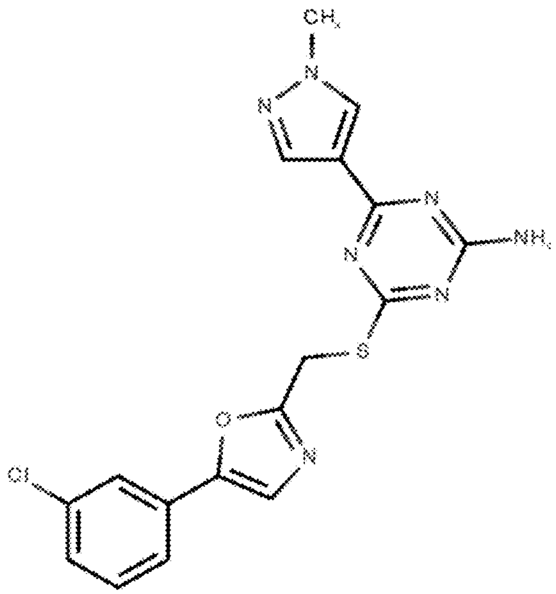
Figure 1:
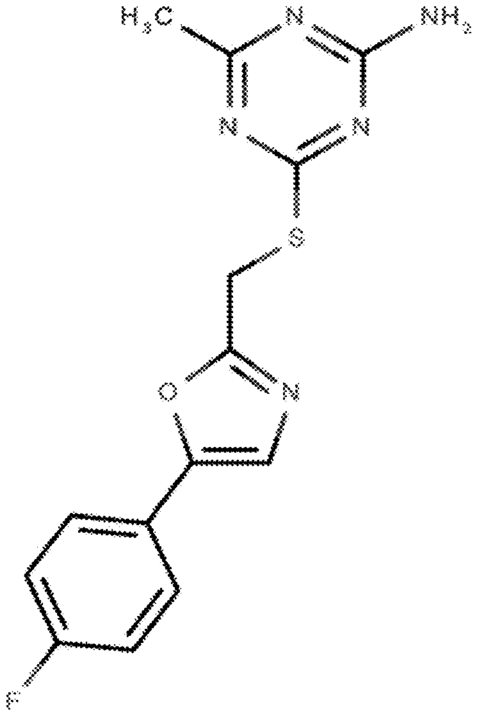
Figure 1:
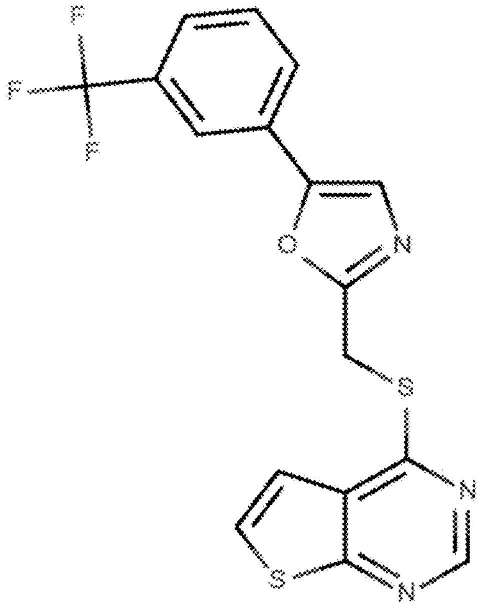
Figure 1:
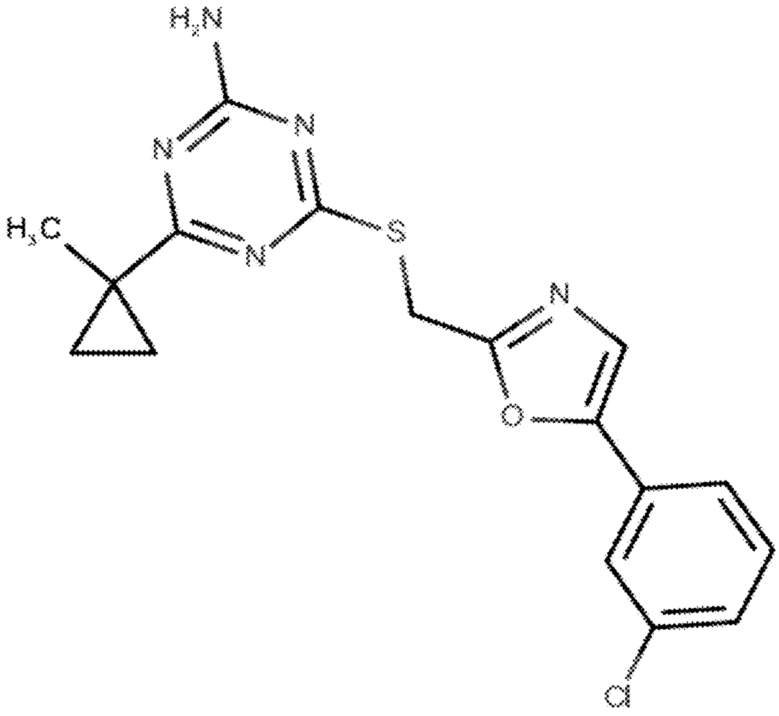
Figure 1:
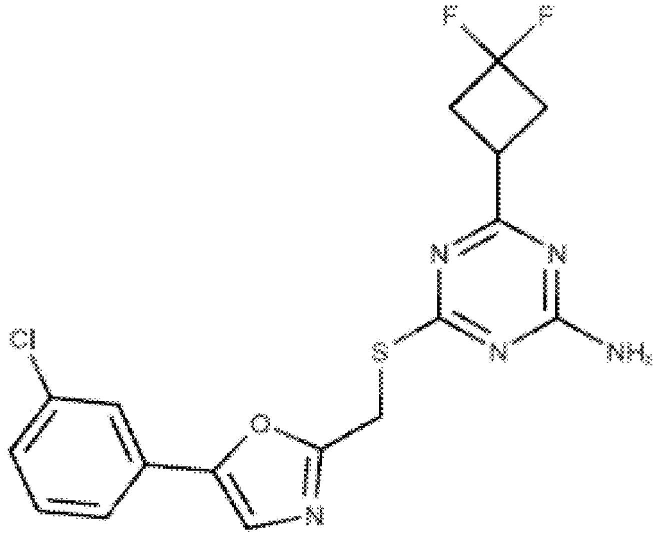
Figure 1:
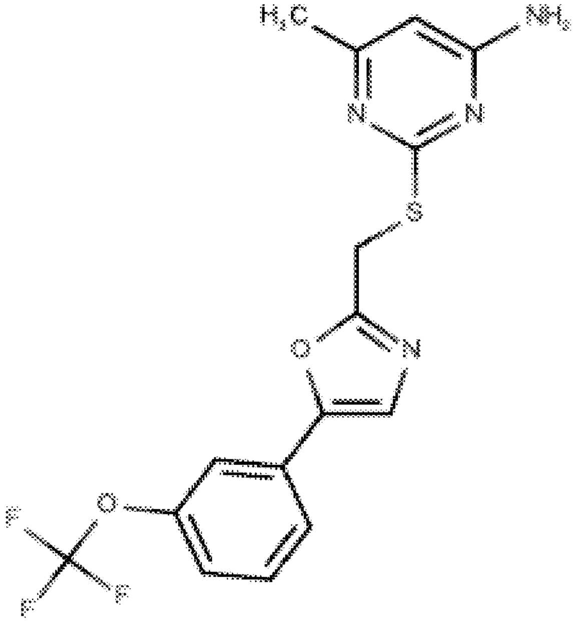
Figure 1:
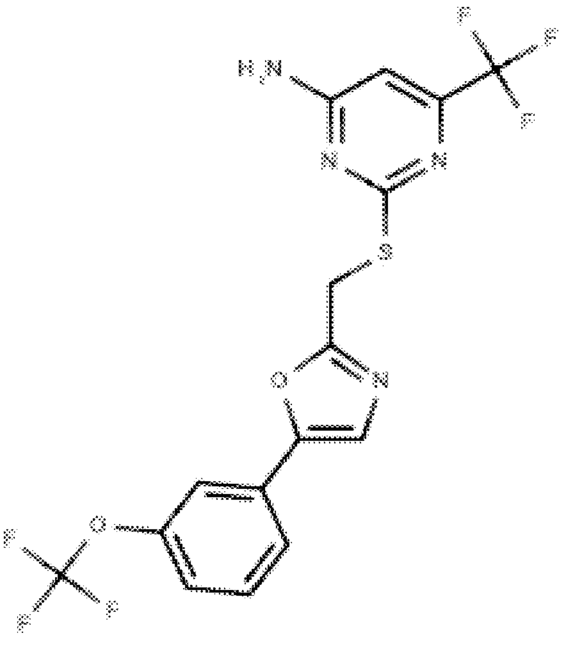
Figure 1:
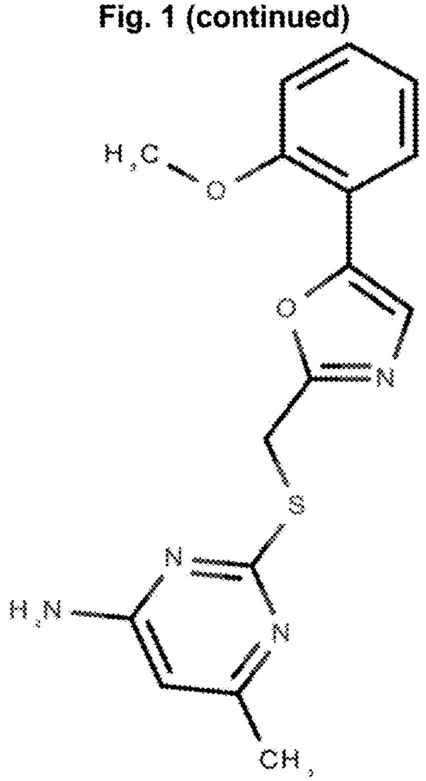
Figure 1:
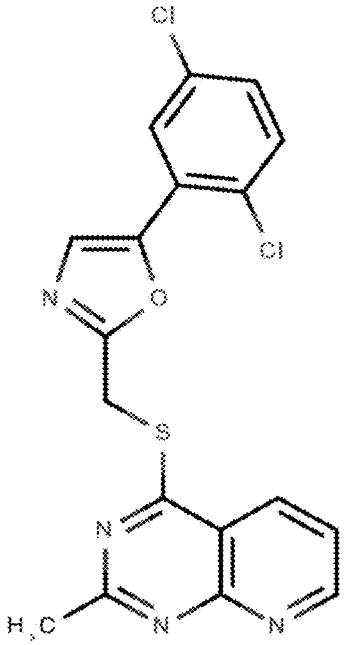
Figure 1:
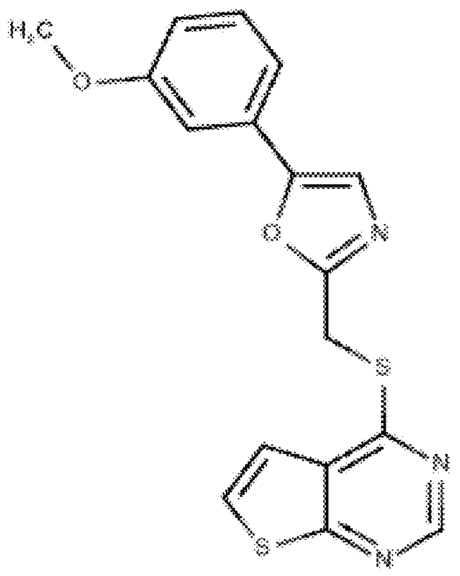
Figure 1:
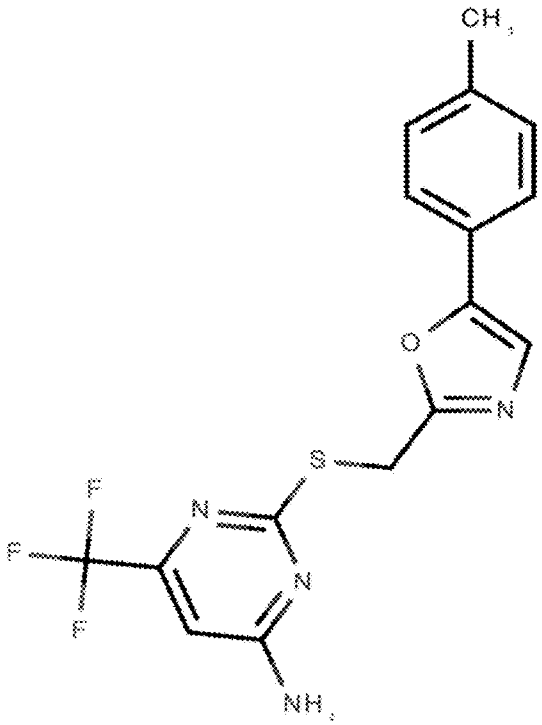
Figure 1:
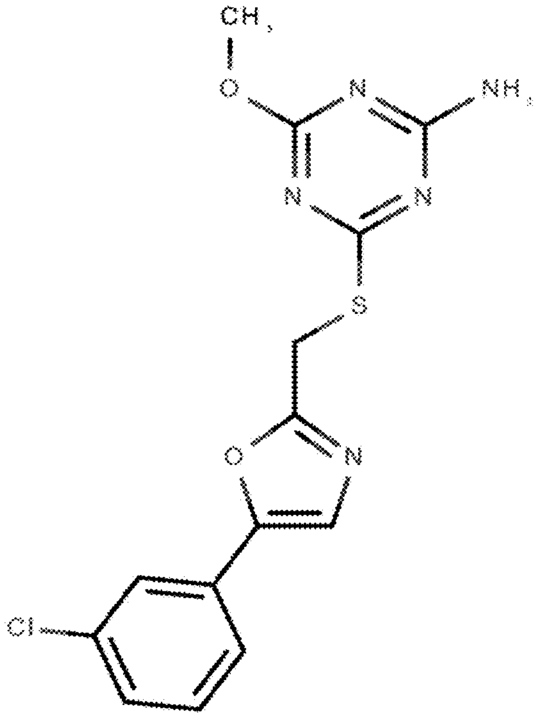
Figure 1:
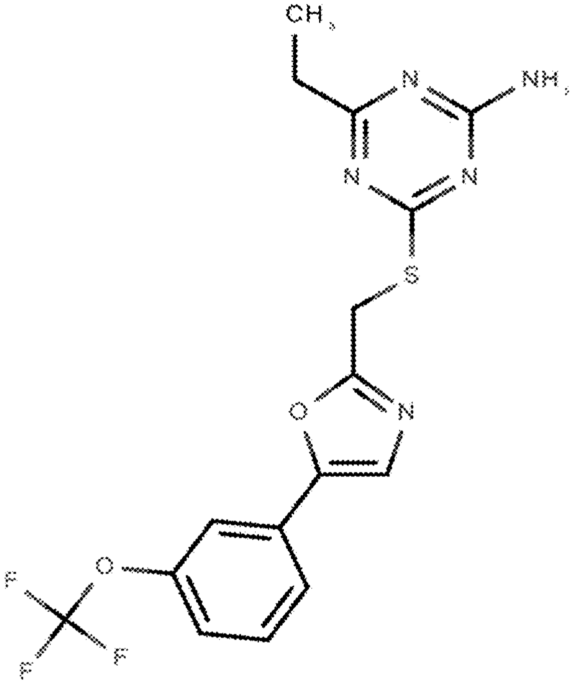
Figure 1:
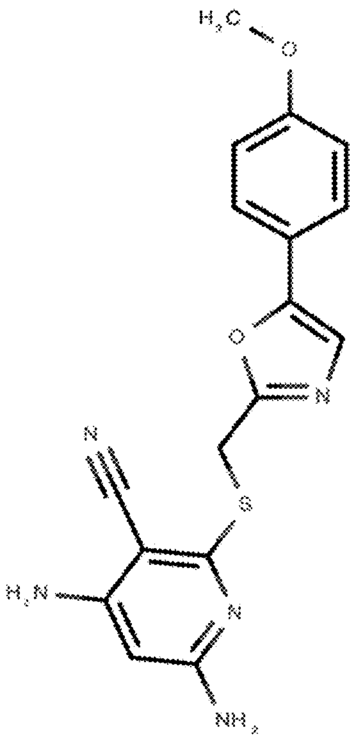
Figure 1:
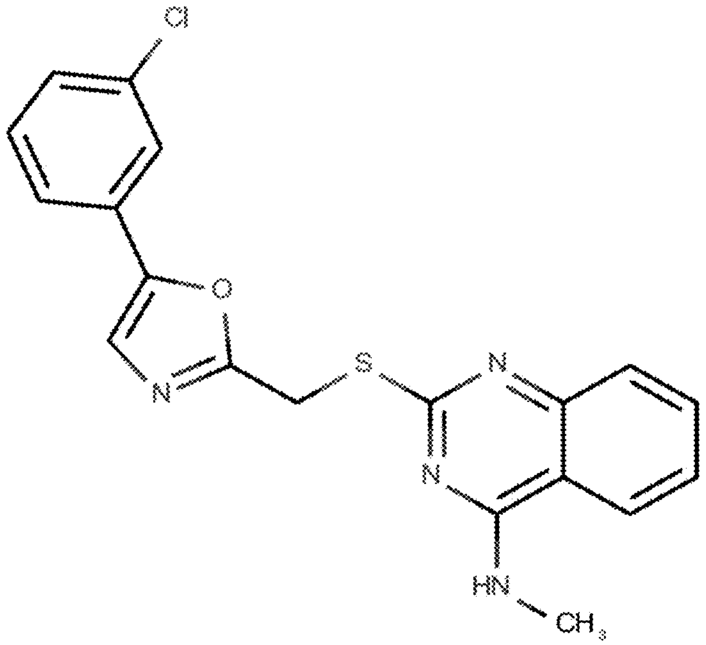
Figure 1:
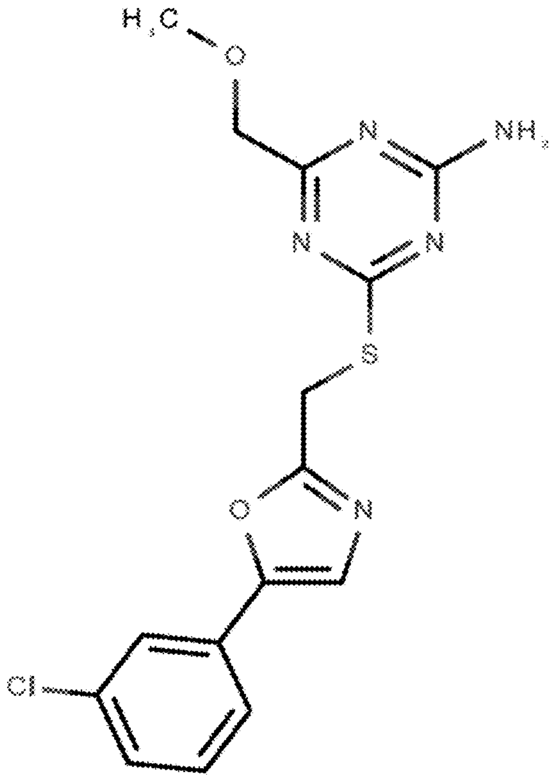
Figure 1:
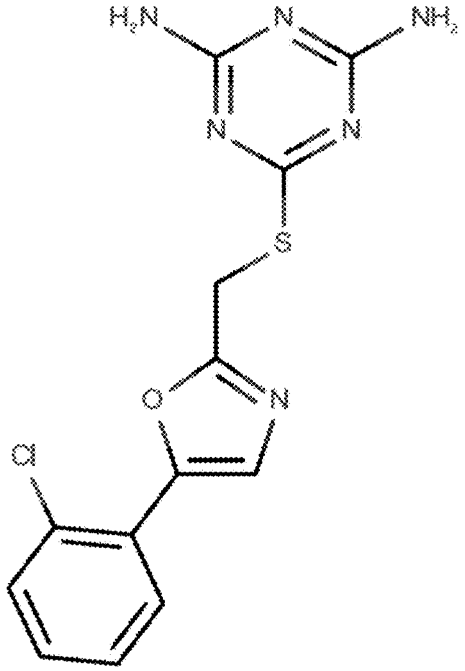
Figure 1:
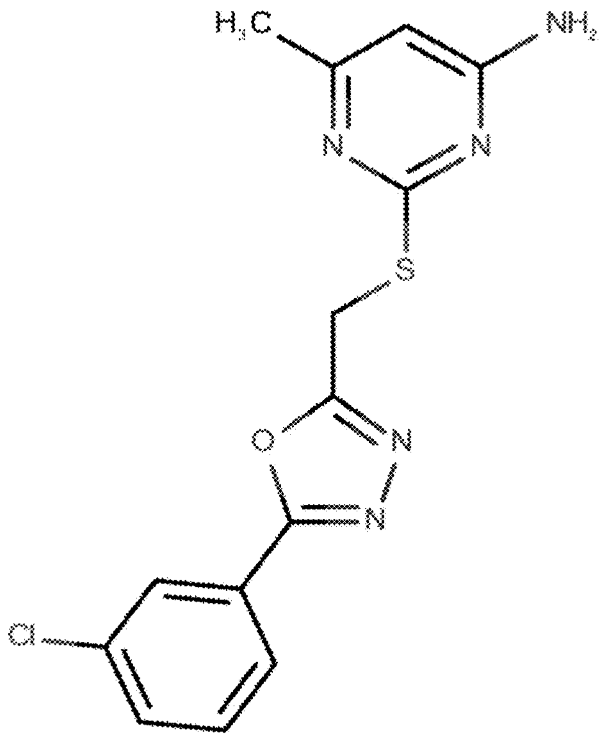
Figure 1:
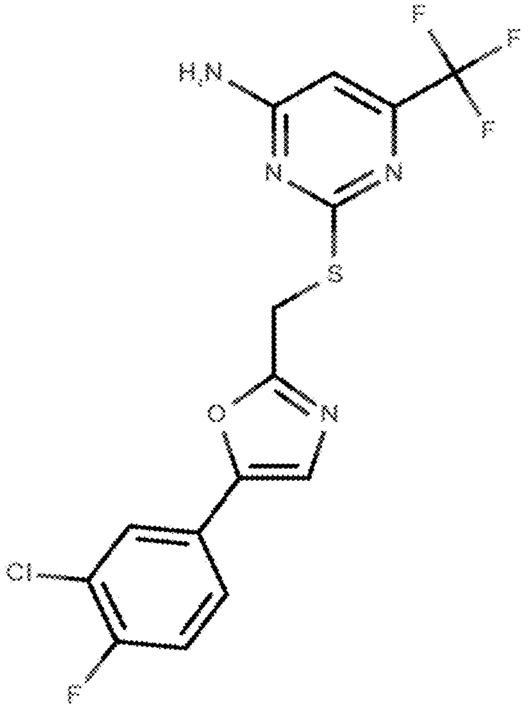
Figure 1:
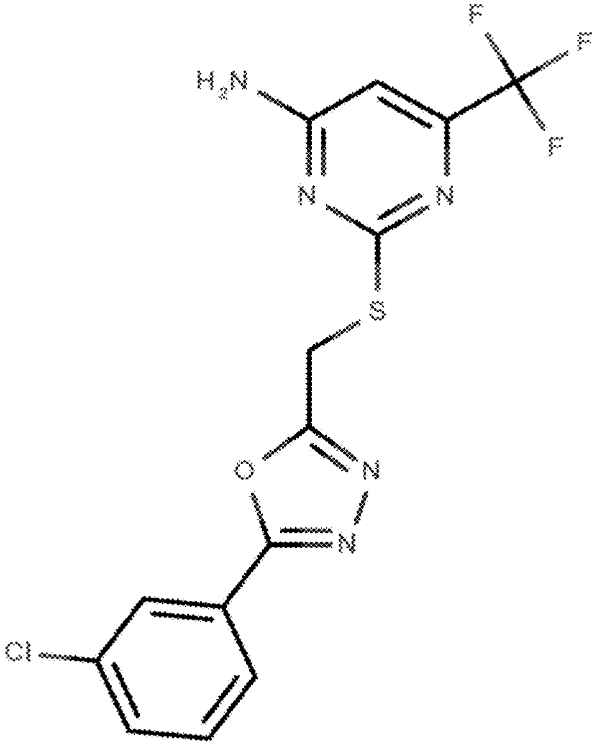
Figure 1:
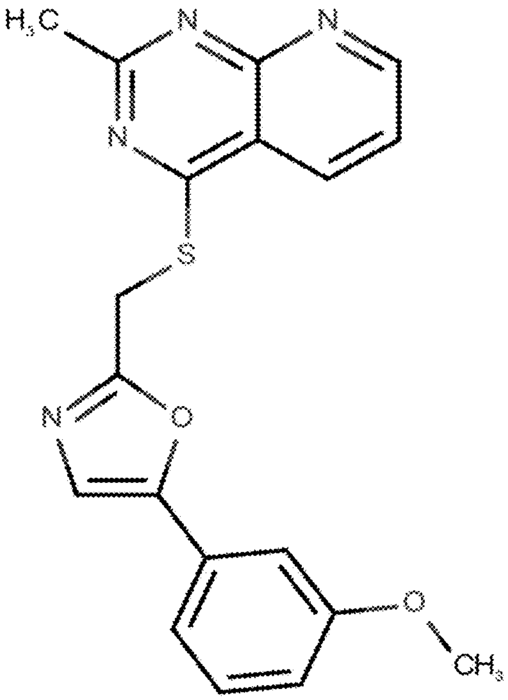

In the context of the present invention, the "$C_1$-$C_6$ alkyl (group)" means, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbuty, or the like. $C_1$-$C_5$-alkyl groups, more preferably those mentioned before, are preferred. It is also to be understood that the above examples and preferred embodiments of "$C_1$-$C_6$ alkyl" also relate to substituents in which such ""$C_1$-$C_6$ alkyl" is present. Any alkyl group as referred to herein having more than 2 carbons may be a linear or branched chain.

In the context of the present invention, the "$C_1$-$C_4$-alkoxy (group)" means, for example, methoxy, ethoxy, propoxy, isopropoxy, butoxy, iso-butoxy, sec-butoxy, tert.-butoxy or the like. $C_1$-$C_3$-alkoxy groups, more preferably those mentioned before, are preferred. Any alkoxy group as referred to herein having more than 2 carbons may be a linear or branched chain.

In the context of the present invention, a "N-mono-$C_1$-$C_3$-alkylamino (group)" means, for example, methylamino, ethylamino, propylamino, isopropylamino or the like.

In the context of the present invention, a "N,N-di-$C_1$-$C_3$-alkylamino (group)" means, for example, dimethylamino, diethylamino, dipropylamino, diisopropylamino, or the like. It is to be understood that the $C_1$-$C_3$-alkyl groups of the N,N-di-$C_1$-$C_3$-alkylamino (group) may also be different from one another.

In the context of the present invention, a "$C_3$-$C_6$-cycloalkyl (group)" means, for example, cyclopropyl, cyclobutyl, cyclopentyl, cyclohexyl or the like. $C_3$-$C_5$-cycloalkyl groups, more preferably those mentioned before, are preferred.

In the context of the present invention, the 6-membered aryl substituent of 1,2,4-triazine or pyrimidine in the definition of $R^2$ of general formula (I) means phenyl.

In the context of the present invention, examples of the "5- or 6-membered heterary1 (group)" means a 5- or 6-membered monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4 -pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), and the like.

In the context of the present invention, a "non-aromatic 5- to 6-membered heterocyclic group" means a 5- or 6-membered monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized). Examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

In preferred embodiments of the invention $R^1$ is 1,3,5-triazinyl substituted as defined above in general formula (I). It is further preferred that, if the 1,3,5-triazinyl group is substituted with more than one substituent, the substituents are different. According to further preferred embodiments, the 1,3,5 triazinyl group is independently substituted with one or two substituents selected from the group consisting of amino, methyl, ethyl, isopropyl and tert.-butyl, which may be in turn substituted with one or more halide, preferably Cl, F and/or Br.

According to particularly preferred compounds of the inventions $R^1$ is selected from the group consisting of

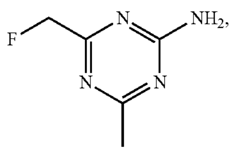

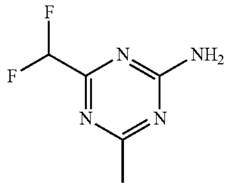

and

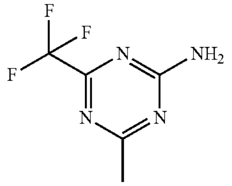

In other preferred embodiments of the invention, $R^1$ is pyrimidinyl substituted as defined above in general formula (I). It is further preferred that, if the pyrimidinyl group is substituted with more than one substituent, the substituents are different. According to further preferred embodiments the pyrimidinyl group is independently substituted by one or more substituents selected from the group consisting of amino (preferably mono- or di-substituted with methyl, more preferably methylamino), methyl and ethyl wherein the latter two groups are substituted with one or more halides as defined above.

According to particular preferred embodiments of the compound of the invention $R^1$ is selected from the group consisting of

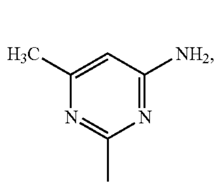

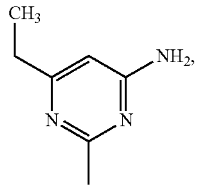

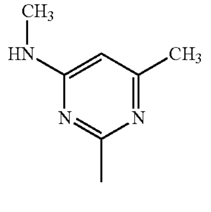

and

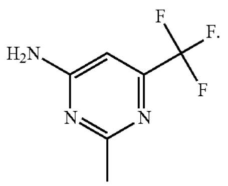

According to further preferred embodiments of the invention are compounds of general formula (I) wherein $R^2$ is independently substituted with one more substituents selected from the group consisting of Cl, Br, F, methyl, trifluormethyl, methoxy and ethoxy. Furthermore, it is preferred that $R^2$ is substituted in at least one meta position and/or at least one ortho position.

According to particularly preferred embodiments of the invention $R^2$ is selected from the group consisting of

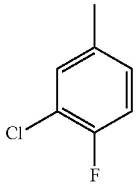
,
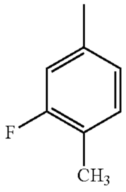
and
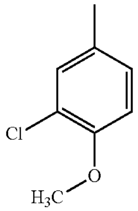
.

Highly active agonists of GPR40 according to the invention are compounds wherein $R^2$ is not substituted in the para position.

Particularly preferred groups for $R^2$ are selected from the group consisting of

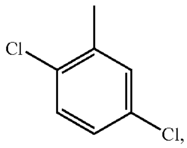
,
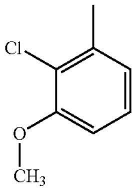
,
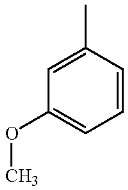
,
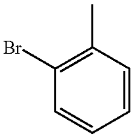
,
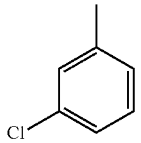
,
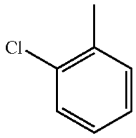
,
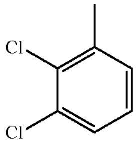
,
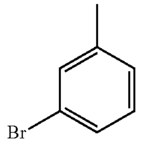
,
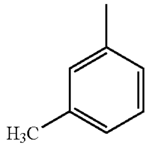
,
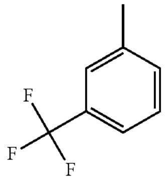
,
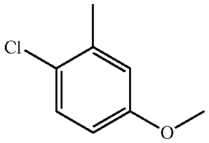
and
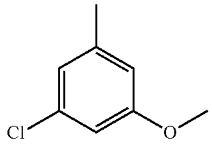
.

Figure 2:
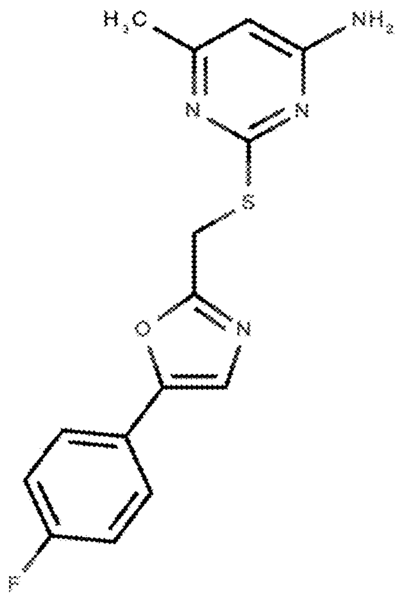
FIG. 2 shows further compounds for use as GRP40 agonists and for use as medicaments, preferably for the treatment and/or prevention of T2DM. nM EC50 values, p(EC50,M) values and % activation compared to TAK-875 are indicated.
Figure 2:
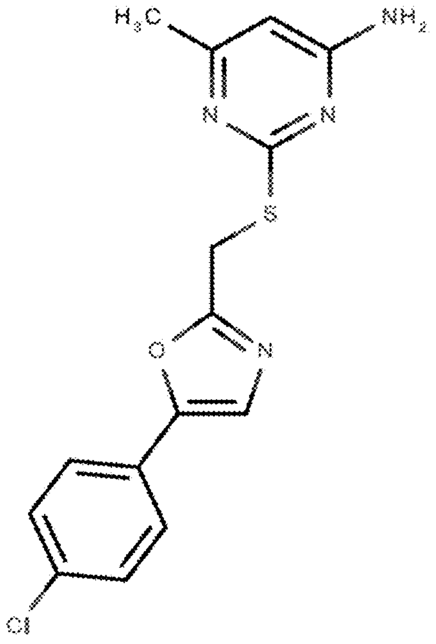
Figure 2:
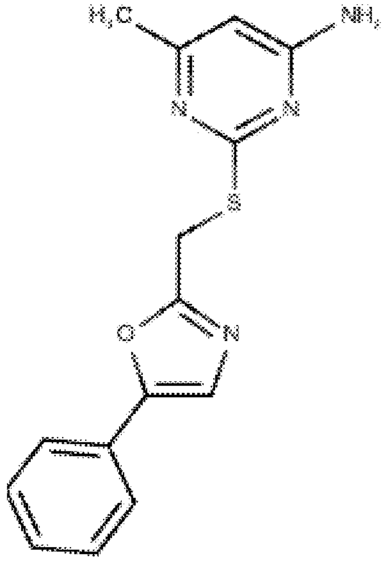

Highly preferred compounds of the invention are compounds shown in FIG. 1. FIG. 2 shows additional compounds specifically preferred for the use as medicaments, in particular for the uses according to the invention as further described below.

Particularly preferred compounds according to the invention are shown in the following Table 1.

TABLE 1

| Compound ID | Name |
|---|---|
| Z3352693410 | 5-(2,5-dichlorophenyl)-2-[({2-methylpyrido[2,3-d]pyrimidin-4-yl}sulfanyl)methyl]-1,3-oxazole |
| Z3331727678 | 2-({[5-(2,3-dichlorophenyl)-1,3-oxazol-2-yl]methyl}sulfanyl)-6-(trifluoromethyl)pyrimidin-4-ol |
| Z3331727680 | 2-({[5-(2,5-dichlorophenyl)-1,3-oxazol-2-yl]methyl}sulfanyl)-6-(trifluoromethyl)pyrimidin-4-amine |
| Z3304784611 | 5-(2-chlorophenyl)-2-[({2-methylpyrido[2,3-d]pyrimidin-4-yl}sulfanyl)methyl]-1,3-oxazole |
| Z3304784618 | 4-({[5-(4-fluorophenyl)-1,3-oxazol-2-yl]methyl}sulfanyl)-1,3,5-triazin-2-amine |
| Z3304784621 | 4-({[5-(3-methoxyphenyl)-1,3-oxazol-2-yl]methyl}sulfanyl)-1,3,5-triazin-2-amine |
| Z3397119005 | 6-methyl-2-[({5-[3-(trifluoromethoxy)phenyl]-1,3-oxazol-2-yl}methyl)sulfanyl]pyrimidin-4-amine |
| Z3352693156 | 4-methyl-6-[({5-[3-(trifluoromethyl)phenyl]-1,3-oxazol-2-yl}methyl)sulfanyl]-1,3,5-triazin-2-amine |
| Z3331727682 | 2-({[5-(2,5-dichlorophenyl)-1,3-oxazol-2-yl]methyl}sulfanyl)-6-(trifluoromethyl)pyrimidin-4-ol |
| Z1263986196 | 2-({[5-(2-chlorophenyl)-1,3-oxazol-2-yl]methyl}sulfanyl)-6-(trifluoromethyl)pyrimidin-4-ol |
| Z3304784610 | 4-({[5-(2-chlorophenyl)-1,3-oxazol-2-yl]methyl}sulfanyl)-1,3,5-triazin-2-amine |
| Z3325085929 | 6-(difluoromethyl)-2-({[5-(3-phenylphenyl)-1,3-oxazol-2-yl]methyl}sulfanyl)pyrimidin-4-ol |
| Z3325085931 | 6-methyl-2-({[5-(3-phenylphenyl)-1,3-oxazol-2-yl]methyl}sulfanyl)pyrimidin-4-amine |

TABLE 1-continued

| Compound ID | Name |
|---|---|
| Z1558782315 | 4-ethyl-6-({[5-(3-methoxyphenyl)-1,3-oxazol-2-yl]methyl}sulfanyl)-1,3,5-triazin-2-amine |
| Z3397119007 | 2-({[5-(2-chloro-3-methoxyphenyl)-1,3-oxazol-2-yl]methyl}sulfanyl)-6-methylpyrimidin-4-amine |
| Z3397119008 | 4-({[5-(2-chloro-3-methoxyphenyl)-1,3-oxazol-2-yl]methyl}sulfanyl)-6-methyl-1,3,5-triazin-2-amine |
| Z71175677 | 2-({[5-(3-chlorophenyl)-1,3-oxazol-2-yl]methyl}sulfanyl)-N-methylquinazolin-4-amine |
| Z74373205 | 2-({[5-(2-chlorophenyl)-1,3,4-oxadiazol-2-yl]methyl}sulfanyl)-6-methylpyrimidin-4-amine |
| Z1231014532 | 2-({[5-(3-chlorophenyl)-1,3,4-oxadiazol-2-yl]methyl}sulfanyl)-6-(trifluoromethyl)pyrimidin-4-ol |
| Z359955408 | 6-methyl-2-({[5-(4-methylphenyl)-1,3,4-oxadiazol-2-yl]methyl}sulfanyl)pyrimidin-4-amine |
| Z3331727647 | 2-({[5-(3-chloro-4-fluorophenyl)-1,3-oxazol-2-yl]methyl}sulfanyl)-6-(trifluoromethyl)pyrimidin-4-ol |
| Z1882973046 | 6-cyclopropyl-2-({[5-(4-methylphenyl)-1,3-oxazol-2-yl]methyl}sulfanyl)pyrimidin-4-ol |
| Z1263986208 | 2-({[5-(3-methoxyphenyl)-1,3-oxazol-2-yl]methyl}sulfanyl)-6-(trifluoromethyl)pyrimidin-4-ol |
| Z2169241286 | 2-({[5-(3-chlorophenyl)-1,3-oxazol-2-yl]methyl}sulfanyl)-6-(difluoromethyl)pyrimidin-4-ol |
| Z3304784619 | 5-(4-fluorophenyl)-2-[({2-methylpyrido[2,3-d]pyrimidin-4-yl}sulfanyl)methyl]-1,3-oxazole |
| Z3325085934 | 6-cyclopropyl-2-[({5-[3-(trifluoromethyl)phenyl]-1,3-oxazol-2-yl}methyl)sulfanyl]pyrimidin-4-ol |
| Z3325085938 | 2-({thieno[2,3-d]pyrimidin-4-ylsulfanyl}methyl)-5-[3-(trifluoromethyl)phenyl]-1,3-oxazole |
| Z3325085930 | 6-methyl-2-({[5-(3-phenylphenyl)-1,3-oxazol-2-yl]methyl}sulfanyl)pyrimidin-4-ol |
| Z3325085942 | 2-({[5-(3-chloro-4-methoxyphenyl)-1,3-oxazol-2-yl]methyl}sulfanyl)-6-methylpyrimidin-4-ol |
| Z3325085928 | 6-cyclopropyl-2-({[5-(3-phenylphenyl)-1,3-oxazol-2-yl]methyl}sulfanyl)pyrimidin-4-ol |
| Z3465744370 | 4-({[5-(2-chloro-5-methoxyphenyl)-1,3-oxazol-2-yl]methyl}sulfanyl)-6-methyl-1,3,5-triazin-2-amine |
| Z3465744375 | 2-({[5-(2-chloro-5-methoxyphenyl)-1,3-oxazol-2-yl]methyl}sulfanyl)-6-(trifluoromethyl)pyrimidin-4-amine |
| Z3446839939 | 4-ethyl-6-[({5-[3-(trifluoromethoxy)phenyl]-1,3-oxazol-2-yl}methyl)sulfanyl]-1,3,5-triazin-2-amine |
| Z3397119003 | 4-({[5-(3-chloro-4-methoxyphenyl)-1,3-oxazol-2-yl]methyl}sulfanyl)-6-ethyl-1,3,5-triazin-2-amine |
| Z3352693152 | 4-({[5-(3-chlorophenyl)-1,3-oxazol-2-yl]methyl}sulfanyl)-6-methyl-1,3,5-triazin-2-amine |
| Z3352693158 | 4-({[5-(3-chloro-4-methoxyphenyl)-1,3-oxazol-2-yl]methyl}sulfanyl)-6-methyl-1,3,5-triazin-2-amine |
| Z3352693149 | 4-({[5-(2,3-dichlorophenyl)-1,3-oxazol-2-yl]methyl}sulfanyl)-6-methyl-1,3,5-triazin-2-amine |
| Z1143973826 | 2-({[5-(3-chlorophenyl)-1,3,4-oxadiazol-2-yl]methyl}sulfanyl)-6-methylpyrimidin-4-amine |
| Z215331784 | 2-({[5-(4-chlorophenyl)-1,3,4-oxadiazol-2-yl]methyl}sulfanyl)-6-methylpyrimidin-4-amine |
| Z1171240450 | 2-({[5-(3-chlorophenyl)-1,3-oxazol-2-yl]methyl}sulfanyl)-6-(trifluoromethyl)pyrimidin-4-ol |
| Z3272467650 | 6-tert-butyl-2-({[5-(4-methylphenyl)-1,3-oxazol-2-yl]methyl}sulfanyl)pyrimidin-4-ol |
| Z3302950788 | 2-({[5-(4-methylphenyl)-1,3-oxazol-2-yl]methyl}sulfanyl)-6-(trifluoromethyl)pyrimidin-4-amine |
| Z1607529540 | 2-({[5-(4-fluorophenyl)-1,3-oxazol-2-yl]methyl}sulfanyl)-5H,6H,7H-cyclopenta[d]pyrimidin-4-ol |
| Z3304784609 | 4-({[5-(2-chlorophenyl)-1,3-oxazol-2-yl]methyl}sulfanyl)-6-methyl-1,3,5-triazin-2-amine |
| Z3304784620 | 4-({[5-(3-methoxyphenyl)-1,3-oxazol-2-yl]methyl}sulfanyl)-6-methyl-1,3,5-triazin-2-amine |
| Z1607530768 | 2-({[5-(3-methoxyphenyl)-1,3-oxazol-2-yl]methyl}sulfanyl)-5H,6H,7H-cyclopenta[d]pyrimidin-4-ol |
| Z1607539139 | 2-({[5-(2-chlorophenyl)-1,3-oxazol-2-yl]methyl}sulfanyl)-5H,6H,7H-cyclopenta[d]pyrimidin-4-ol |
| Z1272915868 | 6-({[5-(4-methylphenyl)-1,3-oxazol-2-yl]methyl}sulfanyl)-1,3,5-triazine-2,4-diamine |
| Z3465744373 | 2-({[5-(2-chloro-5-methoxyphenyl)-1,3-oxazol-2-yl]methyl}sulfanyl)-6-methylpyrimidin-4-amine |
| Z1955117405 | 5-(3-chlorophenyl)-2-[({7-ethyl-[1,2,4]triazolo[4,3-c]pyrimidin-5-yl}sulfanyl)methyl]-1,3-oxazole |
| Z1272945711 | 2-({[5-(3-methoxyphenyl)-1,3,4-oxadiazol-2-yl]methyl}sulfanyl)-6-methylpyrimidin-4-amine |
| Z1272988076 | 2-({[5-(3-methoxyphenyl)-1,3,4-oxadiazol-2-yl]methyl}sulfanyl)-6-(trifluoromethyl)pyrimidin-4-ol |

TABLE 1-continued

| Compound ID | Name |
|---|---|
| Z3331727556 | 2-({[5-(2-chlorophenyl)-1,3,4-oxadiazol-2-yl]methyl}sulfanyl)-6-(trifluoromethyl)pyrimidin-4-amine |
| Z3331727606 | 2-({[5-(3-methoxyphenyl)-1,3,4-oxadiazol-2-yl]methyl}sulfanyl)-6-(trifluoromethyl)pyrimidin-4-amine |
| Z3331727652 | 2-({[5-(2,3-dichlorophenyl)-1,3-oxazol-2-yl]methyl}sulfanyl)-6-(trifluoromethyl)pyrimidin-4-amine |
| Z3331727576 | 2-({[5-(3-chlorophenyl)-1,3,4-oxadiazol-2-yl]methyl}sulfanyl)-6-(trifluoromethyl)pyrimidin-4-amine |
| Z1171240167 | 2-({[5-(4-methylphenyl)-1,3,4-oxadiazol-2-yl]methyl}sulfanyl)-6-(trifluoromethyl)pyrimidin-4-ol |
| Z3272467647 | 6-tert-butyl-2-({[5-(2-chlorophenyl)-1,3-oxazol-2-yl]methyl}sulfanyl)pyrimidin-4-ol |
| Z3272467633 | 6-tert-butyl-2-({[5-(3-chlorophenyl)-1,3-oxazol-2-yl]methyl}sulfanyl)pyrimidin-4-ol |
| Z1882978995 | 6-cyclopropyl-2-({[5-(3-methoxyphenyl)-1,3-oxazol-2-yl]methyl}sulfanyl)pyrimidin-4-ol |
| Z1272925835 | 5-(4-methylphenyl)-2-({thieno[2,3-d]pyrimidin-4-ylsulfanyl}methyl)-1,3-oxazole |
| Z1263936576 | 5-(2-chlorophenyl)-2-({thieno[2,3-d]pyrimidin-4-ylsulfanyl}methyl)-1,3-oxazole |
| Z1607528727 | 2-({[5-(4-methylphenyl)-1,3-oxazol-2-yl]methyl}sulfanyl)-5H,6H,7H-cyclopenta[d]pyrimidin-4-ol |
| Z3304784617 | 4-({[5-(4-fluorophenyl)-1,3-oxazol-2-yl]methyl}sulfanyl)-6-methyl-1,3,5-triazin-2-amine |
| Z3325085936 | 6-methyl-2-[({5-[3-(trifluoromethyl)phenyl]-1,3-oxazol-2-yl}methyl)sulfanyl]pyrimidin-4-ol |
| Z3325085943 | 2-({[5-(3-chloro-4-methoxyphenyl)-1,3-oxazol-2-yl]methyl}sulfanyl)-6-methylpyrimidin-4-amine |
| Z3325085937 | 6-methyl-2-[({5-[3-(trifluoromethyl)phenyl]-1,3-oxazol-2-yl}methyl)sulfanyl]pyrimidin-4-amine |
| Z3465744378 | 4-({[5-(2-chloro-5-methoxyphenyl)-1,3-oxazol-2-yl]methyl}sulfanyl)-6-ethyl-1,3,5-triazin-2-amine |
| Z3465744385 | 2-({[5-(3-chloro-5-methoxyphenyl)-1,3-oxazol-2-yl]methyl}sulfanyl)-6-(trifluoromethyl)pyrimidin-4-amine |
| Z3397119002 | 4-({[5-(2,3-dichlorophenyl)-1,3-oxazol-2-yl]methyl}sulfanyl)-6-ethyl-1,3,5-triazin-2-amine |
| Z3331727663 | 2-({[5-(2,3-dichlorophenyl)-1,3-oxazol-2-yl]methyl}sulfanyl)-6-methylpyrimidin-4-amine |
| Z3331727527 | 2-({[5-(4-fluorophenyl)-1,3,4-oxadiazol-2-yl]methyl}sulfanyl)-6-(trifluoromethyl)pyrimidin-4-amine |
| Z74373206 | 2-({[5-(4-fluorophenyl)-1,3,4-oxadiazol-2-yl]methyl}sulfanyl)-6-methylpyrimidin-4-amine |
| Z3331727681 | 2-({[5-(2,5-dichlorophenyl)-1,3-oxazol-2-yl]methyl}sulfanyl)-6-methylpyrimidin-4-amine |
| Z3331727540 | 2-({[5-(4-chlorophenyl)-1,3,4-oxadiazol-2-yl]methyl}sulfanyl)-6-(trifluoromethyl)pyrimidin-4-amine |
| Z3304784614 | 4-({[5-(4-methylphenyl)-1,3-oxazol-2-yl]methyl}sulfanyl)-1,3,5-triazin-2-amine |
| Z213830254 | 6-({[5-(4-fluorophenyl)-1,3-oxazol-2-yl]methyl}sulfanyl)-1,3,5-triazine-2,4-diamine |
| Z3304784612 | 4-methyl-6-({[5-(4-methylphenyl)-1,3-oxazol-2-yl]methyl}sulfanyl)-1,3,5-triazin-2-amine |
| Z1263936589 | 5-(3-methoxyphenyl)-2-({thieno[2,3-d]pyrimidin-4-ylsulfanyl}methyl)-1,3-oxazole |
| Z3304784622 | 5-(3-methoxyphenyl)-2-[({2-methylpyrido[2,3-d]pyrimidin-4-yl}sulfanyl)methyl]-1,3-oxazole |
| Z3325085933 | 6-(trifluoromethyl)-2-[({5-[3-(trifluoromethyl)phenyl]-1,3-oxazol-2-yl}methyl)sulfanyl]pyrimidin-4-ol |
| Z3325085944 | 5-(3-chloro-4-methoxyphenyl)-2-({thieno[2,3-d]pyrimidin-4-ylsulfanyl}methyl)-1,3-oxazole |
| Z3465744380 | 4-({[5-(3-chloro-5-methoxyphenyl)-1,3-oxazol-2-yl]methyl}sulfanyl)-6-methyl-1,3,5-triazin-2-amine |
| Z3465744387 | 4-({[5-(3-chloro-5-methoxyphenyl)-1,3-oxazol-2-yl]methyl}sulfanyl)-6-ethyl-1,3,5-triazin-2-amine |
| Z3397119006 | 4-methyl-6-[({5-[3-(trifluoromethoxy)phenyl]-1,3-oxazol-2-yl}methyl)sulfanyl]-1,3,5-triazin-2-amine |
| Z3352693408 | 5-(3-bromophenyl)-2-[({2-methylpyrido[2,3-d]pyrimidin-4-yl}sulfanyl)methyl]-1,3-oxazole |
| Z3331727625 | 2-({[5-(3-chloro-4-fluorophenyl)-1,3-oxazol-2-yl]methyl}sulfanyl)-6-(trifluoromethyl)pyrimidin-4-amine |
| Z3331727639 | 2-({[5-(3-chloro-4-fluorophenyl)-1,3-oxazol-2-yl]methyl}sulfanyl)-6-methylpyrimidin-4-amine |
| Z1231014130 | 2-({[5-(4-fluorophenyl)-1,3,4-oxadiazol-2-yl]methyl}sulfanyl)-6-(trifluoromethyl)pyrimidin-4-ol |
| Z3272467645 | 6-tert-butyl-2-({[5-(3-methoxyphenyl)-1,3-oxazol-2-yl]methyl}sulfanyl)pyrimidin-4-ol |
| Z2169232902 | 6-(difluoromethyl)-2-({[5-(3-methoxyphenyl)-1,3-oxazol-2-yl]methyl}sulfanyl)pyrimidin-4-ol |

TABLE 1-continued

| Compound ID | Name |
|---|---|
| Z2169235138 | 6-(difluoromethyl)-2-({[5-(4-methylphenyl)-1,3-oxazol-2-yl]methyl}sulfanyl)pyrimidin-4-ol |
| Z1272988122 | 2-({[5-(4-methylphenyl)-1,3-oxazol-2-yl]methyl}sulfanyl)-6-(trifluoromethyl)pyrimidin-4-ol |
| Z3302950790 | 2-({[5-(3-chlorophenyl)-1,3-oxazol-2-yl]methyl}sulfanyl)-6-(trifluoromethyl)pyrimidin-4-amine |
| Z3304784616 | 5-(4-methylphenyl)-2-[({2-methylpyrido[2,3-d]pyrimidin-4-yl}sulfanyl)methyl]-1,3-oxazole |
| Z1263928611 | 6-({[5-(2-chlorophenyl)-1,3-oxazol-2-yl]methyl}sulfanyl)-1,3,5-triazine-2,4-diamine |
| Z3325085940 | 2-({[5-(3-chloro-4-methoxyphenyl)-1,3-oxazol-2-yl]methyl}sulfanyl)-6-cyclopropylpyrimidin-4-ol |
| Z3325085932 | 5-(3-phenylphenyl)-2-({thieno[2,3-d]pyrimidin-4-ylsulfanyl}methyl)-1,3-oxazole |
| Z3325085939 | 2-({[5-(3-chloro-4-methoxyphenyl)-1,3-oxazol-2-yl]methyl}sulfanyl)-6-(trifluoromethyl)pyrimidin-4-ol |
| Z3325085927 | 2-({[5-(3-phenylphenyl)-1,3-oxazol-2-yl]methyl}sulfanyl)-6-(trifluoromethyl)pyrimidin-4-ol |
| Z3465744366 | 2-[({5-[3-(trifluoromethoxy)phenyl]-1,3-oxazol-2-yl}methyl)sulfanyl]-6-(trifluoromethyl)pyrimidin-4-amine |
| Z3397119004 | 5,6-diamino-2-({[5-(3-chlorophenyl)-1,3-oxazol-2-yl]methyl}sulfanyl)pyrimidin-4-ol |
| Z1558775684 | 4-({[5-(3-chlorophenyl)-1,3-oxazol-2-yl]methyl}sulfanyl)-6-ethyl-1,3,5-triazin-2-amine |
| Z3352693146 | 4-({[5-(2,5-dichlorophenyl)-1,3-oxazol-2-yl]methyl}sulfanyl)-6-methyl-1,3,5-triazin-2-amine |
| Z3352693154 | 4-({[5-(3-bromophenyl)-1,3-oxazol-2-yl]methyl}sulfanyl)-6-methyl-1,3,5-triazin-2-amine |
| Z1171239933 | 2-({[5-(2-chlorophenyl)-1,3,4-oxadiazol-2-yl]methyl}sulfanyl)-6-(trifluoromethyl)pyrimidin-4-ol |
| Z1171240290 | 2-({[5-(4-chlorophenyl)-1,3,4-oxadiazol-2-yl]methyl}sulfanyl)-6-(trifluoromethyl)pyrimidin-4-ol |
| Z3331727590 | 2-({[5-(4-methylphenyl)-1,3,4-oxadiazol-2-yl]methyl}sulfanyl)-6-(trifluoromethyl)pyrimidin-4-amine |
| Z2169238509 | 2-({[5-(2-chlorophenyl)-1,3-oxazol-2-yl]methyl}sulfanyl)-6-(difluoromethyl)pyrimidin-4-ol |
| Z1882973222 | 2-({[5-(2-chlorophenyl)-1,3-oxazol-2-yl]methyl}sulfanyl)-6-cyclopropylpyrimidin-4-ol |
| Z3302950786 | 2-({[5-(2-chlorophenyl)-1,3-oxazol-2-yl]methyl}sulfanyl)-6-(trifluoromethyl)pyrimidin-4-amine |
| Z3302950784 | 2-({[5-(3-methoxyphenyl)-1,3-oxazol-2-yl]methyl}sulfanyl)-6-(trifluoromethyl)pyrimidin-4-amine |
| Z3272467625 | 2-({[5-(3-chlorophenyl)-1,3-oxazol-2-yl]methyl}sulfanyl)-6-cyclopropylpyrimidin-4-ol |
| Z1263928626 | 6-({[5-(3-methoxyphenyl)-1,3-oxazol-2-yl]methyl}sulfanyl)-1,3,5-triazine-2,4-diamine |
| Z92097091 | 5-(4-fluorophenyl)-2-({thieno[2,3-d]pyrimidin-4-ylsulfanyl}methyl)-1,3-oxazole |
| Z3325085935 | 6-(difluoromethyl)-2-[({5-[3-(trifluoromethyl)phenyl]-1,3-oxazol-2-yl}methyl)sulfanyl]pyrimidin-4-ol |
| Z3325085941 | 2-({[5-(3-chloro-4-methoxyphenyl)-1,3-oxazol-2-yl]methyl}sulfanyl)-6-(difluoromethyl)pyrimidin-4-ol |
| Z3465744383 | 2-({[5-(3-chloro-5-methoxyphenyl)-1,3-oxazol-2-yl]methyl}sulfanyl)-6-methylpyrimidin-4-amine |
| Z167994154 | 5-(1-benzofuran-2-yl)-3-{[5-(4-methoxyphenyl)-1,3,4-oxadiazol-2-yl]methyl}-5-methylimidazolidine-2,4-dione |
| Z153632018 | 6-methyl-2-{[(3-phenyl-1,2,4-oxadiazol-5-yl)methyl]sulfanyl}pyrimidin-4-amine |
| Z92291585 | 2-({[3-(4-ethylphenyl)-1,2,4-oxadiazol-5-yl]methyl}sulfanyl)-6-methylpyrimidin-4-amine |
| Z224417008 | 6-[({3-[3-(trifluoromethyl)phenyl]-1,2,4-oxadiazol-5-yl}methyl)sulfanyl]-1,3,5-triazine-2,4-diamine |
| Z74374081 | 2-({[3-(4-methoxyphenyl)-1,2,4-oxadiazol-5-yl]methyl}sulfanyl)-6-methylpyrimidin-4-amine |
| Z1029501714 | 2-({[3-(2H-1,3-benzodioxol-5-yl)-1,2,4-oxadiazol-5-yl]methyl}sulfanyl)-6-methylpyrimidin-4-amine |
| Z1198273125 | 6-methyl-2-{[2-(5-phenyl-1,3-oxazol-2-yl)ethyl]sulfanyl}pyrimidin-4-amine |
| Z1209503309 | 3-({[5-(4-methoxyphenyl)-1,3-oxazol-2-yl]methyl}sulfanyl)-6-methyl-[1,2,4]triazolo[4,3-b][1,2,4]triazin-7-ol |
| Z1231012460 | 2-({3-[3-(4-chlorophenyl)-1,2,4-oxadiazol-5-yl]propyl}sulfanyl)-6-(trifluoromethyl)pyrimidin-4-ol |
| Z1231014625 | 2-({[5-(4-methoxyphenyl)-1,3-oxazol-2-yl]methyl}sulfanyl)-6-(trifluoromethyl)pyrimidin-4-ol |
| Z1231014829 | 2-{[3-(3-phenyl-1,2,4-oxadiazol-5-yl)propyl]sulfanyl}-6-(trifluoromethyl)pyrimidin-4-ol |
| Z1231014839 | 2-({[5-(4-methoxyphenyl)-1,3,4-oxadiazol-2-yl]methyl}sulfanyl)-6-(trifluoromethyl)pyrimidin-4-ol |

TABLE 1-continued

| Compound ID | Name |
|---|---|
| Z1231014954 | 2-{[2-(5-phenyl-1,3-oxazol-2-yl)ethyl]sulfanyl}-6-(trifluoromethyl)pyrimidin-4-ol |
| Z1263951032 | 2-({[5-(2-chlorophenyl)-1,3-oxazol-2-yl]methyl}sulfanyl)-6-methylpyrimidin-4-amine |
| Z1263951043 | 2-({[5-(3-methoxyphenyl)-1,3-oxazol-2-yl]methyl}sulfanyl)-6-methylpyrimidin-4-amine |
| Z1263951047 | 2-({[5-(2-bromophenyl)-1,3-oxazol-2-yl]methyl}sulfanyl)-6-methylpyrimidin-4-amine |
| Z1263951049 | 6-methyl-2-({[5-(2-methylphenyl)-1,3-oxazol-2-yl]methyl}sulfanyl)pyrimidin-4-amine |
| Z1272945742 | 2-({[5-(2-methoxyphenyl)-1,3-oxazol-2-yl]methyl}sulfanyl)-6-methylpyrimidin-4-amine |
| Z1272945752 | 6-methyl-2-({[5-(4-methylphenyl)-1,3-oxazol-2-yl]methyl}sulfanyl)pyrimidin-4-amine |
| Z153632138 | 2-({3-[3-(4-chlorophenyl)-1,2,4-oxadiazol-5-yl]propyl}sulfanyl)-6-methylpyrimidin-4-amine |
| Z1729866458 | 8-({[5-(4-methoxyphenyl)-1,3-oxazol-2-yl]methyl}sulfanyl)-7H-purine |
| Z1882969362 | 6-cyclopropyl-2-({[5-(4-methoxyphenyl)-1,3-oxazol-2-yl]methyl}sulfanyl)pyrimidin-4-ol |
| Z1882977097 | 6-cyclopropyl-2-({[5-(4-methoxyphenyl)-1,3,4-oxadiazol-2-yl]methyl}sulfanyl)pyrimidin-4-ol |
| Z2067312306 | 6-tert-butyl-2-({[5-(4-methoxyphenyl)-1,3,4-oxadiazol-2-yl]methyl}sulfanyl)pyrimidin-4-ol |
| Z213832006 | 6-({[5-(4-methoxyphenyl)-1,3,4-oxadiazol-2-yl]methyl}sulfanyl)-1,3,5-triazine-2,4-diamine |
| Z2169237989 | 6-(difluoromethyl)-2-({[5-(4-methoxyphenyl)-1,3,4-oxadiazol-2-yl]methyl}sulfanyl)pyrimidin-4-ol |
| Z2169243043 | 6-(difluoromethyl)-2-({[5-(4-methoxyphenyl)-1,3-oxazol-2-yl]methyl}sulfanyl)pyrimidin-4-ol |
| Z291790796 | 2-({[5-(4-methoxyphenyl)-1,3,4-oxadiazol-2-yl]methyl}sulfanyl)pyrimidin-4-ol |
| Z3271681128 | 4-({[5-(4-methoxyphenyl)-1,3-oxazol-2-yl]methyl}sulfanyl)-1,3,5-triazin-2-amine |
| Z3271681130 | 4-({[5-(4-methoxyphenyl)-1,3-oxazol-2-yl]methyl}sulfanyl)-6-methyl-1,3,5-triazin-2-amine |
| Z3271681135 | 2-({[5-(4-methoxyphenyl)-1,3-oxazol-2-yl]methyl}sulfanyl)-5-nitropyrimidin-4-amine |
| Z3271681140 | 4-hydroxy-2-({[5-(4-methoxyphenyl)-1,3-oxazol-2-yl]methyl}sulfanyl)pyrimidine-5-carbonitrile |
| Z3271681148 | 4-({[5-(4-methoxyphenyl)-1,3,4-oxadiazol-2-yl]methyl}sulfanyl)-1,3,5-triazin-2-amine |
| Z3271681150 | 4-({[5-(4-methoxyphenyl)-1,3,4-oxadiazol-2-yl]methyl}sulfanyl)-6-methyl-1,3,5-triazin-2-amine |
| Z3271681155 | 2-({[5-(4-methoxyphenyl)-1,3,4-oxadiazol-2-yl]methyl}sulfanyl)-5-nitropyrimidin-4-amine |
| Z3271681160 | 4-hydroxy-2-({[5-(4-methoxyphenyl)-1,3,4-oxadiazol-2-yl]methyl}sulfanyl)pyrimidine-5-carbonitrile |
| Z3271681169 | 6-tert-butyl-2-({[5-(4-methoxyphenyl)-1,3-oxazol-2-yl]methyl}sulfanyl)pyrimidin-4-ol |
| Z3271747780 | 2-({2-[3-(4-methylphenyl)-1,2,4-oxadiazol-5-yl]ethyl}sulfanyl)-6-(trifluoromethyl)pyrimidin-4-ol |
| Z3271747781 | 6-tert-butyl-2-({2-[3-(4-methylphenyl)-1,2,4-oxadiazol-5-yl]ethyl}sulfanyl)pyrimidin-4-ol |
| Z3271747785 | 6-tert-butyl-2-{[3-(3-phenyl-1,2,4-oxadiazol-5-yl)propyl]sulfanyl}pyrimidin-4-ol |
| Z3271747786 | 6-tert-butyl-2-({3-[3-(4-chlorophenyl)-1,2,4-oxadiazol-5-yl]propyl}sulfanyl)pyrimidin-4-ol |
| Z3271747787 | 6-tert-butyl-2-[(3-{3-[3-(trifluoromethyl)phenyl]-1,2,4-oxadiazol-5-yl}propyl)sulfanyl]pyrimidin-4-ol |
| Z3271747788 | 6-(trifluoromethyl)-2-[(3-{3-[3-(trifluoromethyl)phenyl]-1,2,4-oxadiazol-5-yl}propyl)sulfanyl]pyrimidin-4-ol |
| Z3271747791 | 3-({[5-(4-methoxyphenyl)-1,3-oxazol-2-yl]methyl}sulfanyl)-1,2,4-triazin-5-ol |
| Z3271747792 | 3-({[3-(4-methoxyphenyl)-1,2,4-oxadiazol-5-yl]methyl}sulfanyl)-1,2,4-triazin-5-ol |
| Z3271747795 | 5-(4-methoxyphenyl)-2-({7H-[1,2,4]triazolo[4,3-b][1,2,4]triazol-3-ylsulfanyl}methyl)-1,3-oxazole |
| Z3271747796 | 3-(4-methoxyphenyl)-5-({7H-[1,2,4]triazolo[4,3-b][1,2,4]triazol-3-ylsulfanyl}methyl)-1,2,4-oxadiazole |
| Z335843894 | 6-methyl-2-[(3-{3-[3-(trifluoromethyl)phenyl]-1,2,4-oxadiazol-5-yl}propyl)sulfanyl]pyrimidin-4-amine |
| Z3379835074 | 6-methyl-2-({[5-(naphthalen-2-yl)-1,3-oxazol-2-yl]methyl}sulfanyl)pyrimidin-4-amine |
| Z3379835075 | 4-({[5-(4-ethylphenyl)-1,3-oxazol-2-yl]methyl}sulfanyl)-6-methyl-1,3,5-triazin-2-amine |
| Z3379835076 | 4-({[5-(3-chloro-4-fluorophenyl)-1,3-oxazol-2-yl]methyl}sulfanyl)-6-methyl-1,3,5-triazin-2-amine |
| Z3379835077 | 4-({[5-(3-ethoxyphenyl)-1,3-oxazol-2-yl]methyl}sulfanyl)-6-methyl-1,3,5-triazin-2-amine |

TABLE 1-continued

| Compound ID | Name |
|---|---|
| Z3379835078 | 4-methyl-6-({[5-(naphthalen-2-yl)-1,3-oxazol-2-yl]methyl}sulfanyl)-1,3,5-triazin-2-amine |
| Z3379835080 | 2-({[5-(3-ethoxyphenyl)-1,3-oxazol-2-yl]methyl}sulfanyl)-6-methylpyrimidin-4-amine |
| Z74373346 | 2-({[5-(3-chlorophenyl)-1,3-oxazol-2-yl]methyl}sulfanyl)-6-methylpyrimidin-4-amine |
| Z74373790 | 2-({[5-(4-chlorophenyl)-1,3-oxazol-2-yl]methyl}sulfanyl)-6-methylpyrimidin-4-amine |
| Z855789072 | 2-({[5-(4-methoxyphenyl)-1,3-oxazol-2-yl]methyl}sulfanyl)pyrimidin-4-ol |
| Z92291581 | 2-({[5-(4-fluorophenyl)-1,3-oxazol-2-yl]methyl}sulfanyl)-6-methylpyrimidin-4-amine |
| Z97827966 | 6-methyl-2-{[3-(3-phenyl-1,2,4-oxadiazol-5-yl)propyl]sulfanyl}pyrimidin-4-amine |
| Z1029494972 | 3-(2H-1,3-benzodioxol-5-yl)-5-{[(1-methyl-1H-imidazol-2-yl)sulfanyl]methyl}-1,2,4-oxadiazole |
| Z1029495534 | 2-({[3-(2H-1,3-benzodioxol-5-yl)-1,2,4-oxadiazol-5-yl]methyl}sulfanyl)-5-chloro-1,3-benzoxazole |
| Z1029496480 | 3-(2H-1,3-benzodioxol-5-yl)-5-({thieno[2,3-d]pyrimidin-4-ylsulfanyl}methyl)-1,2,4-oxadiazole |
| Z1029496618 | 4-[5-({[3-(2H-1,3-benzodioxol-5-yl)-1,2,4-oxadiazol-5-yl]methyl}sulfanyl)-1,3,4-oxadiazol-2-yl]pyridine |
| Z1029497206 | 2-({[3-(2H-1,3-benzodioxol-5-yl)-1,2,4-oxadiazol-5-yl]methyl}sulfanyl)-3-methyl-3,4-dihydroquinazolin-4-one |
| Z1029497420 | 2-({[3-(2H-1,3-benzodioxol-5-yl)-1,2,4-oxadiazol-5-yl]methyl}sulfanyl)-3-methyl-3H,4H-thieno[2,3-d]pyrimidin-4-one |
| Z1029502292 | 3-({[3-(2H-1,3-benzodioxol-5-yl)-1,2,4-oxadiazol-5-yl]methyl}sulfanyl)-5-(thiophen-2-yl)-1,2,4-triazine |
| Z1029503244 | 2-({[3-(2H-1,3-benzodioxol-5-yl)-1,2,4-oxadiazol-5-yl]methyl}sulfanyl)-5-(ethanesulfonyl)-1,3-benzoxazole |
| Z1029503342 | 2-({[3-(2H-1,3-benzodioxol-5-yl)-1,2,4-oxadiazol-5-yl]methyl}sulfanyl)-4-methyl-6-phenylpyrimidine |
| Z1029503770 | 2-({[3-(2H-1,3-benzodioxol-5-yl)-1,2,4-oxadiazol-5-yl]methyl}sulfanyl)pyridine-3-carbonitrile |
| Z1029506360 | 3-(2H-1,3-benzodioxol-5-yl)-5-{[(1-cyclopropyl-1H-imidazol-2-yl)sulfanyl]methyl}-1,2,4-oxadiazole |
| Z1029506602 | 3-(2H-1,3-benzodioxol-5-yl)-5-{[(4,5-dimethyl-1,3-oxazol-2-yl)sulfanyl]methyl}-1,2,4-oxadiazole |
| Z1029507470 | 2-({[3-(2H-1,3-benzodioxol-5-yl)-1,2,4-oxadiazol-5-yl]methyl}sulfanyl)-3-methylquinoxaline |
| Z1029507482 | 1-({[3-(2H-1,3-benzodioxol-5-yl)-1,2,4-oxadiazol-5-yl]methyl}sulfanyl)phthalazine |
| Z1029507712 | 2-({[3-(2H-1,3-benzodioxol-5-yl)-1,2,4-oxadiazol-5-yl]methyl}sulfanyl)-5,6-dimethylthieno[2,3-d]pyrimidin-4-amine |
| Z1029509832 | 4-({[3-(2H-1,3-benzodioxol-5-yl)-1,2,4-oxadiazol-5-yl]methyl}sulfanyl)-2,6-dimethylpyrimidine |
| Z1029509856 | 3-({[3-(2H-1,3-benzodioxol-5-yl)-1,2,4-oxadiazol-5-yl]methyl}sulfanyl)-5,6-dimethylpyridazine-4-carboxamide |
| Z1029510154 | 2-({[3-(2H-1,3-benzodioxol-5-yl)-1,2,4-oxadiazol-5-yl]methyl}sulfanyl)pyridine-4-carbonitrile |
| Z1031201354 | 2-({[3-(2H-1,3-benzodioxol-5-yl)-1,2,4-oxadiazol-5-yl]methyl}sulfanyl)-4,6-dimethylpyridine-3-carboxamide |
| Z1203023499 | 6-({[3-(2H-1,3-benzodioxol-5-yl)-1,2,4-oxadiazol-5-yl]methyl}sulfanyl)-9H-purine |
| Z1222487486 | 2-({[3-(2H-1,3-benzodioxol-5-yl)-1,2,4-oxadiazol-5-yl]methyl}sulfanyl)-5-chloro-7-methyl-1,3-benzoxazole |
| Z1346686154 | 3-(2H-1,3-benzodioxol-5-yl)-5-[(1H-1,2,3-triazol-5-ylsulfanyl)methyl]-1,2,4-oxadiazole |
| Z1607494891 | 2-({[3-(2H-1,3-benzodioxol-5-yl)-1,2,4-oxadiazol-5-yl]methyl}sulfanyl)-5,6-dimethylpyrimidin-4-ol |
| Z1651266851 | 3-(2H-1,3-benzodioxol-5-yl)-5-[({5-methyl-[1,3]oxazolo[4,5-b]pyridin-2-yl}sulfanyl)methyl]-1,2,4-oxadiazole |
| Z1696915398 | 6-methyl-2-{[(5-phenyl-1,3,4-thiadiazol-2-yl)methyl]sulfanyl}pyrimidin-4-amine |
| Z1715553861 | 2-({[3-(2H-1,3-benzodioxol-5-yl)-1,2,4-oxadiazol-5-yl]methyl}sulfanyl)-7-chloro-1,3-benzoxazole |
| Z1892324362 | 3-(2H-1,3-benzodioxol-5-yl)-5-[(1,3-oxazol-2-ylsulfanyl)methyl]-1,2,4-oxadiazole |
| Z2067308590 | 2-({[3-(2H-1,3-benzodioxol-5-yl)-1,2,4-oxadiazol-5-yl]methyl}sulfanyl)-6-tert-butylpyrimidin-4-ol |
| Z2199288132 | 3-(2H-1,3-benzodioxol-5-yl)-5-({1H,4H,5H,6H-cyclopenta[d]imidazol-2-ylsulfanyl}methyl)-1,2,4-oxadiazole |
| Z74373281 | 6-methyl-2-{[(5-phenyl-1,3,4-oxadiazol-2-yl)methyl]sulfanyl}pyrimidin-4-amine |
| Z74373573 | 6-methyl-2-{[(5-phenyl-1,3-oxazol-2-yl)methyl]sulfanyl}pyrimidin-4-amine |
| Z74373706 | 6-methyl-2-{[(2-phenyl-1,3-thiazol-5-yl)methyl]sulfanyl}pyrimidin-4-amine |

Further particularly preferred compounds of the invention are shown in the following Table 2:

TABLE 2

| Compound ID | Name |
|---|---|
| Z3400108329 | 4-({[5-(3-chlorophenyl)-1,3-oxazol-2-yl]methyl}sulfanyl)-6-[difluoro(phenyl)methyl]-1,3,5-triazin-2-amine |
| Z3400108333 | 4-({[5-(3-chlorophenyl)-1,3-oxazol-2-yl]methyl}sulfanyl)-6-(1,3-thiazol-4-yl)-1,3,5-triazin-2-amine |
| Z3400108337 | 4-({[5-(3-chlorophenyl)-1,3-oxazol-2-yl]methyl}sulfanyl)-6-(1-methyl-1H-imidazol-2-yl)-1,3,5-triazin-2-amine |
| Z3400108303 | 4-({[5-(3-chlorophenyl)-1,3-oxazol-2-yl]methyl}sulfanyl)-6-(3,3-difluorocyclobutyl)-1,3,5-triazin-2-amine |
| Z3400108326 | 4-[chloro(fluoro)methyl]-6-({[5-(3-chlorophenyl)-1,3-oxazol-2-yl]methyl}sulfanyl)-1,3,5-triazin-2-amine |
| Z3400108331 | 4-({[5-(3-chlorophenyl)-1,3-oxazol-2-yl]methyl}sulfanyl)-6-(thiophen-3-yl)-1,3,5-triazin-2-amine |
| Z3400108302 | 4-({[5-(3-chlorophenyl)-1,3-oxazol-2-yl]methyl}sulfanyl)-6-(1-methoxycyclobutyl)-1,3,5-triazin-2-amine |
| Z3400108300 | 4-({[5-(3-chlorophenyl)-1,3-oxazol-2-yl]methyl}sulfanyl)-6-(1-methylcyclopropyl)-1,3,5-triazin-2-amine |
| Z3400108330 | 4-({[5-(3-chlorophenyl)-1,3-oxazol-2-yl]methyl}sulfanyl)-6-(thiophen-2-yl)-1,3,5-triazin-2-amine |
| Z3400108334 | 4-({[5-(3-chlorophenyl)-1,3-oxazol-2-yl]methyl}sulfanyl)-6-(1-methyl-1H-pyrazol-4-yl)-1,3,5-triazin-2-amine |
| Z3400108335 | 4-({[5-(3-chlorophenyl)-1,3-oxazol-2-yl]methyl}sulfanyl)-6-(1-methyl-1H-pyrazol-5-yl)-1,3,5-triazin-2-amine |
| Z3400108325 | 4-({[5-(3-chlorophenyl)-1,3-oxazol-2-yl]methyl}sulfanyl)-6-(2-methanesulfonylpropan-2-yl)-1,3,5-triazin-2-amine |
| Z3400108341 | 4-({[5-(3-chlorophenyl)-1,3-oxazol-2-yl]methyl}sulfanyl)-6-(pyridin-4-yl)-1,3,5-triazin-2-amine |
| Z3400108339 | 4-({[5-(3-chlorophenyl)-1,3-oxazol-2-yl]methyl}sulfanyl)-6-(pyridin-2-yl)-1,3,5-triazin-2-amine |
| Z3400108304 | 4-({[5-(3-chlorophenyl)-1,3-oxazol-2-yl]methyl}sulfanyl)-6-(methoxymethyl)-1,3,5-triazin-2-amine |
| Z3400108306 | 4-({[5-(3-chlorophenyl)-1,3-oxazol-2-yl]methyl}sulfanyl)-6-(oxolan-2-yl)-1,3,5-triazin-2-amine |
| Z3400108301 | 4-({[5-(3-chlorophenyl)-1,3-oxazol-2-yl]methyl}sulfanyl)-6-cyclobutyl-1,3,5-triazin-2-amine |

Further particularly preferred compounds according to the invention are shown in the following Table 3:

TABLE 3

| Coumpound ID | Name |
|---|---|
| Z642432840 | 2-{[5-(4-methylphenyl)-1,3,4-oxadiazol-2-yl]sulfanyl}-1,3-benzoxazole |
| Z1340746590 | 4-{[5-(1-benzofuran-2-yl)-1,3,4-oxadiazol-2-yl]sulfanyl}-6-methylpyrimidine |

Further particularly preferred compounds according to the invention are shown in the following Table 4:

TABLE 4

| Compound ID | Name |
|---|---|
| Z855788832 | 6-({[5-(4-methoxyphenyl)-1,3-oxazol-2-yl]methyl}sulfanyl)-1,3,5-triazine-2,4-diamine |
| Z1029502468 | 4,6-diamino-2-({[3-(2H-1,3-benzodioxol-5-yl)-1,2,4-oxadiazol-5-yl]methyl}sulfanyl)pyridine-3-carbonitrile |

Further particularly preferred compounds according to the invention are shown in the following Table 5:

TABLE 5

| Compound ID | Name |
|---|---|
| Z1029491270 | 2-({[3-(2H-1,3-benzodioxol-5-yl)-1,2,4-oxadiazol-5-yl]methyl}sulfanyl)-1-methyl-1H-1,3-benzodiazole |
| Z1029491492 | 4-({[3-(2H-1,3-benzodioxol-5-yl)-1,2,4-oxadiazol-5-yl]methyl}sulfanyl)-2-methylquinazoline |

TABLE 5-continued

| Compound ID | Name |
|---|---|
| Z1029492422 | 2-({[3-(2H-1,3-benzodioxol-5-yl)-1,2,4-oxadiazol-5-yl]methyl}sulfanyl)-6-chloro-1,3-benzoxazole |
| Z1029493690 | 6-({[3-(2H-1,3-benzodioxol-5-yl)-1,2,4-oxadiazol-5-yl]methyl}sulfanyl)-1,3,5-triazine-2,4-diamine |
| Z1029494394 | 2-({[3-(2H-1,3-benzodioxol-5-yl)-1,2,4-oxadiazol-5-yl]methyl}sulfanyl)quinoline |
| Z1029494414 | 2-({[3-(2H-1,3-benzodioxol-5-yl)-1,2,4-oxadiazol-5-yl]methyl}sulfanyl)-1,3-benzoxazole |
| Z1029494424 | 2-({[3-(2H-1,3-benzodioxol-5-yl)-1,2,4-oxadiazol-5-yl]methyl}sulfanyl)-1,3-benzothiazole |
| Z1029495632 | 4-({[3-(2H-1,3-benzodioxol-5-yl)-1,2,4-oxadiazol-5-yl]methyl}sulfanyl)quinazoline |
| Z1029496466 | 2-({[3-(2H-1,3-benzodioxol-5-yl)-1,2,4-oxadiazol-5-yl]methyl}sulfanyl)-4-methylquinoline |
| Z1029496890 | 2-({[3-(2H-1,3-benzodioxol-5-yl)-1,2,4-oxadiazol-5-yl]methyl}sulfanyl)-1-(propan-2-yl)-1H-1,3-benzodiazole |
| Z1029499752 | 2-({[3-(2H-1,3-benzodioxol-5-yl)-1,2,4-oxadiazol-5-yl]methyl}sulfanyl)-5-cyclohexyl-1,3,4-oxadiazole |
| Z1029500204 | 3-(2H-1,3-benzodioxol-5-yl)-5-({imidazo[1,5-a]pyridin-3-ylsulfanyl}methyl)-1,2,4-oxadiazole |
| Z1029500216 | 3-(2H-1,3-benzodioxol-5-yl)-5-{[(1-propyl-1H-imidazol-2-yl)sulfanyl]methyl}-1,2,4-oxadiazole |
| Z1029500474 | 2-({[3-(2H-1,3-benzodioxol-5-yl)-1,2,4-oxadiazol-5-yl]methyl}sulfanyl)-N-methylquinazolin-4-amine |
| Z1029501304 | 2-({[3-(2H-1,3-benzodioxol-5-yl)-1,2,4-oxadiazol-5-yl]methyl}sulfanyl)-5-(trifluoromethyl)pyridine |
| Z1029501700 | 6-({[3-(2H-1,3-benzodioxol-5-yl)-1,2,4-oxadiazol-5-yl]methyl}sulfanyl)-N,N-dimethylpyridine-3-sulfonamide |
| Z1029504560 | 4-({[3-(2H-1,3-benzodioxol-5-yl)-1,2,4-oxadiazol-5-yl]methyl}sulfanyl)-6-methyl-2-(propan-2-yl)pyrimidine |
| Z1029504794 | 2-({[3-(2H-1,3-benzodioxol-5-yl)-1,2,4-oxadiazol-5-yl]methyl}sulfanyl)-1-(difluoromethyl)-1H-1,3-benzodiazole |
| Z1029505062 | 3-(2H-1,3-benzodioxol-5-yl)-5-({thieno[3,2-d]pyrimidin-4-ylsulfanyl}methyl)-1,2,4-oxadiazole |
| Z1029506108 | 2-({[3-(2H-1,3-benzodioxol-5-yl)-1,2,4-oxadiazol-5-yl]methyl}sulfanyl)-3-chloropyridine |
| Z1029506216 | 3-(2H-1,3-benzodioxol-5-yl)-5-[({1-methyl-1H-pyrazolo[3,4-d]pyrimidin-4-yl}sulfanyl)methyl]-1,2,4-oxadiazole |
| Z1029507034 | 2-({[3-(2H-1,3-benzodioxol-5-yl)-1,2,4-oxadiazol-5-yl]methyl}sulfanyl)-4-(trifluoromethyl)pyrimidine |
| Z1029508010 | 2-({[3-(2H-1,3-benzodioxol-5-yl)-1,2,4-oxadiazol-5-yl]methyl}sulfanyl)-5-chloropyridine |
| Z1029510124 | 2-({[3-(2H-1,3-benzodioxol-5-yl)-1,2,4-oxadiazol-5-yl]methyl}sulfanyl)-5-methylpyridine |
| Z1029510468 | 2-({[3-(2H-1,3-benzodioxol-5-yl)-1,2,4-oxadiazol-5-yl]methyl}sulfanyl)-5-methylpyrimidine |
| Z1029510526 | 3-(2H-1,3-benzodioxol-5-yl)-5-{[(5-tert-butyl-1,3,4-oxadiazol-2-yl)sulfanyl]methyl}-1,2,4-oxadiazole |
| Z1029511174 | 3-(2H-1,3-benzodioxol-5-yl)-5-{[(5-phenyl-1,3-oxazol-2-yl)sulfanyl]methyl}-1,2,4-oxadiazole |
| Z1029519298 | 2-({[3-(2H-1,3-benzodioxol-5-yl)-1,2,4-oxadiazol-5-yl]methyl}sulfanyl)-1-ethyl-1,4-dihydropyrimidin-4-one |
| Z1032412320 | 6-({[3-(2H-1,3-benzodioxol-5-yl)-1,2,4-oxadiazol-5-yl]methyl}sulfanyl)pyridine-3-sulfonamide |
| Z1170218673 | 2-({[3-(2H-1,3-benzodioxol-5-yl)-1,2,4-oxadiazol-5-yl]methyl}sulfanyl)-4,6-dimethylpyrimidine |
| Z1203037016 | 6-methyl-2-({[3-(pyridin-4-yl)-1,2,4-oxadiazol-5-yl]methyl}sulfanyl)pyrimidin-4-amine |
| Z1231014585 | 2-({[3-(2H-1,3-benzodioxol-5-yl)-1,2,4-oxadiazol-5-yl]methyl}sulfanyl)-6-(trifluoromethyl)pyrimidin-4-ol |
| Z1263951070 | 6-methyl-2-({[3-(2,2,2-trifluoroethyl)-1,2,4-oxadiazol-5-yl]methyl}sulfanyl)pyrimidin-4-amine |
| Z1268440212 | 2-({[3-(2H-1,3-benzodioxol-5-yl)-1,2,4-oxadiazol-5-yl]methyl}sulfanyl)-4-methylpyrimidine |
| Z1329003512 | 3-(2H-1,3-benzodioxol-5-yl)-5-({[1-methyl-5-(propan-2-yl)-1H-imidazol-2-yl]sulfanyl}methyl)-1,2,4-oxadiazole |
| Z1425912580 | 3-(2H-1,3-benzodioxol-5-yl)-5-{[(5-tert-butyl-1,3-oxazol-2-yl)sulfanyl]methyl}-1,2,4-oxadiazole |
| Z1431854261 | 2-({[2-(4-chlorophenyl)-1H-imidazol-4-yl]methyl}sulfanyl)-6-methylpyrimidin-4-amine |
| Z1478208661 | 6-methyl-2-{[(5-phenyl-1,3-thiazol-2-yl)methyl]sulfanyl}pyrimidin-4-amine |
| Z1497574643 | 2-{[(3-cyclopentyl-1,2,4-oxadiazol-5-yl)methyl]sulfanyl}-6-methylpyrimidin-4-amine |
| Z1509671877 | 2-[({3-[(3,5-dimethylphenoxy)methyl]-1,2,4-oxadiazol-5-yl}methyl)sulfanyl]-6-methylpyrimidin-4-amine |
| Z1518617719 | 3-(2H-1,3-benzodioxol-5-yl)-5-[({1-ethyl-1H-imidazo[4,5-c]pyridin-2-yl}sulfanyl)methyl]-1,2,4-oxadiazole |

TABLE 5-continued

| Compound ID | Name |
|---|---|
| Z153632010 | 6-methyl-2-({[3-(thiophen-2-yl)-1,2,4-oxadiazol-5-yl]methyl}sulfanyl)pyrimidin-4-amine |
| Z1537370343 | 3-(2H-1,3-benzodioxol-5-yl)-5-[({6-methylthieno[2,3-d]pyrimidin-4-yl}sulfanyl)methyl]-1,2,4-oxadiazole |
| Z1606901941 | 2-({[3-(methoxymethyl)-1,2,4-oxadiazol-5-yl]methyl}sulfanyl)-6-methylpyrimidin-4-amine |
| Z1607523924 | 2-({[3-(2H-1,3-benzodioxol-5-yl)-1,2,4-oxadiazol-5-yl]methyl}sulfanyl)-5H,6H,7H-cyclopenta[d]pyrimidin-4-ol |
| Z1636448291 | 3-({[3-(2H-1,3-benzodioxol-5-yl)-1,2,4-oxadiazol-5-yl]methyl}sulfanyl)pyridazine |
| Z165913012 | 6-methyl-2-{[(5-phenyl-1,2,4-oxadiazol-3-yl)methyl]sulfanyl}pyrimidin-4-amine |
| Z167919650 | 2-({[5-(4-methoxyphenyl)-1,3,4-oxadiazol-2-yl]methyl}sulfanyl)-6-methylpyrimidin-4-amine |
| Z1686590093 | 3-(2H-1,3-benzodioxol-5-yl)-5-{[(5-methyl-1,3,4-oxadiazol-2-yl)sulfanyl]methyl}-1,2,4-oxadiazole |
| Z1737959431 | 3-(2H-1,3-benzodioxol-5-yl)-5-({imidazo[1,2-a]pyrazin-8-ylsulfanyl}methyl)-1,2,4-oxadiazole |
| Z1742797621 | 3-({[3-(2H-1,3-benzodioxol-5-yl)-1,2,4-oxadiazol-5-yl]methyl}sulfanyl)-6-(trifluoromethyl)pyridazine |
| Z1815466224 | 2-({[3-(2H-1,3-benzodioxol-5-yl)-1,2,4-oxadiazol-5-yl]methyl}sulfanyl)-4,6-dimethylpyridine |
| Z1818892697 | 2-({[3-(2H-1,3-benzodioxol-5-yl)-1,2,4-oxadiazol-5-yl]methyl}sulfanyl)-6-cyclopropylpyrimidin-4-ol |
| Z1838461414 | 3-(2H-1,3-benzodioxol-5-yl)-5-{[(4-methyl-1,3-oxazol-2-yl)sulfanyl]methyl}-1,2,4-oxadiazole |
| Z1881568735 | 6-methyl-2-{[(4-phenyl-1,3-thiazol-2-yl)methyl]sulfanyl}pyrimidin-4-amine |
| Z1883024789 | 3-(2H-1,3-benzodioxol-5-yl)-5-{[(4-phenyl-1,3-oxazol-2-yl)sulfanyl]methyl}-1,2,4-oxadiazole |
| Z1913692254 | 3-({[3-(2H-1,3-benzodioxol-5-yl)-1,2,4-oxadiazol-5-yl]methyl}sulfanyl)pyrazin-2-amine |
| Z215143852 | 2-({[3-(4-methoxyphenyl)-1,2-oxazol-5-yl]methyl}sulfanyl)-6-methylpyrimidin-4-amine |
| Z215143872 | 6-methyl-2-{[(3-phenyl-1,2-oxazol-5-yl)methyl]sulfanyl}pyrimidin-4-amine |
| Z2199309979 | 2-({[3-(2H-1,3-benzodioxol-5-yl)-1,2,4-oxadiazol-5-yl]methyl}sulfanyl)-5-fluoro-1,3-benzoxazole |
| Z2217546941 | 3-(2H-1,3-benzodioxol-5-yl)-5-{[(4,5-dimethyl-1H-imidazol-2-yl)sulfanyl]methyl}-1,2,4-oxadiazole |
| Z2234585705 | 2-({[3-(2H-1,3-benzodioxol-5-yl)-1,2,4-oxadiazol-5-yl]methyl}sulfanyl)pyrimidin-4-ol |
| Z225946944 | 6-methyl-2-({[3-(pyridin-3-yl)-1,2,4-oxadiazol-5-yl]methyl}sulfanyl)pyrimidin-4-amine |
| Z236243226 | 6-methyl-2-{[(5-methyl-2-phenyl-1,3-oxazol-4-yl)methyl]sulfanyl}pyrimidin-4-amine |
| Z243492726 | 6-methyl-2-({[3-(2-methylpropyl)-1,2,4-oxadiazol-5-yl]methyl}sulfanyl)pyrimidin-4-amine |
| Z2736147791 | 2-({[3-(2H-1,3-benzodioxol-5-yl)-1,2,4-oxadiazol-5-yl]methyl}sulfanyl)-6-methylpyrimidin-4-ol |
| Z2769120597 | 2-{[(3-cyclobutyl-1,2,4-oxadiazol-5-yl)methyl]sulfanyl}-6-methylpyrimidin-4-amine |
| Z281391700 | 2-({[2-(4-methoxyphenyl)-1,3-oxazol-4-yl]methyl}sulfanyl)-6-methylpyrimidin-4-amine |
| Z285633030 | 2-({[5-(4-methoxyphenyl)-1,2,4-oxadiazol-3-yl]methyl}sulfanyl)-6-methylpyrimidin-4-amine |
| Z285633032 | 2-{[(3-tert-butyl-1,2,4-oxadiazol-5-yl)methyl]sulfanyl}-6-methylpyrimidin-4-amine |
| Z2902738608 | 1-({[3-(2H-1,3-benzodioxol-5-yl)-1,2,4-oxadiazol-5-yl]methyl}sulfanyl)isoquinoline |
| Z2918137285 | 6-methyl-2-[({3-[(propan-2-yloxy)methyl]-1,2,4-oxadiazol-5-yl}methyl)sulfanyl]pyrimidin-4-amine |
| Z3213802691 | 2-({[3-(2H-1,3-benzodioxol-5-yl)-1,2,4-oxadiazol-5-yl]methyl}sulfanyl)-N-phenylquinazolin-4-amine |
| Z3213802693 | 6-amino-2-({[3-(2H-1,3-benzodioxol-5-yl)-1,2,4-oxadiazol-5-yl]methyl}sulfanyl)pyrimidin-4-ol |
| Z3213802695 | 4-({[3-(2H-1,3-benzodioxol-5-yl)-1,2,4-oxadiazol-5-yl]methyl}sulfanyl)-6-methyl-1,3,5-triazin-2-amine |
| Z3213802699 | 2-({[3-(2H-1,3-benzodioxol-5-yl)-1,2,4-oxadiazol-5-yl]methyl}sulfanyl)-5-(4-chlorophenyl)-6-ethylpyrimidin-4-amine |
| Z3213802705 | 2-({[3-(2H-1,3-benzodioxol-5-yl)-1,2,4-oxadiazol-5-yl]methyl}sulfanyl)-4-methylpyridine |
| Z3213802707 | 2-({[3-(2H-1,3-benzodioxol-5-yl)-1,2,4-oxadiazol-5-yl] methyl}sulfanyl) pyridin-3-ol |
| Z3213802708 | 3-({[3-(2H-1,3-benzodioxol-5-yl)-1,2,4-oxadiazol-5-yl]methyl}sulfanyl)-1,2,4-triazin-5-ol |
| Z3213802710 | 4-({[3-(2H-1,3-benzodioxol-5-yl)-1,2,4-oxadiazol-5-yl]methyl}sulfanyl)-1,3,5-triazin-2-amine |
| Z3213802729 | 5-({[3-(2H-1,3-benzodioxol-5-yl)-1,2,4-oxadiazol-5-yl]methyl}sulfanyl)-[1,3]thiazolo[5,4-d]pyrimidin-7-ol |

TABLE 5-continued

| Compound ID | Name |
|---|---|
| Z3213802731 | 2-({[3-(2H-1,3-benzodioxol-5-yl)-1,2,4-oxadiazol-5-yl]methyl}sulfanyl)-4-(trifluoromethyl)pyridine |
| Z3213802738 | 4-({[3-(2H-1,3-benzodioxol-5-yl)-1,2,4-oxadiazol-5-yl]methyl}sulfanyl)-6-(trifluoromethyl)pyrimidine |
| Z3213802739 | 2-({[3-(2H-1,3-benzodioxol-5-yl)-1,2,4-oxadiazol-5-yl]methyl}sulfanyl)-4-tert-butylpyrimidine |
| Z3213802750 | 2-({[3-(2H-1,3-benzodioxol-5-yl)-1,2,4-oxadiazol-5-yl]methyl}sulfanyl)-4-(pyridin-4-yl) pyrimidine |
| Z3213802754 | 3-(2H-1,3-benzodioxol-5-yl)-5-({[1,3]thiazolo[5,4-b]pyridin-2-ylsulfanyl}methyl)-1,2,4-oxadiazole |
| Z3213802764 | 2-({[3-(2H-1,3-benzodioxol-5-yl)-1,2,4-oxadiazol-5-yl]methyl}sulfanyl)-6-fluoro-1,3-benzoxazole |
| Z3213802766 | 3-(2H-1,3-benzodioxol-5-yl)-5-[({1-methyl-1H-imidazo[4,5-c]pyridin-2-yl}sulfanyl)methyl]-1,2,4-oxadiazole |
| Z3213802783 | 2-({[3-(2H-1,3-benzodioxol-5-yl)-1,2,4-oxadiazol-5-yl]methyl}sulfanyl)-5-cyclopropyl-1,3,4-oxadiazole |
| Z3213802789 | 3-(2H-1,3-benzodioxol-5-yl)-5-{[(4-tert-butyl-1,3-oxazol-2-yl)sulfanyl]methyl}-1,2,4-oxadiazole |
| Z3213802799 | 3-(2H-1,3-benzodioxol-5-yl)-5-({1H,4H,6H,7H-pyrano[3,4-d]imidazol-2-ylsulfanyl}methyl)-1,2,4-oxadiazole |
| Z3213805248 | 2-({[3-(2-methoxypropan-2-yl)-1,2,4-oxadiazol-5-yl]methyl}sulfanyl)-6-methylpyrimidin-4-amine |
| Z3213805251 | 6-methyl-2-({[3-(1-methyl-1H-imidazol-5-yl)-1,2,4-oxadiazol-5-yl]methyl}sulfanyl)pyrimidin-4-amine |
| Z3213805252 | 2-({[3-(6-methoxypyridazin-3-yl)-1,2,4-oxadiazol-5-yl]methyl}sulfanyl)-6-methylpyrimidin-4-amine |
| Z326667474 | 2-[({3-[(4-fluorophenoxy)methyl]-1,2,4-oxadiazol-5-yl}methyl)sulfanyl]-6-methylpyrimidin-4-amine |
| Z326667486 | 2-{[(3-cyclopropyl-1,2,4-oxadiazol-5-yl)methyl]sulfanyl}-6-methylpyrimidin-4-amine |
| Z362900180 | 6-methyl-2-({[3-(pyridin-2-yl)-1,2,4-oxadiazol-5-yl]methyl}sulfanyl)pyrimidin-4-amine |
| Z74373912 | 2-({[2-(4-methoxyphenyl)-1,3-thiazol-4-yl]methyl}sulfanyl)-6-methylpyrimidin-4-amine |
| Z74373920 | 6-methyl-2-{[(2-phenyl-1,3-oxazol-4-yl)methyl]sulfanyl}pyrimidin-4-amine |
| Z855791334 | 2-({[5-(4-methoxyphenyl)-1,3-oxazol-2-yl]methyl}sulfanyl)-6-methylpyrimidin-4-amine |
| Z97827862 | 6-methyl-2-{[(5-phenyl-1,2-oxazol-3-yl)methyl]sulfanyl}pyrimidin-4-amine |
| Z990622086 | 6-methyl-2-{[(4-methyl-5-phenyl-4H-1,2,4-triazol-3-yl)methyl]sulfanyl}pyrimidin-4-amine |

Further particularly preferred compounds according to the invention are shown in the following Table 6:

TABLE 6

| Compound ID | Name |
|---|---|
| Z1137177241 | 2-(((3-(furan-3-yl)-1,2,4-oxadiazol-5-yl)methyl)thio)-6-methylpyrimidin-4-amine |
| Z3214047394 | 6-methyl-2-((2-(3-(p-tolyl)-1,2,4-oxadiazol-5-yl)ethyl)thio)pyrimidin-4(1H)-imine |
| Z1453477070 | 2-((1-(3-(4-methoxyphenyl)-1,2,4-oxadiazol-5-yl)ethyl)thio)-6-methylpyrimidin-4(1H)-imine |

According to the invention compounds disclosed herein are to be understood as also including the respective enantiomers, diastereomers, hydrates, solvates, pharmaceutically acceptable co-crystals or salts, prodrugs and complexes thereof.

Pharmaceutically acceptable salts are typically salts of an organic or inorganic acids generally known in the art as pharmaceutically acceptable, preferably those disclosed in P. H. Stahl and C. G. Wermuth, editors, *Handbook of Pharmaceutical Salts: Properties, Selection and Use*, Weinheim/Zurich:Wiley-VCH/VHCA, 2002. A preferred salt of the invention is the hydrochloride salt of a compound as disclosed herein.

The compounds as defined herein are particularly useful as agonists of GPR40, wherein, according to preferred embodiments, the compound shows a higher selectivity for GPR40 than for GPR120.

More preferably, the compound as defined herein shows a % activation of GPR40 being at least 3 fold higher than the % activation of GPR120, with % activation being the hundredfold ratio of activation of GPR40 or GPR120, respectively, by said compound to the activation of GPR40 or GPR120, respectively, by AMG 837. AMG 837 is a known potent agonist of GPR40 [22].

The compounds of the present invention are potent and selective agonists and are preferably provided as such agonists, of FFAR1 (GPR40). In particular, the compounds as disclosed herein are more selective and potent agonists of FFAR1 than of FFAR4. In preferred embodiments of the invention, a compound as disclosed herein shows an at least 3 fold %, more preferably a 3 to 5 fold, % activation of FFAR1 in comparison to its % activation of FFAR4 (GPR120), with % activation always being the 100 fold ratio of activation of the respective receptor by the compound as disclosed herein and the activation of the respective receptor by AMG 837. According to alternative embodiments of the invention, the % activation as used herein may also be expressed by reference to the activation by TAK-875.

The compounds as disclosed herein are useful as medicaments, preferably for the prevention, improvement of symptoms, suppression of progression or treatment of conditions or diseases in a mammalian (such as, e.g., human, mouse, rat, rabbit, dog, cat, bovine, horse, swine, monkey) subject as further outlined below.

For medical use the compounds of this disclosure may be used as such or as an active ingredient of a pharmaceutical composition comprising at least one compound of general formula (I) and at least one pharmaceutically acceptable carrier.

Useful pharmaceutically acceptable carriers are various organic or inorganic carrier substances which are conventionally used as preparation materials in the pharmaceutical art. These may be incorporated as excipients, lubricants, binders and disintegrants for solid preparations, or solvents, solubilizing agents, suspending agents, isotonicity agents, buffers and soothing agents for liquid preparations, and the like, in the present pharmaceutical composition. Further ingredients are preferably selected from preparation additives such as preservatives, antioxidants, colorants, sweetening agents and the like, which can be added as necessary.

Preferred examples of excipients include, but are not limited to, lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferred examples of lubricants include, but are not limited to, magnesium stearate, calcium stearate, talc and colloidal silica.

Preferred binders include, but are not limited to, gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferred disintegrants include, but are not limited to, lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferred examples of useful solvents include, but are not limited to, water for injection, physiological brine, Ringer's solution, Ringer lactate, alcohol, propylene glycol, polyethylene glycol, sesame oil, corn oil, olive oil and cottonseed oil.

Preferred solubilizing agents include, but are not limited to, polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferred suspending agents for use in the present inventiuon include, but are not limited to, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates; and polyoxyethylene hydrogenated castor oil.

Preferred examples of isotonicity agents are sodium chloride, glycerol, D-mannitol, D-sorbitol and glucose.

Preferred buffer substances include buffers such as phosphate, acetate, carbonate, citrate and the like.

A preferred soothing agent in the context of the invention is benzyl alcohol.

Preferred examples of preservatives for use in the pharmaceutical composition include, but are not limited to, p-oxybenzoates, chlorobutanol, benzyl alcohol, phenethyl alcohol, dehydroacetic acid and sorbic acid.

Preferred antioxidants for use in the invention include, but are not limited to, sulfite and ascorbate.

Preferred colorants include, e.g., aqueous water-soluble food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the aforementioned water-soluble food tar color) and natural dyes (e.g., β-carotene, chlorophyll, ferric oxide red).

Preferred sweetening agents are, e.g., saccharin sodium, dipotassium glycyrrhizinate, aspartame and *stevia*.

Preferred dosage forms of the pharmaceutical composition include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like, and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop.

Pharmaceutical compositions of the invention may be in the form of release control preparations (e.g., sustained-release microcapsule) such as an immediate-release preparation, a sustained-release preparation and the like The pharmaceutical composition can be produced according to a method conventionally used in the field of pharmaceutical formulation.

While the content of the compound of the present invention in the pharmaceutical composition varies depending on the dosage form, dose of the compound of the present invention or as disclosed herein and further parameters such as the specific aids as outlined above, it is typically contained in the pharmaceutical composition at about 0.1 to about 100 wt %.

Oral pharmaceutical compositions of the invention may comprise one or more coatings which may be applied as necessary for the purpose of various parameters such as masking of taste, enteric property or durability.

Further specific guidance concerning the ingredients, but also routes for administration, dosage etc., of the pharmaceutical composition can be found in the latest edition of Remington's Pharmaceutical Sciences (Mack Publishing Co., Eastern, PA, USA).

The compounds disclosed herein are for use in the prevention, improvement of symptoms, suppression of progression or treatment of conditions or diseases amenable to higher GPR40 (FFAR1) activity.

It is to be understood that, throughout the present disclosure, the term "treatment" means the treatment of the respective conditions or diseases as such as well as the prevention and/or improvement of symptoms and/or suppression of progression of such conditions or diseases. The same applies to the term "use in the treatment" which relates to the use in the treatment of the respective conditions or diseases as such as well as the to the use in the prevention and/or improvement of symptoms and/or suppression of progression of such conditions or diseases.

In particular, according to one preferred aspect of the invention, the compounds as disclosed are for use in the treatment of conditions or diseases involving energy household and metabolism, preferably conditions or diseases involving impaired control of glucose blood levels, more preferably diabetes, most preferred T2DM, and pre-diabetic conditions such as obesity and insulin resistance. The present invention therefore also relates to a method for the prevention, improvement of symptoms, suppression of progression or treatment of diseases or conditions amenable to higher GPR40 (FFAR1) activity, in particular, conditions or diseases involving energy household and metabolism, preferably conditions or diseases involving impaired control of glucose blood levels, more preferably diabetes, most preferred T2DM, and pre-diabetic conditions such as obesity and insulin resistance, which method comprises the step of administering an effective amount of a compound as disclosed herein to a subject, preferably human subject, in need thereof.

The present invention also relates to the use of the disclosed compounds for the preparation of a medicament for the prevention, improvement of symptoms, suppression of progression or treatment of diseases or conditions amenable to higher GPR40 (FFAR1) activity, in particular, conditions or diseases involving energy household and metabolism, preferably conditions or diseases involving impaired control of glucose blood levels, more preferably diabetes, most preferred T2DM, and pre-diabetic conditions such as obesity and insulin resistance.

Other preferred diseases of energy household and/or metabolism for which the compounds of the invention can be applied to include metabolic syndrome and dyslipidemia Further preferred diseases and/or conditions involving GPR40 (FFAR1) to which the compounds of the invention can be applied include kidney diseases such as preferably chronic kidney disease (CKD) and diabetic nephropathy (diabetic kidney disease), fibrotic and sclerotic diseases or conditions such as preferably idiopathic pulmonary fibrosis (IPF), lung fibrosis, heart fibrosis, liver fibrosis, kidney fibrosis and systemic schlerosis, and hepatic and biliary diseases such as preferably hepatic steatosis, non-alcoholic fatty liver disease (NAFLD), non-alcoholic fatty liver (NAFL), and non-alcoholic steatohepatitis (NASH), primary biliary cholangitis (PBC) and primary sclerosing cholangitis (PSC).

The administration of the compound disclosed herein is preferably systemic, with oral administration being particularly preferred.

The "effective amount" of the compound disclosed herein varies depending on the administration subject, route of administration, target disease, symptoms, sex of the subject etc. For example, when it is administered orally to an adult patient (body weight 60 kg), its dose is typically about 0.01 to about 100 mg/kg body weight per dose, preferably about 0.05 to about 30 mg/kg body weight per dose, more preferably about 0.1 to about 10 mg/kg body weight per dose, with such exemplary or preferable effective amounts being preferably administered in 1 to 3 doses per day.

When the compound of formula (I) as disclosed herein is applied to a condition or diseases as outlined above, it can be used in an appropriate combination with a medicament or a treatment method generally employed for the condition or disease, respectively, whereby the compound of the invention (or compound being useful in the invention) can administered with the second, third or more medicament simultaneously or non-simultaneously.

Preferred combination therapies for treatment of conditions or diseases involving impaired control of glucose blood levels, more preferably diabetes, most preferred T2DM, according to the invention employ at least one compound of formula (I) and one or more other active agents useful in the treatment of conditions or diseases involving impaired control of glucose blood levels, more preferably diabetes, most preferred T2DM, such as preferably one or more selected from; biduanides such as preferably Metformin, SGTL2 inhibitors (gliflozins) such as preferably one or more selected from dapagliflohin, licogliflozin, luseogliflozin, remogliflozin etabonate, sotagliflozin and tofogliflozin; DPP-4 inhibitors such as preferably one or more selected from Sitagliptin, Vildagliptin, Saxagliptin and Linagliptin; α-glucosidase inhibitors such as preferably one or more selected from Acarbose, Miglitol and Voglibose; sulfonylurea compounds such as preferably one or more selected from acetohexamide, carbutamide, chlorpropamide, glycyclamide metahexamide, tolazamide, tolbutamide glibenclamide, glibornuride, gliclazide, glipizide, gliquidone, glisoxepide, glyclopyramide and glimipiride; glinides such as preferably one or more selected from repaglinide, nateglinide and mitiglinide; other agonists of GPR40 and/or GPR120 such as preferably one or more of TAK-875, LY2881835, AMG6837, GW9608, grifolic acid, NCG21, GSK-137677A and TUG391; GLP-1 receptor agonists such as preferably one or more selected from albiglutide, dulaglutide, exenatide, extended-release exenatide, liraglutide, lixisenatide and semaglutide; glucokinase modulators such as preferably dorzagliatin; thiazolidinediones such as preferably one or more selected rosiglitazone, troglitazone, and pioglitazone; incretin mimetics, such as preferably one or more selected from liraglutide, exenatide, semaglutide, dulaglutide, albiglutide and lixisenatide; insulin and insulin derivatives such as preferably one or more selected from Insulin glulisine, Insulin aspart, Insulin lispro, Novolin R, Humulin R, NPH insulin, Insulin detemir, Insulin U-100 and Insulin glargine U-300; and other compounds for T2DM therapy such as preferably Pramlintide It is to be understood that the present invention also relates to pharmaceutical compositions containing at least one compound of formula (1) and one or more other active components useful in the treatment of conditions or diseases involving impaired control of glucose blood levels, more preferably diabetes, most preferably T2DM, and pre-diabetic conditions, preferably insulin resistance, such as preferably one or more of the active agents as outlined above.

Preferred combination therapies for treatment of metabolic syndrome and/or obesity and/or and/or dyslipidemia according to the invention employ at least one compound of formula (1) and one or more other active agents useful in the treatment of metabolic syndrome and/or obesity and/or and/or dyslipidemia, such as preferably one or more selected from; statins such as preferably one or more selected from atorvastatin, fluvastatin, lovastatin, pitavastatin, pravastatin, rosuvastatin calcium and simvastatin; bile acid sequestrants such as preferably one or more selected from cholestyramine, colesevelam, colestipol, fibrates; other PPAR alpha agonists such as preferably one or more selected from bezafibrate, ciprofibrate, clinofibrate, clofibrate, fenofibrate, gemfibrozil and ronifibrate; PCSK9 inhibitors such as preferably one or more selected from alirocumab, bococizumab and evolocumab; lipase inhibitors such as preferably orlistat; 5-HT2C receptor agonists such as preferably lorcaserin; amphetamines and/or phenethylamines such as preferably one or more selected from amfepramone, benzphetamine, dextroamphetamine, ephedrine, pseudoephedrine, phentermine, phenmetrazine and MDMA; anticonvulsants such as preferably topiramate; opioid receptor antagonists such as preferably naltrexone; norepinephrine-dopamine reuptake inhibitors such as preferably bupropion; and other compounds for treatment of metabolic syndrome and/or obesity and/or and/or dyslipidemia, such as preferably ezetimibe and niacin.

It is to be understood that the present invention also relates to pharmaceutical compositions containing at least one compound of formula (1) and one or more other active components useful in the treatment of metabolic syndrome and/or obesity and/or and/or dyslipidemia, such as preferably one or more of the active agents as outlined above.

Preferred combination therapies for treatment of kidney diseases such as preferably chronic kidney disease (CKD) and diabetic nephropathy (diabetic kidney disease), according to the invention employ at least one compound of formula (1) and one or more other active agents useful in the treatment of kidney diseases, such as preferably one or more selected from; angiotensin-converting-enzyme inhibitors (ACE inhibitors) such as preferably one or more selected from benazepril, captopril, enalapril, lisinopril, perindopril, ramipril, trandolapril, and zofenopril; angiotensin II receptor blockers (ARBs) such as preferably one or more selected from losartan, irbesartan, olmesartan, candesartan, valsartan, fimasartan and azilsartan; thiazide diuretics such as preferably one or more selected from hydrochlorothiazide, bendroflumethiazide, methyclothiazide, trichlormethiazide and indapamide; calcium channel blockers such as preferably one or more selected from amlodipine, aranidipine, azelnidipine, barnidipine, fendiline, verapamil and diltiazem; antioxidants such as preferably N-acetylcysteine; protein kinase C inhibitors such as preferably ruboxistaurin; TNF-alpha blockers such as preferably pentoxifylline; thiazolidinediones such as preferably pioglitazone; DPP-4 inhibitors such as preferably vildagliptin; SGTL2 inhibitors (gliflozins) such as preferably one or more selected from dapagliflohin, licogliflozin, luseogliflozin, remogliflozin etabonate, sotagliflozin and tofogliflozin; incretin mimetics such as preferably one or more selected from liraglutide, exenatide, semaglutide, dulaglutide, albiglutide and lixisenatide; mineralocorticoid receptor antagonists such as preferably esaxerenone (CS-3150); and other compounds useful in the prevention and/or treatment of kidney diseases, preferably kidney disease (CKD) and diabetic nephropathy (diabetic kidney disease), such as preferably sulodexide.

It is to be understood that the present invention also relates to pharmaceutical compositions containing at least one compound of formula (1) and one or more other active components useful in the treatment of kidney diseases, such as preferably chronic kidney disease (CKD) and diabetic nephropathy (diabetic kidney disease), such as preferably one or more of the above active agents as outlined above.

Preferred combination therapies for treatment of fibrotic and sclerotic diseases or conditions such as preferably idiopathic pulmonary fibrosis (IPF), lung fibrosis, heart fibrosis, liver fibrosis, kidney fibrosis and systemic sclerosis, according to the invention employ at least one compound of formula (1) and one or more other active agents useful in the treatment of fibrotic and sclerotic diseases or conditions such as preferably idiopathic pulmonary fibrosis (IPF), lung fibrosis, heart fibrosis, liver fibrosis, kidney fibrosis and systemic sclerosis, such as preferably one or more selected from; tissue growth factor (TGF) inhibitors such as preferably one or more selected from F-351, P-144, GC-1008 and pamrevlumab; tyrosine-kinase inhibitors such as preferably one or more selected from nintedanib, or TAS-115, sorafenib; imatinib, BOT-191, nilotinib, dasatinib and sorafenib, integrin inhibitors such as preferably one or more selected from IDL-2965, CWHM-12, BGO00011, STX-100 and dioscin; ALK5 inhibitors such as preferably SB-431542; bone morphogenetic protein-7 agonists such as preferably THR-184; CTGF inhibitors such as preferably one or more selected from PF-06473871, RXI-109 and FG-3019; TNF inhibitors such as preferably one or more selected from thalidomide, pomalidomide, etanercept and belimumab; HGF mimetics such as preferably refanalin; interleukin inhibitors such as preferably one or more selected from dectrekumab, tralokinumab, anakinra, rilonacept, lebrikizumab and SAR156597; CC chemokine inhibitors such as preferably one or more selected from carlumab, bindarit, maraviroc and RS-504393; interferons such as preferably actimmune and/or interferon alpha, MMP/TIMP inhibitors such as preferably batimastat and/or marimastat; endothelin antagonists such as preferably one or more selected from macitentan, bosentan, ambrisentan, sparsentan and atrasentan; angiotensin II receptor blockers (ARBs) such as preferably one or more selected from losartan, irbesartan, olmesartan, candesartan, valsartan, fimasartan and azilsartan; LPAR antagonists such as preferably BMS-986020; CB1 receptor antagonists such as preferably curcumin and/or silymarin; CB2 receptor antagonists such as preferably beta-caryophyllene; prostacyclin receptor agonists such as preferably one or more selected from beraprost, iloprost and treprostinil; VIP receptor agonists such as preferably aviptadil; leukocyte elastase inhibitors such as preferably sivelestat; TAFI inhibitors such as preferably UK-396082; relaxin receptor stimulants such as preferably serelaxin, recombinant pentraxins and/or mimetics thereof such as preferably PRM-151; TGM inhibitors such as preferably NTU281; autotaxin inhibitors such as preferably BBT-877 and/or GLPG1690, GPR84 inhibitors such as preferably GLPG1205; GPR40 agonists such as preferably PBI-4050; connective galectin inhibitors such as preferably TD139; Rho-associated kinase inhibitors such as preferably KD025; c-Jun kinase inhibitors such as preferably CC-90001; somatostatin analogues such as preferably octreitude; cyclophilin inhibitors such as preferably CRV431; and other compounds for use in the treatment of fibrotic and sclerotic conditions or diseases, preferably those mentioned above, such as preferably one or more selected from pirfenidone, Tripelukast, and bardoxolonemethyl.

It is to be understood that the present invention also relates to pharmaceutical compositions containing at least one compound of formula (1) and one or more other active components useful in the treatment of fibrotic and sclerotic diseases or conditions such as preferably idiopathic pulmonary fibrosis (IPF), lung fibrosis, heart fibrosis, liver fibrosis, kidney fibrosis and systemic sclerosis, such as one or more of the above active agents as outlined above.

Preferred combination therapies for treatment of hepatic and biliary diseases, preferably hepatic steatosis, non-alcoholic fatty liver disease (NAFLD), non-alcoholic fatty liver (NAFL), and non-alcoholic steatohepatitis (NASH), primary biliary cholangitis (PBC) and primary sclerosing cholangitis (PSC), according to the invention employ at least one compound of formula (1) and one or more other active agents useful in the treatment of hepatic and biliary diseases, preferably hepatic steatosis, non-alcoholic fatty liver disease (NAFLD), non-alcoholic fatty liver (NAFL), and non-alcoholic steatohepatitis (NASH), primary biliary cholangitis (PBC) and primary sclerosing cholangitis (PSC), such as preferably one or more selected from; androgen receptor agonists such as preferably LPCN 1144; fatty-acid/bile-acid conjugates (FABACs) such as preferably aramchol; bile acids such as preferably ursodeoxycholic acid (UDCA) and/or nor-ursodeoxycholic acid; FXR ligands such as preferably one or more selected from obeticholic acid, GS9674, tropifexor, AKN-083, EYP001 and TERN-101; FGF-19 mimetics such as preferably NGM282; TGR5 agonists such as preferably INT-767 and/or INT-777; PPAR agonists such as preferably one or more selected from banzfibrate, MBX-8025, elafibranor, lanifibranor, saroglitazar and seladelpar; ASBT inhibitors such as preferably one or more selected from A4250, maralixibat and GSK2330672; immunomodulators such as FFP-104 and/or foralumab; CCR2/CCR5 receptor inhibitors such as cenicriviroc; caspase inhibitors such as preferably one or more selected from emricasan, GS-9450 and VX-166; GLP-1 receptor agonists such as preferably one or more selected from albiglutide, dulaglutide, exenatide, extended-release exenatide, liraglutide, lixisenatide and semaglutide; thiazolidinediones such as preferably one or more selected from rosiglitazone, troglitazone, MSDC-0602K and pioglitazone; thyroid hormone receptor β agonists such as preferably resmetirom and/or MGL-3196; ASK1 inhibitors such as preferably selonsertib; SSAO/VAP-1 inhibitors such as preferably BI 1467335; human fibroblast growth factor mimetics such as preferably BMS-986036; P2RY13 protein agonists such as preferably CER-209; cyclosporine A analogues such as preferably CRV-431; galectin inhibitors such as preferably GR-MD-02; acetyl-CoA carboxylase (ACC) inhibitors such as preferably GS-0976 and/or PF-05221304; lipid modulators such as preferably HTD1801; anti-CD3 antibodies such as preferably foralumab; FGFR1c/KLB activators such as preferably NGM313; Diacylglycerol O-Acyltransferase 2 (DGAT2) inhibitors such as preferably PF-06865571; ketohexokinase (KHK) inhibitors such as preferably PF-06835919; integrin inhibitors such as preferably PLN-1474; mitochondrial pyruvate carrier inhibitors such as preferably PXL-065; and other compounds for use in fibrotic and/or sclerotic diseases or conditions such preferably those mentioned above, such as preferably vitamin E.

It is to be understood that the present invention also relates to pharmaceutical compositions containing at least one compound of formula (1) and one or more other active components useful in the treatment hepatic and biliary diseases, preferably hepatic steatosis, non-alcoholic fatty liver disease (NAFLD), non-alcoholic fatty liver (NAFL), and non-alcoholic steatohepatitis (NASH), primary biliary cholangitis (PBC) and primary sclerosing cholangitis (PSC), such as one or more of the above active agents as outlined above.

It is to be understood that with respect to all uses and treatment methods according to the invention, a "compound as disclosed herein" refers to the compound of general formula (I) as defined above also expressis verbis including the following compounds

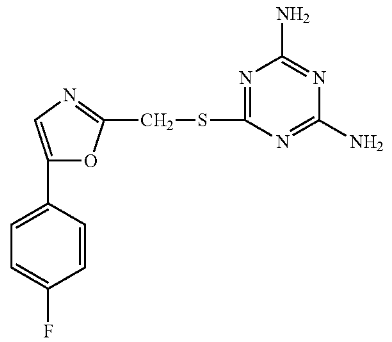

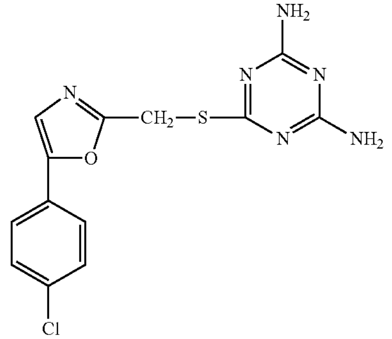

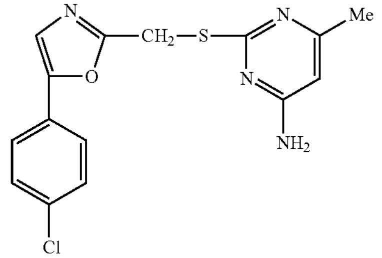

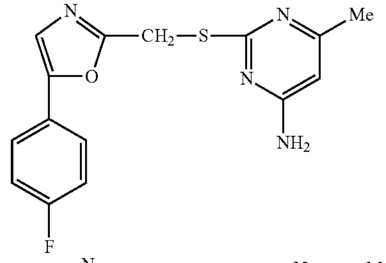

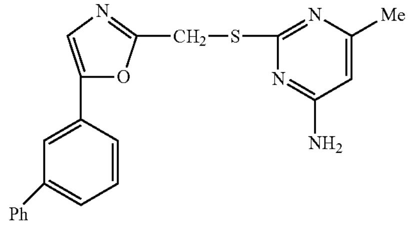

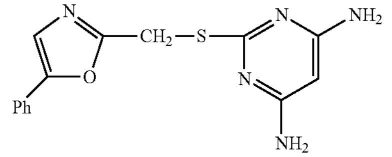

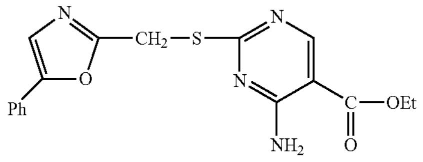

-continued

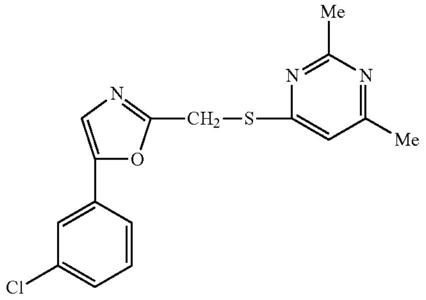

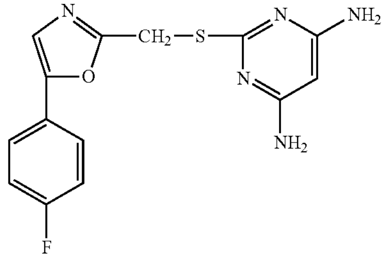

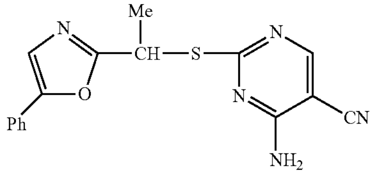

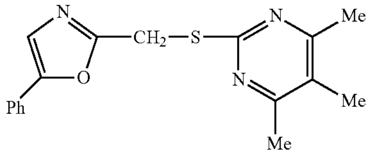

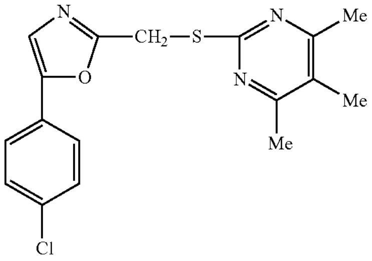

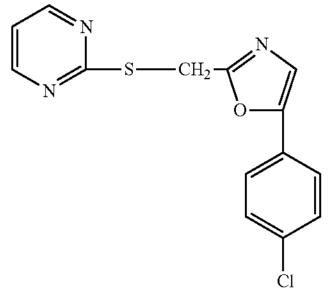

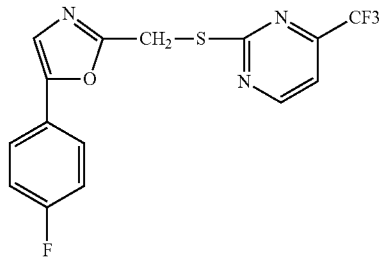

-continued

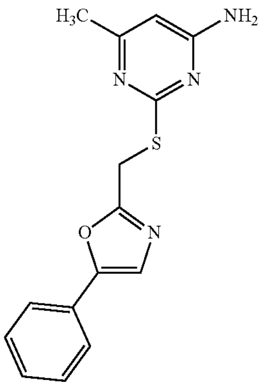

Preferred embodiments of the compounds of the present disclosure wherein OXA in general formula (1) is 1,3-oxazolyl are preferably prepared according to one the following general synthesis schemes:

Scheme 1

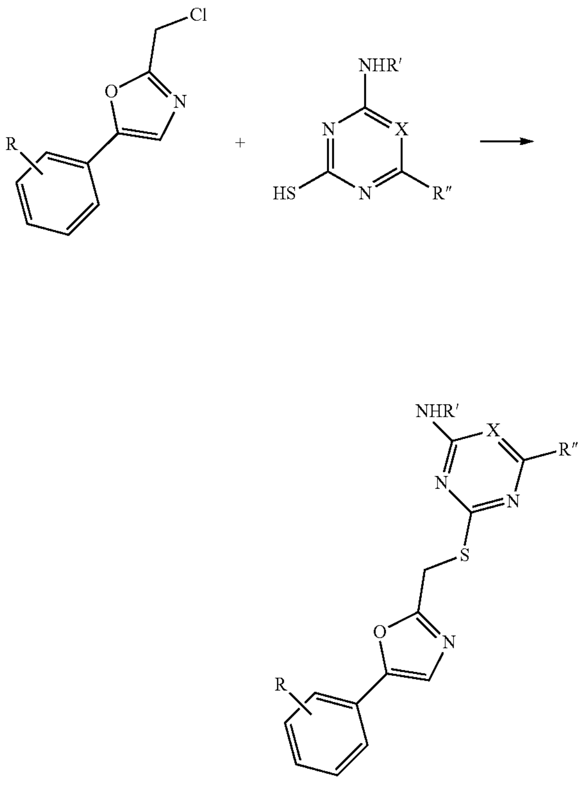

X = CH, N wherein R is as defined as the substituents at the phenyl group as defined in $R^2$ according to general formula (I), R' is H or $C_1$-$C_3$-alkyl, and R" is a substituent selected from hydroxyl, amino, $C_1$-$C_5$-alkyl, $C_3$-$C_5$-cycloalkyl, $C_1$-$C_3$-alkoxy, N-mono- or N,N-di-substituted $C_1$-$C_3$-alkylamino, non-aromatic 5- to 6-membered heterocyclyl, 6-membered aryl and 5- to 6-membered heteroaryl, optionally substituted with one or more groups selected from halide, cyano and $C_1$ to $C_6$-alkyl.

Scheme 2

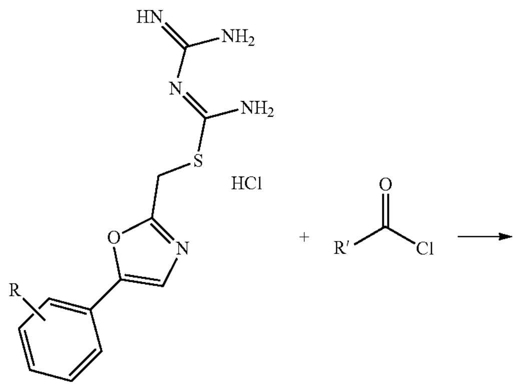

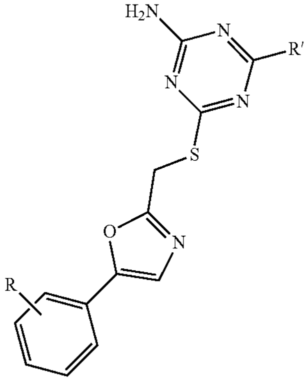

wherein R is as defined as the substituents at the phenyl group as defined in $R^2$ according to general formula (I), R' is a substituent selected from hydroxyl, amino, $C_1$-$C_5$-alkyl, $C_3$-$C_5$-cycloalkyl, $C_1$-$C_3$-alkoxy, N-mono- or N,N-di-substituted $C_1$-$C_3$-alkylamino, non-aromatic 5- to 6-membered heterocyclyl, 6-membered aryl and 5- to 6-membered heteroaryl, optionally substituted with one or more groups selected from halide, cyano and $C_1$ to $C_6$-alkyl.

Scheme 3

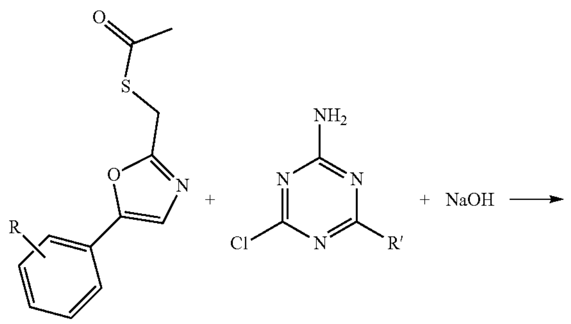

-continued

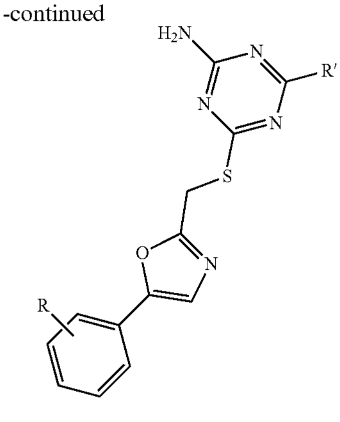

wherein R is as defined as the substituents at the phenyl group as defined in $R_2$ according to general formula (I), R' is a substituent selected from hydroxyl, amino, $C_1$-$C_5$-alkyl, $C_3$-$C_5$-cycloalkyl, $C_1$-$C_3$-alkoxy, N-mono- or N,N-di-substituted $C_1$-$C_3$-alkylamino, non-aromatic 5- to 6-membered heterocyclyl, 6-membered aryl and 5- to 6-membered heteroaryl, optionally substituted with one or more groups selected from halide, cyano and $C_1$ to $C_6$-alkyl.

The Figures show:

FIG. 1: shows preferred compounds of the invention. nM EC50, p(EC50,M) and % activation compared to AMG 837 are indicated.

FIG. 2 shows further compounds for use as GRP40 agonists and for use as medicaments, preferably for the treatment and/or prevention of T2DM. nM EC50 values, p(EC50,M) values and % activation compared to TAK-875 are indicated.

Figure 3:
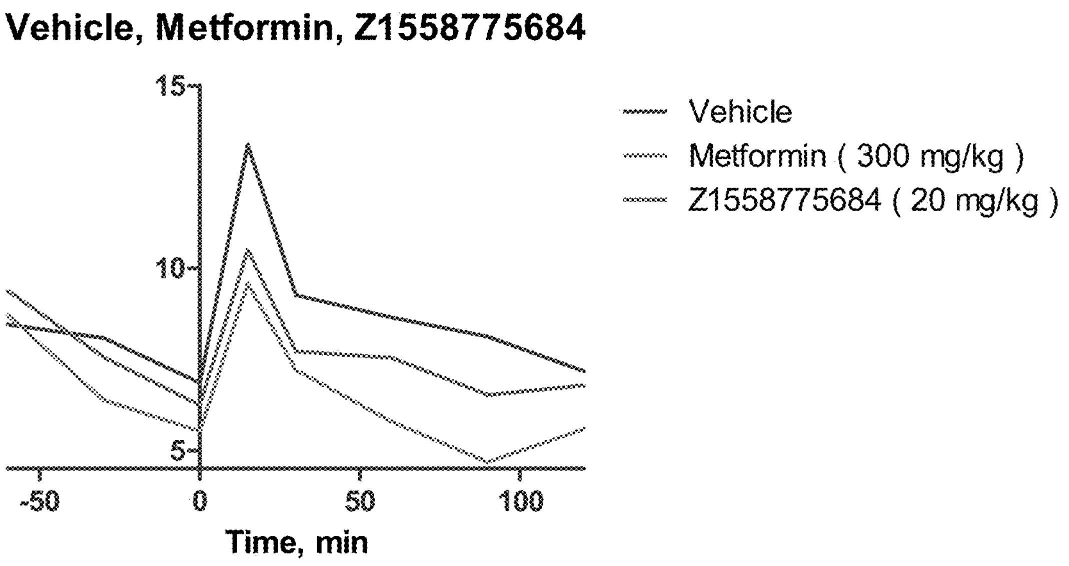
FIG. 3 shows a graphic representation of glucose levels during oral glucose tolerance test (OGTT) according to the experiment of Example 87. Values are expressed as means of 5 animals tested. For glucose tolerance test (GTT), mice were orally treated with glucose at dose of 2 g/kg at the dose volume of 10 ml/kg after a 6-hour fasting. Glucose measurements were performed immediately before compound treatment (−60 min), at −30 min, 0 min (before glucose administration), and then 15, 30, 60, 90 and 120 min after glucose administration.

FIG. 3 shows a graphic representation of glucose levels during oral glucose tolerance test (OGTT) according to the experiment of Example 87. Values are expressed as means of 5 animals tested. For glucose tolerance test (GTT), mice were orally treated with glucose at dose of 2 g/kg at the dose volume of 10 ml/kg after a 6-hour fasting. Glucose measurements were performed immediately before compound treatment (−60 min), at −30 min, 0 min (before glucose administration), and then 15, 30, 60, 90 and 120 min after glucose administration.

The present invention is further illustrated by the following non-limiting examples:

A. Synthesis of intermediate compounds:

Example 1: 2-Amino-1-(3-chloro-4-methoxyphenyl)ethanone hydrochloride

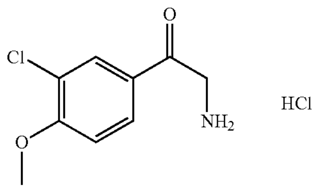

To a stirred solution of 2-bromo-1-(3-chloro-4-methoxyphenyl)ethanone (10.76 g, 40.832 mmol) in anhydrous acetonitrile (100 mL) was added sodium diformylamide (5.432 g, 57.165 mmol). The mixture was stirred at ambient temperature for 14 h. Inorganics was filtered off, and the filtrate was concentrated in vacuo. 5N Hydrochloric acid (100 mL) was added to the dark oily residue, and the resulting mixture was heated to reflux for 3 h. The hot solution was separated from dark viscous oil, and was allowed to cool down to ambient temperature. The precipitate formed was filtered and successively washed with 5N hydrochloric acid and diethyl ether affording 2-amino-1-(3-chloro-4-methoxyphenyl)ethanone hydrochloride (5.193 g, 100% purity, 54% yield) as yellow crystals. $^{1}H$ NMR (400 MHz, DMSO-$d_6$) δ 8.45 (br s, 3H), 8.07 (s, 1H), 8.02 (d, J=8.7 Hz, 1H), 7.33 (d, J=8.7 Hz, 1H), 4.55 (m, 2H), 3.98 (s, 3H). MS (Cl): m/z=200 $[M+H]^+$.

Example 2: N-(2-Oxo-2-(3-chloro-4-methoxyphenyl)ethyl) chloroacetamide

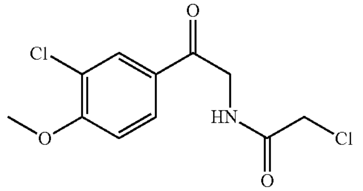 [SMILES: COc1ccc(C(=O)CNC(=O)CCl)cc1Cl]

To an ice-chilled stirred slurry of 2-amino-1-(3-chloro-4-methoxyphenyl) ethanone hydrochloride (5.193 g, 21.995 mmol) and sodium hydrocarbonate (4.065 g, 48.389 mmol) in a mixture of ethyl acetate (150 mL) and water (50 mL), chloroacetyl chloride (1.92 mL, 24.194 mmol) was added dropwise. The reaction mixture was stirred at 0-5° C. for 1 h 30 min. After the completion of the reaction, the ethyl acetate layer was separated and dried over sodium sulfate. Sodium sulfate was filtered off, and the filtrate was concentrated in vacuo affording N-(2-oxo-2-(3-chloro-4-methoxyphenyl)ethyl)chloroacetamide (2.65 g, 100% purity, 44% yield) as a pink solid. $^{1}H$ NMR (400 MHz, $CDCl_3$) δ 8.03 (d, J=2.1 Hz, 1H), 7.89 (dd, J=8.7, 2.1 Hz, 1H), 7.61 (br s, 1H), 7.00 (d, J=8.7 Hz, 1H), 4.72 (d, J=4.3 Hz, 2H), 4.13 (s, 2H), 3.99 (s, 3H). MS (Cl): m/z=276 $[M+H]^+$.

Example 3: 5-(3-Chloro-4-methoxyphenyl)-2-(chloromethyl)-1,3-oxazole

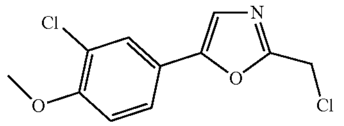 [SMILES: COc1ccc(-c2cnc(CCl)o2)cc1Cl]

A stirred slurry of N-(2-oxo-2-(3-chloro-4-methoxyphenyl)ethyl)chloroacetamide (2.568 g, 9.3 mmol) in phosphoryl chloride (11.7 mL, 125.55 mmol) was heated under reflux for 2 h. Gas evolution was observed. Then, the reaction mixture was allowed to cool down to RT, and was poured into crashed ice (200 g). The precipitate was filtered and washed with water affording 5-(3-chloro-4-methoxyphenyl)-2-(chloromethyl)-1,3-oxazole (1.984 g, 100% purity, 83% yield) as a brown solid. $^{1}H$ NMR (400 MHz, $CDCl_3$) δ 7.65 (s, 1H), 7.49 (d, J=8.5 Hz, 1H), 7.20 (s, 1H), 6.96 (d, J=8.5 Hz, 1H), 4.64 (s, 2H), 3.93 (s, 3H). MS (Cl): m/z=258 $[M+H]^+$.

Example 4: N-(2-Oxo-2-(3-trifluoromethylphenyl) ethyl)chloroacetamide

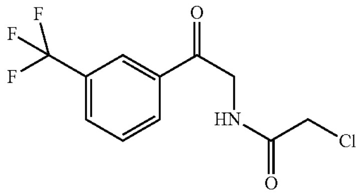 [SMILES: O=C(CCl)NCC(=O)c1cccc(C(F)(F)F)c1]

To an ice-chilled stirred slurry of 2-amino-1-(3-trifluoromethylphenyl)ethanone hydrochloride (2.55 g, 10.641 mmol) and sodium hydrocarbonate (1.967 g, 23.41 mmol) in ethyl acetate (75 mL)/water (25 mL) mixture, chloroacetyl chloride (0.93 mL, 11.705 mmol) was added dropwise. The reaction mixture was stirred at 0-5° C. for 1 h 30 min. The ethyl acetate layer was separated and dried over sodium sulfate. Sodium sulfate was filtered off, and the filtrate was concentrated in vacuo affording N-(2-oxo-2-(3-trifluoromethylphenyl)ethyl)chloroacetamide (2.691 g, 95% purity, 90% yield) as a yellow solid. $^{1}H$ NMR (500 MHz, $CDCl_3$) δ 8.26 (s, 1H), 8.18 (d, J=7.8 Hz, 1H), 7.91 (d, J=7.8 Hz, 1H), 7.70 (m, 1H), 7.61 (br s, 1H), 4.84 (d, J=3.6 Hz, 2H), 4.17 (s, 2H). MS (Cl): m/z=280 $[M+H]^+$.

Example 5: 2-(Chloromethyl)-5-[3-(trifluoromethyl) phenyl]-1,3-oxazole

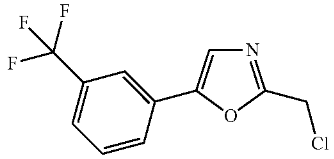 [SMILES: FC(F)(F)c1cccc(-c2cnc(CCl)o2)c1]

A stirred slurry of N-(2-oxo-2-(3-(trifluoromethylphenyl) ethyl)chloroacetamide (2.654 g, 9.49 mmol) in phosphoryl chloride (11.94 mL, 128.115 mmol) was heated to reflux for 2 h. Gas evolution was observed. Then the reaction mixture was allowed to cool down to ambient temperature, and was poured into crashed ice (200 g). The precipitate was filtered and washed with water affording 2-(chloromethyl)-5-[3-(trifluoromethyl)phenyl]-1,3-oxazole (2.308 g, 100% purity, 93% yield) as a brown solid. $^{1}H$ NMR (400 MHz, $CDCl_3$) δ 7.88 (s, 1H), 7.81 (d, J=7.5 Hz, 1H), 7.66-7.51 (m, 2H), 7.39 (s, 1H), 4.67 (d, J=2.6 Hz, 2H). MS (Cl): m/z=262 $[M+H]^+$.

Example 6: N-(2-Oxo-2-(2,3-dichlorophenyl)ethyl) chloroacetamide

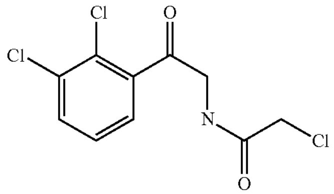 [SMILES: O=C(CCl)NCC(=O)c1cccc(Cl)c1Cl]

To an ice-chilled stirred slurry of 2-amino-1-(2,3-dichlorophenyl)ethanone hydrochloride (4.68 g, 19.458 mmol) and sodium hydrocarbonate (3.596 g, 42.808 mmol) in ethyl acetate (225 mL)/water (75 mL) mixture, chloroacetyl chloride (1.70 mL, 21.404 mmol) was added dropwise. The reaction mixture was stirred at 0-5° C. for 1 h 30 min. The ethyl acetate layer was separated and dried over sodium sulfate. Sodium sulfate was filtered off, and the filtrate was concentrated in vacuo affording N-(2-oxo-2-(2,3-dichlorophenyl)ethyl)chloroacetamide (5.0 g, 98% purity, 92% yield) as a colorless solid. $^1$H NMR (500 MHz, $CDCl_3$) δ 7.65 (dd, J=7.9, 1.6 Hz, 1H), 7.48 (dd, J=7.9, 1.6 Hz, 1H), 7.44 (br s, 1H), 7.34 (t, J=7.9 Hz, 1H), 4.70 (d, J=4.9 Hz, 2H), 4.13 (s, 2H). MS (Cl): m/z=280 $[M+H]^+$.

Example 7: 2-(Chloromethyl)-5-(2,3-dichlorophenyl)-1,3-oxazole

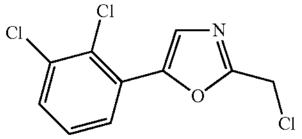 [SMILES: ClCc1ncc(-c2cccc(Cl)c2Cl)o1]

A stirred slurry of N-(2-oxo-2-(2,3-dichlorophenyl)ethyl) chloroacetamide (4.943 g, 17.62 mmol) in phosphoryl chloride (25 mL, 268.176 mmol) was heated to reflux for 2 h. Gas evolution was observed. Then the reaction mixture was allowed to cool down to ambient temperature, and was poured into crashed ice (250 g). The precipitate was filtered and washed with water affording 2-(chloromethyl)-5-(2,3-dichlorophenyl)-1,3-oxazole (4.052 g, 99% purity, 88% yield) as a brown solid. $^1$H NMR (400 MHz, $CDCl_3$) δ 7.77 (s, 1H), 7.73 (dd, J=8.0, 1.5 Hz, 1H), 7.46 (dd, J=8.0, 1.6 Hz, 1H), 7.29 (t, J=8.0 Hz, 1H), 4.67 (d, J=1.3 Hz, 2H). MS (Cl): m/z=262 $[M+H]^+$.

Example 8: 2-Amino-1-(2,5-dichlorophenyl)ethanone hydrochloride

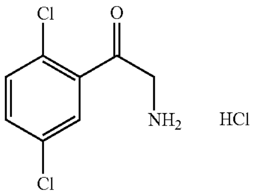 [SMILES: NCC(=O)c1cc(Cl)ccc1Cl ; Cl]

To a stirred solution of 2-bromo-1-(2,5-dichlorophenyl) ethanone (9.045 g, 33.758 mmol) in anhydrous acetonitrile (100 mL) was added sodium diformylamide (8.02 g, 84.395 mmol). The mixture was stirred at ambient temperature for 40 h. Inorganics was filtered off, and the filtrate was concentrated in vacuo. 5N hydrochloric acid (100 mL) was added to the dark oily residue, and the resulting mixture was heated to reflux for 3 h. The hot solution was separated from dark viscous oil, and was allowed to cool down to ambient temperature. The precipitate formed was filtered and successively washed with 5N hydrochloric acid and diethyl ether affording 2-amino-1-(2,5-dichlorophenyl)ethanone hydrochloride (2.973 g, 100% purity, 37% yield) as colorless crystals. $^1$H NMR (500 MHz, DMSO-$d_6$) δ 8.55 (br s, 3H), 8.05 (t, J=2.5 Hz, 1H), 7.72 (dd, J=8.8, 2.5 Hz, 1H), 7.66 (d, J=8.8 Hz, 1H), 4.52 (s, 2H). MS (Cl): m/z=204 $[M]^+$.

Example 9: N-(2-Oxo-2-(2,5-dichlorophenyl)ethyl) chloroacetamide

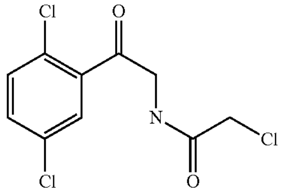 [SMILES: O=C(CCl)NCC(=O)c1cc(Cl)ccc1Cl]

To an ice-chilled stirred slurry of 2-amino-1-(2,5-dichlorophenyl)ethanone hydrochloride (2.976 g, 12.373 mmol) and sodium hydrocarbonate (2.287 g, 27.221 mmol) in ethyl acetate (150 mL)/water (50 mL) mixture, chloroacetyl chloride (1.08 mL, 13.61 mmol) was added dropwise. The reaction mixture was stirred at 0-5° C. for 1 h 30 min. The ethyl acetate layer was separated and dried over sodium sulfate. Sodium sulfate was filtered off, and the filtrate was concentrated in vacuo affording N-(2-oxo-2-(2,5-dichlorophenyl)ethyl)chloroacetamide (2.9 g, 100% purity, 84% yield) as a yellow solid. $^1$H NMR (500 MHz, $CDCl_3$) δ 7.67 (t, J=2.3 Hz, 1H), 7.44 (m, 3H), 4.74 (d, J=4.8, 2H), 4.14 (s, 2H). MS (Cl): m/z=280 $[M+H]^+$.

Example 10: 2-(Chloromethyl)-5-(2,5-dichlorophenyl)-1,3-oxazole

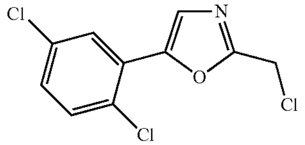 [SMILES: ClCc1ncc(-c2cc(Cl)ccc2Cl)o1]

A stirred slurry of N-(2-oxo-2-(2,5-dichlorophenyl)ethyl) chloroacetamide (2.675 g, 9.535 mmol) in phosphoryl chloride (20 mL, 214.537 mmol) was heated to reflux for 2 h. Gas evolution was observed. Then the reaction mixture was allowed to cool down to ambient temperature, and was poured into crashed ice (200 g). The precipitate was filtered and washed with water affording 2-(chloromethyl)-5-(2,5-dichlorophenyl)-1,3-oxazole (2.288 g, 100% purity, 91% yield) as a brown solid. $^1$H NMR (400 MHz $CDCl_3$) δ 7.83-7.76 (m, 2H), 7.39 (d, J=8.6 Hz, 1H), 7.26-7.20 (m, 1H), 4.67 (s, 2H). MS (Cl): m/z=262 $[M+H]^+$.

Example 11: 2-Amino-1-(4-ethylphenyl)ethanone hydrochloride

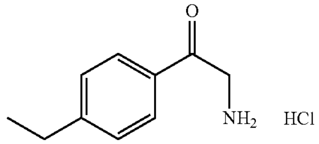

To a stirred solution of 2-bromo-1-(4-ethylphenyl)ethanone (7.95 g, 35.07 mmol) in anhydrous acetonitrile (100 mL) was added sodium diformylamide (8.317 g, 87.517 mmol). The mixture was stirred at ambient temperature for 15 h. Inorganics was filtered off, and the filtrate was concentrated in vacuo. 5N hydrochloric acid (70 mL) was added to the dark oily residue, and the resulting mixture was heated to reflux for 2.5 h. The hot solution was separated from dark viscous oil, and was allowed to cool down to ambient temperature. The reaction mixture was concentrated in vacuo, and the residue was crystallized from 5N hydrochloric acid affording 2-amino-1-(4-ethylphenyl)ethanone hydrochloride (2.848 g, 100% purity, 41% yield) as yellow crystals. 1H NMR (500 MHz, DMSO-$d_6$) δ 8.44 (br s, 3H), 7.94 (d, J=7.8 Hz, 2H), 7.43 (d, J=7.8 Hz, 2H), 4.54 (m, 2H), 2.70 (q, J=7.6 Hz, 2H), 1.20 (t, J=7.6 Hz, 3H). MS (Cl): m/z=164 $[M]^+$.

Example 12: N-(2-Oxo-2-(4-ethylphenyl)ethyl)chloroacetamide

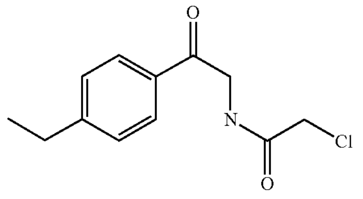

To an ice-chilled stirred slurry of 2-amino-1-(4-ethylphenyl)ethanone hydrochloride (2.848 g, 14.262 mmol) and sodium hydrocarbonate (2.636 g, 31.376 mmol) in ethyl acetate (150 mL)/water (50 mL) mixture, chloroacetyl chloride (1.25 mL, 15.688 mmol) was added dropwise. The reaction mixture was stirred at 0-5° C. for 2 h. The ethyl acetate layer was separated and dried over sodium sulfate. Sodium sulfate was filtered off, and the filtrate was concentrated in vacuo affording N-(2-oxo-2-(4-ethylphenyl)ethyl) chloroacetamide (3.091 g, 100% purity, 90% yield) as a beige solid. $^1$H NMR (500 MHz, $CDCl_3$) δ 7.92 (d, J=8.2, 2H), 7.67 (br s, 1H), 7.34 (d, J=8.2, 2H), 4.77 (d, J=3.9 Hz, 2H), 4.14 (s, 2H), 2.74 (q, J=7.7, 2H), 1.28 (t, J=7.6, 3H). MS (Cl): m/z=240 $[M+H]^+$.

Example 13: 5-(4-Ethylphenyl)-2-(chloromethyl)-1,3-oxazole

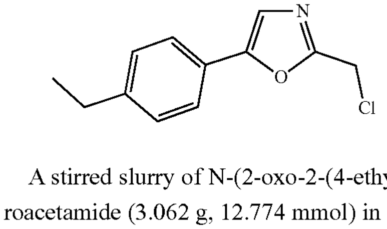

A stirred slurry of N-(2-oxo-2-(4-ethylphenyl)ethyl)chloroacetamide (3.062 g, 12.774 mmol) in phosphoryl chloride (22 mL, 236.064 mmol) was heated to reflux for 2 h. Gas evolution was observed. Then the reaction mixture was allowed to cool down to ambient temperature, and was poured into crashed ice (300 g). The precipitate was filtered and washed with water affording 5-(4-ethylphenyl)-2-(chloromethyl)-1,3-oxazole (2.513 g, 100% purity, 89% yield) as a brown solid. $^1$H NMR (400 MHz, $CDCl_3$) δ 7.55 (d, J=8.0 Hz, 2H), 7.36-7.07 (m, 3H), 4.65 (s, 2H), 2.66 (q, J=7.6 Hz, 2H), 1.24 (t, J=7.6 Hz, 3H). MS (Cl): m/z=222 [M+H]+.

Example 14: N-(2-Oxo-2-(3-ethoxyphenyl)ethyl)chloroacetamide

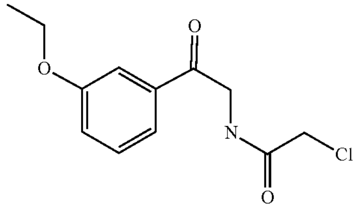

To an ice-chilled stirred slurry of 2-amino-1-(3-ethoxyphenyl)ethanone hydrochloride (2.563 g, 11.883 mmol) and sodium hydrocarbonate (2.196 g, 26.143 mmol) in ethyl acetate (150 mL)/water (50 mL) mixture, chloroacetyl chloride (1.04 mL, 13.071 mmol) was added dropwise. The reaction mixture was stirred at 0-5° C. for 2 h. The ethyl acetate layer was separated and dried over sodium sulfate. Sodium sulfate was filtered off, and the filtrate was concentrated in vacuo affording N-(2-oxo-2-(3-ethoxyphenyl) ethyl)chloroacetamide (2.79 g, 100% purity, 92% yield) as a yellow solid. $^1$H NMR (400 MHz, $CDCl_3$) δ 7.61 (br s, 1H), 7.52 (d, J=7.7 Hz, 1H), 7.46 (t, J=2.0 Hz, 1H), 7.38 (t, J=8.0 Hz, 1H), 7.14 (dd, J=8.2, 2.6 Hz, 1H), 4.75 (d, J=4.4 Hz, 2H), 4.11 (s, 2H), 4.07 (q, J=7.0 Hz, 2H), 1.42 (t, J=7.0 Hz, 3H). MS (Cl): m/z=256 [M+H]+.

Example 15: 5-(3-Ethoxyphenyl)-2-(chloromethyl)-1,3-oxazole

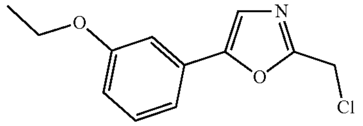 [SMILES: CCOc1cccc(-c2cnc(CCl)o2)c1]

A stirred slurry of N-(2-oxo-2-(3-ethoxyphenyl)ethyl) chloroacetamide (2.737 g, 10.704 mmol) in phosphoryl chloride (15 mL, 160.56 mmol) was heated to reflux for 2 h. Gas evolution was observed. Then the reaction mixture was allowed to cool down to ambient temperature, and was poured into crashed ice (200 g). Chloroform (150 mL) was added, and the resulting mixture was stirred for 0.25 h. The organic layer was separated and dried over sodium sulfate. Sodium sulfate was filtered off, and the filtrate was concentrated in vacuo affording 5-(3-ethoxyphenyl)-2-(chloromethyl)-1,3-oxazole (2.418 g, 100% purity, 95% yield) as a brown oil. $^1$H NMR (400 MHz, $CDCl_3$) δ 7.31 (t, J=8.0 Hz, 1H), 7.25-7.18 (m, 2H), 7.15 (t, J=2.1 Hz, 1H), 6.87 (dd, J=8.4, 2.5 Hz, 1H), 4.65 (s, 2H), 4.07 (q, J=7.0 Hz, 2H), 1.42 (t, J=7.0 Hz, 3H). MS (Cl): m/z=238 [M+H]+.

Example 16: 2-Amino-1-biphenyl-3-ylethanone hydrochloride

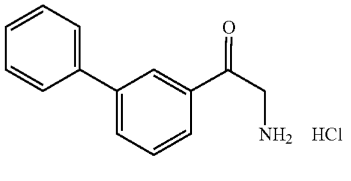 [SMILES: NCC(=O)c1cccc(-c2ccccc2)c1 ; Cl]

To a stirred solution of 1-biphenyl-3-yl-2-bromoethanone (15.287 g, 38.89 mmol) in anhydrous acetonitrile (100 mL) was added sodium diformylamide (10.163 g, 106.948 mmol). The mixture was stirred at rt for 72 h. Inorganics was filtered off, and the filtrate was concentrated in vacuo. 5N hydrochloric acid (100 mL) was added to the dark oily residue, and the resulting mixture was heated to reflux for 5 h. The hot solution was separated from dark viscous oil, and was allowed to cool down to rt. The precipitate formed was filtered and successively washed with 5N hydrochloric acid and diethyl ether affording 2-amino-1-biphenyl-3-ylethanone hydrochloride (6.35 g, 100% purity, 66% yield) as brown crystals. $^1H$ NMR (500 MHz, DMSO-$d_6$) δ 8.44 (br s, 3H), 8.25 (s, 1H), 8.07-7.96 (m, 2H), 7.78 (d, J=7.0 Hz, 2H), 7.69 (t, J=7.6 Hz, 1H), 7.52 (t, J=7.3 Hz, 2H), 7.44 (t, J=7.1 Hz, 1H), 4.74-4.65 (m, 2H). MS (CI): m/z=212 [M]+.

Example 17: N-(2-Oxo-2-biphenyl-3-ylethyl)chloroacetamide

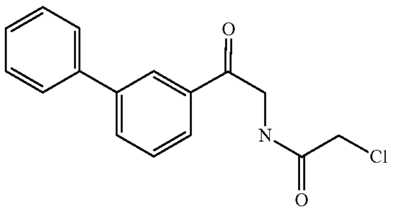

To an ice-chilled stirred slurry of 2-amino-1-biphenyl-3-ylethanone hydrochloride (6.349 g, 25.63 mmol) and sodium hydrocarbonate (4.737 g, 56.386 mmol) in ethyl acetate (150 mL)/water (50 mL) mixture, chloroacetyl chloride (2.31 mL, 28.193 mmol) was added dropwise. The reaction mixture was stirred at 0-5° C. for 2 h 15 min. The ethyl acetate layer was separated and dried over sodium sulfate. Sodium sulfate was filtered off, and the filtrate was concentrated in vacuo affording N-(2-oxo-2-biphenyl-3-ylethyl)chloroacetamide (6.858 g, 100% purity, 93% yield) as a yellow solid. $^1H$ NMR (500 MHz, $CDCl_3$) δ 8.21 (s, 1H), 7.97 (d, J=7.6 Hz, 1H), 7.88 (d, J=7.6 Hz, 1H), 7.68 (br s, 1H), 7.62 (m, 3H), 7.50 (t, J=7.5 Hz, 2H), 7.42 (t, J=7.3 Hz, 1H), 4.86 (d, J=4.4 Hz, 2H), 4.16 (s, 2H). MS (CI): m/z=288 $[M+H]^+$.

Example 18: 5-Biphenyl-3-yl-2-(chloromethyl)-1,3-oxazole

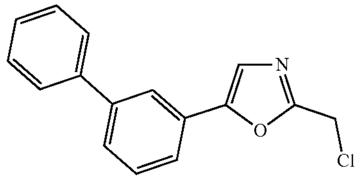 [SMILES: ClCc1ncc(-c2cccc(-c3ccccc3)c2)o1]

A stirred slurry of N-(2-oxo-2-biphenyl-3-ylethyl)chloroacetamide (6.858 g, 23.833 mmol) in phosphoryl chloride (30 mL, 321.746 mmol) was heated to reflux for 2 h. Gas evolution was observed. Then the reaction mixture was allowed to cool down to ambient temperature, and was poured into crashed ice (300 g). The precipitate was filtered and washed with water affording 5-biphenyl-3-yl-2-(chloromethyl)-1,3-oxazole as (6.092 g, 100% purity, 95% yield) a brown solid. $^1H$ NMR (500 MHz, $CDCl_3$) δ 7.88 (s, 1H), 7.68-7.62 (m, 3H), 7.60 (d, J=8.3 Hz, 1H), 7.56-7.46 (m, 3H), 7.45-7.35 (m, 2H), 4.71 (s, 2H). MS (CI): m/z=270 [M+H]+.

Example 19: 2-Amino-1-(3-dichloro-4-fluorophenyl)ethanone hydrochloride

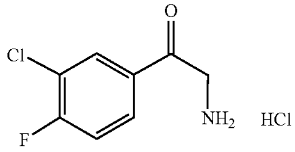 [SMILES: NCC(=O)c1ccc(F)c(Cl)c1 ; Cl]

To a stirred solution of 2-bromo-1-(3-chloro-4-fluorophenyl)ethanone (15.215 g, 27.83 mmol) in anhydrous acetonitrile (100 mL) was added sodium diformylamide (8.701 g, 91.561 mmol). The mixture was stirred at ambient temperature for 72 h. Inorganics was filtered off, and the filtrate was concentrated in vacuo. 5N hydrochloric acid (100 mL) was added to the dark oily residue, and the resulting mixture was heated to reflux for 5 h. The hot solution was separated from dark viscous oil, and was allowed to cool down to ambient temperature. The reaction mixture was concentrated in vacuo, and the residue was crystallized from 5N hydrochloric acid affording 2-amino-1-(3-dichloro-4-fluorophenyl) ethanone hydrochloride (1.683 g, 100% purity, 27% yield) as colorless crystals. $^1H$ NMR (500 MHz, DMSO-$d_6$) δ 8.41 (brs, 3H), 8.31-8.20 (m, 1H), 8.06 (ddt, J=8.8, 4.8, 2.3 Hz, 1H), 7.66 (t, J=8.8 Hz, 1H), 4.61 (s, 2H). MS (CI): m/z=188 [M]+.

Example 20: N-(2-Oxo-2-(3-chloro-4-fluorophenyl) ethyl) chloroacetamide

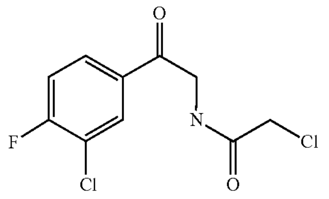

To an ice-chilled stirred slurry of 2-amino-1-(3-chloro-4-fluorophenyl)ethanone hydrochloride (1.71 g, 7.632 mmol) and sodium hydrocarbonate (1.411 g, 16.79 mmol) in ethyl acetate (150 mL)/water (50 mL) mixture, chloroacetyl chloride (0.67 mL, 8.395 mmol) was added dropwise. The reaction mixture was stirred at 0-5° C. for 1 h 30 min. The ethyl acetate layer was separated and dried over sodium sulfate. Sodium sulfate was filtered off and the filtrate was concentrated in vacuo affording N-(2-oxo-2-(3-chloro-4-fluorophenyl)ethyl)chloroacetamide (1.95 g, 100% purity, 97% yield) as a colorless solid. $^{1}$H NMR (500 MHz, $CDCl_3$) δ 8.12-8.06 (m, 1H), 7.91 (m, 1H), 7.58 (br s, 1H), 7.30 (t, J=8.8 Hz, 1H), 4.76 (d, J=4.2 Hz, 2H), 4.16 (s, 2H). MS (Cl): m/z=264 [M+H]+.

Example 21: 5-(3-Chloro-4-fluorophenyl)-2-(chloromethyl)-1,3-oxazole

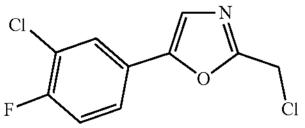 [SMILES: Fc1ccc(-c2cnc(CCl)o2)cc1Cl]

A stirred slurry of N-(2-oxo-2-(3-chloro-4-fluorophenyl) ethyl)chloroacetamide (1.946 g, 7.369 mmol) in phosphoryl chloride (16 mL, 171.698 mmol) was heated to reflux for 1.5 h. Gas evolution was observed. Then the reaction mixture was allowed to cool down to ambient temperature and was poured into crashed ice (200 g). The precipitate was filtered and washed with water affording 5-(3-chloro-4-fluorophenyl)-2-(chloromethyl)-1,3-oxazole (1.449 g, 100% purity, 80% yield) as a brown solid. $^{1}$H NMR (400 MHz, $CDCl_3$) δ 7.69 (dd, J=6.9, 2.2 Hz, 1H), 7.50 (ddd, J=8.7, 4.5, 2.2 Hz, 1H), 7.27 (s, 1H), 7.19 (t, J=8.6 Hz, 1H), 4.64 (s, 2H). MS (Cl): m/z=246 $[M+H]^+$.

Example 22: N-(2-Oxo-2-(1-naphthyl)ethyl)chloroacetamide

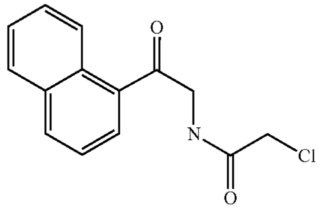

To an ice-chilled stirred slurry of 2-amino-1-(1-naphthyl) ethanone hydrochloride (7.4 g, 33.38 mmol) and sodium hydrocarbonate (6.169 g, 73.436 mmol) in ethyl acetate (300 mL)/water (100 mL) mixture, chloroacetyl chloride (2.92 mL, 36.718 mmol) was added dropwise. The reaction mixture was stirred at 0-5° C. for 1 h 30 min. The ethyl acetate layer was separated and dried over sodium sulfate. Sodium sulfate was filtered off and the filtrate was concentrated in vacuo affording N-(2-oxo-2-(1-naphthyl)ethyl)chloroacetamide (7.17 g, 100% purity, 82% yield) as a brown solid. m=7.17 g (yield 82%). $^{1}$H NMR (500 MHz, $CDCl_3$) δ 8.85 (d, J=8.7 Hz, 1H), 8.10 (d, J=8.2 Hz, 1H), 8.03 (d, J=7.3 Hz, 1H), 7.92 (d, J=8.2 Hz, 1H), 7.74 (br s, 1H), 7.67 (m, 1H), 7.63-7.53 (m, 2H), 4.87 (d, J=4.6 Hz, 2H), 4.19 (s, 2H). MS (Cl): m/z=262 $[M+H]^+$.

Example 23: 2-(Chloromethyl)-5-(1-naphthyl)-1,3-oxazole

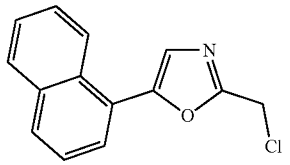 [SMILES: ClCc1ncc(-c2cccc3ccccc23)o1]

A stirred slurry of N-(2-oxo-2-(1-naphthyl)ethyl)chloroacetamide (6.744 g, 25.769 mmol) in phosphoryl chloride (35 mL, 375.454 mmol) was heated to reflux for 2 h. Gas evolution was observed. Then the reaction mixture was allowed to cool down to ambient temperature, and was poured into crashed ice (300 g). Chloroform (300 mL) was added, and the resulting mixture was stirred for 0.5 h. The organic layer was separated and dried over sodium sulfate. Sodium sulfate was filtered off, and the filtrate was concentrated in vacuo affording 2-(chloromethyl)-5-(1-naphthyl)-1,3-oxazole (6.045 g, 100% purity, 96% yield) as a black oil. $^{1}$H NMR (400 MHz, $CDCl_3$) δ 8.23 (d, J=7.8 Hz, 1H), 7.90 (m, 2H), 7.74 (dd, J=7.2, 1.2 Hz, 1H), 7.61-7.49 (m, 3H), 7.40 (s, 1H), 4.73 (s, 2H). MS (Cl): m/z=244 $[M+H]^+$.

Example 24: N-(2-Oxo-2-(2-naphthyl)ethyl)chloroacetamide

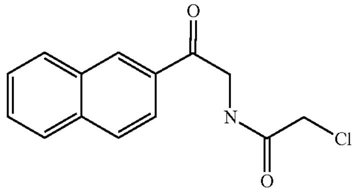

To an ice-chilled stirred slurry of 2-amino-1-(2-naphthyl) ethanone hydrochloride (2.57 g, 11.593 mmol) and sodium hydrocarbonate (2.143 g, 25.505 mmol) in ethyl acetate (150 mL)/water (50 mL) mixture, chloroacetyl chloride (1.02 mL, 12.752 mmol) was added dropwise. The reaction mixture was stirred at 0-5° C. for 1 h 30 min. The ethyl acetate layer was separated and dried over sodium sulfate. Sodium sulfate was filtered off, and the filtrate was concentrated in vacuo affording crude N-(2-oxo-2-(2-naphthyl)ethyl)chloroacetamide (2.131 g, 96% purity, 67% yield) as a brown solid. $^{1}$H NMR (500 MHz, $CDCl_3$) δ 8.53 (s, 1H), 8.04 (dd, J=8.7, 1.9 Hz, 1H), 8.00 (d, J=8.2 Hz, 1H), 7.95 (d, J=8.6 Hz, 1H), 7.91 (d, J=8.2 Hz, 1H), 7.76 (br s, 1H), 7.66 (t, J=7.5 Hz, 1H), 7.61 (t, J=7.5 Hz, 1H), 4.95 (d, J=4.3 Hz, 2H), 4.19 (s, 2H). MS (Cl): m/z=262 $[M+H]^+$.

Example 25: 2-(Chloromethyl)-5-(2-naphthyl)-1,3-oxazole

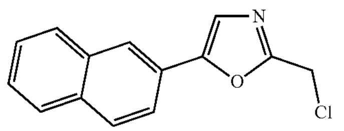 [SMILES: ClCc1ncc(-c2ccc3ccccc3c2)o1]

A stirred slurry of N-(2-oxo-2-(2-naphthyl)ethyl)chloroacetamide (2.082 g, 7.955 mmol) in phosphoryl chloride (15 mL, 160.93 mmol) was heated to reflux for 3 h. Gas evolution was observed. Then the reaction mixture was allowed to cool down to ambient temperature, and was poured into crashed ice (200 g). The mixture was allowed to warm up to ambient temperature, and was extracted with dichloromethane (3×100 mL). The dichloromethane solution was dried over sodium sulfate. Sodium sulfate was filtered off, and the filtrate was concentrated in vacuo affording crude 2-(chloromethyl)-5-(2-naphthyl)-1,3-oxazole as a brown oil. It was subjected to column chromatography on Silicagel (0.040-0.060) (ethyl acetate/hexane) affording 2-(chloromethyl)-5-(2-naphthyl)-1,3-oxazole (1.281 g, 97% purity, 66% yield) as a yellow solid. $^1H$ NMR (400 MHz, $CDCl_3$) δ 8.13 (s, 1H), 7.87 (m, 2H), 7.85-7.79 (m, 1H), 7.70 (dd, J=8.6, 1.7 Hz, 1H), 7.50 (tt, J=7.3, 3.6 Hz, 2H), 7.41 (d, J=1.3 Hz, 1H), 4.70 (d, J=1.3 Hz, 2H). MS (Cl): m/z=244 $[M+H]^+$.

Example 26: 2-Amino-1-(3-trifluoromethoxyphenyl)ethanone hydrochloride

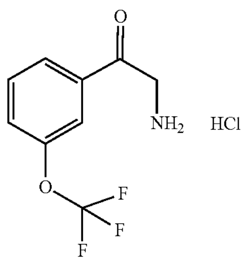 [SMILES: NCC(=O)c1cccc(OC(F)(F)F)c1 ; Cl]

To a stirred solution of 2-bromo-1-(3-trifluoromethoxyphenyl)ethanone (11.45 g, 34.384 mmol) in anhydrous ethyl acetate (100 mL) was added sodium diformylamide (8.169 g, 85.96 mmol). The mixture was stirred at ambient temperature for 96 h. Inorganics was filtered off, and the filtrate was concentrated in vacuo. 5N hydrochloric acid (100 mL) was added to the dark oily residue, and the resulting mixture was heated to reflux for 4 h. The hot solution was separated from dark viscous oil, and was allowed to cool down to 0° C. The precipitate formed was filtered and successively washed with 10N hydrochloric acid and diethyl ether affording 2-amino-1-(3-trifluoromethoxyphenyl)ethanone hydrochloride (2.785 g, 100% purity, 32% yield) as colorless crystals. $^1H$ NMR (400 MHz, DMSO-$d_6$) δ 8.49 (s, 3H), 8.06 (m, 1H), 7.94 (br s, 1H), 7.75 (m, 2H), 4.62 (s, 2H). $^{19}F$ NMR (376 MHz, DMSO-$d_6$) δ −57.34. MS (Cl): m/z=220 $[M]^+$.

Example 27: N-(2-Oxo-2-(3-trifluoromethoxyphenyl)ethyl) chloroacetamide

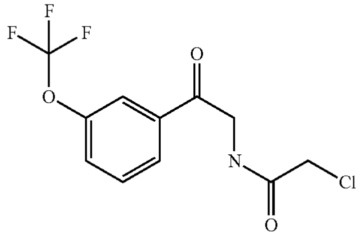

To an ice-chilled stirred slurry of 2-amino-1-(3-trifluoromethoxyphenyl)ethanone hydrochloride (2.785 g, 10.895 mmol) and sodium hydrocarbonate (2.014 g, 23.969 mmol) in ethyl acetate (150 mL)/water (50 mL) mixture, chloroacetyl chloride (0.95 mL, 11.985 mmol) was added dropwise. The reaction mixture was stirred at 0-5° C. for 1.5 h. The ethyl acetate layer was separated and dried over sodium sulfate. Sodium sulfate was filtered off, and the filtrate was concentrated in vacuo affording N-(2-oxo-2-(3-trifluoromethoxyphenyl)ethyl)chloroacetamide (3.139 g, 94% purity, 92% yield) as a yellow solid. $^1H$ NMR (500 MHz, $CDCl_3$) δ 7.96-7.89 (d, J=7.7 Hz, 1H), 7.85 (s, 1H), 7.60 (m, 2H), 7.51 (d, J=8.0 Hz, 1H), 4.81 (d, J=4.4 Hz, 2H), 4.16 (s, 2H). $^{19}F$ NMR (470 MHz, $CDCl_3$) δ −57.94. MS (Cl): m/z=296 $[M+H]^+$.

Example 28: 2-(Chloromethyl)-5-(3-trifluoromethoxyphenyl)-1,3-oxazole

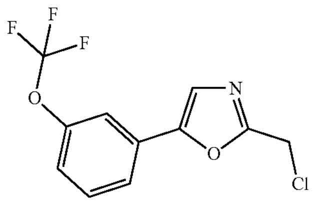 [SMILES: FC(F)(F)Oc1cccc(-c2cnc(CCl)o2)c1]

A stirred slurry of N-(2-oxo-2-(3-trifluoromethoxyphenyl)ethyl)chloroacetamide (3.139 g, 9.998 mmol) in phosphoryl chloride (22 mL, 236.027 mmol) was heated under reflux for 2 h. Gas evolution was observed. Then, the reaction mixture was allowed to cool down to ambient temperature and was poured into crashed ice (300 g). The mixture was allowed to warm up to ambient temperature and was extracted with chloroform (2×75 mL). The dichloromethane solution was dried over sodium sulfate. Sodium sulfate was filtered off and the filtrate was concentrated in vacuo affording brown oil. m=2.68 g. It was subjected to column chromatography on Silicagel (0.040-0.060) (ethyl acetate/hexane) affording 2-(chloromethyl)-5-(3-trifluoromethoxyphenyl)-1,3-oxazole (1.973 g, 100% purity, 71% yield) as a brown oil. $^1H$ NMR (400 MHz, $CDCl_3$) δ 7.57 (dt, J=7.9, 1.3 Hz, 1H), 7.48 (s, 1H), 7.45 (t, J=8.1 Hz, 1H), 7.35 (s, 1H), 7.19 (d, J=8.3 Hz, 1H), 4.66 (s, 2H). $^{19}F$ NMR (376 MHz, $CDCl_3$) δ −58.27. MS (Cl): m/z=278 $[M+H]^+$.

Example 29: 2-Amino-1-(2-chloro-5-methoxyphenyl)ethan-1-one hydrochloride

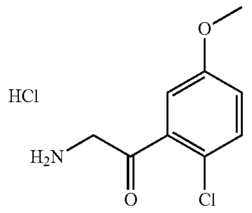

To a stirred solution of 2-bromo-1-(2-chloro-5-methoxyphenyl)ethan-1-one (3.31 g, 12.57 mmol) in anhydrous acetonitrile (70 mL) was added sodium diformylamide (2.99 g, 31.42 mmol) in one portion. The reaction mixture was stirred at ambient temperature for 60 h. The precipitate was filtered off and the filtrate was concentrated in vacuo. Then, 5N hydrochloric acid (50 mL) was added to the dark oily residue, and the resulting mixture was heated under reflux for 3.5 h. The hot solution was separated from dark viscous oil and was allowed to cool down to 0° C. The formed precipitate was filtered and washed with diethyl ether affording 2-amino-1-(2-chloro-5-methoxyphenyl)ethan-1-one hydrochloride (1.25 g, 100% purity, 42% yield) as colorless crystals. $^1H$ NMR (400 MHz, DMSO-$d_6$) δ 8.37 (br.s, 3H), 7.53 (d, J=8.9 Hz, 1H), 7.46 (d, J= 3.1 Hz, 1H), 7.23 (dd, J=8.9, 3.1 Hz, 1H), 4.53 (s, 2H), 3.83 (s, 3H). MS (Cl): m/z=200 $[M+H]^+$.

Example 30: 2-Chloro-N-[2-(2-chloro-5-methoxyphenyl)-2-oxoethyl]acetamide

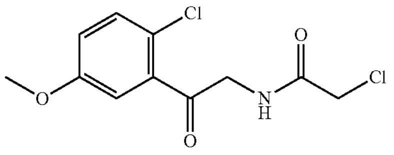 [SMILES: COc1ccc(Cl)c(C(=O)CNC(=O)CCl)c1]

To an ice-chilled stirred slurry of 2-amino-1-(2-chloro-5-methoxyphenyl)ethan-1-one hydrochloride (1.21 g, 5.11 mmol) and sodium hydrogen carbonate (945.1 mg, 11.25 mmol) in a mixture of ethyl acetate (75 mL)/water (25 mL), 2-chloroacetyl chloride (635.32 mg, 5.63 mmol, 450.0 μl) was added dropwise. The reaction mixture was stirred at 0-5° C. for 1.5 h. The ethyl acetate layer was separated and dried over sodium sulfate. Sodium sulfate was filtered off, and the filtrate was concentrated in vacuo affording 2-chloro-N-[2-(2-chloro-5-methoxyphenyl)-2-oxoethyl]acetamide (1.2 g, 100% purity, 85% yield) as a beige solid. $^1H$ NMR (500 MHz, $CDCl_3$) δ 7.52 (s, 1H), 7.37 (d, J=8.9 Hz, 1H), 7.19 (d, J=3.1 Hz, 1H), 7.02 (dd, J=8.8, 3.1 Hz, 1H), 4.77 (d, J=4.8 Hz, 2H), 4.14 (s, 2H), 3.84 (s, 3H). MS (Cl): m/z=276 $[M+H]^+$.

Example 31: 5-(2-Chloro-5-methoxyphenyl)-2-(chloromethyl)-1,3-oxazole

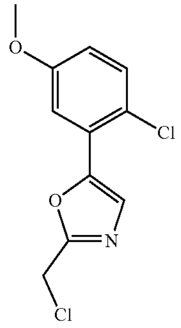 [SMILES: COc1ccc(Cl)c(-c2cnc(CCl)o2)c1]

A stirred slurry of 2-chloro-N-[2-(2-chloro-5-methoxyphenyl)-2-oxoethyl]acetamide (1.17 g, 4.24 mmol) in phosphoryl trichloride (24.63 g, 160.6 mmol, 14.97 ml) was heated under reflux for 2 h. Gas evolution was observed. Then, the reaction mixture was allowed to cool down to ambient temperature and was poured into crashed ice (250 g). The precipitate was filtered and washed with water affording 5-(2-chloro-5-methoxyphenyl)-2-(chloromethyl)-1,3-oxazole (980.0 mg, 100% purity, 90% yield) as a beige solid. $^1H$ NMR (500 MHz, $CDCl_3$) δ 7.78 (s, 1H), 7.38 (d, J=8.9 Hz, 1H), 7.34 (d, J=3.1 Hz, 1H), 6.86 (dd, J=8.9, 3.1 Hz, 1H), 4.70 (s, 2H), 3.88 (s, 3H). MS (Cl): m/z=258 $[M+H]^+$.

Example 32: 2-Amino-1-(3-chloro-5-methoxyphenyl)ethan-1-one hydrochloride

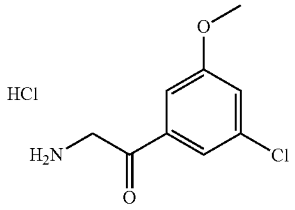

To a stirred solution of 2-bromo-1-(3-chloro-5-methoxyphenyl)ethan-1-one (2.89 g, 10.96 mmol) in anhydrous acetonitrile (56 mL) was added sodium diformylamide (4.01 g, 42.18 mmol) in one portion. The reaction mixture was stirred at rt for 66 h. The precipitate was filtered off and the filtrate was concentrated in vacuo. 5N hydrochloric acid (45 mL) was added to the dark oily residue and the resulting mixture was heated to reflux for 2.5 h. The hot solution was separated from dark viscous oil, and was allowed to cool down to 0° C. The formed precipitate was filtered and washed with diethyl ether affording 2-amino-1-(3-chloro-5-methoxyphenyl)ethan-1-one hydrochloride (1.01 g, 100% purity, 39% yield) as colorless crystals. $^1H$ NMR (400 MHz, DMSO-$d_6$) δ 8.43 (br.s, 3H), 7.62 (s, 1H), 7.47 (s, 1H), 7.41 (s, 1H), 4.60 (s, 2H), 3.86 (s, 3H). MS (Cl): m/z=200 $[M+H]^+$.

Example 33: 2-Chloro-N-[2-(3-chloro-5-methoxyphenyl)-2-oxoethyl]acetamide

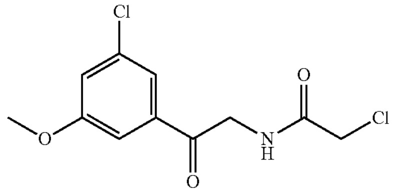 [SMILES: COc1cc(Cl)cc(C(=O)CNC(=O)CCl)c1]

To an ice-chilled stirred slurry of 2-amino-1-(3-chloro-5-methoxyphenyl)ethan-1-one hydrochloride (998.71 mg, 4.23 mmol) and sodium hydrogen carbonate (781.79 mg, 9.31 mmol) in a mixture of ethyl acetate (60 mL)/water (20 mL), 2-chloroacetyl chloride (525.47 mg, 4.65 mmol, 370.0 µl) was added dropwise. The reaction mixture was stirred at 0-5° C. for 1.5 h. The ethyl acetate layer was separated and dried over sodium sulfate. Sodium sulfate was filtered off, and the filtrate was concentrated in vacuo affording 2-chloro-N-[2-(3-chloro-5-methoxyphenyl)-2-oxoethyl]acetamide (1.05 g, 100% purity, 90% yield) as a yellow solid. $^1$H NMR (500 MHz, $CDCl_3$) δ 7.58 (br.s, 1H), 7.54 (s, 1H), 7.39 (s, 1H), 7.17 (s, 1H), 4.76 (d, J=4.2 Hz, 2H), 4.15 (s, 2H), 3.88 (s, 3H). MS (CI): m/z=276 $[M+H]^+$.

Example 34: 5-(3-Chloro-5-methoxyphenyl)-2-(chloromethyl)-1,3-oxazole

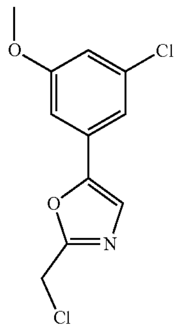 [SMILES: COc1cc(Cl)cc(-c2cnc(CCl)o2)c1]

A stirred slurry of 2-chloro-N-[2-(3-chloro-5-methoxyphenyl)-2-oxoethyl]acetamide (986.36 mg, 3.57 mmol) in phosphoryl trichloride (19.74 g, 128.74 mmol, 12.0 ml) was heated under reflux for 2.5 h. Gas evolution was observed. Then, the reaction mixture was allowed to cool down to ambient temperature and was poured into crashed ice (250 g). The precipitate was filtered and washed with water affording 5-(3-chloro-5-methoxyphenyl)-2-(chloromethyl)-1,3-oxazole (890.0 mg, 99% purity, 97% yield) as a yellow solid. $^1$H NMR (400 MHz, $CDCl_3$) δ 7.31 (s, 1H), 7.22 (s, 1H), 7.04 (s, 1H), 6.86 (s, 1H), 4.65 (s, 2H), 3.83 (s, 3H). MS (CI): m/z=258 $[M+H]^+$.

Example 35: 2-Amino-1-(2-chloro-3-methoxyphenyl)ethan-1-one hydrochloride

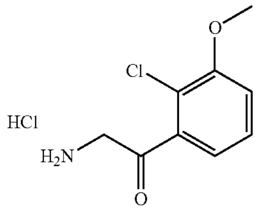

To a stirred solution of 2-bromo-1-(2-chloro-3-methoxyphenyl)ethan-1-one (6.39 g, 24.25 mmol) in anhydrous acetonitrile (70 mL) was added sodium diformylamide (5.18 g, 54.56 mmol) in one portion. The reaction mixture was stirred at ambient temperature for 48 h. The precipitate was filtered off and the filtrate was concentrated in vacuo. 5N hydrochloric acid (50 mL) was added to the dark oily residue and the resulting mixture was heated to reflux for 4 h. The hot solution was separated from dark viscous oil, and was allowed to cool down to 0° C. The formed precipitate was filtered and successively washed with 10N hydrochloric acid and diethyl ether affording 2-amino-1-(2-chloro-3-methoxyphenyl)ethan-1-one hydrochloride (1.82 g, 100% purity, 32% yield) as yellow crystals. $^1$H NMR (500 MHz, DMSO-$d_6$) δ 8.50 (s, 3H), 7.49 (t, J=7.9 Hz, 1H), 7.45-7.37 (m, 2H), 4.45 (q, J=5.5 Hz, 2H), 3.90 (s, 3H). MS (CI): m/z=200 $[M+H]^+$.

Example 36: 2-Chloro-N-[2-(2-chloro-3-methoxyphenyl)-2-oxoethyl]acetamide

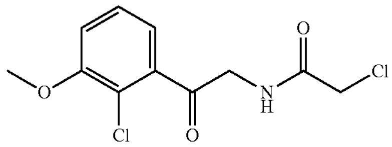 [SMILES: COc1cccc(C(=O)CNC(=O)CCl)c1Cl]

To an ice-chilled stirred slurry of 2-amino-1-(2-chloro-3-methoxyphenyl)ethan-1-one hydrochloride (1.82 g, 7.7 mmol) and sodium hydrogen carbonate (1.42 g, 16.95 mmol) in ethyl acetate (100 mL)/water (30 mL) mixture, 2-chloroacetyl chloride (957.03 mg, 8.47 mmol, 670.0 µl) was added dropwise. The reaction mixture was stirred at 0-5° C. for 1.5 h. The ethyl acetate layer was separated and dried over sodium sulfate. Sodium sulfate was filtered off and the filtrate was concentrated in vacuo affording 2-chloro-N-[2-(2-chloro-3-methoxyphenyl)-2-oxoethyl]acetamide (1.77 g, 98% purity, 81% yield) as a beige solid. $^1$H NMR (500 MHz, $CDCl_3$) δ 7.51 (br s, 1H), 7.35 (td, J=8.0, 2.3 Hz, 1H), 7.20-7.14 (m, 1H), 7.10 (dt, J=8.3, 1.9 Hz, 1H), 4.71 (s, 2H), 4.14 (s, 2H), 3.95 (s, 3H). MS (CI): m/z=276 $[M+H]^+$.

Example 37: 5-(2-Chloro-3-methoxyphenyl)-2-(chloromethyl)-1,3-oxazole

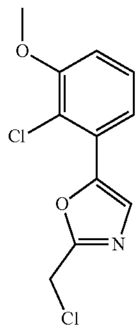 [SMILES: COc1cccc(-c2cnc(CCl)o2)c1Cl]

A stirred slurry of 2-chloro-N-[2-(2-chloro-3-methoxyphenyl)-2-oxoethyl]acetamide (1.77 g, 6.39 mmol) in phosphoryl trichloride (26.34 g, 171.76 mmol, 16.01 ml) was heated under reflux for 2 h. Gas evolution was observed. Then, the reaction mixture was allowed to cool down to ambient temperature and was poured into crashed ice (300 g). The precipitate was filtered and washed with water affording 5-(2-chloro-3-methoxyphenyl)-2-(chloromethyl)-1,3-oxazole (1.36 g, 100% purity, 83% yield) as a brown solid. $^1$H NMR (500 MHz, $CDCl_3$) δ 7.79 (s, 1H), 7.44 (d, J=8.0 Hz, 1H), 7.32 (t, J=8.0 Hz, 1H), 6.95 (d, J=8.2 Hz, 1H), 4.69 (s, 2H), 3.95 (s, 3H). MS (Cl): m/z=258 $[M+H]^+$.

Example 38: 1-[3-Chloro-4-(3-methanesulfonylpropoxy)phenyl]ethan-1-one

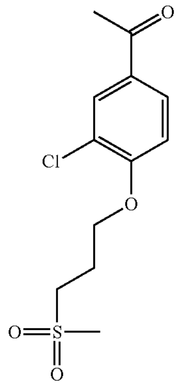 [SMILES: CC(=O)c1ccc(OCCCS(C)(=O)=O)c(Cl)c1]

To a stirred solution of 3'-chloro-4'-hydroxyacetophenone (5.5 g, 32.24 mmol) in anhydrous DMF (75 mL) were successively added 1-bromo-3-methanesulfonylpropane (7.78 g, 38.69 mmol) and anhydrous potassium carbonate (8.91 g, 64.48 mmol). The reaction mixture was heated 70° C. for 48 h. Inorganics was filtered off and the filtrate was concentrated in vacuo. The residue was dissolved in dichloromethane (200 mL) and was successively washed with water (2×200 mL), 1% aq. NaOH (200 mL) and dried over sodium sulfate. Sodium sulfate was filtered off and the filtrate was concentrated in vacuo affording 1-[3-chloro-4-(3-methanesulfonylpropoxy)phenyl]ethan-1-one (9.31 g, 98% purity, 97% yield) as a yellow solid. $^1$H NMR (400 MHz, $CDCl_3$) δ 7.98 (d, J=2.1 Hz, 1H), 7.83 (dd, J=8.6, 2.1 Hz, 1H), 6.93 (d, J=8.6 Hz, 1H), 4.25 (t, J=5.8 Hz, 2H), 3.30 (t, J=7.5 Hz, 2H), 2.96 (s, 3H), 2.54 (s, 3H), 2.43 (p, J=6.2 Hz, 2H). MS (Cl): m/z=291 $[M+H]^+$.

Example 39: 2-Bromo-1-[3-chloro-4-(3-methanesulfonylpropoxy) phenyl]ethan-1-one

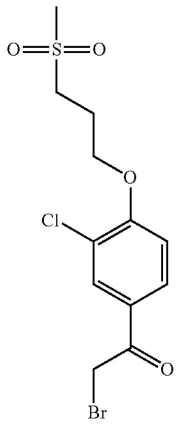 [SMILES: CS(=O)(=O)CCCOc1ccc(C(=O)CBr)cc1Cl]

To an ice-chilled solution of 1-[3-chloro-4-(3-methanesulfonylpropoxy) phenyl]ethan-1-one (9.3 g, 31.98 mmol) in anhydrous THE (200 mL) N,N,N-trimethylanilinium dibromane bromide (12.62 g, 33.58 mmol) was added portionwise. Then, the reaction mixture was allowed to warm up to ambient temperature and stirred for 18 h. The precipitate was filtered off and the filtrate was concentrated in vacuo affording crude target bromoketone as a dark solid. m=16.3 g. It was subjected to column chromatography on Silicagel (0.040-0.060) affording 2-bromo-1-[3-chloro-4-(3-methanesulfonylpropoxy) phenyl]ethan-1-one (4.33 g, 85% purity, 31% yield) as a colorless solid. It was used in the next step without further purification. $^1$H NMR (400 MHz, $CDCl_3$) δ 8.06-7.98 (m, 1H), 7.87 (d, J=8.7 Hz, 1H), 7.01-6.92 (m, 1H), 4.35 (s, 2H), 4.28 (q, J=5.9 Hz, 2H), 3.30 (t, J=7.5 Hz, 2H), 2.97 (s, 3H), 2.44 (t, J=7.3 Hz, 2H). MS (Cl): m/z=369 $[M]^+$.

Example 40: 2-Amino-1-[3-chloro-4-(3-methanesulfonylpropoxy) phenyl]ethan-1-one hydrochloride

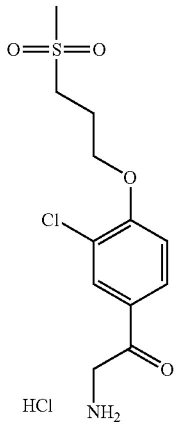 [SMILES: CS(=O)(=O)CCCOc1ccc(C(=O)CN)cc1Cl ; Cl]

To a stirred solution of 2-bromo-1-[3-chloro-4-(3-methanesulfonylpropoxy)phenyl]ethan-1-one (4.33 g, 11.71 mmol) in anhydrous acetonitrile (110 mL) was added sodium diformylamide (2.84 g, 29.86 mmol) in one portion. The reaction mixture was stirred at ambient temperature for 72 h. The precipitate was filtered off and the filtrate was concentrated in vacuo. 5N Hydrochloric acid (70 mL) was added to the dark oily residue, and the resulting mixture was heated to reflux for 5 h. The hot solution was separated from dark viscous oil and was allowed to cool down to ambient temperature. The precipitate formed was filtered and washed with diethyl ether affording 2-amino-1-[3-chloro-4-(3-methanesulfonylpropoxy)phenyl]ethan-1-one hydrochloride (2.92 g, 90% purity, 77% yield) as a yellow solid. $^1$H NMR (500 MHz, DMSO-$d_6$) δ 8.40 (br s, 3H), 8.08 (d, J=2.3 Hz, 1H), 8.00 (dq, J=7.3, 5.2, 3.8 Hz, 1H), 7.33 (dd, J=8.8, 2.0 Hz, 1H), 4.54 (s, 2H), 4.33 (t, J=6.3 Hz, 2H), 3.32-3.27 (m, 2H), 3.03 (s, 3H), 2.22 (dq, J=12.9, 6.5 Hz, 2H). MS (Cl): m/z=306 [M+H]$^+$.

Example 41: 2-Chloro-N-2-[3-chloro-4-(3-methanesulfonylpropoxy)phenyl]-2-oxoethylacetamide

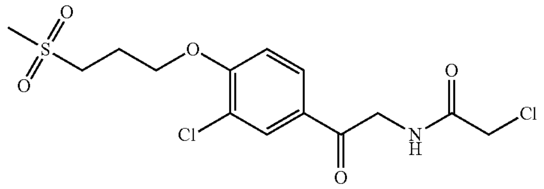 [SMILES: CS(=O)(=O)CCCOc1ccc(C(=O)CNC(=O)CCl)cc1Cl]

To an ice-chilled stirred slurry of 2-amino-1-[3-chloro-4-(3-methanesulfonylpropoxy)phenyl]ethan-1-one hydrochloride (2.9 g, 8.47 mmol) and sodium hydrogen carbonate (1.57 g, 18.64 mmol) in a mixture of ethyl acetate (120 mL)/water (40 mL), 2-chloroacetyl chloride (1.05 g, 9.32 mmol, 740.0 µl) was added dropwise. The reaction mixture was stirred at 0-5° C. for 1.5 h. The precipitate was filtered and washed with diethyl ether affording crude 2-chloro-N-2-[3-chloro-4-(3-methanesulfonylpropoxy)phenyl]-2-oxoethylacetamide (2.28 g, 83% purity, 58% yield) as a beige solid. The product was used in the next step without further purification. $^1$H NMR (400 MHz, DMSO-$d_6$) δ 8.53 (s, 1H), 8.28 (s, 1H), 8.12-7.93 (m, 1H), 7.29 (d, J=8.7 Hz, 1H), 4.64 (d, J=5.5 Hz, 2H), 4.31 (t, J=6.7 Hz, 2H), 4.19 (s, 2H), 3.27 (m, 2H), 3.03 (s, 3H), 2.23 (d, J=8.6 Hz, 2H). MS (Cl): m/z=382 [M+H]$^+$.

Example 42: 5-[3-Chloro-4-(3-methanesulfonylpropoxy)phenyl]-2-(chloromethyl)-1,3-oxazole

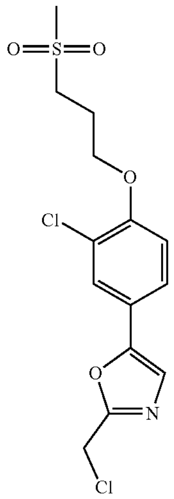 [SMILES: CS(=O)(=O)CCCOc1ccc(-c2cnc(CCl)o2)cc1Cl]

A stirred slurry of 2-chloro-N-2-[3-chloro-4-(3-methanesulfonylpropoxy)phenyl]-2-oxoethylacetamide (2.28 g, 5.96 mmol) in phosphoryl trichloride (23.03 g, 150.2 mmol, 14.0 ml) was heated to reflux for 1 h. Gas evolution was observed. Then, the reaction mixture was allowed to cool down to ambient temperature and was poured into crashed ice (250 g). Then, chloroform (200 mL) was added and the resulting mixture was stirred for 30 min. The organic layer was separated and dried over sodium sulfate. Sodium sulfate was filtered off and the filtrate was concentrated in vacuo affording 5-[3-chloro-4-(3-methanesulfonylpropoxy)phenyl]-2-(chloromethyl)-1,3-oxazole (1.64 g, 96% purity, 87% yield) as a brown solid. $^1$H NMR (500 MHz, $CDCl_3$) δ 7.69 (d, J=2.1 Hz, 1H), 7.52 (dd, J=8.6, 2.1 Hz, 1H), 7.24 (s, 1H), 6.98 (dd, J=8.6, 1.7 Hz, 1H), 4.67 (d, J=1.8 Hz, 2H), 4.25 (t, J=5.8 Hz, 2H), 3.34 (t, J=7.6 Hz, 2H), 2.99 (s, 3H), 2.44 (ddd, J=13.1, 9.5, 5.7 Hz, 2H). MS (Cl): m/z=364 [M+H]$^+$.

Example 43: 4-Methyl-6-(methylamino)pyrimidine-2-thiol

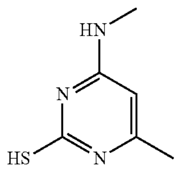

A stirred mixture of 2-chloro-N,6-dimethylpyrimidin-4-amine (5.17 g, 32.804 mmol) and thiourea (2.747 g, 36.084 mmol) in anhydrous ethanol (70 mL) was heated under reflux for 15 h. The reaction mixture was concentrated in vacuo and the residue was subjected to column chromatography affording 4-methyl-6-(methylamino)pyrimidine-2-thiol (0.45 g, 92% purity, 9% yield) as a colorless solid. 1H NMR (500 MHz, DMSO-$d_6$) δ 11.88 (s, 1H), 7.83-7.76 (m, 1H), 5.72 (s, 1H), 2.80 (d, J=3.2 Hz, 3H), 2.05 (s, 3H). MS (Cl): m/z=156 [M+H]$^+$.

Example 44: (E)-N-[Amino([5-(3-methoxyphenyl)-1,3-oxazol-2-yl]methylsulfanyl)methyl-idene]guanidine hydrochloride

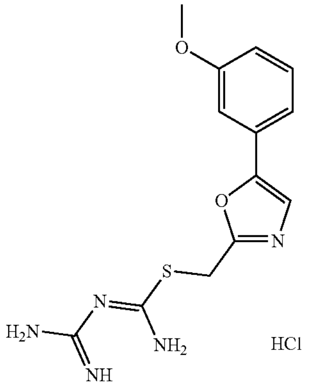 [SMILES: COc1cccc(-c2cnc(CS/C(N)=N/C(=N)N)o2)c1 ; Cl]

To a stirred solution of 2-(chloromethyl)-5-(3-methoxyphenyl)-1,3-oxazole (420.0 mg, 1.88 mmol) in anhydrous acetonitrile (4 mL) was added of 1-(diaminomethylene) thiourea (221.73 mg, 1.88 mmol). The reaction mixture was heated 60° C. for 4 h. The precipitate was filtered and successively washed with acetonitrile (2×5 mL) and acetone (3×5 mL) affording (E)-N-[amino([5-(3-methoxyphenyl)-1,3-oxazol-2 -yl]methylsulfanyl)methylidene]guanidine hydrochloride (309.0 mg, 75% purity, 40% yield) as a brown solid. It was used in the next step without further purification. $^1$H NMR (500 MHz, DMSO-$d_6$) δ 8.17 (s, 2H), 8.10-7.71 (m, 4H), 7.66 (s, 1H), 7.38 (t, J=8.0 Hz, 1H), 7.26 (d, J=8.0 Hz, 1H), 7.22 (s, 1H), 7.00-6.91 (m, 1H), 4.47 (s, 2H), 3.80 (s, 3H). MS (Cl): m/z=306 $[M+H]^+$.

Example 45: N-[Amino([5-(3-chlorophenyl)-1,3-oxazol-2-yl]methylsulfanyl)methylidene]-guanidine hydrochloride

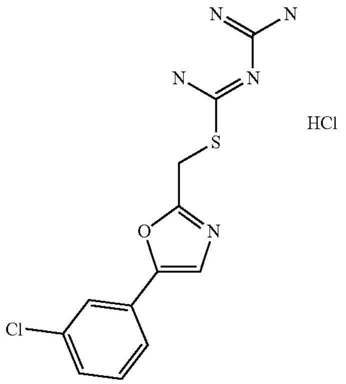 [SMILES: N=C(N)/N=C(\N)SCc1ncc(-c2cccc(Cl)c2)o1 ; Cl]

To a stirred solution of 2-(chloromethyl)-5-(3-chlorophenyl)-1,3-oxazole (3.29 g, 14.43 mmol) in anhydrous acetonitrile (100 mL) was added 1-(diaminomethylene)thiourea (1.7 g, 14.42 mmol). The reaction mixture was stirred at ambient temperature for 15 h. The precipitate was filtered off and the filtrate was concentrated in vacuo and treated with acetone (100 mL). The obtained precipitate was filtered and washed with acetone (3×50 mL) affording N-[amino([5-(3-chlorophenyl)-1,3-oxazol-2-yl]methylsulfanyl)methylidene]guanidine hydrochloride (1.93 g, 95% purity, 37% yield) as a brown solid. $^1$H NMR (500 MHz, DMSO-$d_6$) δ 8.20 (s, 2H), 8.12-7.86 (m, 4H), 7.77 (s, 2H), 7.65 (d, J=7.7 Hz, 1H), 7.51 (t, J=7.9 Hz, 1H), 7.43 (d, J=8.3 Hz, 1H), 4.48 (s, 2H). MS (Cl): m/z=310 $[M+H]^+$.

Example 46: 1-([5-(3-Chlorophenyl)-1,3-oxazol-2-yl]methylsulfanyl)ethan-1-one

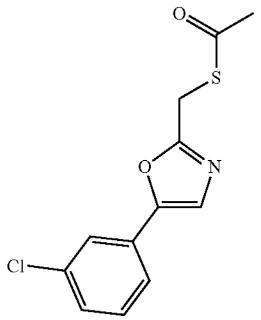 [SMILES: CC(=O)SCc1ncc(-c2cccc(Cl)c2)o1]

To a stirred solution of 2-(chloromethyl)-5-(3-chlorophenyl)-1,3-oxazole (2.11 g, 9.26 mmol) in anhydrous DMF (55 mL) was added potassium acetylsulfanide (1.16 g, 10.18 mmol). The reaction mixture was stirred at ambient temperature for 22 h. Inorganics was filtered off and the filtrate was concentrated in vacuo. The dark oily residue was dissolved in dichloromethane (150 mL) and washed with water (200 mL). The organic layer was dried over sodium sulfate. Sodium sulfate was filtered off and the filtrate was concentrated in vacuo affording 1-([5-(3-chlorophenyl)-1,3-oxazol-2-yl]methylsulfanyl)ethan-1-one (2.29 g, 100% purity, 92% yield) as a dark oil. $^1$H NMR (500 MHz, $CDCl_3$) δ 7.63-7.58 (m, 1H), 7.51-7.47 (m, 1H), 7.35 (td, J=7.9, 2.3 Hz, 1H), 7.32-7.29 (m, 1H), 7.29-7.25 (m, 1H), 4.32 (s, 2H), 2.44 (s, 3H). MS (Cl): m/z=268 $[M+H]^+$.

Example 47: 1-([5-(2-Chloro-5-methoxyphenyl)-1,3-oxazol-2-yl]methylsulfanyl)ethan-1-one

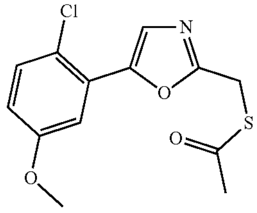 [SMILES: COc1ccc(Cl)c(-c2cnc(CSC(C)=O)o2)c1]

To a stirred solution of 5-(2-chloro-5-methoxyphenyl)-2-(chloromethyl)-1,3-oxazole (0.668 g, 2.588 mmol) in anhydrous DMF (20 mL) was added potassium acetylsulfanide (0.325 g, 2.847 mmol). The reaction mixture was stirred at ambient temperature for 40 h. Inorganics was filtered off and the filtrate was concentrated in vacuo. The dark oily residue was dissolved in dichloromethane (50 mL) and washed with water (150 mL). The organic layer was dried over sodium sulfate. Sodium sulfate was filtered off and the filtrate was concentrated in vacuo affording 1-([5-(2-chloro-5-methoxyphenyl)-1,3-oxazol-2-yl]methylsulfanyl)ethan-1-one (0.617 g, 97% purity, 80% yield) as a dark oil. $^1$H NMR (400 MHz, $CDCl_3$) δ 7.68 (s, 1H), 7.32 (d, J=8.8 Hz, 1H), 7.26 (d, J=3.0 Hz, 1H), 6.79 (dd, J=8.89, 3.0 Hz, 1H), 4.30 (s, 2H), 3.83 (s, 3H), 2.40 (s, 3H). MS (Cl): m/z=298 [M+H]$^+$.

Example 48: 1-([5-(2,5-Dichlorophenyl)-1,3-oxazol-2-yl]methylsulfanyl)ethan-1-one

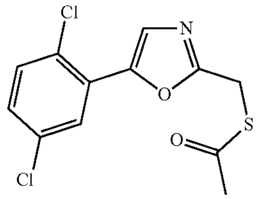 [SMILES: CC(=O)SCc1ncc(-c2cc(Cl)ccc2Cl)o1]

To a stirred solution of 2-(chloromethyl)-5-(2,5-dichlorophenyl)-1,3-oxazole (1.21 g, 4.609 mmol) in anhydrous DMF (40 mL) was added potassium acetylsulfanide (0.579 g, 5.07 mmol). The reaction mixture was stirred at ambient temperature for 40 h. Inorganics was filtered off and the filtrate was concentrated in vacuo. The dark oily residue was dissolved in dichloromethane (100 mL) and washed with water (200 mL). The organic layer was dried over sodium sulfate. Sodium sulfate was filtered off and the filtrate was concentrated in vacuo affording 1-([5-(2,5-dichlorophenyl)-1,3-oxazol-2-yl]methylsulfanyl)ethan-1-one (1.234 g, 100% purity, 89% yield) as a yellow solid. $^1$H NMR (400 MHz, $CDCl_3$) δ 7.74 (d, J=2.5 Hz, 1H), 7.71 (s, 1H), 7.37 (d, J=8.6 Hz, 1H), 7.20 (dd, J=8.6, 2.5 Hz, 1H), 4.30 (s, 2H), 2.41 (s, 3H). MS (Cl): m/z=302 [M+H]$^+$.

Example 49: 2-(Iodomethyl)-6-methylpyrimidin-4(1H)-imine

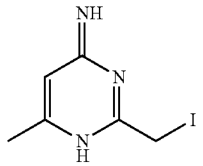

$I_2$ (19.0 g, 0.15 mmol, 1.5 equiv) and $CCl_4$ (2.0 mL) were added to the solution of 2,6-dimethylpyrimidin-4-amine (24.6 g, 0.2 mol, 2.0 equiv) in 20% aqueous solution of $H_2SO_4$ (75.0 mL). The resulting mixture was heated to reflux and 20 mL of the 20% aqueous solution of $H_2O_2$ (11.3 g, 0.1 mol, 1.0 equiv) were added dropwise monitoring that the organic phase was dark red. The resulting mixture was stirred under reflux for 2 h (until the organic phase became yellow). Then, the reaction mixture was cooled to room temperature, aqueous layer was separated and diluted with aqueous solution of NaOH to pH 11. The formed precipitate was filtered on, washed with $H_2O$ (5.0 mL) and dried in vacuo at 70° C. to obtain pure product (10.9 g, 44.0%): m/z=249.99 [M+H]$^+$.

Example 50: tert-Butyl 4-((4-amino-6-methylpyrimidin-2-yl)thio)piperidine-1-carboxylate

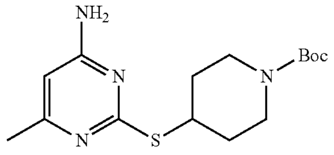 [SMILES: Cc1cc(N)nc(SC2CCN(C(=O)OC(C)(C)C)CC2)n1]

4-Amino-6-methylpyrimidine-2-thiol (1.15 g, 8.16 mmol, 1.15 equiv), NaOH (340.4 mg, 8.51 mmol, 1.2 equiv) and EtOH (20 mL) were mixed together. The resulting mixture was stirred for 10 min at room temperature followed by the dropwise addition of the solution tert-butyl 4-iodopiperidine-1-carboxylate (2.20 g, 7.09 mmol, 1.0 equiv) in hot EtOH (10 mL). Then, the reaction mixture was stirred for 3 h at 70° C. After all starting material was consumed, as was shown by LCMS, the resulting mixture was allowed to cool down to room temperature and the volatiles were removed under reduced pressure. The obtained residue was subjected to HPLC (Waters Sunfire 19·100 C18 5 mkm column and mixture of $H_2O$—$CH_3OH$ as a mobile phase) to afford pure product (1.05 g, 43.6%): m/z=325.16 [M+H]$^+$.

Example 51: 6-Methyl-2-(piperidin-4-ylthio)pyrimidin-4-amine

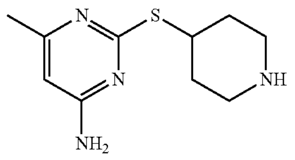

tert-Butyl 4-((4-amino-6-methylpyrimidin-2-yl)thio)piperidine-1-carboxylate (1.0 g, 3.08 mmol, 1.0 equiv) was dissolved in a 4.0 M solution of HCl in dioxane (20.0 mL). The resulting mixture was stirred overnight at room temperature. After the completion of the reaction, monitored by LCMS, the formed precipitate was filtered off, washed wit $E_2O$ (10.0 mL) and air-dried to afford pure product (822.97 mg, 90%, 2HCl): m/z=225.11 [M+H]$^+$.

B. Synthesis of Final Compounds:

Example 52: 4-([5-(2,5-Dichlorophenyl)-1,3-oxazol-2-yl]methylsulfanyl)-6-ethyl-1,3,5-triazin-2-amine (Z3397119001)

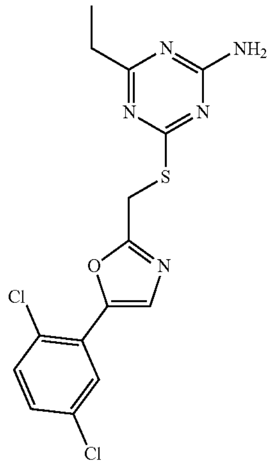 [SMILES: CCc1nc(N)nc(SCc2ncc(-c3cc(Cl)ccc3Cl)o2)n1]

To a stirred solution of 2-(chloromethyl)-5-(2,5-dichlorophenyl)-1,3-oxazole (201.22 mg, 766.48 μmol) in anhydrous DMF (5 mL) were successively added 6-amino-4-ethyl-1,2-dihydro-1,3,5-triazine-2-thione (119.73 mg, 766.48 μmol) and N,N-diisopropylethylamine (118.72 mg, 918.58 μmol, 160.0 μl). The resulting mixture was stirred at ambient temperature for 11 h. The volatiles were removed in vacuo. The oily residue was treated with water (5×25 mL) and the formed precipitate was filtered affording 4-([5-(2,5-dichlorophenyl)-1,3-oxazol-2-yl]methylsulfanyl)-6-ethyl-1,3,5-triazin-2-amine (260.0 mg, 97% purity, 86% yield) as a beige solid. $^1$H NMR (500 MHz, DMSO-$d_6$) δ 7.79 (d, J=2.6 Hz, 1H), 7.73 (d, J=2.7 Hz, 1H), 7.62 (dd, J=8.6, 2.6 Hz, 1H), 7.57-7.40 (m, 3H), 4.59 (s, 2H), 3.29-3.14 (m, 2H), 1.12 (t, J=7.6 Hz, 3H). MS (Cl): m/z=382 $[M+H]^+$.

Example 53: 2-([5-(3-Methoxyphenyl)-1,3-oxazol-2-yl]methylsulfanyl)-N,6-dimethylpyrimidin-4-amine (Z3375851526)

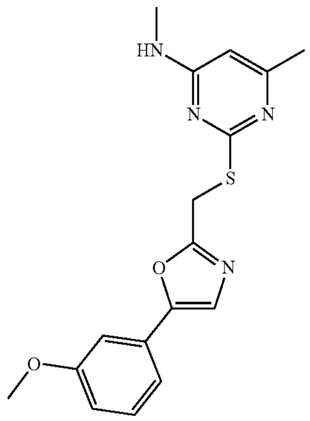

To a stirred solution of 4-methyl-6-(methylamino)pyrimidine-2-thiol (83.28 mg, 536.54 μmol) in anhydrous DMF (2 mL) were successively added 2-(chloromethyl)-5-(3-methoxyphenyl)-1,3-oxazole (100.0 mg, 447.12 μmol) and N,N-diisopropylethylamine (86.68 mg, 670.68 μmol, 120.0 μl). The resulting mixture was stirred at ambient temperature for 18 h. The precipitate was filtered off and the filtrate was concentrated in vacuo The dark oily residue was purified by HPLC (eluent MeCN/$H_2O$ 30%=>40%) affording 2-([5-(3-methoxyphenyl)-1,3-oxazol-2-yl]methylsulfanyl)-N,6-dimethylpyrimidin-4-amine (66.0 mg, 96% purity, 41% yield) as a beige solid. $^1$H NMR (400 MHz, DMSO-$d_6$) δ 7.60 (s, 1H), 7.40-7.29 (m, 2H), 7.22 (d, J=7.7 Hz, 1H), 7.17 (t, J=2.0 Hz, 1H), 6.95-6.89 (m, 1H), 6.03 (s, 1H), 4.52 (s, 2H), 3.79 (s, 3H), 2.76 (d, J=4.6 Hz, 3H), 2.13 (s, 3H). MS (Cl): m/z=343 $[M+H]^+$.

Example 54: 6-([5-(3-Chlorophenyl)-1,3-oxazol-2-yl]methylsulfanyl)-2-methylpyrimidin-4-amine (Z3402157929)

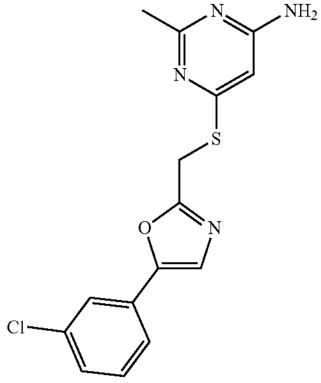 [SMILES: Cc1nc(N)cc(SCc2ncc(-c3cccc(Cl)c3)o2)n1]

To a stirred solution of 6-amino-2-methylpyrimidine-4-thiol (81.87 mg, 579.82 μmol) in anhydrous DMF (3 mL) were successively added 2-(chloromethyl)-5-(3-chlorophenyl)-1,3-oxazole (115.0 mg, 504.22 μmol) and N,N-diisopropylethylamine (97.75 mg, 756.29 μmol, 130.0 μl). The resulted mixture was stirred at ambient temperature for 15 h. The precipitate was filtered off and the filtrate was concentrated in vacuo. The dark oily residue was purified by HPLC (eluent MeCN/$H_2O$ 45%=>55%) affording 6-([5-(3-chlorophenyl)-1,3-oxazol-2-yl]methylsulfanyl)-2-methylpyrimidin-4-amine (12.0 mg, 100% purity, 7% yield) as a grey solid. $^1$H NMR (400 MHz, DMSO-$d_6$) δ 7.77-7.73 (m, 2H), 7.63 (d, J=7.7 Hz, 1H), 7.55 (br.s, 2H), 7.50 (t, J=7.9 Hz, 1H), 7.43 (d, J=8.0 Hz, 1H), 6.43 (s, 1H), 4.63 (s, 2H), 2.33 (s, 3H). MS (Cl): m/z=333 $[M+H]^+$.

Example 55: 4-([5-(2,5-Dichlorophenyl)-1,3-oxazol-2-yl]methylsulfanyl)-6-methyl-1,3,5-triazin-2-amine (Z3485538332)

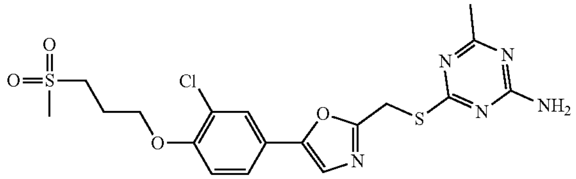

To a stirred solution of 5-[3-chloro-4-(3-methanesulfonylpropoxy)phenyl]-2-(chloromethyl)-1,3-oxazole (100 mg, 275 μmol) in anhydrous DMF (1 mL) were successively added 6-amino-4-methyl-1,2-dihydro-1,3,5-triazine-2-thione (39 mg, 275 μmol) and N,N-diisopropylethylamine (43 mg, 330 μmol). The resulting mixture was stirred at ambient temperature for 12 h. The volatiles were removed in vacuo. The oily residue was treated with water (5×10 mL), and the precipitate formed was filtered affording 4-([5-(2,5-dichlorophenyl)-1,3-oxazol-2-yl]methylsulfanyl)-6-methyl-1,3,5-triazin-2-amine (104 mg, 100% purity, 80% yield) as a beige solid. $^1$H NMR (400 MHz, DMSO-$d_6$) δ 7.76 (s, 1H), 7.63-7.47 (m, 4H), 7.25 (d, J=8.7 Hz, 1H), 4.56 (s, 2H), 4.22 (t, J=6.3 Hz, 2H), 3.30-3.18 (m, 2H), 3.03 (s, 3H), 2.30-2.09 (m, 5H). MS (Cl): m/z=470 [M+H]$^+$.

Example 56: 4-([5-(2,5-Dichlorophenyl)-1,3-oxazol-2-yl]methylsulfanyl)-6-ethyl-1,3,5-triazin-2-amine (Z3485538333)

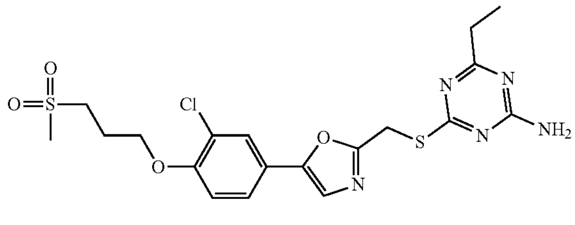 [SMILES: CCc1nc(N)nc(SCc2ncc(-c3ccc(OCCCS(C)(=O)=O)c(Cl)c3)o2)n1]

To a stirred solution of 5-[3-chloro-4-(3-methanesulfonylpropoxy)phenyl]-2-(chloromethyl)-1,3-oxazole (100 mg, 275 μmol) in anhydrous DMF (1 mL) were successively added 6-amino-4-ethyl-1,2-dihydro-1,3,5-triazine-2-thione (43 mg, 275 μmol) and N,N-diisopropylethylamine (43 mg, 330 μmol). The resulting mixture was stirred at ambient temperature for 12 h. The volatiles were removed in vacuo. The oily residue was treated with water (5×10 mL) and the precipitate formed was filtered affording 4-([5-(2,5-dichlorophenyl)-1,3-oxazol-2-yl]methylsulfanyl)-6-ethyl-1,3,5-triazin-2-amine (80 mg, 100% purity, 60% yield) as a beige solid. $^1$H NMR (400 MHz, DMSO-$d_6$) δ 7.75 (s, 1H), 7.69-7.43 (m, 4H), 7.32-7.20 (m, 1H), 4.56 (s, 2H), 4.22 (s, 2H), 3.36-3.17 (m, 4H), 3.03 (s, 3H), 2.30-2.07 (m, 2H), 1.27-0.98 (m, 3H). MS (Cl): m/z=484 [M+H]$^+$.

Example 57: 2-[({5-[3-Chloro-4-(3-methanesulfonylpropoxy)phenyl]-1,3-oxazol-2-yl}methyl)sulfanyl]-6-methylpyrimidin-4-amine (Z3485538331)

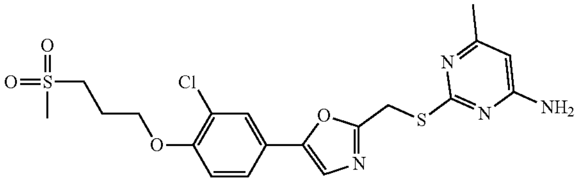 [SMILES: Cc1cc(N)nc(SCc2ncc(-c3ccc(OCCCS(C)(=O)=O)c(Cl)c3)o2)n1]

To a stirred solution of 5-[3-chloro-4-(3-methanesulfonylpropoxy)phenyl]-2-(chloromethyl)-1,3-oxazole (100 mg, 275 μmol) in anhydrous DMF (1 mL) were successively added 4-amino-6-methylpyrimidine-2-thiol (39 mg, 275 μmol) and N,N-diisopropylethylamine (43 mg, 330 μmol). The resulting mixture was stirred at ambient temperature for 12 h. The volatiles were removed in vacuo. The oily residue was treated with water (5×10 mL) and the formed precipitate was filtered affording 2-[({5-[3-chloro-4-(3-methanesulfonylpropoxy)phenyl]-1,3-oxazol-2-yl}methyl)sulfanyl]-6-methylpyrimidin-4-amine (102 mg, 100% purity, 79% yield) as a beige solid.

$^1$H NMR (400 MHz, DMSO-$d_6$) δ 7.74 (s, 1H), 7.65-7.45 (m, 2H), 7.24 (s, 1H), 7.00-6.76 (m, 2H), 6.02 (s, 1H), 4.52 (s, 2H), 4.22 (s, 2H), 3.26 (m, 2H), 3.03 (s, 3H), 2.34-1.89 (m, 5H). MS (Cl): m/z=469 [M+H]$^+$.

Example 58: 2-[({5-[3-Chloro-4-(3-methanesulfonylpropoxy)phenyl]-1,3-oxazol-2-yl}methyl)sulfanyl]-6-(trifluoromethyl)pyrimidin-4-amine (Z3485538334)

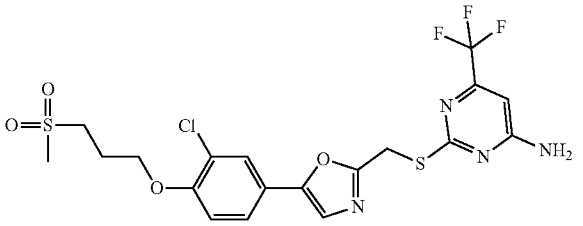 [SMILES: CS(=O)(=O)CCCOc1ccc(-c2cnc(CSc3nc(N)cc(C(F)(F)F)n3)o2)cc1Cl]

To a stirred solution of 5-[3-chloro-4-(3-methanesulfonylpropoxy)phenyl]-2-(chloromethyl)-1,3-oxazole (60 mg, 165 μmol) in anhydrous DMF (1 mL) were successively added 4-amino-6-(trifluoromethyl)pyrimidine-2-thiol (32 mg, 165 μmol) and N,N-diisopropylethylamine (26 mg, 198 μmol, 4 μl). The resulting mixture was stirred at ambient temperature for 12 h. The volatiles were removed in vacuo and the oily residue was subjected to HPLC (eluent MeCN/$H_2O$) to afford 2-[({5-[3-chloro-4-(3-methanesulfonylpropoxy)phenyl]-1,3-oxazol-2-yl}methyl)sulfanyl]-6-(trifluoromethyl)pyrimidin-4-amine (21 mg, 100% purity, 24% yield) as a solid. $^1$H NMR (400 MHz, DMSO-$d_6$) 7.70-7.78 (br.s 2H), δ 7.73 (d, J=2.2 Hz, 1H), 7.60-7.55 (m, 2H), 7.25 (d, J=8.7 Hz, 1H), 6.57 (s, 1H), 4.54 (s, 2H), 4.23 (t, J=6.3 Hz, 2H), 3.31-3.27 (m, 2H), 3.03 (s, 3H), 2.19 (t, J=7.7 Hz, 2H). MS (Cl): m/z=523 [M+H]$^+$.

Example 59: 4-Cyclopropyl-6-([5-(3-methoxyphenyl)-1,3-oxazol-2-yl]methylsulfanyl)-1,3,5-triazin-2-amine (Z3399992230)

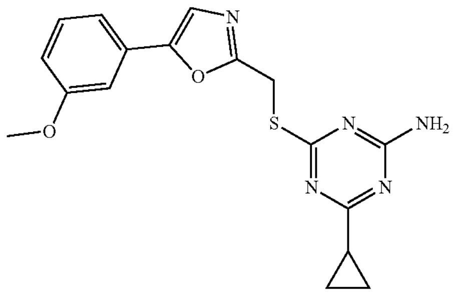 [SMILES: COc1cccc(-c2cnc(CSc3nc(N)nc(C4CC4)n3)o2)c1]

To a stirred slurry of (E)-N-[amino([5-(3-methoxyphenyl)-1,3-oxazol-2-yl]methylsulfanyl)methylidene]guanidine hydrochloride (70.0 mg, 204.79 μmol) in anhydrous THE (1 mL) were successively added cyclopropanecarbonyl chloride (29.98 mg, 286.76 μmol, 30.0 μl), triethylamine (51.82 mg, 512.08 μmol, 70.0 μl) and sodium sulfate (87.28 mg, 614.49 μmol). The reaction mixture was stirred 45 min at ambient temperature and then was heated 55° C. for 5.5 h. The precipitate was filtered off and the filtrate was concentrated in vacuo. The dark oily residue was purified by HPLC (eluent MeCN/$_{H2O}$ $_{30}$%=>45%) affording 4-cyclopropyl-6-([5-(3-methoxyphenyl)-1,3-oxazol-2-yl]methylsulfanyl)-1,3,5-triazin-2-amine (11.0 mg, 100% purity, 15% yield) as a yellow oil. $^1$H NMR (400 MHz, $CDCl_3$) δ 7.29 (t, J=8.0 Hz, 1H), 7.23 (s, 1H), 7.17 (d, J=7.7 Hz, 1H), 7.10 (t, J=2.1 Hz, 1H), 6.84 (dd, J=8.4, 2.6 Hz, 1H), 5.32 (s, 2H), 4.47 (s, 2H), 3.82 (s, 3H), 1.84 (tt, J=8.4, 4.6 Hz, 1H), 1.13 (dt, J=6.6, 3.4 Hz, 2H), 0.97 (dq, J=7.3, 3.8 Hz, 2H). MS (CI): m/z=356 $[M+H]^+$.

Example 60: 4-([5-(3-Chlorophenyl)-1,3-oxazol-2-yl]methylsulfanyl)-6-(trifluoromethyl)-1,3,5-triazin-2-amine (Z3400108327)

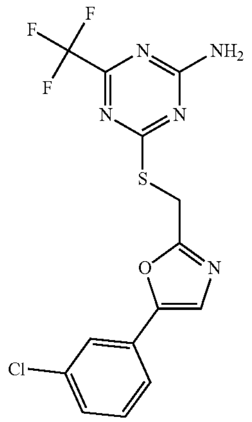 [SMILES: Nc1nc(SCc2ncc(-c3cccc(Cl)c3)o2)nc(C(F)(F)F)n1]

To a stirred slurry of N-[amino([5-(3-chlorophenyl)-1,3-oxazol-2-yl]methylsulfanyl)methylidene]guanidine hydrochloride (83.0 mg, 239.72 μmol) in anhydrous THE (1 mL) were successively added trifluoroacetyl 2,2,2-trifluoroacetate (51.38 mg, 244.63 μmol, 30.0 μl), triethylamine (92.22 mg, 911.37 μmol, 130.0 μl) and sodium sulfate (102.2 mg, 719.5 μmol). The reaction mixture was stirred 10 min at ambient temperature, and then was heated 50° C. for 6.5 h. The precipitate was filtered off and the filtrate was concentrated in vacuo. The dark oily residue was purified by HPLC (eluent MeCN/$H_2O$ 30%=>40%) affording 4-([5-(3-chlorophenyl)-1,3-oxazol-2-yl]methylsulfanyl)-6-(trifluoromethyl)-1,3,5-triazin-2-amine (2.38 mg, 95% purity, 2% yield) as a grey solid. $^1$H NMR (400 MHz, DMSO-$d_6$) δ 8.44 (s, 1H), 8.35 (s, 1H), 7.75 (d, J=2.0 Hz, 2H), 7.63 (dt, J=7.8, 1.4 Hz, 1H), 7.49 (t, J=7.9 Hz, 1H), 7.45-7.38 (m, 1H), 4.63 (s, 2H). MS (CI): m/z=388 $[M+H]^+$.

Example 61: 4-([5-(3-Chlorophenyl)-1,3-oxazol-2-yl]methylsulfanyl)-6-(fluoromethyl)-1,3,5-triazin-2-amine (Z3481547512)

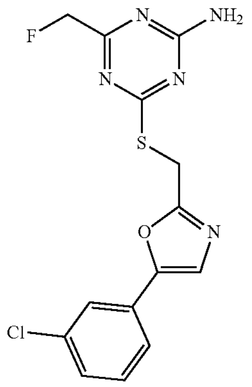 [SMILES: Nc1nc(CF)nc(SCc2ncc(-c3cccc(Cl)c3)o2)n1]

To a stirred under argon solution of 1-([5-(3-chlorophenyl)-1,3-oxazol-2-yl]methylsulfanyl)ethan-1-one (364 mg, 1360 μmol) in DMSO (3 mL) were successively added 4-chloro-6-(fluoromethyl)-1,3,5-triazin-2-amine (221 mg, 1360 μmol) and a solution of potassium hydroxide (114 mg, 2040 μmol) in water (0.3 mL). The mixture was stirred at ambient temperature for 16 h. The precipitate was filtered off, and the filtrate was subjected to HPLC (eluent MeCN/$H_2O$ 40%=>50%) affording 4-([5-(3-chlorophenyl)-1,3-oxazol-2-yl]methylsulfanyl)-6-(fluoromethyl)-1,3,5-triazin-2-amine (21 mg, 100% purity, 4% yield) as a brown solid. $^1$H NMR (400 MHz, DMSO-$d_6$) δ 7.90 (s, 1H), 7.80 (s, 1H), 7.75 (s, 1H), 7.74 (s, 1H), 7.63 (d, J=7.7 Hz, 1H), 7.49 (t, J=7.9 Hz, 1H), 7.42 (d, J=8.1 Hz, 1H), 5.18 (d, J=46.5 Hz, 2H), 4.60 (s, 2H). MS (CI): m/z=352 $[M+H]^+$.

Example 62: 4-([5-(3-Chlorophenyl)-1,3-oxazol-2-yl]methylsulfanyl)-6-(difluoromethyl)-1,3,5-triazin-2-amine (Z3400108328)

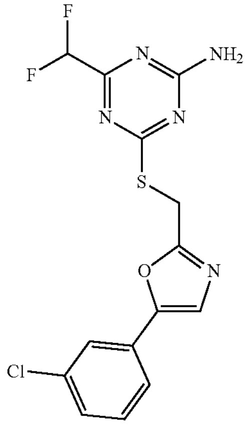 [SMILES: Nc1nc(SCc2ncc(-c3cccc(Cl)c3)o2)nc(C(F)F)n1]

To a stirred under argon solution of 1-([5-(3-chlorophenyl)-1,3-oxazol-2-yl]methylsulfanyl)ethan-1-one (142.35 mg, 531.67 μmol) in DMSO (1 mL) were successively added 4-chloro-6-(difluoromethyl)-1,3,5-triazin-2-amine (96.0 mg, 531.73 μmol) and a solution of potassium hydroxide (44.74 mg, 797.51 μmol) in water (0.1 mL). The mixture was stirred at ambient temperature for 16 h. The precipitate was filtered off and the filtrate was subjected to HPLC (eluent MeCN/$H_2O$ 40%=>50%) affording 4-([5-(3-chlorophenyl)-1,3-oxazol-2-yl]methylsulfanyl)-6-(difluoromethyl)-1,3,5-triazin-2-amine (21.7 mg, 100% purity, 11% yield) as a brown solid. $^1H$ NMR (400 MHz, DMSO-$d_6$) δ 8.19 (s, 1H), 8.10 (s, 1H), 7.78-7.72 (m, 2H), 7.63 (d, J=7.8 Hz, 1H), 7.49 (t, J=7.8 Hz, 1H), 7.42 (d, J=8.0 Hz, 1H), 6.56 (t, J=53.7 Hz, 1H), 4.62 (s, 2H). MS (Cl): m/z=370 $[M+H]^+$.

Example 63: 4-([5-(3-Chlorophenyl)-1,3-oxazol-2-yl]methylsulfanyl)-6-(4-methylpiperazin-1-yl)-1,3,5-triazin-2-amine (Z3400108321)

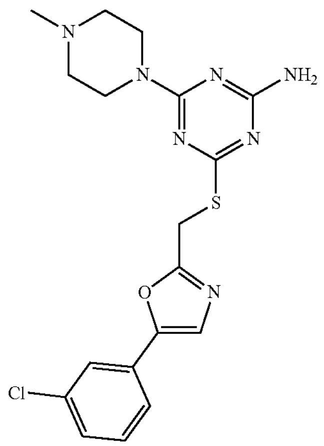 [SMILES: CN1CCN(c2nc(N)nc(SCc3ncc(-c4cccc(Cl)c4)o3)n2)CC1]

To a stirred under argon solution of 1-([5-(3-chlorophenyl)-1,3-oxazol-2-yl]methylsulfanyl)ethan-1-one (107.0 mg, 399.65 μmol) in DMSO (1 mL) were successively added 4-chloro-6-(4-methylpiperazin-1-yl)-1,3,5-triazin-2-amine (91.38 mg, 399.6 μmol) and a solution of potassium hydroxide (33.63 mg, 599.4 μmol) in water (0.1 mL). The mixture was stirred at ambient temperature for 12 h. The precipitate was filtered off and the filtrate was subjected to HPLC (eluent MeCN/$H_2O$ 30%=>50%) affording 4-([5-(3-chlorophenyl)-1,3-oxazol-2-yl]methylsulfanyl)-6-(4-methylpiperazin-1-yl)-1,3,5-triazin-2-amine (34.9 mg, 100% purity, 21% yield) as a colorless solid. $^1H$ NMR (400 MHz, DMSO-$d_6$) δ 7.72 (s, 2H), 7.62 (d, J=7.8 Hz, 1H), 7.49 (t, J=7.9 Hz, 1H), 7.42 (d, J=8.1 Hz, 1H), 6.92 (br.s, 2H), 4.46 (s, 2H), 3.75-3.58 (m, 4H), 2.32-2.14 (m, 4H), 2.12 (s, 3H). MS (Cl): m/z=418 $[M+H]^+$.

Example 64: 2-[4-Amino-6-([5-(3-chlorophenyl)-1,3-oxazol-2-yl]methylsulfanyl)-1,3,5-triazin-2-yl]aminoethan-1-ol (Z3446839933)

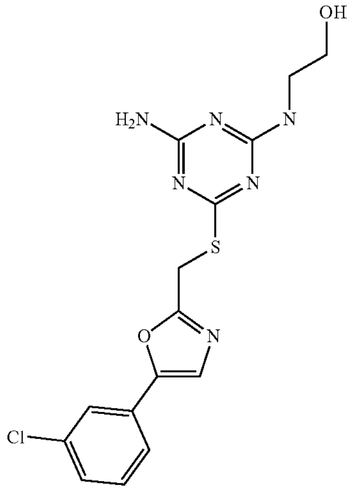 [SMILES: Nc1nc(NCCO)nc(SCc2ncc(-c3cccc(Cl)c3)o2)n1]

To a stirred under argon solution of 1-([5-(3-chlorophenyl)-1,3-oxazol-2-yl]methylsulfanyl)ethan-1-one (100.0 mg, 373.51 μmol) in DMSO (1 mL) were successively added 2-[(4-amino-6-chloro-1,3,5-triazin-2-yl)amino]ethan-1-ol (70.57 mg, 372.19 μmol) and a solution of potassium hydroxide (31.32 mg, 558.29 μmol) in water (0.1 mL). The mixture was stirred at ambient temperature for 12 h. The precipitate was filtered off, and the filtrate was subjected to HPLC (eluent MeCN/$H_2O$ 30%=>45%) affording 2-[4-amino-6-([5-(3-chlorophenyl)-1,3-oxazol-2-yl]methylsulfanyl)-1,3,5-triazin-2-yl]aminoethan-1-ol (18.4 mg, 100% purity, 13% yield) as a colorless solid. $^1H$ NMR (400 MHz, DMSO-$d_6$) δ 7.75 (s, 1H), 7.73 (s, 1H), 7.63 (d, J=7.7 Hz, 1H), 7.49 (t, J=7.8 Hz, 1H), 7.42 (d, J=7.8 Hz, 1H), 7.24-7.04 (m, 1H), 6.93 (s, 1H), 6.75 (s, 1H), 4.67-4.57 (m, 1H), 4.55 (s, 1H), 4.51 (s, 1H), 3.51-3.39 (m, 2H), 3.30-3.21 (m, 2H). MS (Cl): m/z=379 $[M+H]^+$.

Example 65: 4-([5-(3-Chlorophenyl)-1,3-oxazol-2-yl]methylsulfanyl)-6-(morpholin-4-yl)-1,3,5-triazin-2-amine (Z3400108313)

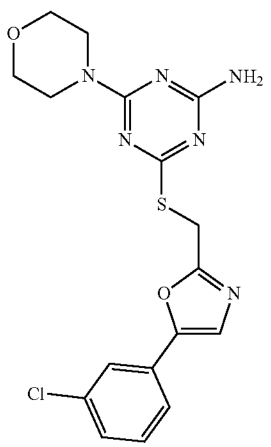 [SMILES: Nc1nc(SCc2ncc(-c3cccc(Cl)c3)o2)nc(N2CCOCC2)n1]

To a stirred under argon solution of 1-([5-(3-chlorophenyl)-1,3-oxazol-2-yl]methylsulfanyl)ethan-1-one (100.0 mg, 373.51 μmol) in DMSO (1 mL) were successively added 4-chloro-6-(morpholin-4-yl)-1,3,5-triazin-2-amine (80.53 mg, 373.45 μmol) and a solution of potassium hydroxide (31.43 mg, 560.17 μmol) in water (0.1 mL). The mixture was stirred at ambient temperature for 12 h. The precipitate was filtered off, and the filtrate was subjected to HPLC (eluent MeCN/$H_2O$ 30%=>50%) affording 4-([5-(3-chlorophenyl)-1,3-oxazol-2-yl]methylsulfanyl)-6-(morpholin-4-yl)-1,3,5-triazin-2-amine (25.2 mg, 100% purity, 17% yield) as a colorless solid. $^1$H NMR (400 MHz, DMSO-$d_6$) δ 7.73 (s, 2H), 7.62 (d, J=7.8 Hz, 1H), 7.50 (t, J=7.9 Hz, 1H), 7.42 (d, J=8.2 Hz, 1H), 6.97 (br s, 2H), 4.47 (s, 2H), 3.63 (s, 4H), 3.57-3.39 (m, 4H). MS (Cl): m/z=405 $[M+H]^+$.

Example 66: 4-([5-(3-Chlorophenyl)-1,3-oxazol-2-yl]methylsulfanyl)-6-methoxy-1,3,5-triazin-2-amine (Z3400108307)

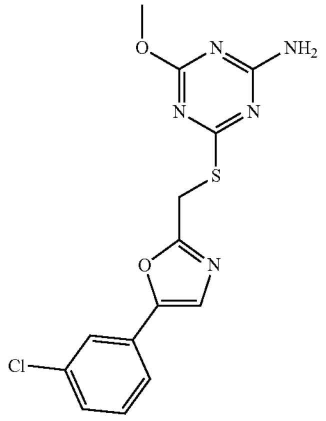 [SMILES: COc1nc(N)nc(SCc2ncc(-c3cccc(Cl)c3)o2)n1]

To a stirred under argon solution of 1-([5-(3-chlorophenyl)-1,3-oxazol-2-yl]methylsulfanyl)ethan-1-one (278.6 mg, 1.04 mmol) in methanol (2 mL) was added a solution of potassium hydroxide (80.0 mg, 1.43 mmol) in water (1 mL). The mixture was stirred at rt for 1.5 h. Then a solution of 4-chloro-6-methoxy-1,3,5-triazin-2-amine (173.0 mg, 1.08 mmol) in DMSO (4 mL) was added via a syringe. The resulted mixture was stirred at ambient temperature for additional 12 h. The precipitate was filtered off and washed with methanol, and the filtrate was concentrated in vacuo. The dark oily residue was subjected to HPLC (eluent MeCN/$H_2O$ 30%=>45%) affording 4-([5-(3-chlorophenyl)-1,3-oxazol-2-yl]methylsulfanyl)-6-methoxy-1,3,5-triazin-2-amine (103.0 mg, 100% purity, 28% yield) as a colorless solid. $^1$H NMR (400 MHz, DMSO-$d_6$) δ 7.78-7.69 (m, 2H), 7.62 (dt, J=7.8, 1.4 Hz, 1H), 7.57 (s, 2H), 7.49 (t, J=7.9 Hz, 1H), 7.41 (dt, J=7.9, 1.6 Hz, 1H), 4.57 (s, 2H), 3.81 (s, 3H). MS (Cl): m/z=350 $[M+H]^+$.

Example 67: 6-({[5-(2,5-Dichlorophenyl)-1,3-oxazol-2-yl]methyl}thio)-N,N-dimethyl-1,3,5-triazine-2,4-diamine (Z3485538342)

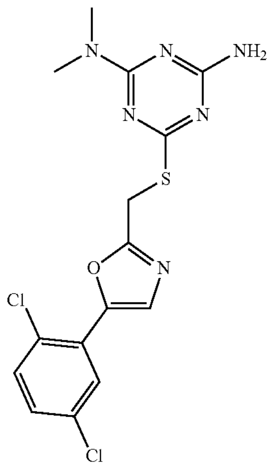 [SMILES: CN(C)c1nc(N)nc(SCc2ncc(-c3cc(Cl)ccc3Cl)o2)n1]

To a stirred under argon solution of 1-([5-(2,5-dichlorophenyl)-1,3-oxazol-2-yl]methylsulfanyl)ethan-1-one (100.0 mg, 331 μmol) in DMSO (1 mL) were successively added 6-chloro-$N^2$,$N^2$-dimethyl-1,3,5-triazine-2,4-diamine (57 mg, 331 μmol) and a solution of potassium hydroxide (28 mg, 496 μmol) in water (0.1 mL). The mixture was stirred at ambient temperature for 12 h. The precipitate was filtered off and the filtrate was subjected to HPLC (eluent MeCN/$H_2O$) affording 6-({[5-(2,5-dichlorophenyl)-1,3-oxazol-2-yl]methyl}thio)-N,N-dimethyl-1,3,5-triazine-2,4-diamine (24 mg, 97% purity, 18% yield) as a solid. $^1$H NMR (400 MHz, $CDCl_3$) δ 7.72 (s, 2H), 7.36 (d, J=8.6 Hz, 1H), 7.19 (dd, J=8.7, 2.5 Hz, 1H), 4.90 (br.s, 2H), 4.48 (s, 2H), 3.15 (s, 3H), 3.07 (s, 3H). MS (Cl): m/z=397 $[M+H]^+$.

Example 68: 4-([5-(2,5-Dichlorophenyl)-1,3-oxazol-2-yl]methylsulfanyl)-6-(morpholin-4-yl)-1,3,5-triazin-2-amine (Z3485538340)

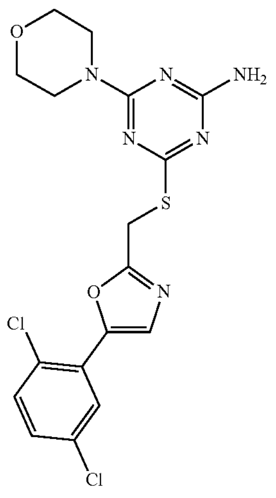 [SMILES: Nc1nc(SCc2ncc(-c3cc(Cl)ccc3Cl)o2)nc(N2CCOCC2)n1]

To a stirred under argon solution of 1-([5-(2,5-dichlorophenyl)-1,3-oxazol-2-yl]methylsulfanyl)ethan-1-one (100.0 mg, 331 μmol) in DMSO (1 mL) were successively added 4-chloro-6-(morpholin-4-yl)-1,3,5-triazin-2-amine (71 mg, 331 μmol) and a solution of potassium hydroxide (28 mg, 496 μmol) in water (0.1 mL). The mixture was stirred at ambient temperature for 12 h. The precipitate was filtered off, and the filtrate was subjected to HPLC (eluent MeCN/$H_2O$) affording 4-([5-(2,5-dichlorophenyl)-1,3-oxazol-2-yl]methylsulfanyl)-6-(morpholin-4-yl)-1,3,5-triazin-2-amine (11 mg, 100% purity, 8% yield) as a solid. $^1$H NMR (400 MHz, $CDCl_3$) δ 7.71 (s, 2H), 7.36 (d, J=8.8 Hz, 1H), 7.19 (d, J=9.2 Hz, 1H), 4.95 (s, 2H), 4.43 (s, 2H), 3.76 (s, 4H), 3.64 (s, 4H). MS (Cl): m/z=439 [M+H]$^+$.

Example 69: 4-([5-(2,5-Dichlorophenyl)-1,3-oxazol-2-yl]methylsulfanyl)-6-(4-methylpiperazin-1-yl)-1,3,5-triazin-2-amine (Z3485538341)

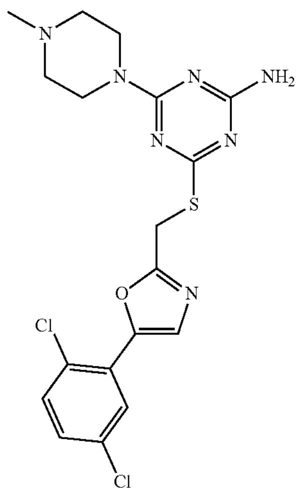 [SMILES: CN1CCN(c2nc(N)nc(SCc3ncc(-c4cc(Cl)ccc4Cl)o3)n2)CC1]

To a stirred under argon solution of 1-([5-(2,5-dichlorophenyl)-1,3-oxazol-2-yl]methylsulfanyl)ethan-1-one (100.0 mg, 331 μmol) in DMSO (1 mL) were successively added 4-chloro-6-(4-methylpiperazin-1-yl)-1,3,5-triazin-2-amine (76 mg, 331 μmol) and a solution of potassium hydroxide (28 mg, 496 μmol) in water (0.1 mL). The mixture was stirred at ambient temperature for 12 h. The precipitate was filtered off, and the filtrate was subjected to HPLC (eluent MeCN/$H_2O$) affording 4-([5-(2,5-dichlorophenyl)-1,3-oxazol-2-yl]methylsulfanyl)-6-(4-methylpiperazin-1-yl)-1,3,5-triazin-2-amine (5 mg, 100% purity, 3% yield) as a solid. $^1$H NMR (400 MHz, $CDCl_3$) δ 7.73-7.68 (m, 2H), 7.36 (d, J=8.5 Hz, 1H), 7.19 (dd, J=8.5, 2.5 Hz, 1H), 4.96 (s, 2H), 4.43 (s, 2H), 3.97-3.76 (m, 4H), 2.56-2.43 (m, 4H), 2.37 (s, 3H). MS (Cl): m/z=452 [M+H]$^+$.

Example 70: 4-([5-(2,5-Dichlorophenyl)-1,3-oxazol-2-yl]methylsulfanyl)-6-(difluoromethyl)-1,3,5-triazin-2-amine (Z3485538343)

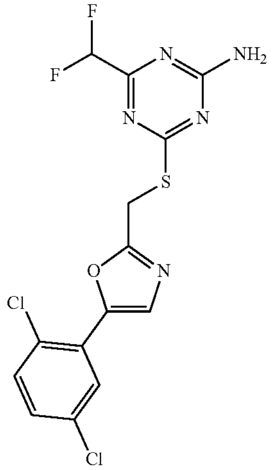 [SMILES: Nc1nc(SCc2ncc(-c3cc(Cl)ccc3Cl)o2)nc(C(F)F)n1]

To a stirred under argon solution of 1-([5-(2,5-dichlorophenyl)-1,3-oxazol-2-yl]methylsulfanyl)ethan-1-one (100.0 mg, 331 μmol) in DMSO (1 mL) were successively added 4-chloro-6-(difluoromethyl)-1,3,5-triazin-2-amine (57 mg, 331 μmol) and a solution of potassium hydroxide (28 mg, 496 μmol) in water (0.1 mL). The mixture was stirred at ambient temperature for 12 h. The precipitate was filtered off and the filtrate was subjected to HPLC (eluent MeCN/$H_2O$) affording 4-([5-(2,5-dichlorophenyl)-1,3-oxazol-2-yl]methylsulfanyl)-6-(difluoromethyl)-1,3,5-triazin-2-amine (17 mg, 95% purity, 13% yield) as a solid. $^1$H NMR (400 MHz, $CDCl_3$) δ 7.72 (s, 2H), 7.37 (d, J=8.5 Hz, 1H), 7.21 (dd, J=9.1, 2.4 Hz, 1H), 6.24 (t, J=54.3 Hz, 1H), 5.67 (br s, 2H), 4.54 (s, 2H). MS (Cl): m/z=404 [M+H]$^+$.

Example 71: 4-([5-(2,5-Dichlorophenyl)-1,3-oxazol-2-yl]methylsulfanyl)-6-(fluoromethyl)-1,3,5-triazin-2-amine (Z3485538344)

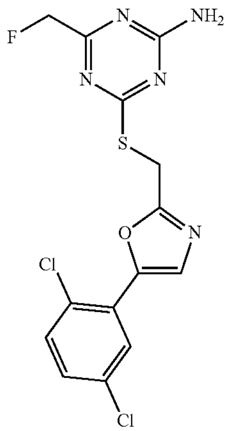 [SMILES: Nc1nc(CF)nc(SCc2ncc(-c3cc(Cl)ccc3Cl)o2)n1]

To a stirred under argon solution of 1-([5-(2,5-dichlorophenyl)-1,3-oxazol-2-yl]methylsulfanyl)ethan-1-one (100.0 mg, 331 μmol) in DMSO (1 mL) were successively added 4-chloro-6-(fluoromethyl)-1,3,5-triazin-2-amine (54 mg, 331 μmol) and a solution of potassium hydroxide (28 mg, 496 μmol) in water (0.1 mL). The mixture was stirred at ambient temperature for 12 h. The precipitate was filtered off, and the filtrate was subjected to HPLC (eluent MeCN/$H_2O$) affording 4-([5-(2,5-dichlorophenyl)-1,3-oxazol-2-yl]methylsulfanyl)-6-(fluoromethyl)-1,3,5-triazin-2-amine (21 mg, 100% purity, 16% yield) as a solid. $^1H$ NMR (400 MHz, $CDCl_3$) δ 7.72 (s, 2H), 7.37 (d, J=8.6 Hz, 1H), 7.20 (dd, J=8.3, 2.3 Hz, 1H), 6.00 (br s, 1H), 5.61 (br s, 1H), 5.20 (d, J=46.7 Hz, 2H), 4.53 (s, 2H). MS (Cl): m/z=386 $[M+H]^+$.

Example 72: 4-({[5-(2-Chloro-5-methoxyphenyl)-1,3-oxazol-2-yl]methyl}sulfanyl)-6-(fluoromethyl)-1,3,5-triazin-2-amine (Z3485538337)

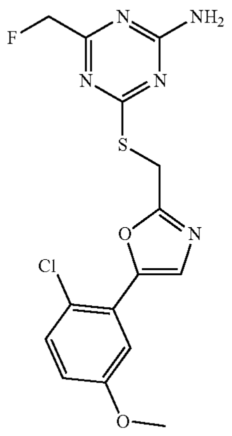 [SMILES: COc1ccc(Cl)c(-c2cnc(CSc3nc(N)nc(CF)n3)o2)c1]

To a stirred under argon solution of 1-([5-(2-chloro-5-methoxyphenyl)-1,3-oxazol-2-yl]methylsulfanyl)ethan-1-one (121.0 mg, 406 μmol) in DMSO (1.2 mL) were successively added 4-chloro-6-(fluoromethyl)-1,3,5-triazin-2-amine (66 mg, 406 μmol) and a solution of potassium hydroxide (34 mg, 609 μmol) in water (0.12 mL). The mixture was stirred at ambient temperature for 12 h. The precipitate was filtered off, and the filtrate was subjected to HPLC (eluent MeCN/$H_2O$) affording 4-({[5-(2-chloro-5-methoxyphenyl)-1,3-oxazol-2-yl]methyl}sulfanyl)-6-(fluoromethyl)-1,3,5-triazin-2-amine (27 mg, 100% purity, 17% yield) as a solid. $^1H$ NMR (400 MHz, $CDCl_3$) δ 7.69 (s, 1H), 7.33 (d, J=8.7 Hz, 1H), 7.24 (s, 1H), 6.79 (dd, J=8.9, 3.2 Hz, 1H), 5.52 (br s, 2H), 5.19 (d, J=46.6 Hz, 2H), 4.54 (s, 2H), 3.82 (s, 3H). MS (Cl): m/z=382 $[M+H]^+$.

Example 73: 4-({[5-(2-Chloro-5-methoxyphenyl)-1,3-oxazol-2-yl]methyl}sulfanyl)-6-(4-methylpiperazin-1-yl)-1,3,5-triazin-2-amine (Z3485538338)

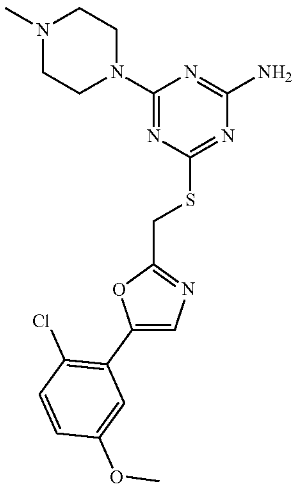 [SMILES: COc1ccc(Cl)c(-c2cnc(CSc3nc(N)nc(N4CCN(C)CC4)n3)o2)c1]

To a stirred under argon solution of 1-([5-(2-chloro-5-methoxyphenyl)-1,3-oxazol-2-yl]methylsulfanyl)ethan-1-one (242.0 mg, 812 μmol) in DMSO (2.4 mL) were successively added 4-chloro-6-(4-methylpiperazin-1-yl)-1,3,5-triazin-2-amine (186 mg, 812 μmol) and a solution of potassium hydroxide (68 mg, 1218 μmol) in water (0.25 mL). The mixture was stirred at ambient temperature for 12 h. The precipitate was filtered off, and the filtrate was subjected to HPLC (eluent MeCN/$H_2O$) affording 4-({[5-(2-chloro-5-methoxyphenyl)-1,3-oxazol-2-yl]methyl}sulfanyl)-6-(4-methylpiperazin-1-yl)-1,3,5-triazin-2-amine (24 mg, 95% purity, 7% yield) as a solid. $^1H$ NMR (400 MHz, $CDCl_3$) δ 7.68 (s, 1H), 7.32 (d, J=8.9 Hz, 1H), 7.23 (m, 1H), 7.65 (dd, J=8.5, 2.5 Hz, 1H), 4.87 (s, 2H), 4.44 (s, 2H), 3.81 (s, 3H), 3.46-3.59 (m, 4H), 2.35-2.31 (m, 4H), 2.27 (s, 3H). MS (Cl): m/z=248 $[M+H]^+$.

Example 74: 4-({[5-(2-Chloro-5-methoxyphenyl)-1,3-oxazol-2-yl]methyl}sulfanyl)-6-(morpholin-4-yl)-1,3,5-triazin-2-amine (Z3485538336)

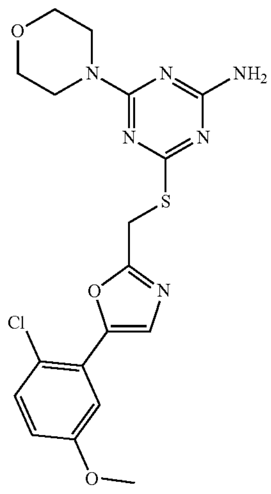 [SMILES: COc1ccc(Cl)c(-c2cnc(CSc3nc(N)nc(N4CCOCC4)n3)o2)c1]

To a stirred under argon solution of 1-([5-(2-chloro-5-methoxyphenyl)-1,3-oxazol-2-yl]methylsulfanyl)ethan-1-one (121.0 mg, 406 μmol) in DMSO (1.2 mL) were successively added 4-chloro-6-(morpholin-4-yl)-1,3,5-triazin-2-amine (88 mg, 406 μmol) and a solution of potassium hydroxide (34 mg, 609 μmol) in water (0.12 mL). The mixture was stirred at ambient temperature for 12 h. The precipitate was filtered off, and the filtrate was subjected to HPLC (eluent MeCN/$H_2O$) affording 4-({[5-(2-chloro-5-methoxyphenyl)-1,3-oxazol-2-yl]methyl}sulfanyl)-6-(morpholin-4-yl)-1,3,5-triazin-2-amine (30 mg, 100% purity, 17% yield) as a solid. $^1$H NMR (400 MHz, $CDCl_3$) δ 7.67 (s, 1H), 7.32 (d, J=8.9 Hz, 1H), 7.23 (s, 1H), 6.78 (dd, J=8.9, 3.1 Hz, 1H), 4.96 (s, 2H), 4.43 (s, 2H), 3.81 (s, 3H), 3.79-3.68 (m, 4H), 3.68-3.52 (m, 4H). MS (Cl): m/z=435 $[M+H]^+$.

Example 75: 4-({[5-(2-Chloro-5-methoxyphenyl)-1,3-oxazol-2-yl]methyl}sulfanyl)-6-(difluoromethyl)-1,3,5-triazin-2-amine (Z3485538339)

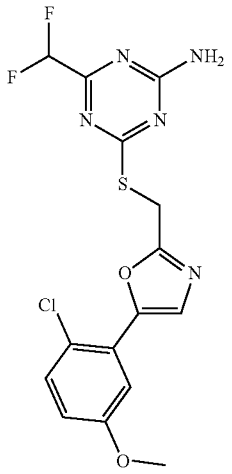 [SMILES: COc1ccc(Cl)c(-c2cnc(CSc3nc(N)nc(C(F)F)n3)o2)c1]

To a stirred under argon solution of 1-([5-(2-chloro-5-methoxyphenyl)-1,3-oxazol-2-yl]methylsulfanyl)ethan-1-one (121.0 mg, 406 μmol) in DMSO (1.2 mL) were successively added 4-chloro-6-(difluoromethyl)-1,3,5-triazin-2-amine (73 mg, 406 μmol) and a solution of potassium hydroxide (34 mg, 609 μmol) in water (0.12 mL). The mixture was stirred at ambient temperature for 12 h. The precipitate was filtered off, and the filtrate was subjected to HPLC (eluent MeCN/$H_2O$) affording 4-({[5-(2-chloro-5-methoxyphenyl)-1,3-oxazol-2-yl]methyl}sulfanyl)-6-(difluoromethyl)-1,3,5-triazin-2-amine (24 mg, 100% purity, 15% yield) as a solid. $^1$H NMR (400 MHz, $CDCl_3$) δ 7.69 (s, 1H), 7.33 (d, J=9.1 Hz, 1H), 7.24-7.23 (m, 1H), 6.80 (dd, J=8.3, 2.3 Hz, 1H), 6.23 (t, J=54.1 Hz, 1H), 5.61 (br s, 2H), 4.56 (s, 2H), 3.81 (s, 3H). MS (Cl): m/z=400 $[M+H]^+$.

Example 76: 6-Methyl-2-((2-(3-(p-tolyl)-1,2,4-oxadiazol-5-yl)ethyl)thio)pyrimidin-4(1H)-imine (Z3214047394)

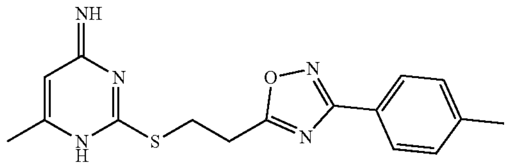

4-Imino-6-methyl-1,4-dihydropyrimidine-2-thiol (28.59 mg, 0.203 mmol, 1.15 equiv), NaOH (8.48 mg, 0.212 mmol, 1.2 equiv) and EtOH (5 mL) were mixed together. The resulting mixture was stirred for 10 min at room temperature followed by the dropwise addition of the solution of 5-(2-chloroethyl)-3-(p-tolyl)-1,2,4-oxadiazole (39.3 mg, 0.176 mmol, 1.0 equiv) in hot EtOH (3 mL). Then, the reaction mixture was stirred for 3 h at 70° C. After all starting material was consumed, as was shown by LCMS, the resulting mixture was allowed to cool down to room temperature and the volatiles were removed under reduced pressure. The obtained residue was subjected to HPLC (Waters Sunfire 19·100 C18 5 mkm column and mixture of $H_2O$—$CH_3OH$ as a mobile phase) to afford pure product (36.2 mg, 24.0%): m/z=290 $[M+H]^+$.

Following the above procedure all compounds of the series were obtained. The molar ratio of the reagents and reaction conditions were kept the same in each reaction of the series. ~~The exact amounts of the reagents and the yields of the products are in the attached Excel file.~~

Example 77: 6-Methyl-2-((3-phenyl-1,2,4-oxadiazol-5-yl)methoxy)pyrimidin-4-amine (Z3214047395)

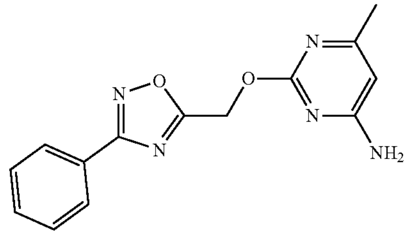 [SMILES: Cc1cc(N)nc(OCc2nc(-c3ccccc3)no2)n1]

DMF (3.0 mL), NaH (88.8 mg, 3.7 mmol, 1.05 equiv) and (3-phenyl-1,2,4-oxadiazol-5-yl)methanol (650.0 mg, 3.7 mmol, 1.05 equiv) were mixed together in a round-bottom flask. After the completion of gas evolution, 2-chloro-6-methylpyrimidin-4-amine (500.0 mg, 3.5 mmol, 1.0 equiv) was added and the resulting mixture was stirred at room temperature overnight. Then, the reaction mixture was diluted with a mixture of EtOAc (30.0 mL) and $H_2O$ (50.0 mL). The organic phase was separated, dried over $Na_2SO_4$, filtered off and concentrated under reduced pressure. The residue was purified using HPLC (Waters Sunfire 19·100 C18 5 mkm column and mixture of $H_2O$—$CH_3OH$ as a mobile phase) to obtain pure product (180.6 mg, 18.23%): m/z=284.20 $[M+H]^+$.

Example 78: 2-(((3-(4-Ethylphenyl)-1,2,4-oxadiazol-5-yl)thio)methyl)-6-methylpyrimidin-4-amine (Z3214047396)

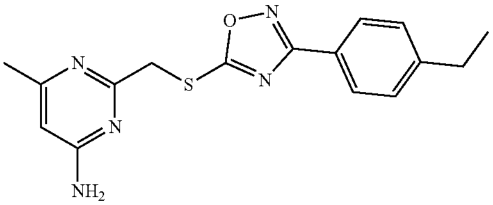 [SMILES: CCc1ccc(-c2noc(SCc3nc(C)cc(N)n3)n2)cc1]

3-(4-Ethylphenyl)-1,2,4-oxadiazole-5-thiol (466.7 mg, 2.26 mmol, 1.15 equiv), NaOH (94 mg, 2.36 mmol, 1.2 equiv) and EtOH (20 mL) were mixed together. The resulting mixture was stirred for 10 min at room temperature followed by the dropwise addition of the solution 2-(iodomethyl)-6-methylpyrimidin-4(1H)-imine (492.3 mg, 1.97 mmol, 1.0 equiv) in hot EtOH (10 mL). Then, the reaction mixture was stirred for 3 h at 70° C. After all starting material was consumed, as was shown by LCMS, the resulting mixture was allowed to cool down to room temperature and the volatiles were removed under reduced pressure. The obtained residue was subjected to HPLC (Waters Sunfire 19·100 C18 5 mkm column and mixture of $H_2O$—$CH_3OH$ as a mobile phase) to afford pure product (174.5 mg, 23.6%): m/z=328.20 $[M+H]^+$.

Example 79: 2-((1-((3-(Benzo[d][1,3]dioxol-5-yl)-1,2,4-oxadiazol-5-yl)methyl)piperidin-4-yl)thio)-6-methylpyrimidin-4-amine (Z3214047397)

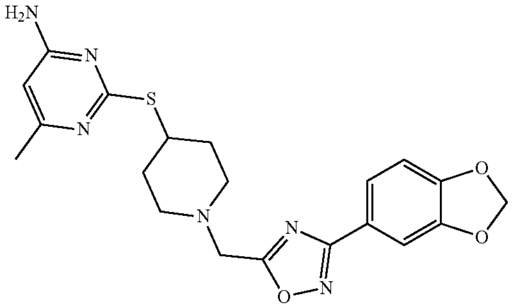 [SMILES: Cc1cc(N)nc(SC2CCN(Cc3nc(-c4ccc5c(c4)OCO5)no3)CC2)n1]

TEA (1.56 g, 15.4 mmol, 5.5 equiv) and 3-(benzo[d][1,3]dioxol-5-yl)-5-(chloromethyl)-1,2,4-oxadiazole (667.4 mg, 2.8 mmol, 1.0 equiv) were added to the solution of 26-methyl-2-(piperidin-4-ylthio)pyrimidin-4-amine (831.9 g, 2.8 mmol, 1.0 equiv, 2HCl) in DMF (10.0 mL). The resulting mixture was stirred at 40° C. for 16 h. After LCMS showed full conversion of starting material, the reaction mixture was allowed to cool down to room temperature and diluted with a mixture of EtOAc (80.0 mL) and $H_2O$ (100.0 mL). The organic phase was separated, dried over $Na_2SO_4$, filtered off and concentrated in vacuo. The obtained solid was subjected to HPLC (Waters Sunfire 19·100 C18 5 mkm column and mixture of $H_2O$—$CH_3OH$ as a mobile phase) to afford pure product (174.5 mg, 14.62%): m/z=427.20 $[M+H]^+$.

Parallel Syntheses:

Example 80: 2-(((5-(3-Chloro-4-methoxyphenyl)oxazol-2-yl)methyl)thio)-6-methylpyrimidin-4(3H)-one (Z3325085942)

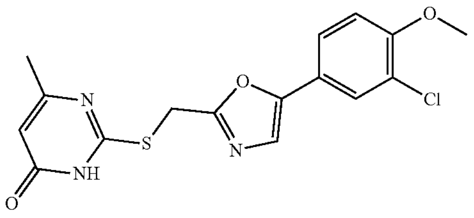 [SMILES: COc1ccc(-c2cnc(CSc3nc(C)cc(=O)[nH]3)o2)cc1Cl]

5-(3-Chloro-4-methoxyphenyl)-2-(chloromethyl)oxazole (72.61 mg, 0.282 mmol, 1.0 equiv) and 2-mercapto-6-methylpyrimidin-4(3H)-one (40.0 mg, 0.282 mmol, 1.0 equiv) were mixed together in anhydrous DMF (1.5 mL). The resulting mixture was stirred for 5 min followed by the addition of DIPEA (43.63 mg, 0.337 mmol, 2.0 equiv). Then, the reaction mixture was heated 90° C. in sealed vial for 12 h. After the completion of the reaction, monitored by LCMS, the volatiles were removed under reduced pressure. The residue was subjected to HPLC (Waters Sunfire 19·100 C18 5 mkm column and mixture of $H_2O$—$CH_3OH$ as a mobile phase) to afford pure product (57.7 mg, 56.37% yield):): m/z=364.00 $[M+H]^+$.

Example 81: 4-(((5-(3-Chlorophenyl)oxazol-2-yl)methyl)thio)-6-(thiophen-3-yl)-1,3,5-triazin-2-amine (Z3400108331)

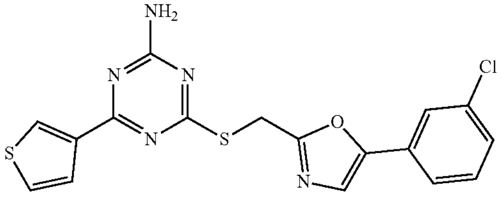 [SMILES: Nc1nc(SCc2ncc(-c3cccc(Cl)c3)o2)nc(-c2ccsc2)n1]

DIPEA (51.70 mg, 04 mmol, 2.0 equiv) was added to a stirred slurry of N-[amino({[5-(3-chlorophenyl)-1,3-oxazol-2-yl]methyl}sulfanyl)methylidene]guanidine (69.25 mg, 0.2 mmol, 1.0 equiv, HCl) and thiophene-3-carbonyl chloride (29.3 mg, 0.2 mmol, 1.0 equiv) in anhydrous THE (1.5 mL). The reaction mixture was heated 70° C. in sealed vial for 12 h. After all starting material was consumed, as was shown by LCMS, the solvent was removed in vacuo. The obtained solid was dissolved in DMSO (1.0 mL) and filtered off. The filtrate was subjected to HPLC (Waters Sunfire 19·100 C18 5 mkm column and mixture of $H_2O$—$CH_3OH$ as a mobile phase) to afford pure product (6.4 mg, 7.18% yield): m/z=402.00 $[M+H]^+$.

Example 82: 2-((5-(p-Tolyl)-1,3,4-oxadiazol-2-yl)thio)benzo[d]oxazole (Z642432840)

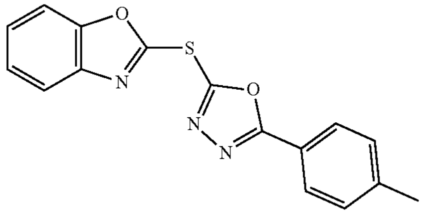 [SMILES: Cc1ccc(-c2nnc(Sc3nc4ccccc4o3)o2)cc1]

5-(p-Tolyl)-1,3,4-oxadiazole-2-thiol (372.0 mg, 1.93 mmol, 1.0 equiv), DMSO (0.5 mL) and TEA (235.0 mg, 2.32 mmol, 1.2 equiv) were mixed together in an 8 mL vessel. The resulting mixture was stirred for 20 min followed by the addition of 2-chlorobenzo[d]oxazole (297.0 mg, 1.93 mmol, 1.0 equiv). The resulting mixture was stirred at 100° C. for 9 h. After the completion of the reaction, monitored by LCMS, the resulting suspension was filtered off and the obtained filtrate was subjected to HPLC (Waters Sunfire 19·100 C18 5 mkm column and mixture of $H_2O$—$CH_3OH$ as a mobile phase) to afford pure product (34.0 mg, 6.80%): m/z=310.00 $[M+H]^+$.

Example 83: 6-(((5-(4-Methoxyphenyl)oxazol-2-yl)methyl)thio)-1,3,5-triazine-2,4-diamine (Z855788832)

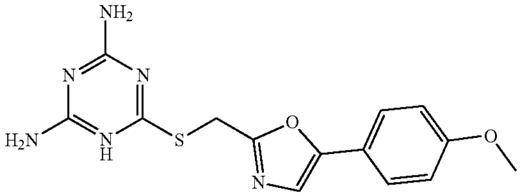 [SMILES: COc1ccc(-c2cnc(CSc3nc(N)nc(N)n3)o2)cc1]

4,6-Diamino-1,3,5-triazine-2-thiol (45.0 mg, 0.314 mmol, 1.0 equiv), DMSO (0.5 mL) and 2-(chloromethyl)-5-(4-methoxyphenyl)oxazole (70.3 mg, 0.314 mmol, 1.0 equiv) were mixed together and stirred for 20 min at room temperature. Then, the 4.0 M solution of KOH (91.7 mg, 1.63 mmol, 5.2 equiv) was added and the reaction mixture was stirred at 100° C. for 8 h. The obtained mixture was placed in autoclave and $CO_2$ was blown in. The resulting mixture was stirred for 6 h in the autoclave. After the completion of the reaction, the reaction mixture was filtered off and the obtained filtrate was subjected to HPLC (Waters Sunfire 19·100 C18 5 mkm column and mixture of $H_2O$—$CH_3OH$ as a mobile phase) to afford pure product (17.1 mg, 17.1%): m/z=331.00 $[M+H]^+$.

Example 84: 3-(Benzo[d][1,3]dioxol-5-yl)-5-(((1-methyl-1H-benzo[d]imidazol-2-yl)thio)methyl)-1,2,4-oxadiazole (Z1029491270)

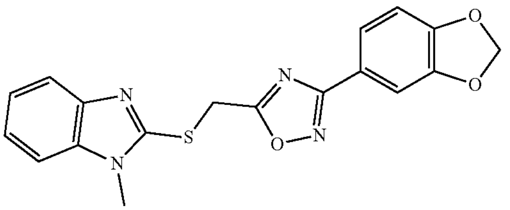 [SMILES: Cn1c(SCc2nc(-c3ccc4c(c3)OCO4)no2)nc2ccccc21]

DIPEA (61.7 mg, 0.477 mmol, 3.5 equiv) was added to the solution of 1-methyl-1H-benzo[d]imidazole-2-thiol (22.4 mg, 0.136 mmol, 1.0 equiv) and 3-(benzo[d][1,3]dioxol-5-yl)-5-(chloromethyl)-1,2,4-oxadiazole (39.1 mg, 0.163 mmol, 1.2 equiv) in DMF (1.0 mL). The resulting mixture was stirred at 90° C. overnight. After the completion of the reaction, monitored by LCMS, the reaction mixture was concentrated under reduced pressure. The residue was dissolved in DMSO (1.0 mL) and filtered off. The filtrate was subjected to HPLC (Waters Sunfire 19·100 C18 5 mkm column and mixture of $H_2O$—$CH_3OH$ as a mobile phase) to afford pure product (24.6 mg, 49.2%): m/z=367.00 $[M+H]^+$.

Example 85: 4-(((5-(3-chlorophenyl)oxazol-2-yl)methyl)thio)-6-ethyl-1,3,5-triazin-2-amine (Z1558775684)

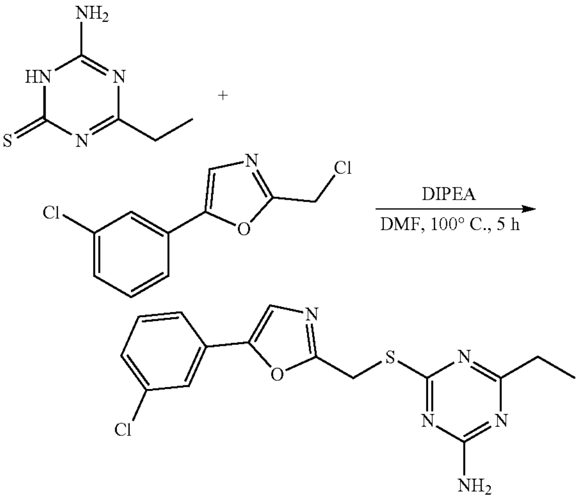

DIPEA (44.7 mg, 345.8 mmol) was added to the solution of 6-amino-4-ethyl-1,3,5-triazine-2(1H)-thione (45.0 mg, 288.1 mmol) in DMSO (0.5 mL). The resulting mixture was stirred for 30 min followed by the addition of 2 -(chloromethyl)-5-(3-chlorophenyl)oxazole (69.5 mg, 304.7 mmol). The reaction mixture was stirred at room temperature for 1 h and then for 5 h at 100° C. After all starting material was consumed, as was shown by LCMS, the resulting mixture was filtered off and the filtrate was subjected to HPLC (Waters SunFire C18 19·100 5 mkm column and $H_2O$-MeCN as a mobile phase, Run Time=5 min) to afford pure product (22.3 mg, 22.3%); LCMS: 348 (M+1)

Example 86: Measurement of Agonistic Activity of Compounds of the Invention on GPR40

Assays for agonistic activity of compounds as described herein on GPR40 are carried out in mammalian cells which provide a readout for GPR40 activation. Primarily stable cell lines of HEK cells, which measure B-arrestin recruitment to heterologously expressed GPR40 via BRET readout. This involves co-expressing in one cell two components, namely a B-arrestin tagged with one element of the BRET assay (fluorescent protein or Luciferase) and the GPR40 tagged with the other element of the assay (fluorescent protein or Luciferase). A fluorescent protein (FP) was fused to the C-terminus of the receptor and was co-expressed in HEK293T cells with luciferase (Luc) fused the N-terminus of G-protein subunit G gamma 2 (Gγ). Furthermore, a fluorescent protein (FP) was fused to the C-terminus of the receptor and was co-expressed in HEK293T cells with luciferase (Luc) fused to the N-terminus of beta-Arrestin-2. 48 h after transfections, cells were incubated with increasing doses of GPR40 reference ligand AMG 837 or a compound as disclosed herein and changes in BRET were measured.

pEC50 data and % activation (% activation=(activation of GPR40 by compound of invention/activation of GPR40 by AMG-837)*100) data of preferred compounds of the invention are shown in FIG. 1 and of preferred compounds for use in the invention are shown in FIG. 2.

Example 87: OGTT Testing in C57Bl/6N Male Mice

1. Materials 1.1. Test Substances.

Compound Z1558775684 was synthesized according to Example 85. Metformin was acquired from Teva Pharmaceutical Industries Ltd., Petach Tikwa, Israel, Lot 78133817 03 2020.

1.2. Reagents Used for Formulation of the Test Substances

METHOCEL F4M Hydroxypropyl methylcellulose (Dow Chemical Company, Midland, USA).

1.4. Other Reagents and Materials

Syringes for injection, 1 ml without needle, Medicare S-3S11, (Dopomoga-1 Ltd, Ukraine). Stainless steel animal feeding tube 20 ga×38 mm (Intech Solomon, USA)

D-(+)-Glucose monohydrate (Sigma, 16301-250G). On Call Plus glucometer (Acon Laboratories, Inc., USA) and specific test strips (REF G133-111). Sterile plastic tubes different volumes (Falcon, Eppendorf). Ethanol, 96% (Ukrorgsynthesis Ltd, Ukraine) Stainless Steel Scissors for microsurgery.

1.5. Equipment

Balance Sartorius LE225D, d=0.01 mg. Water purification system NANOpure Diamond D11911 (Thermo Scientific Barnstead, USA). Ultrasonic bath (Daihan, Korea; WUC-A03H). Micropipettes 0.5-5 μL, 2-20 μL, 20-200, 100-1000 μL (Eppendorf, Hamburg, Germany)

2. Test Systems 2.1. Animals

Species/strain Mice/C57BL/6N: All Males

Age at arrival5 months

Number of animals in the study 25

Animal care: Study design, animal selection, handling and treatment were all in accordance with the Bienta toxicity study protocols and animal care guidelines.

Breeders: The animals were obtained from the animal facility of the Institute of Pharmacology and Toxicology, National Academy of Medical Sciences of Ukraine.

Hygienic class. Conventional at arrival. The animals were kept in good conventional conditions during the study.

2.2. Reason for Animal Species and Strain Selection

C57BL/6N is a mouse strain commonly used in glucose metabolism studies.

2.3. Animal Identification

The animals were individually identified by earmarking. The cages were labeled with tags indicating the ID numbers and earmarks of mice, the study code, sex, and route of administration, start and end date of the experimental period.

2.4. Housing Conditions

Hygienic level: Good conventional

Type of animal cages: Polycarbonate bottoms with stainless steel wire mesh lids

Cage size: H×W×D: 12.0×17.5×28.0 cm

Cleaning: By changing the bedding twice a week

Number of animals per cage: 3-5

Environmental conditions:

Air exchange: 15-20 times/hour

Temperature: 22±3C

Relative humidity: 40-60%

Lighting: 12-hour light/dark cycles.

Feed. Mice were given free access to standardized rodent diet.

Drinking. Mice had free access to acidified boiled tap water.

2.5. Acclimatization Period

During the acclimatization period (7 days) 3-5 animals were kept in each cage. All animals were monitored daily. Animals free from any clinical symptoms of sickness were used in the study.

2.6. Randomization

Animals were randomly assigned to groups according to the standard procedure 7 days prior to the starting day of the study. Each cage contained animals from a uniform experimental group.

3. Study Design 3.1. Dose Levels, Group Division, and Sampling

Each experimental group consisted of five male C57Bl/6N mice. Animals were dosed once perorally with 20 mg/kg of tested compound Z1558775684. A control group was dosed with vehicle on the same schedule. Metformin at the dosage of 300 mg/kg was used as reference compound. All mice were observed for clinical signs of gross toxicity before administration.

3.2. Groups Characteristic

Mice were 5 months old, body weight ranged from 24.0 g to 32.2 g at arrival. Average body weight across all experimental groups was 28.0 g (SD=2.12 g, CV=7.6%).

4. Compound Administration 4.1. Drug Formulation, Route and Volume of Administration Compound Z1558775684 was dissolved/suspended in DMSO—PEG400—physiological saline (20%:50%:30%) at concentration 4 mg/ml. Metformin was dissolved in the same vehicle at concentration 60 mg/ml. The test samples were administered per os in the volume corresponding to 5 ml/kg body weight.

4.2. Frequency and Duration of Application

Single doses of test samples were administered 60 min before glucose treatment at 3 p.m.

4.3. Duration of Experimental Period

Seven days of acclimatization, 1 treatment day, 1 day for data analysis.

5. Observations, Examinations 5.1. Determination of Blood Glucose Level

The blood glucose level was measured after 6-hour fasting using Call Plus glucometer and specific test strips. Blood was obtained from the tail vein by incision of the tail tip, 5-6 μl of blood was used for each assay.

6. Statistical Analysis

Non-parametric statistical analysis (criteria of Wilcoxon-Mann-Whitney U) for independent samples was used to calculate the significance. The experiments were performed according to the Bienta Standard Operating Procedures/Manuals.

7. Results

The results are presented in FIG. 3. Statistically significant decrease in glucose level was observed in the Metformin-, and Z1558775684-treated groups compared with the Vehicle-treated group.

REFERENCES

1 Covington et al. (2006) Biochem. Soc. Trans. 34 (Pt 5), 770-773

2 Ang et al. (2017) The FASEB Journal. 32, 201700252RR. doi:10.1096/fj

3 Davenport et al. (2013) International Union of Basic and Clinical Pharmacology. LXXXVIII. G protein-coupled receptor list: recommendations for new pairings with cognate ligands. Pharmacol. Rev., 65 (3), 967-86

4 Stoddart et al. (2008) International Union of Pharmacology. LXXI. Free fatty acid receptors FFA1, -2, and -3: pharmacology and pathophysiological functions. Pharmacol. Rev., 60 (4): 405-17

Briscoe et al. (2003) J Biol Chem 278, 11303-11311

6 Itoh et al. (2003) Nature 422, 173-176

7 Kotarsky et al. (2003) Biochem Biophys Res Commun 301, 406-410

8 Hirasawa et al. (2005) Nat Med 11, 90-94

9 Ichimura et al. (2012) Nature, 483 (7389) 350-354

10 Oh et al. (2010) Cell, 142 (5), 687-98

11 Brown et al. (2003) J Biol Chem 278, 11312-11319

12 Le Poul et al. (2003) J Biol Chem 278, 25481-25489

13 Nilsson et al. (2003) Biochem Biophys Res Commun 303, 1047-1052

14 Srivastava et al. (2014) Nature 513 (7516), 124-127

15 Burant et al. (2012) Lancet 379, 1403-1411

16 Houze et al. (2012) Bioorg Med Chem Lett 22, 1267-1270

17 Briscoe et al. (2006) British Journal of Pharmacology 148, 619-628

18 Hara et al. (2009) Naunyn Schmiedebergs Arch Pharmacol 380, 247-255

19 Sun et al. (2010) Mol Pharmacol 78, 804-810

Martin et al. (2012) J Lipid Res 53, 2256-2265

21 Shimpukade et al. (2012) J Med Chem 55, 4511-4515

22 Houze et al (2012) Biorg Med Chem Lett. 22 (2), 1267-70

The invention claimed is:

1. A pharmaceutical composition comprising at least one compound of general formula (I)

$$R^1—S—CH_2—OXA\text{-}R^2 \quad (I)$$

including enantiomers, diastereomers, hydrates, solvates, and pharmaceutically acceptable salts, thereof; and at least one further active component selected from the group consisting of one or more agonists of GPR40 and/or GPR120, one or more biguanides, one or more DPP-4 inhibitors, one or more a-glucosidase inhibitors, one or more sulfonylurea compounds, one or more glinides, one or more GLP-1 receptor agonists, one or more glucokinase modulators, one or more thiazolidinediones, one or more incretin mimetics, insulin, one or more insulin derivatives and Pramlintide;

and at least one pharmaceutical carrier;

wherein the at least one compound of general formula (I) is further characterized in that OXA is selected from the group consisting of 1,3-oxazolyl, 1,2,4-oxadiazolyl or 1,3,4-oxadiazolyl;

when OXA is 1,3-oxazolyl, the group $R^1—S—CH_2$ is bound to $C^2$ of the 1,3-oxazolyl and the group $R^2$ is bound to $C^5$ of the 1,3-oxazolyl;

when OXA is 1,2,4-oxadiazolyl the group $R^1—S—CH_2$ is bound to $C^5$ of the 1,2,4-oxadiazolyl and the group $R^2$ is bound to $C^3$ of the 1,2,4-oxadiazolyl;

when OXA is 1,3,4-oxadiazolyl the group $R^1—S—CH_2$ is bound to $C^5$ of the 1,3,4-oxadiazolyl and the group $R^2$ is bound to $C^2$ of the 1,3,4-oxadiazolyl;

$R^1$ is a 6 membered heteroaryl group selected from the group consisting of 1,3,5-triazinyl and pyrimidinyl being independently substituted with one or more substituents selected from the group consisting of hydroxyl, amino, $C_1$-$C_6$-alkyl, C3-C6-cycloalkyl, $C_1$-$C_4$-alkoxy, N-mono-or N, N-di-substituted $C_1$-C3-alkylamino, non-aromatic 5- to 6-membered heterocyclyl, 6-membered aryl and 5- to 6-membered heteroaryl which substituents may be unsubstituted or substituted with one or more groups selected from the group consisting of halide, cyano and $C_1$-$C_6$-alkyl, wherein the 6-membered aryl and 5- to 6-membered heteroaryl group, respectively, may be fused to said 1,3,5-triazinyl or pyrimidyl group, respectively, and $R^2$ is phenyl being unsubstituted or being substituted with one or more substituents selected from the group consisting of halide, cyano, amino, $C_1$-$C_6$-alkyl, $C_3$-$C_6$-cycloalkyl which may be optionally substituted with one or more halides, $C_1$-$C_4$-alkoxy which may optionally substituted with one or more halides, hydroxy-$C_1$-$C_6$-alkyl, sulfonyl-$C_1$-$C_6$-alkyl, sulphamidyl-N—$C_1$-$C_6$-alkyl and carboxamidyl-N-mono-or N,N-di-$C_1$-$C_6$-alkyl;

with the proviso that the following compounds are excluded:

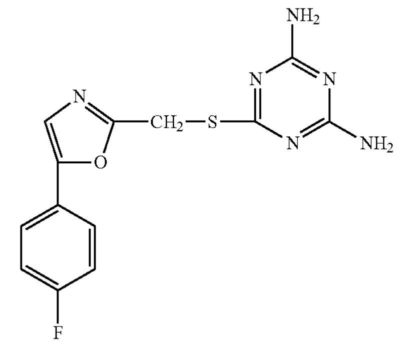

-continued
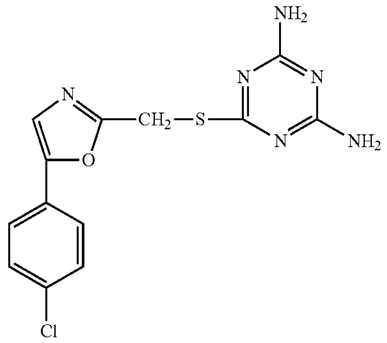
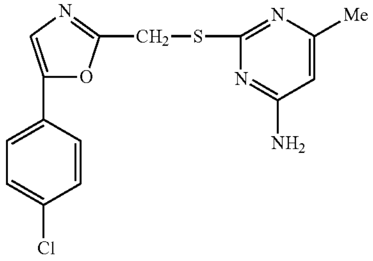
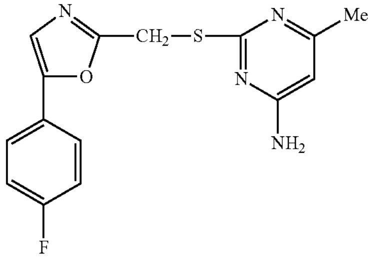
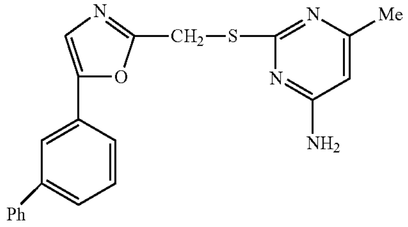
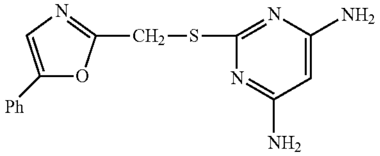
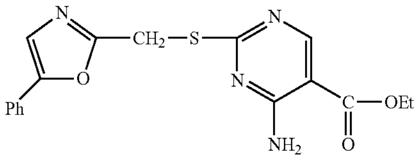
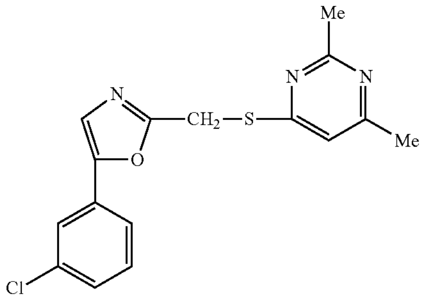
-continued
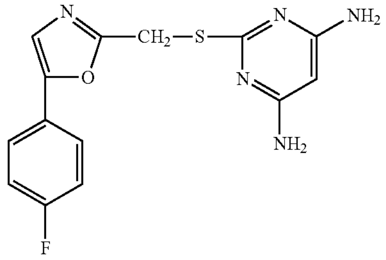
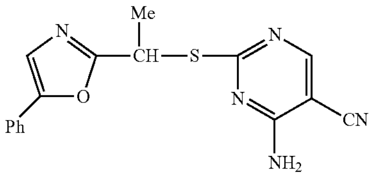
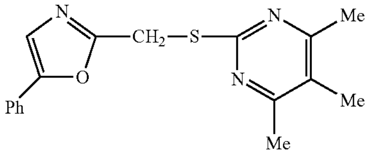
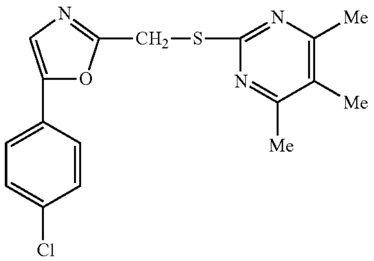
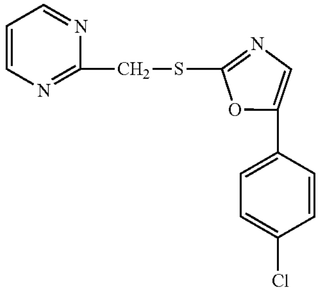
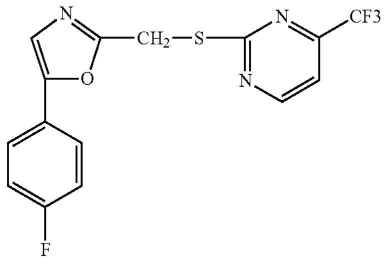

-continued

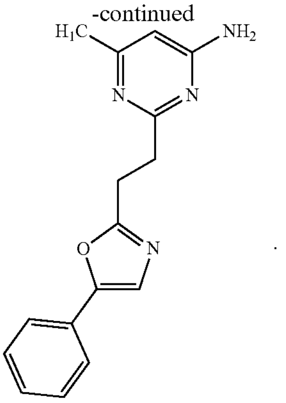

.

2. The composition of claim 1 wherein the halide is selected from CI, Br and F.

3. The composition of claim 1 wherein $R^1$ is 1,3,5-triazinyl independently substituted with one or more substituents selected from the group consisting of hydroxyl, amino, C1-C6-alkyl, C3-C6-cycloalkyl, C1-C4-alkoxy, N-mono-or N,N-di-substituted C1-C3-alkylamino, non-aromatic 5- to 6-membered heterocyclyl, 6-membered aryl and 5- to 6-membered heteroaryl which substituents may be unsubstituted or substituted with one or more groups selected from the group consisting of halide, cyano and C1-C6-alkyl, wherein the 6-membered aryl and 5- to 6-membered heteroaryl group, respectively, may be fused to said 1,3,5-triazinyl.

4. The composition of claim 3 wherein, if the 1,3,5-triazinyl group is substituted with more than one substituent, the substituents are different.

5. The composition of claim 3 wherein the 1,3,5-triazinyl group is independently substituted with one or two substituents selected from the group consisting of amino, methyl, ethyl, isopropyl and tert-butyl, which substituent(s) is/are optionally substituted with one or more halide.

6. The composition of claim 3 wherein $R^1$ is selected from the group consisting of

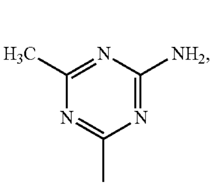

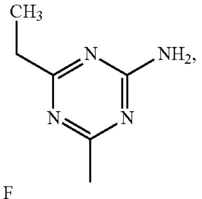

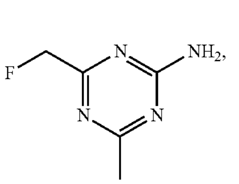

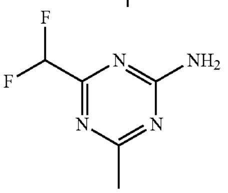

and

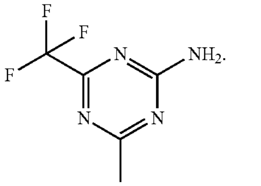

7. The composition according to claim 1 wherein $R^1$ is pyrimidinyl independently substituted with one or more substituents selected from the group consisting of hydroxyl, amino, C1-C6-alkyl, C3-C6-cycloalkyl, C1-C4-alkoxy, N-mono-or N, N-di-substituted $C_1$-C3-alkylamino, non-aromatic 5- to 6-membered heterocyclyl, 6-membered aryl and 5- to 6-membered heteroaryl which substituents may be unsubstituted or substituted with one or more groups selected from the group consisting of halide, cyano and C1-C6-alkyl, wherein the 6-membered aryl and 5- to 6-membered heteroaryl group, respectively, may be fused to said pyrimidinyl.

8. The composition of claim 7 wherein, if the pyrimidinyl group is substituted with more than one substituent, the substituents are different.

9. The composition of claim 7 wherein the pyrimidinyl group is independently substituted by one or more substituents selected from the group consisting of amino, methyl and ethyl.

10. The composition of claim 9 wherein the amino group is substituted with methyl.

11. The composition of claim 9 wherein the methyl or ethyl group is substituted with one or more halides selected from CI, Br and F.

12. The composition of claim 7 wherein $R^1$ is selected from the group consisting of

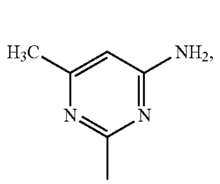

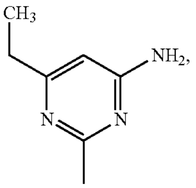

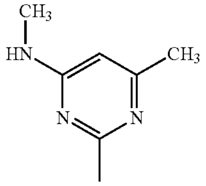

and

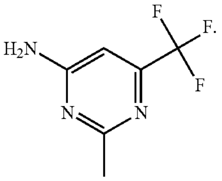

13. The composition according to claim 1 wherein $R^2$ is independently substituted with one or more substituents selected from the group consisting of CI, Br, F, methyl, trifluormethyl, methoxy and ethoxy.

14. The composition of claim 1 wherein $R^2$ is substituted in at least one meta position and/or at least one ortho position.

15. The composition of claim 14 wherein $R^2$ is selected from the group consisting of

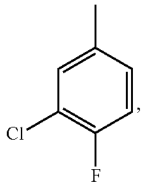

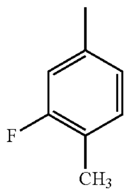

and

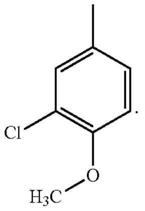

16. The composition of claim 14 wherein $R^2$ is not substituted in the para position.

17. The composition of claim 16 wherein $R^2$ is selected from the group consisting of

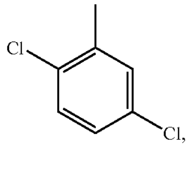,
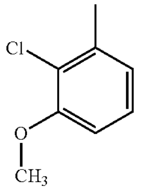,
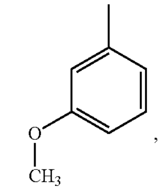,
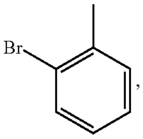,
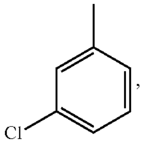,
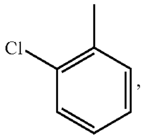,
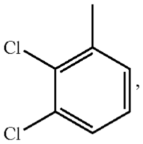,
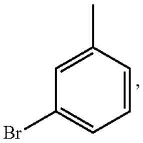,
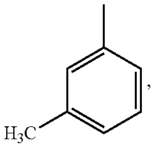,
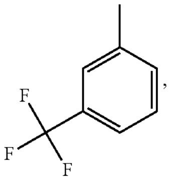,
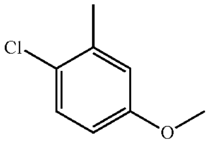
and
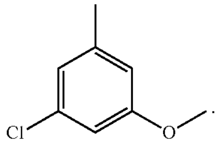.
18. The composition of claim 1 wherein OXA is 1,3-oxazolyl.
19. The composition of claim 18, selected from the group consisting of:
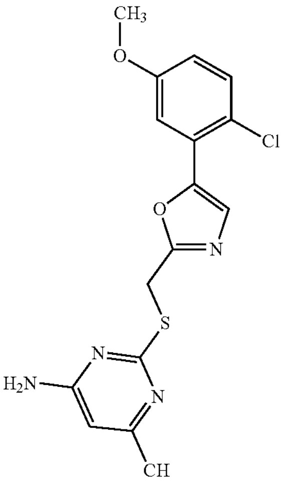
Z3465744373
-continued
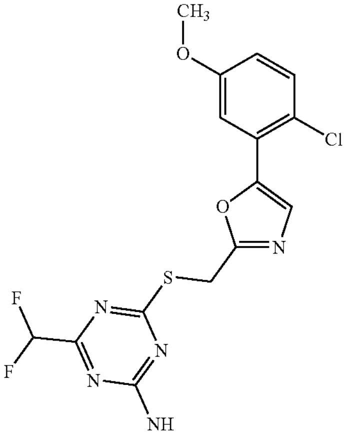
Z3485538339
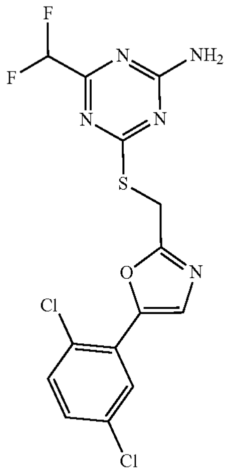
Z3485538343
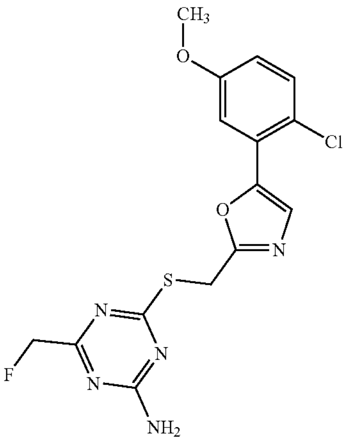
Z3485538337

-continued
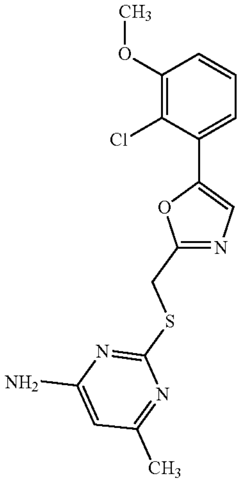
Z3397119007
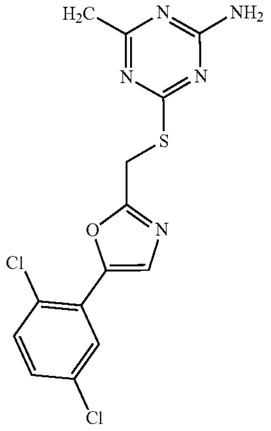
Z3352693146
Z3465744378
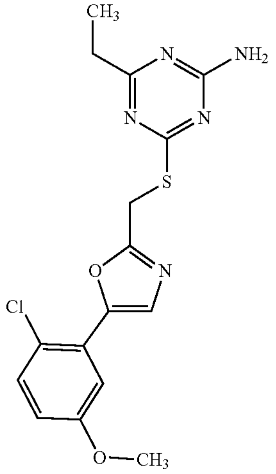
-continued
Z3465744370
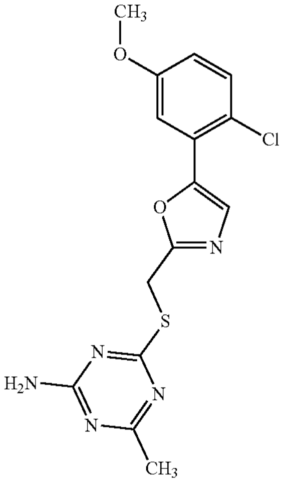
Z3352693158
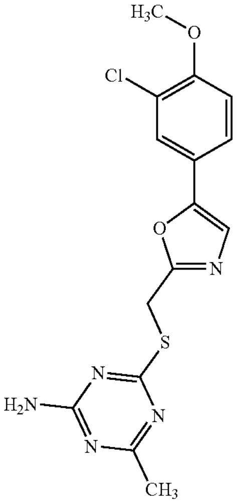
Z3465744375
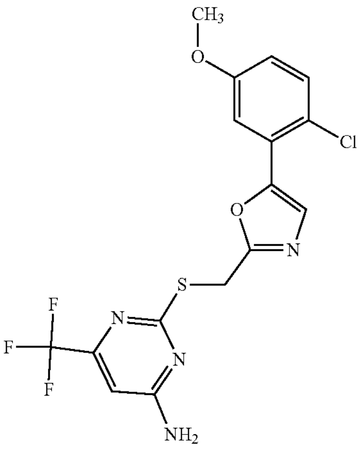

-continued
Z3485538344
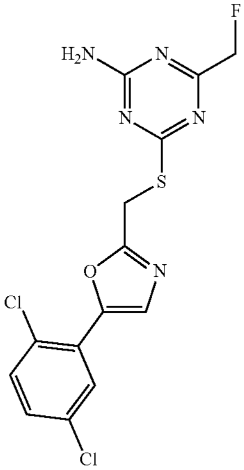
Z3331727681
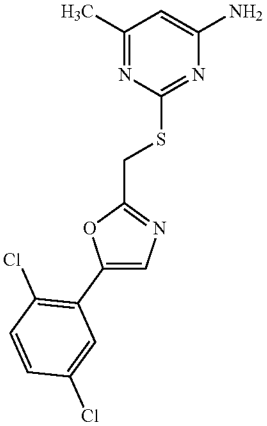
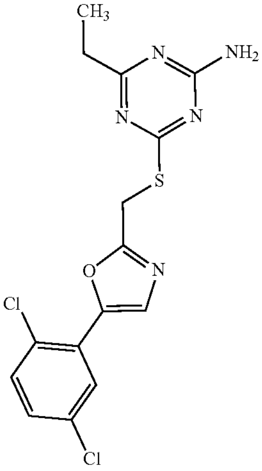
Z3397119001
-continued
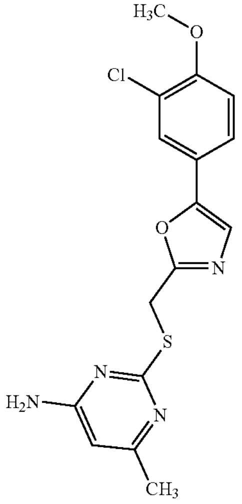
Z3325085943
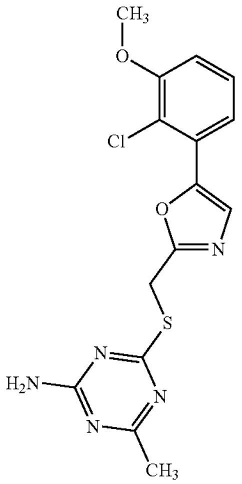
Z3397119008
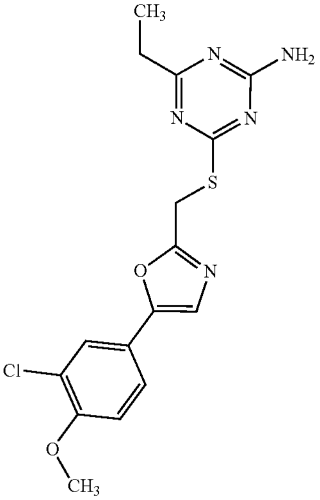
Z3397119003

-continued
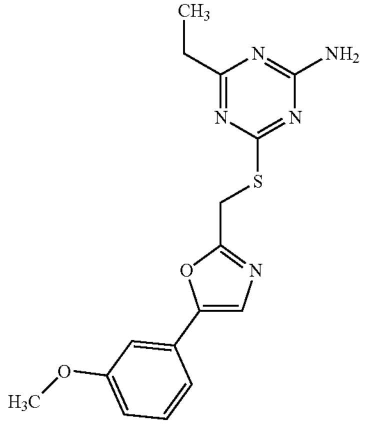
Z1558782315
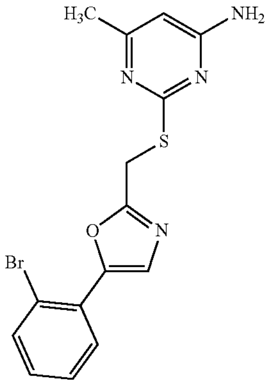
Z1263951047
Z1263951043
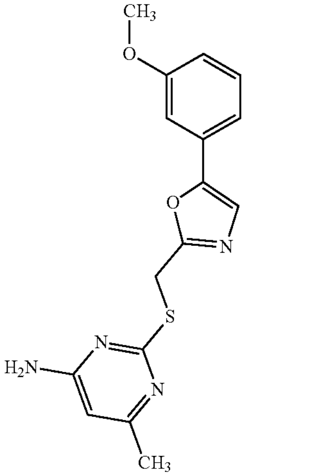
-continued
Z3400108341
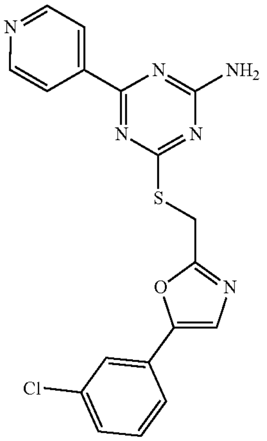
Z3465744387
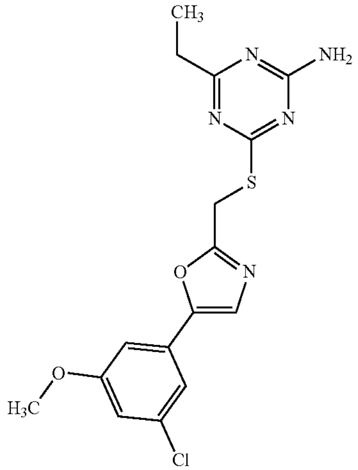
Z1558775684
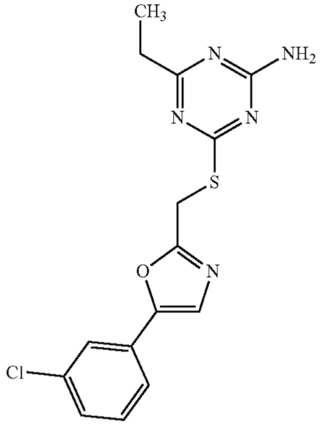

-continued
Z3379835076
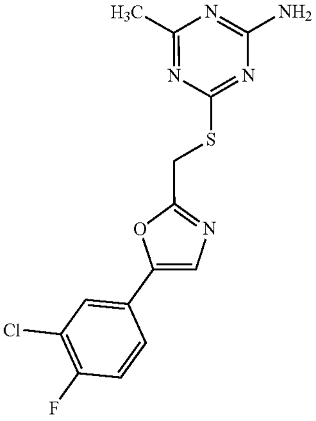
Z1272945752
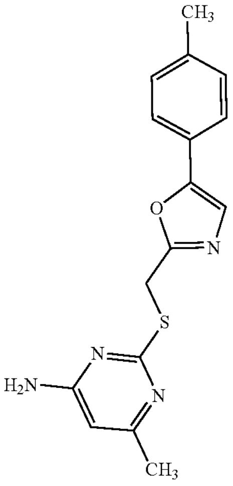
Z74373346
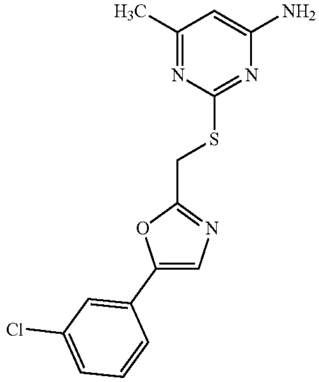
-continued
Z3400108335
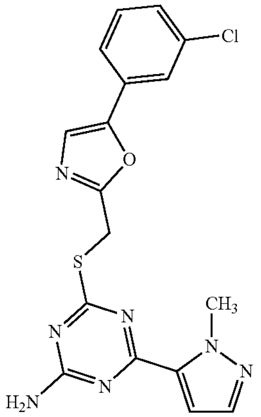
Z3485538331
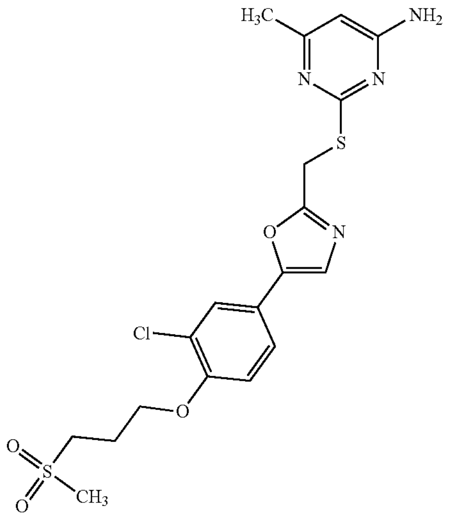
Z3379835080
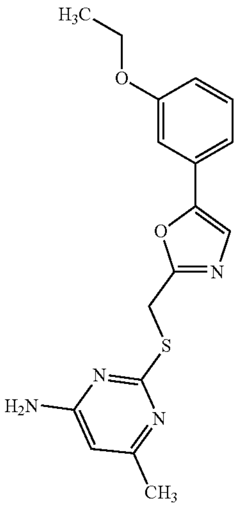

Z3331727639
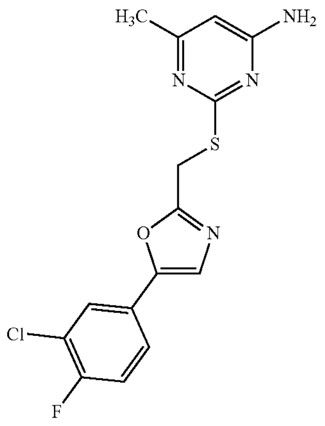
Z335269152
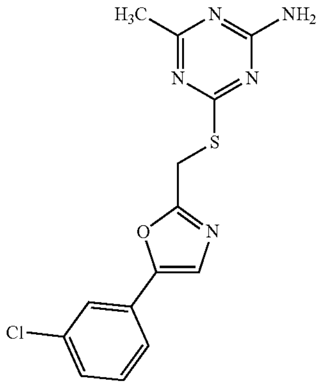
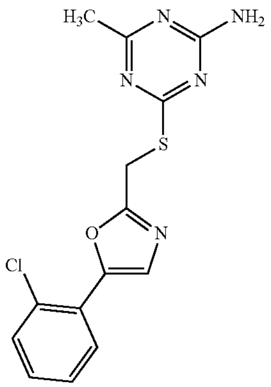
Z3304784609
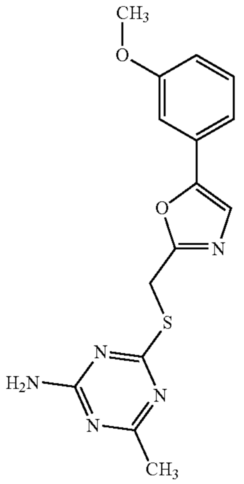
Z3304784620
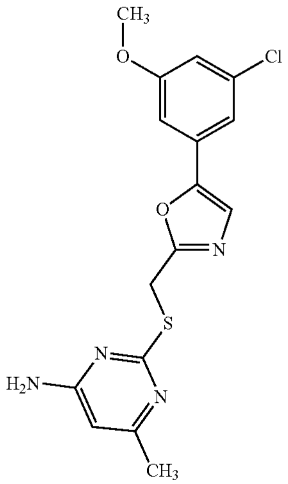
Z3465744383
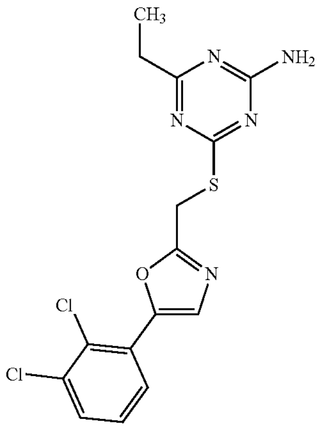
Z3397119002

-continued
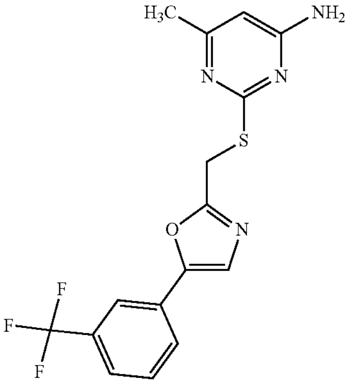
Z3325085937
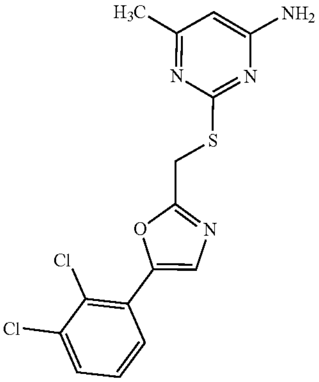
Z3331727663
Z3352693156
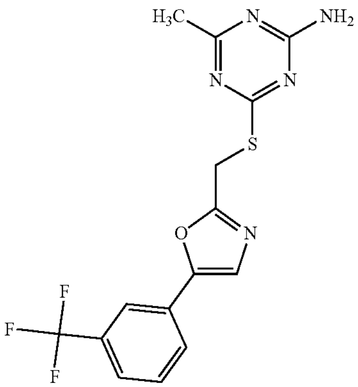
-continued
Z3352693154
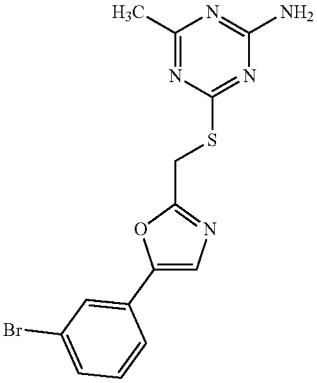
Z3379835077
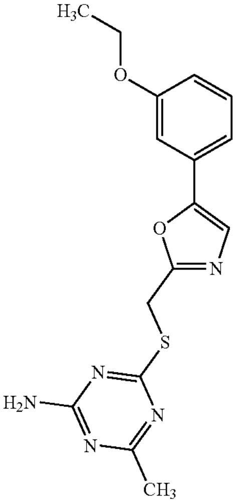
Z3352693149
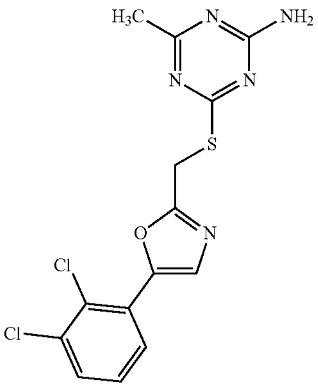

-continued
Z3331727680
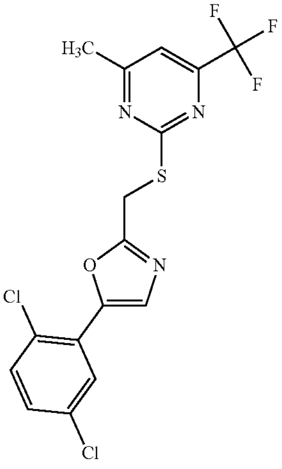
Z3400108326
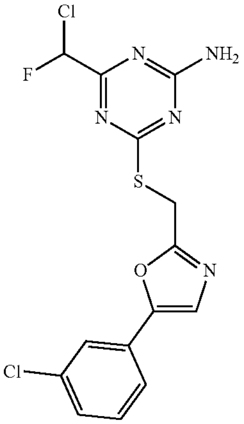
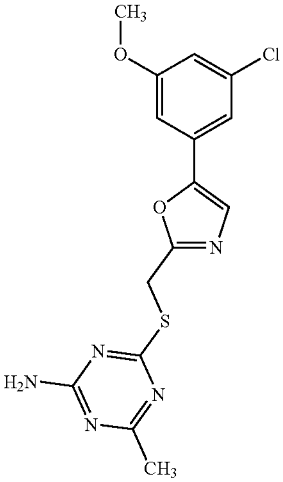
Z3465744380
-continued
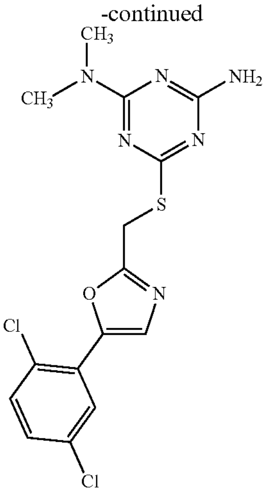
Z3485538342
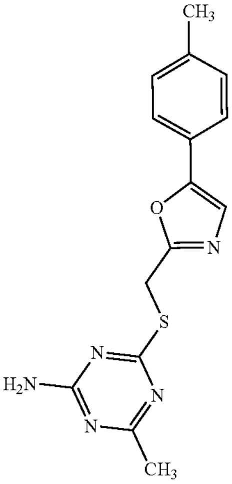
Z3304784612
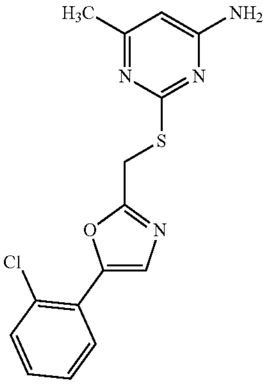
Z1263951032

-continued
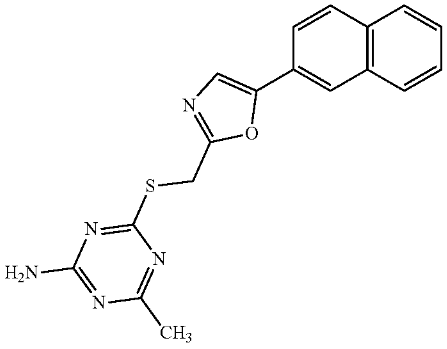
Z3379835078
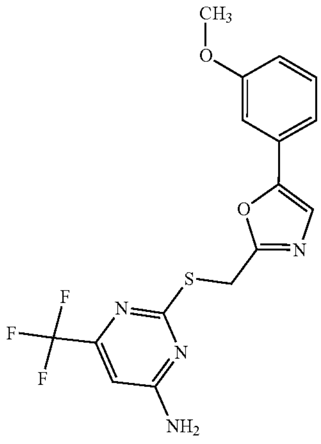
Z3302950784
Z3397119006
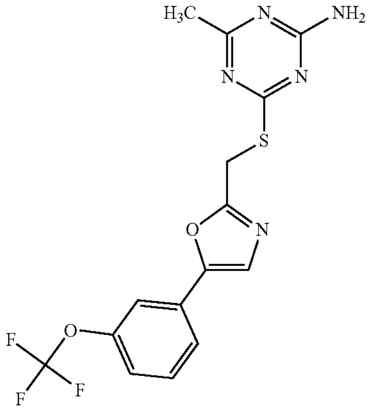
-continued
Z855791334
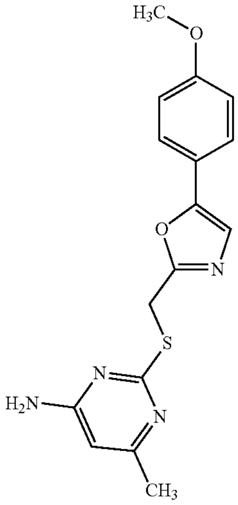
Z3271681130
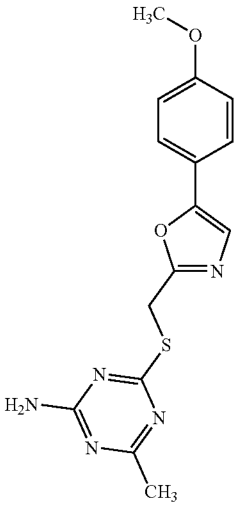
Z3379835074
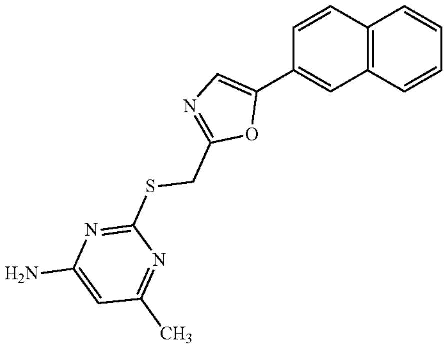

-continued
Z1263951049
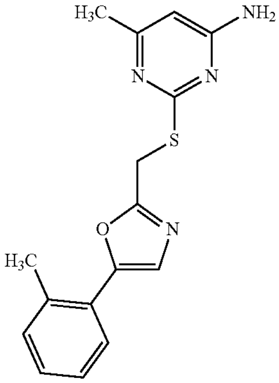
Z3400108327
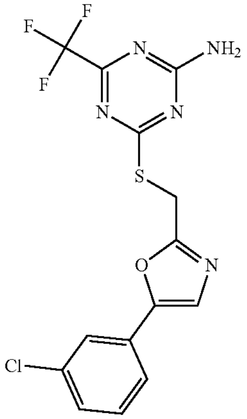
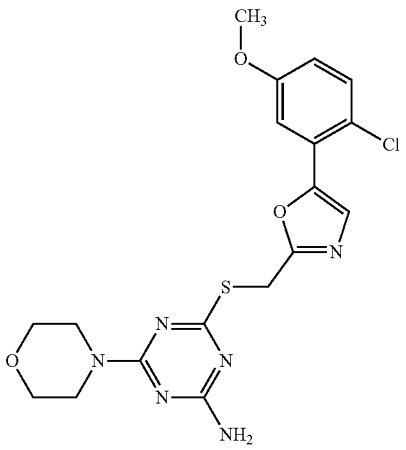
Z3485538336
-continued
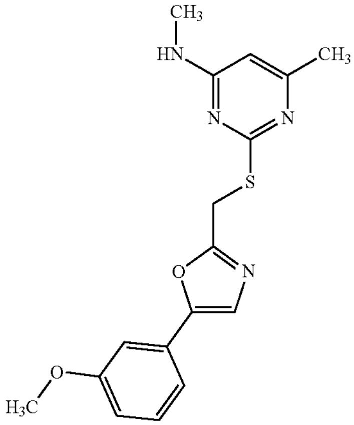
Z3375851526
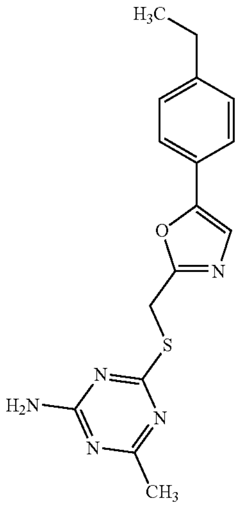
Z3379835075
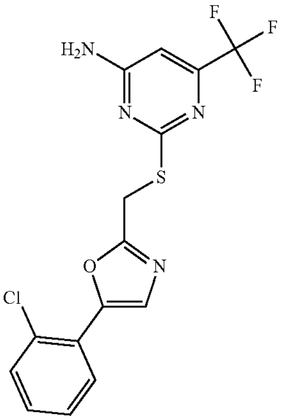
Z3302950786

-continued
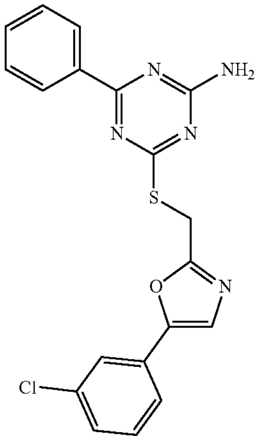
Z3397119009
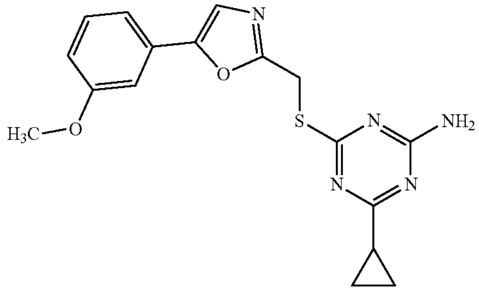
Z3399992230
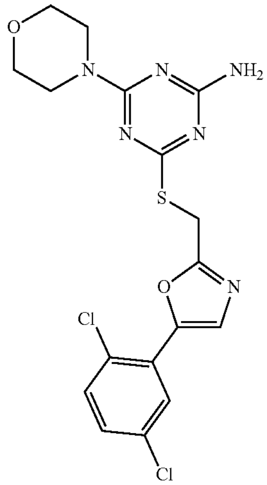
Z3485538340
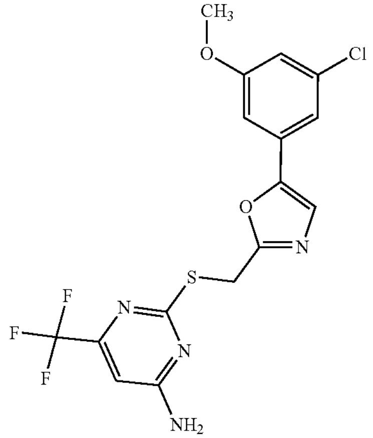
Z3465744385
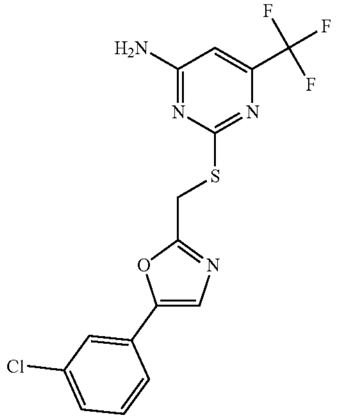
Z3302950790
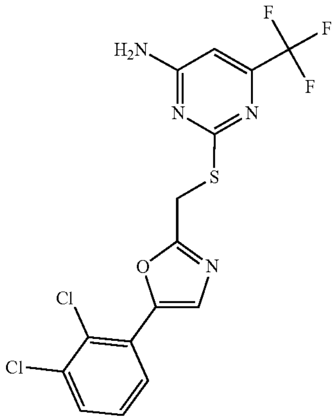
Z3331727652

-continued
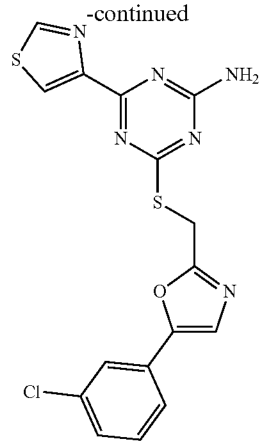
Z3400108333
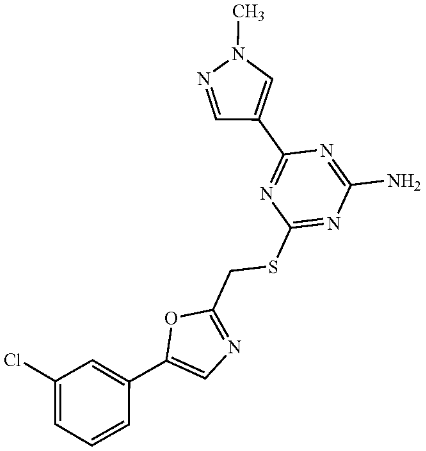
Z3400108334
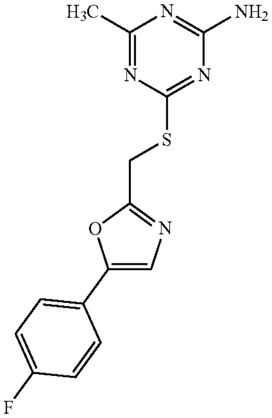
Z3304784617
-continued
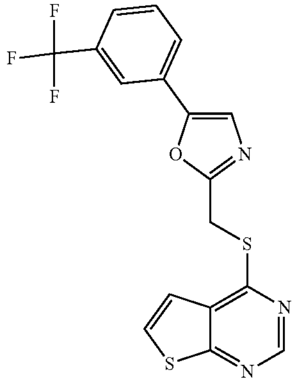
Z3325085938
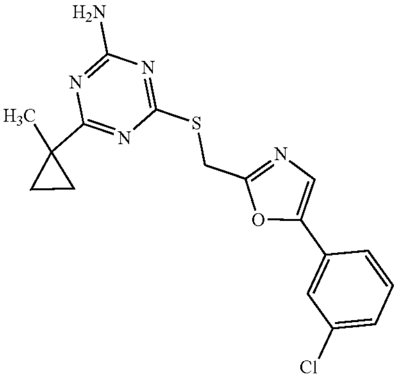
Z3400108300
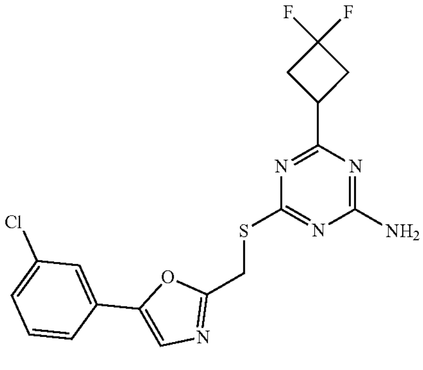
Z3400108303
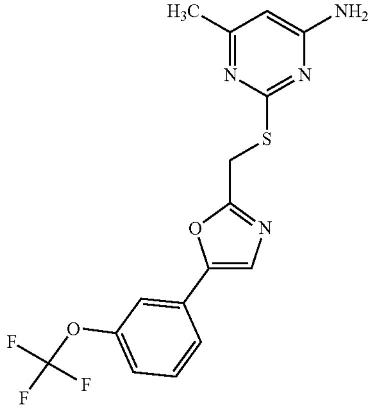
Z3397119005

-continued
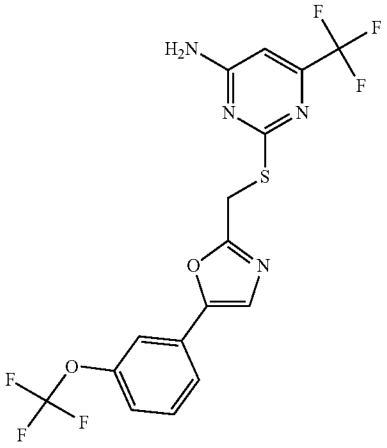
Z3465744366
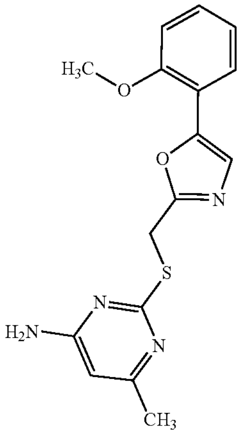
Z1272945742
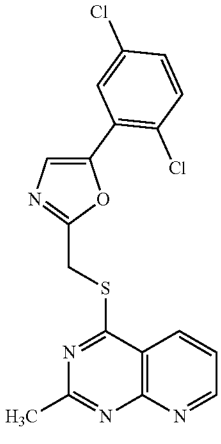
Z3352693410
-continued
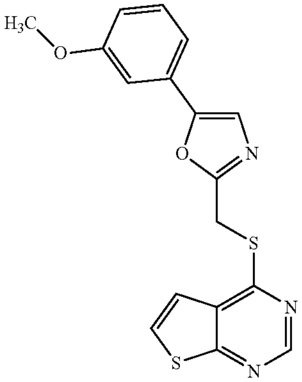
Z1263936589
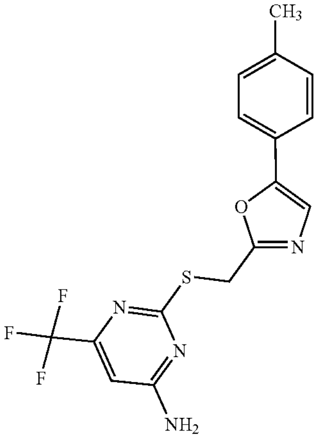
Z3302950788
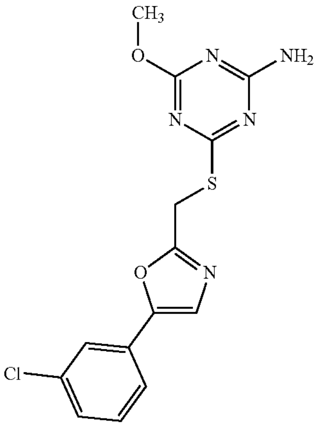
Z3400108307

-continued
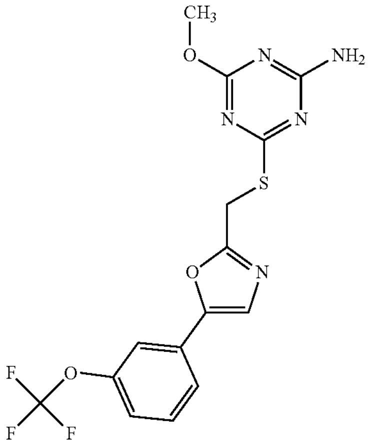
Z3446839939
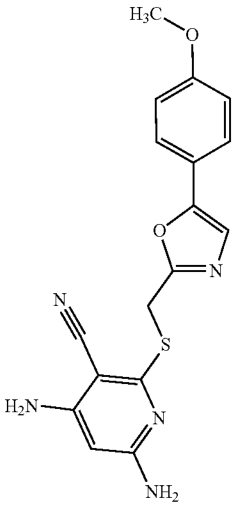
Z855791540
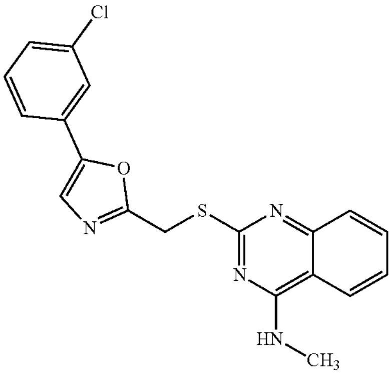
Z71175677
-continued
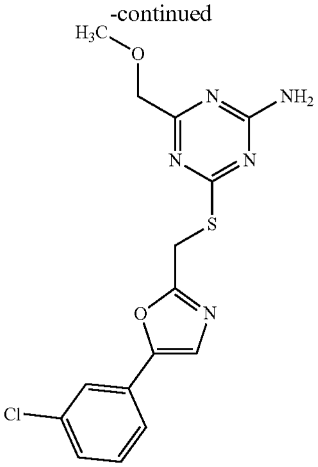
Z3400108304
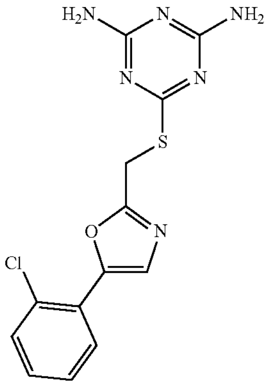
Z1263928611
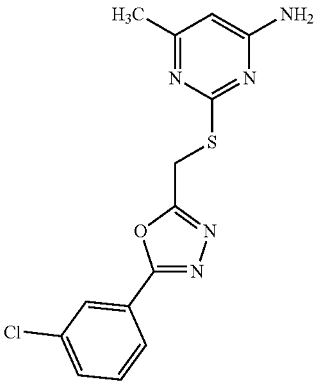
Z1143973826

-continued

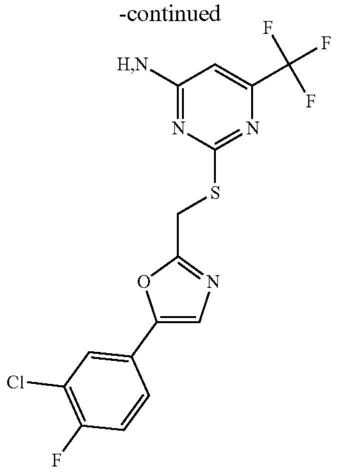

Z3331727625

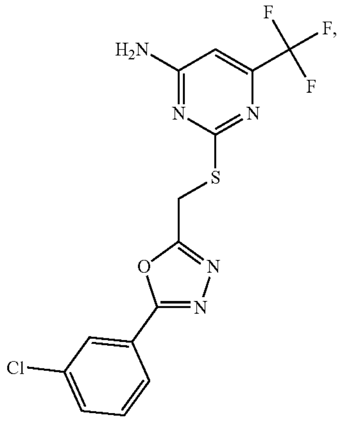

and

Z3331727576

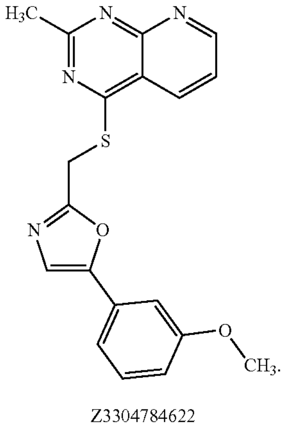

Z3304784622

20. The composition of claim 1 wherein the composition contains at least one further active component selected from the group consisting of one or more angiotensin converting-enzyme inhibitors (ACE inhibitors), one or more angiotensin II receptor blockers (ARBs), one or more thiazide diuretics, one or more calcium channel blockers, one or more antioxidants, one or more protein kinase C inhibitors, one or more TNF-alpha blockers, one or more SGTL2 inhibitors, one or more incretin mimetics, one or more mineralocorticoid receptor antagonists and sulodexide.

21. The composition of claim 1 wherein the composition contains at least one further active component selected from the group consisting of one or more tissue growth factor (TGF) inhibitors, one or more tyrosine-kinase inhibitors, one or more integrin inhibitors, one or more ALK5 inhibitors, one or more bone morphogenetic protein-7 agonists, one or more CTGF inhibitors, one or more TNF inhibitors, one or more HGF mimetics, one or more interleukin inhibitors, one or more CC chemokine inhibitors, one or more interferons, one or more MMP/TIMP inhibitors, one or more endothelin antagonists, one or more LPAR antagonists, one or more CB1 receptor antagonists, one or more CB2 receptor antagonists, one or more prostacyclin receptor agonists, one or more VIP receptor agonists, one or more leukocyte elastase inhibitors, one or more TAFI inhibitors, one or more relaxin receptor stimulants, one or more recombinant pentraxins or mimetics thereof, one or more TGM inhibitors, one or more autotaxin inhibitors, one or more GPR84 inhibitors, one or more GPR40 agonists, one or more connective galectin inhibitors, one or more Rho-associated kinase inhibitors, one or more c-Jun kinase inhibitors, one or more somatostatin analogues, one or more cyclophilin inhibitors, pirfenidone, Tripelukast and bardoxolonemethyl.

22. The composition of claim 1 wherein the composition contains at least one further active component selected from the group consisting of one or more androgen receptor agonists, one or more fatty-acid/bile-acid conjugates (FABACs), one or more bile-acids, one or more FXR ligands, one or more FGF-19 mimetics, one or more TGR5 agonists, one or more PPAR agonists, one or more ASBT inhibitors, one or more immunomodulators, one or more CCR2/CCR5 receptor inhibitors, one or more caspase inhibitors, one or more thyroid hormone receptor β agonists, one or more ASK1 inhibitors, one or more SSAO/VAP-1 inhibitors, one or more human fibroblast growth factor mimetics, one or more P2RY13 protein agonists, one or more cyclosporine A analogues, one or more galectin inhibitors, one or more acetyl-CoA carboxylase (ACC) inhibitors, one or more lipid modulators, one or more anti-CD3 antibodies, one or more FGFR1c/KLB activators, one or more Diacylglycerol O-Acyltransferase 2 (DGAT2) inhibitors, one or more ketohexokinase (KHK) inhibitors, one or more integrin inhibitors, one or more mitochondrial pyruvate carrier inhibitors and vitamin E.

* * * * *